US011371062B2

(12) United States Patent
Doudna et al.

(10) Patent No.: US 11,371,062 B2
(45) Date of Patent: Jun. 28, 2022

(54) RNA-GUIDED NUCLEIC ACID MODIFYING ENZYMES AND METHODS OF USE THEREOF

(71) Applicant: The Regents of the University of California, Oakland, CA (US)

(72) Inventors: Jennifer A. Doudna, Berkeley, CA (US); Jillian F. Banfield, Berkeley, CA (US); David Burstein, Berkeley, CA (US); Lucas Benjamin Harrington, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 572 days.

(21) Appl. No.: 16/335,630

(22) PCT Filed: Sep. 28, 2017

(86) PCT No.: PCT/US2017/054047
§ 371 (c)(1),
(2) Date: Mar. 21, 2019

(87) PCT Pub. No.: WO2018/064352
PCT Pub. Date: Apr. 5, 2018

(65) Prior Publication Data

US 2019/0300908 A1 Oct. 3, 2019

Related U.S. Application Data

(60) Provisional application No. 62/402,849, filed on Sep. 30, 2016.

(51) Int. Cl.
*C12N 9/22* (2006.01)
*C12N 15/113* (2010.01)
*C12N 15/90* (2006.01)
*A61K 38/46* (2006.01)

(52) U.S. Cl.
CPC ............ *C12N 15/902* (2013.01); *A61K 38/46* (2013.01); *C12N 9/22* (2013.01); *C12N 15/113* (2013.01); *C12N 2310/20* (2017.05); *C12N 2740/16043* (2013.01); *C12N 2750/14143* (2013.01)

(58) Field of Classification Search
CPC ...... C12N 15/902; C12N 9/22; C12N 15/113; C12N 2310/20; C12N 2740/16043; C12N 2750/14143; A61K 38/46
See application file for complete search history.

(56) References Cited

U.S. PATENT DOCUMENTS

| | | | |
|---|---|---|---|
| 6,773,885 B1 | 8/2004 | Walder et al. | |
| 8,597,886 B2 | 12/2013 | Smith et al. | |
| 8,815,782 B2 | 8/2014 | Zeiner et al. | |
| 9,730,967 B2 | 8/2017 | Kovarik et al. | |
| 9,790,490 B2 | 10/2017 | Zhang et al. | |
| 10,253,365 B1 | 4/2019 | Doudna et al. | |
| 10,316,324 B2 | 6/2019 | Begemann et al. | |
| 10,337,051 B2 | 7/2019 | Doudna et al. | |
| 10,494,664 B2 | 12/2019 | Doudna et al. | |
| 10,570,415 B2 | 2/2020 | Doudna et al. | |
| 2013/0261196 A1 | 10/2013 | Diamond et al. | |
| 2014/0068797 A1 | 3/2014 | Doudna et al. | |
| 2014/0093883 A1 | 4/2014 | Maples et al. | |
| 2014/0273226 A1 | 9/2014 | Wu | |
| 2015/0211058 A1 | 7/2015 | Carstens | |
| 2016/0138008 A1 | 5/2016 | Charpentier et al. | |
| 2016/0208243 A1* | 7/2016 | Zhang | C12N 15/8201 |
| 2016/0289659 A1* | 10/2016 | Doudna | C12N 15/113 |
| 2017/0037432 A1 | 2/2017 | Donohoue et al. | |
| 2017/0051276 A1 | 2/2017 | May et al. | |
| 2017/0175104 A1 | 6/2017 | Doudna et al. | |
| 2017/0198277 A1 | 7/2017 | Kmiec et al. | |
| 2017/0211142 A1 | 7/2017 | Smargon et al. | |
| 2017/0233756 A1 | 8/2017 | Begemann et al. | |
| 2017/0306335 A1 | 10/2017 | Zhang et al. | |
| 2017/0321198 A1 | 11/2017 | Severinov et al. | |
| 2017/0321214 A1 | 11/2017 | Zhang et al. | |
| 2017/0369870 A1 | 12/2017 | Gill et al. | |

(Continued)

FOREIGN PATENT DOCUMENTS

| | | |
|---|---|---|
| CN | 106701830 A | 5/2017 |
| EP | 3009511 | 4/2016 |

(Continued)

OTHER PUBLICATIONS

Makarova et al., 2015. An updated evolutionary classification of CRISPR-Cas systems. Rev Microbiol 13(11): 722-736 (Year: 2015).*
Zetsche et al., 2015. Cpf1 Is a Single RNA-Guided Endonuclease of a Class 2 CRISPR-Cas System. Cell 163, 759-771 (Year: 2015).*
Yamano et al., May 2016, Crystal Structure of Cpf1 in Complex with Guide RNA and Target DNA. Cell 165, 949-962 (Year: 2016).*

(Continued)

*Primary Examiner* — Neil P Hammell
*Assistant Examiner* — Catherine A Konopka
(74) *Attorney, Agent, or Firm* — Bozicevic, Field & Francis LLP; Shweta Chandra

(57) ABSTRACT

The present disclosure provides CasY proteins, nucleic acids encoding the CasY proteins, and modified host cells comprising the CasY proteins and/or nucleic acids encoding same. CasY proteins are useful in a variety of applications, which are provided. The present disclosure provides CasY guide RNAs that bind to and provide sequence specificity to the CasY proteins, nucleic acids encoding the CasY guide RNAs, and modified host cells comprising the CasY guide RNAs and/or nucleic acids encoding same. CasY guide RNAs are useful in a variety of applications, which are provided. The present disclosure provides methods of identifying a CRISPR RNA-guided endonuclease.

28 Claims, 56 Drawing Sheets

Specification includes a Sequence Listing.

(56) References Cited

U.S. PATENT DOCUMENTS

| | | | |
|---|---|---|---|
| 2018/0340218 | A1 | 11/2018 | Abudayyeh et al. |
| 2019/0276842 | A1 | 9/2019 | Doudna et al. |
| 2019/0300908 | A1 | 10/2019 | Doudna et al. |
| 2020/0017879 | A1 | 1/2020 | Doudna et al. |
| 2020/0087640 | A1 | 3/2020 | Doudna et al. |
| 2021/0166783 | A1 | 6/2021 | Shmakov et al. |

FOREIGN PATENT DOCUMENTS

| | | | | |
|---|---|---|---|---|
| JP | 2004521606 A | 7/2004 | | |
| WO | WO 2015/071474 | 5/2015 | | |
| WO | WO 2015/139139 | 9/2015 | | |
| WO | WO-2015139139 A1 * | 9/2015 | .......... | C12N 15/102 |
| WO | WO 2015/191693 | 12/2015 | | |
| WO | WO 2016/094872 | 12/2015 | | |
| WO | WO 2016/106236 | 12/2015 | | |
| WO | WO 2016/028843 | 2/2016 | | |
| WO | WO 2016/094867 | 6/2016 | | |
| WO | WO 2016/205711 | 6/2016 | | |
| WO | WO 2016/123243 | 8/2016 | | |
| WO | WO 2016/205613 | 12/2016 | | |
| WO | WO 2016/205749 | 12/2016 | | |
| WO | WO 2016/205764 | 12/2016 | | |
| WO | WO 2017/070605 | 4/2017 | | |
| WO | WO 2017/205668 | 5/2017 | | |
| WO | WO 2017/120410 | 7/2017 | | |
| WO | WO 2017/147345 | 8/2017 | | |
| WO | WO 2017/176529 | 10/2017 | | |
| WO | WO 2017/218573 | 12/2017 | | |
| WO | WO 2017/219027 | 12/2017 | | |
| WO | WO 2017/223538 | 12/2017 | | |
| WO | WO 2018/064352 | 4/2018 | | |
| WO | WO 2018/064371 | 4/2018 | | |
| WO | WO 2018/107129 | 6/2018 | | |
| WO | WO 2018/195545 | 10/2018 | | |
| WO | WO 2019/089796 | 5/2019 | | |
| WO | WO 2019/089804 | 5/2019 | | |
| WO | WO 2019/089808 | 5/2019 | | |
| WO | WO 2019/089820 | 5/2019 | | |
| WO | WO 2019/126577 | 6/2019 | | |

OTHER PUBLICATIONS

Wright et al., 2016. Biology and Applications of CRISPR Systems: Harnessing Nature's Toolbox for Genome Engineering. Cell 164, 29-44 (Year: 2016).*

Abudayyeh et al., Aug. 2016, C2c2 is a single-component programmable RNA-guided RNA-targeting CRISPR effector. 353(6299) Science (Year: 2016).*

Sampson et al., 2013. A CRISPR/Cas system mediates bacterial innate immune evasion and virulence. Nature 497, 254-257 (Year: 2013).*

Price et al., 2015. Cas9-mediated targeting of viral RNA in eukaryotic cells. PNAS 112(19), 6164-6169 (Year: 2015).*

CLUSTL Omega Multiple Sequence Alignment. https://www.ebi.ac.uk/Tools/msa/clustalo/ [Retrieved from internet Feb. 2, 2022]. Alignment and Percent identity matrix. (Year: 2022).*

Makarova, et al.; "Snapshot: Class 2 CRISPR-Cas Systems"; Cell; vol. 168, 2 pages (Jan. 12, 2017).

Mohanraju, et al.; "Diverse evolutionary roots and mechanistic variations of the CRISPR-Cas systems"; Science; vol. 353, No. 6299, 14 pages (Aug. 5, 2016).

Abudayyeh, et al.; "C2c2 is a single-component programmable RNA-guided RNA-targeting CRISPR effector"; Science; vol. 353, No. 6299, 23 pages (Aug. 5, 2016).

Abudayyeh, et al.; "C2c2 is a single-component programmable RNA-guided RNA-targeting CRISPR effector; Supplementary Information"; Science; vol. 353, vol. 6299, 31 pages (Aug. 5, 2016).

Abudayyeh, et al.; "RNA targeting with CRISPR-Cas13"; Nature; vol. 550, 18 pages (Oct. 12, 2017).

Ambion; "RnaseAlert Lab Test Kit v2, User Guide"; 12 pages (Mar. 1, 2013).

Anantharaman, et al.; "Thousands of microbial genomes shed light on interconnected biogeochemical processes in an aquifer system"; Nature Communications; vol. 7, No. 13210, 11 pages (Oct. 24, 2016).

Applied Biosystems/Ambion; "RNaseAlert Lab Test Kit"; 12 pages (2008).

Armitage, et al.; "Hairpin-Forming Peptide Nucleic Acid Oligomers"; Biochemistry; vol. 37, No. 26, pp. 9417-9425 (1998).

Baker, et al.; "Enigmatic, ultrasmall, uncultivated Archaea"; PNAS; vol. 107, No. 19, pp. 8806-8811 (May 11, 2010).

Barrangou, et al.; "Expanding the CRISPR Toolbox: Targeting RNA with Cas13b"; Molecular Cell; vol. 65, No. 4, pp. 582-584 (Feb. 16, 2017).

Bautista, et al.; "Virus-Induced Dormancy in the Archaeon Sulfolobus islandicus"; mBio; vol. 6, No. 2, 8 pages (2015).

Choudhury, et al.; "CRISPR-dCas9 mediated TET1 targeting for selective DNA demethylation at BRCA1 promoter"; Oncotarget; vol. 7, No. 29, pp. 46545-46556 (2016).

Chylinski, et al.; "Classification and evolution of type II CRISPR-Cas systems"; Nucleic Acids Research; vol. 42, No. 10, pp. 6091-6105 (2014).

Cong, et al.; "Multiplex Genome Engineering Using CRISPR/Cas Systems"; Science; vol. 339, No. 6121, pp. 819-823 (Feb. 15, 2013).

Cox, et al.; "RNA editing with CRISPR-Cas13"; Science; vol. 358, No. 6366, 15 pages (Nov. 24, 2017).

CRZ3554.1 (hypothetical protein HHT344_2368 [Herbinix hemicellulosilytica], Gen Bank Accession sequence, priority to Jul. 24, 2015, 1 page) (Year: 2015).

East-Seletsky, et al.; "RNA Targeting by Functionally Orthogonal Type VI-A CRISPR-Cas Enzymes"; Molecular Cell; vol. 66, pp. 373-383 (May 4, 2017).

East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).

Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).

GenBank CRZ35554 1; "Hypothetical protein HHT355_2368 [Herbinix hemicellulosilytica]"; 1 page (Oct. 11, 2018).

GenBank OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).

Gootenberg, et al.; "Multiplexed and portable nucleic acid detection platform with Cas13, Cas12a, and Csm6"; Science; vol. 360, pp. 439-444 (2018).

Gootenberg, et al.; "Nucleic acid detection with CRISPR-Cas13a/C2c2"; Science; 9 pages (Apr. 13, 2017).

Hale, et al.; "RNA-Guided RNA Cleavage by a CRISPR RNA-Cas Protein Complex"; Cell; vol. 139, No. 5, pp. 945-956 (Nov. 25, 2009).

Hale, et al.; "Target RNA capture and cleavage by the Cmr type III-B CRISPR-Cas effector complex"; Genes & Development; vol. 28, No. 21, pp. 2432-2443 (Nov. 1, 2014).

Harrington, et al.; "Programmed DNA destruction by miniature CRISPR-Cas14 enzymes"; Science; vol. 362, pp. 839-842 (Nov. 16, 2018).

Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).

Karvelis, et al.; "PAM recognition by miniature CRISPR-Cas12f nucleases triggers programmable double-stranded DNA target cleavage"; Nucleic Acids Research; pp. 1-8 (2020).

Kelemen, et al.; "Hypersensitive substrate for ribonucleases"; Nucleic Acids Research; vol. 27, No. 18, pp. 3696-3701 (1999).

Kim, et al.; "Specific and sensitive detection of nucleic acids and RNases using gold nanoparticle-RNA-fluorescentdye conjugates"; Chemical Communications; vol. 14, No. 42, pp. 4342-4344 (Sep. 19, 2007).

(56) References Cited

OTHER PUBLICATIONS

Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Koonin, et al.; "Diversity, classification and evolution of CRISPR-Cas systems"; Current Opinion in Microbiology; vol. 37, pp. 67-78 (2017).
Le Cong, et al.; "Multiplex Genome Engineering Using CRISPR/Cas Systems"; Science; vol. 339, pp. 819-823 (Feb. 15, 2013).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "CasX enzymes comprise a distinct family of RNA-guided genome editors"; Nature; vol. 566, pp. 23 pages (Feb. 14, 2019).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Makarova, et al.; "Evolutionary classification of CRISPR-Cas systems: a burst of class 2 and derived variants"; Nature Reviews Microbiology; vol. 18, pp. 67-83 (Feb. 2020).
Ngo, et al.; "Computational Complexity, Protein Structure Prediction, and the Levinthal Paradox"; The Protein Folding Problem and Tertiary Structure Prediction; pp. 433 and 492-495 (1994).
O'Connell; "Molecular Mechanisms of RNA Targeting by Cas13-containing Type VI CRISPR-Cas Systems"; J Mol Biol; vol. 431, pp. 66-87 (2019).
OHA03494.1 (hypothetical protein A3J58_03210 [Candidatus Sung bacteria bacterium RIFCSPH IGHO2_02_FU LL_52_23], NCBI Reference Sequence, priority to Oct. 21, 2016, 2 pages) (Year: 2016).
RNaseAlert Lab Test Kit (Applied Biosystems, Fluorometric RNase Detection Assay, 2008, 12 pages). (Year: 2008).
Sato, et al.; "Highly Sensitive Nuclease Assays Based on Chemically Modified DNA or RNA"; Sensors; vol. 14, No. 7, pp. 12437-12450 (2014).
Shmakov, et al.; "Diversity and evolution of class 2 CRISPR-Cas systems"; Nature Reviews Microbiology; vol. 15, pp. 169-182 (2017).
Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Strauß, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
Third Party Observations filed on Oct. 15, 2018 in UK patent application No. GB 1804822.3 (18 pages).
Yan, et al.; "Cas13d Is a Compact RNA-Targeting Type VI CRISPR Effector Positively Modulated by a WYL-Domain-Containing Accessory Protein"; Molecular Cell; vol. 70, pp. 327-339 (2018).
Yang, et al.; "Using Molecular Beacons for Sensitive Fluorescence Assays of the Enzymatic Cleavage of Nucleic Acids"; Methods in Molecular Biology, Fluorescent Energy Transfer Nucleic Acid Probes: Designs and Protocols; vol. 335, pp. 71-81 (2006).
Zhang, et al.; "Design of a Molecular Beacon DNA Probe with Two Fluorophores"; Angew. Chem.; vol. 113, No. 2, pp. 416-419 (2001).
Burstein, et al.; "New CRISPR-Cas systems from uncultivated microbes"; Nature; vol. 542, No. 7640, pp. 237-241 (Dec. 22, 2016).
Deltcheva, et al.; "CRISPR RNA maturation by trans-encoded small RNA and host factor RNase III"; Nature; vol. 471, pp. 1-19 (Mar. 31, 2011).
Shmakov, et al.; "Discovery and functional characterization of diverse Class 2 CRISPR-Cas systems"; Mol. Cell.; vol. 60, No. 3, pp. 385-397 (Nov. 5, 2015).
Yang, et al.; "New CRISPR-Cas systems discovered"; Cell Res.; vol. 27, pp. 313-314 (Feb. 21, 2017).
Koonin, et al.; "Origins and evolution of CRISPR-Cas systems"; Phil. Trans. R. Soc. B.; vol. 374, No. 1772, 6 pages (Mar. 25, 2019).
Chen, et al.; "CRISPR-Cas12a target binding unleashes indiscriminate single-stranded DNase activity"; Science; vol. 360, pp. 436-439 (2018).
Liu, et al.; "Delivery strategies of the CRISPR-Cas9 gene-editing system for therapeutic applications"; Journal of Controlled Release; vol. 266, pp. 17-26 (2017).
Makarova, et al.; "An updated evolutionary classification of CRISPR-Cas systems"; Nat. Rev. Microbiol.; vol. 13, No. 11, pp. 722-736 (Nov. 2015).
Price, et al.; "Cas9-mediated targeting of viral RNA in eukaryotic cells"; PNAS; vol. 112, No. 19, pp. 6164-6169 (May 12, 2015).
Sampson, et al.; "A CRISPR/Cas system mediates bacterial innate immune evasion and virulence"; Nature; vol. 497, No. 7448; pp. 254-257 (May 9, 2013).
Wright, et al.; "Biology and Applications of CRISPR Systems: Harnessing Nature's Toolbox for Genome Engineering"; Cell; vol. 164, pp. 29-44 (2016).
Yamano, et al.; "Crystal Structure of Cpf1 in Complex with Guide RNA and Target DNA"; Cell; vol. 165, pp. 949-962 (2016).
Zetsche, et al.; "Cpf1 Is a Single RNA-Guided Endonuclease of a Class 2 CRISPR-Cas System"; Cell; vol. 163, pp. 759-771 (Oct. 22, 2015).
Koonin, et al.; "CRISPR-Cas: an adaptive immunity system in prokaryotes"; F1000 Biology Reports; vol. 1, No. 95, 6 pages (Dec. 9, 2009).
NCBI Reference Sequence: WP_012985477.1 (May 18, 2013).
NCBI Reference Sequence: WP_015770004.1 (May 20, 2013).
NCBI Reference Sequence: WP_023911507.1 (Oct. 23, 2013).
NCBI Reference Sequence: WP_034560163.1 (Oct. 22, 2015).
Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).

* cited by examiner

FIG. 1A

>CasY1
MRKKLFKGYILHNKRLVYTGKAAIRSIKYPLVAPNKTALNNLSEKIIYDYEHLFGPLNVA
SYARNSNRYSLVDFWIDSLRAGVIWQSKSTSLIDLISKLEGSKSPSEKIFEQIDFELKNK
LDKEQFKDIILLNTGIRSSSNVRSLRGRFLKCFKEEFRDTEEVIACVDKWSKDLIVEGKS
ILVSKQFLYWEEEFGIKIFPHFKDNHDLPKLTFFVEPSLEFSPHLPLANCLERLKKFDIS
RESLLGLDNNFSAFSNYFNELFNLLSRGEIKKIVTAVLAVSKSWENEPELEKRLHFLSEK
AKLLGYPKLTSSWADYRMIIGGKIKSWHSNYTEQLIKVREDLKKHQIALDKLQEDLKKVV
DSSLREQIEAQREALLPLLDTMLKEKDFSDDLELYRFILSDFKSLLNGSYQRYIQTEEER
KEDRDVTKKYKDLYSNLRNIPRFFGESKKEQFNKFINKSLPTIDVGLKILEDIRNALETV
SVRKPPSITEEYVTKQLEKLSRKYKINAFNSNRFKQITEQVLRKYNNGELPKISEVFYRY
PRESHVAIRILPVKISNPRKDISYLLDKYQISPDWKNSNPGEVVDLIEIYKLTLGWLLSC
NKDFSMDFSSYDLKLFPEAASLIKNFGSCLSGYYLSKMIFNCITSEIKGMITLYTRDKFV
VRYVTQMIGSNQKFPLLCLVGEKQTKNFSRNWGVLIEEKGDLGEEKNQEKCLIFKDKTDF
AKAKEVEIFKNNIWRIRTSKYQIQFLNRLFKKTKEWDLMNLVLSEPSLVLEEEWGVSWDK
DKLLPLLKKEKSCEERLYYSLPLNLVPATDYKEQSAEIEQRNTYLGLDVGEFGVAYAVVR
IVRDRIELLSWGFLKDPALRKIRERVQDMKKKQVMAVFSSSSTAVARVREMAIHSLRNQI
HSIALAYKAKIIYEISISNFETGGNRMAKIYRSIKVSDVYRESGADTLVSEMIWGKKNKQ
MGNHISSYATSYTCCNCARTPFELVIDNDKEYEKGGDEFIFNVGDEKKVRGFLQKSLLGK
TIKGKEVLKSIKEYARPPIREVLLEGEDVEQLLKRRGNSYIYRCPFCGYKTDADIQAALN
IACRGYISDNAKDAVKEGERKLDYILEVRKLWEKNGAVLRSAKFL (SEQ ID NO: 1)

>CasY2
MQKVRKTLSEVHKNPYGTKVRNAKTGYSLQIERLSYTGKEGMRSFKIPLENKNKEVFDEF
VKKIRNDYISQVGLLNLSDWYEHYQEKQEHYSLADFWLDSLRAGVIFAHKETEIKNLISK
IRGDKSIVDKFNASIKKKHADLYALVDIKALYDFLTSDARRGLKTEEEFFNSKRNTLFPK
FRKKDNKAVDLWVKKFIGLDNKDKLNFTKKFIGFDPNPQIKYDHTFFFHQDINFDLERIT
TPKELISTYKKFLGKNKDLYGSDETTEDQLKMVLGFHNNHGAFSKYFNASLEAFRGRDNS
LVEQIINNSPYWNSHRKELEKRIIFLQVQSKKIKETELGKPHEYLASFGGKFESWVSNYL
RQEEEVKRQLFGYEENKKGQKKFIVGNKQELDKIIRGTDEYEIKAISKETIGLTQKCLKL
LEQLKDSVDDYTLSLYRQLIVELRIRLNVEFQETYPELIGKSEKDKEKDAKNKRADKRYP
QIFKDIKLIPNFLGETKQMVYKKFIRSADILYEGINFIDQIDKQITQNLLPCFKNDKERI
EFTEKQFETLRRKYYLMNSSRFHHVIEGIINNRKLIEMKKRENSELKTFSDSKFVLSKLF
LKKGKKYENEVYYTFYINPKARDQRRIKIVLDINGNNSVGILQDLVQKLKPKWDDIIKKN
DMGELIDAIEIEKVRLGILIALYCEHKFKIKKELLSLDLFASAYQYLELEDDPEELSGTN
LGRFLQSLVCSEIKGAINKISRTEYIERYTVQPMNTEKNYPLLINKEGKATWHIAAKDDL
SKKKGGGTVAMNQKIGKNFFGKQDYKTVFMLQDKRFDLLTSKYHLQFLSKTLDTGGGSWW
KNKNIDLNLSSYSFIFEQKVKVEWDLTNLDHPIKIKPSENSDDRRLFVSIPFVIKPKQTK
RKDLQTRVNYMGIDIGEYGLAWTIINIDLKNKKINKISKQGFIYEPLTHKVRDYVATIKD
NQVRGTFGMPDTKLARLRENAITSLRNQVHDIAMRYDAKPVYEFEISNFETGSNKVKVIY
DSVKRADIGRGQNNTEADNTEVNLVWGKTSKQFGSQIGAYATSYICSFCGYSPYYEFENS
KSGDEEGARDNLYQMKKLSRPSLEDFLQGNPVYKTFRDFDKYKNDQRLQKTGDKDGEWKT
HRGNTAIYACQKCRHISDADIQASYWIALKQVVRDFYKDKEMDGDLIQGDNKDKRKVNEL
NRLIGVHKDVPIINKNLITSLDINLL (SEQ ID NO: 2)

FIG. 1B

>CasY3
MKAKKSFYNQKRKFGKRGYRLHDERIAYSGGIGSMRSIKYELKDSYGIAGLRNR
IADATISDNKWLYGNINLNDYLEWRSSKTDKQIEDGDRESSLLGFWLEALRLGFVFSKQS
HAPNDFNETALQDLFETLDDDLKHVLDRKKWCDFIKIGTPKTNDQGRLKKQIKNLLKGNK
REEIEKTLNESDDELKEKINRIADVFAKNKSDKYTIFKLDKPNTEKYPRINDVQVAFFCH
PDFEEITERDRTKTLDLIINRFNKRYEITENKKDDKTSNRMALYSLNQGYIPRVLNDLFL
FVKDNEDDFSQFLSDLENFFSFSNEQIKIIKERLKKLKKYAEPIPGKPQLADKWDDYASD
FGGKLESWYSNRIEKLKKIPESVSDLRNNLEKIRNVLKKQNNASKILELSQKIIEYIRDY
GVSFEKPEIIKFSWINKTKDGQKKVFYVAKMADREFIEKLDLWMADLRSQLNEYNQDNKV
SFKKKGKKIEELGVLDFALNKAKKNKSTKNENGWQQKLSESIQSAPLFFGEGNRVRNEEV
YNLKDLLFSEIKNVENILMSSEAEDLKNIKIEYKEDGAKKGNYVLNVLARFYARFNEDGY
GGWNKVKTVLENIAREAGTDFSKYGNNNNRNAGRFYLNGRERQVFTLIKFEKSITVEKIL
ELVKLPSLLDEAYRDLVNENKNHKLRDVIQLSKTIMALVLSHSDKEKQIGGNYIHSKLSG
YNALISKRDFISRYSVQTTNGTQCKLAIGKGKSKKGNEIDRYFYAFQFFKNDDSKINLKV
IKNNSHKNIDFNDNENKINALQVYSSNYQIQFLDWFFEKHQGKKTSLEVGGSFTIAEKSL
TIDWSGSNPRVGFKRSDTEEKRVFVSQPFTLIPDDEDKERRKERMIKTKNRFIGIDIGEY
GLAWSLIEVDNGDKNNRGIRQLESGFITDNQQQVLKKNVKSWRQNQIRQTFTSPDTKIAR
LRESLIGSYKNQLESLMVAKKANLSFEYEVSGFEVGGKRVAKIYDSIKRGSVRKKDNNSQ
NDQSWGKKGINEWSFETTAAGTSQFCTHCKRWSSLAIVDIEEYELKDYNDNLFKVKINDG
EVRLLGKKGWRSGEKIKGKELFGPVKDAMRPNVDGLGMKIVKRKYLKLDLRDWVSRYGNM
AIFICPYVDCHHISHADKQAAFNIAV (SEQ ID NO: 3)

>CasY4
MSKRHPRISGVKGYRLHAQRLEYTGKSGAMRTIKYPLYSSPSGGRTVPREIVSAINDDYV
GLYGLSNFDDLYNAEKRNEEKVYSVLDFWYDCVQYGAVFSYTAPGLLKNVAEVRGGSYEL
TKTLKGSHLYDELQIDKVIKFLNKKEISRANGSLDKLKKDIIDCFKAEYRERHKDQCNKL
ADDIKNAKKDAGASLGERQKKLFRDFFGISEQSENDKPSFTNPLNLTCCLLPFDTVNNNR
NRGEVLFNKLKEYAQKLDKNEGSLEMWEYIGIGNSGTAFSNFLGEGFLGRLRENKITELK
KAMMDITDAWRGQEQEEELEKRLRILAALTIKLREPKFDNHWGGYRSDINGKLSSWLQNY
INQTVKIKEDLKGHKKDLKKAKEMINRFGESDTKEEAVVSSLLESIEKIVPDDSADDEKP
DIPAIAIYRRFLSDGRLTLNRFVQREDVQEALIKERLEAEKKKKPKKRKKKSDAEDEKET
IDFKELFPHLAKPLKLVPNFYGDSKRELYKKYKNAAIYTDALWKAVEKIYKSAFSSSLKN
SFFDTDFDKDFFIKRLQKIFSVYRRFNTDKWKPIVKNSFAPYCDIVSLAENEVLYKPKQS
RSRKSAAIDKNRVRLPSTENIAKAGIALARELSVAGFDWKDLLKKEEHEEYIDLIELHKT
ALALLLAVTETQLDISALDFVENGTVKDFMKTRDGNLVLEGRFLEMFSQSIVFSELRGLA
GLMSRKEFITRSAIQTMNGKQAELLYIPHEFQSAKITTPKEMSRAFLDLAPAEFATSLEP
ESLSEKSLLKLKQMRYYPHYFGYELTRTGQGIDGGVAENALRLEKSPVKKREIKCKQYKT
LGRGQNKIVLYVRSSYYQTQFLEWFLHRPKNVQTDVAVSGSFLIDEKKVKTRWNYDALTV
ALEPVSGSERVFVSQPFTIFPEKSAEEEGQRYLGIDIGEYGIAYTALEITGDSAKILDQN
FISDPQLKTLREEVKGLKLDQRRGTFAMPSTKIARIRESLVHSLRNRIHHLALKHKAKIV
YELEVSRFEEGKQKIKKVYATLKKADVYSEIDADKNLQTTVWGKLAVASEISASYTSQFC
GACKKLWRAEMQVDETITTQELIGTVRVIKGGTLIDAIKDFMRPPIFDENDTPFPKYRDF
CDKHHISKKMRGNSCLFICPFCRANADADIQASQTIALLRYVKEEKKVEDYFERFRKLKN
IKVLGQMKKI (SEQ ID NO: 4)

FIG. 1C

>CasY5
MAESKQMQCRKCGASMKYEVIGLGKKSCRYMCPDCGNHTSARKIQNKKKRD
KKYGSASKAQSQRIAVAGALYPDKKVQTIKTYKYPADLNGEVHDSGVAEKIAQAIQEDEI
GLLGPSSEYACWIASQKQSEPYSVVDFWFDAVCAGGVFAYSGARLLSTVLQLSGEESVLR
AALASSPFVDDINLAQAEKFLAVSRRTGQDKLGKRIGECFAEGRLEALGIKDRMREFVQA
IDVAQTAGQRFAAKLKIFGISQMPEAKQWNNDSGLTVCILPDYYVPEENRADQLVVLLRR
LREIAYCMGIEDEAGFEHLGIDPGALSNFSNGNPKRGFLGRLLNNDIIALANNMSAMTPY
WEGRKGELIERLAWLKHRAEGLYLKEPHFGNSWADHRSRIFSRIAGWLSGCAGKLKIAKD
QISGVRTDLFLLKRLLDAVPQSAPSPDFIASISALDRFLEAAESSQDPAEQVRALYAFHL
NAPAVRSIANKAVQRSDSQEWLIKELDAVDHLEFNKAFPFFSDTGKKKKKGANSNGAPSE
EEYTETESIQQPEDAEQEVNGQEGNGASKNQKKFQRIPRFFGEGSRSEYRILTEAPQYFD
MFCNNMRAIFMQLESQPRKAPRDFKCFLQNRLQKLYKQTFLNARSNKCRALLESVLISWG
EFYTYGANEKKFRLRHEASERSSDPDYVVQQALEIARRLFLFGFEWRDCSAGERVDLVEI
HKKAISFLLAITQAEVSVGSYNWLGNSTVSRYLSVAGTDTLYGTQLEEFLNATVLSQMRG
LAIRLSSQELKDGFDVQLESSCQDNLQHLLVYRASRDLAACKRATCPAELDPKILVLPVG
AFIASVMKMIERGDEPLAGAYLRHRPHSFGWQIRVRGVAEVGMDQGTALAFQKPTESEPF
KIKPFSAQYGPVLWLNSSSYSQSQYLDGFLSQPKNWSMRVLPQAGSVRVEQRVALIWNLQ
AGKMRLERSGARAFFMPVPFSFRPSGSGDEAVLAPNRYLGLFPHSGGIEYAVVDVLDSAG
FKILERGTIAVNGFSQKRGERQEEAHREKQRRGISDIGRKKPVQAEVDAANELHRKYTDV
ATRLGCRIVVQWAPQPKPGTAPTAQTVYARAVRTEAPRSGNQEDHARMKSSWGYTWGTYW
EKRKPEDILGISTQVYWTGGIGESCPAVAVALLGHIRATSTQTEWEKEEVVFGRLKKFFP
S (SEQ ID NO: 6)

>CasY6
MAESKQMQCRKCGASMKYEVIGLGKKSCRYMCPDCGNHTSARKIQNKKKRD
KKYGSASKAQSQRIAVAGALYPDKKVQTIKTYKYPADLNGEVHDRGVAEKIEQAIQEDEI
GLLGPSSEYACWIASQKQSEPYSVVDFWFDAVCAGGVFAYSGARLLSTVLQLSGEESVLR
AALASSPFVDDINLAQAEKFLAVSRRTGQDKLGKRIGECFAEGRLEALGIKDRMREFVQA
IDVAQTAGQRFAAKLKIFGISQMPEAKQWNNDSGLTVCILPDYYVPEENRADQLVVLLRR
LREIAYCMGIEDEAGFEHLGIDPGALSNFSNGNPKRGFLGRLLNNDIIALANNMSAMTPY
WEGRKGELIERLAWLKHRAEGLYLKEPHFGNSWADHRSRIFSRIAGWLSGCAGKLKIAKD
QISGVRTDLFLLKRLLDAVPQSAPSPDFIASISALDRFLEAAESSQDPAEQVRALYAFHL
NAPAVRSIANKAVQRSDSQEWLIKELDAVDHLEFNKAFPFFSDTGKKKKKGANSNGAPSE
EEYTETESIQQPEDAEQEVNGQEGNGASKNQKKFQRIPRFFGEGSRSEYRILTEAPQYFD
MFCNNMRAIFMQLESQPRKAPRDFKCFLQNRLQKLYKQTFLNARSNKCRALLESVLISWG
EFYTYGANEKKFRLRHEASERSSDPDYVVQQALEIARRLFLFGFEWRDCSAGERVDLVEI
HKKAISFLLAITQAEVSVGSYNWLGNSTVSRYLSVAGTDTLYGTQLEEFLNATVLSQMRG
LAIRLSSQELKDGFDVQLESSCQDNLQHLLVYRASRDLAACKRATCPAELDPKILVLPAG
AFIASVMKMIERGDEPLAGAYLRHRPHSFGWQIRVRGVAEVGMDQGTALAFQKPTESEPF
KIKPFSAQYGPVLWLNSSSYSQSQYLDGFLSQPKNWSMRVLPQAGSVRVEQRVALIWNLQ
AGKMRLERSGARAFFMPVPFSFRPSGSGDEAVLAPNRYLGLFPHSGGIEYAVVDVLDSAG
FKILERGTIAVNGFSQKRGERQEEAHREKQRRGISDIGRKKPVQAEVDAANELHRKYTDV
ATRLGCRIVVQWAPQPKPGTAPTAQTVYARAVRTEAPRSGNQEDHARMKSSWGYTWSTYW
EKRKPEDILGISTQVYWTGGIGESCPAVAVALLGHIRATSTQTEWEKEEVVFGRLKKFFP
S (SEQ ID NO: 7)

FIG. 1D

>CasY7
MKRILNSLKVAALRLLFRGKGSELVKTVKYPLVSPVQGAVEELAEAIRHDNLHLFGQKEI
VDLMEKDEGTQVYSVVDFWLDTLRLGMFFSPSANALKITLGKFNSDQVSPFRKVLEQSPF
FLAGRLKVEPAERILSVEIRKIGKRENRVENYAADVETCFIGQLSSDEKQSIQKLANDIW
DSKDHEEQRMLKADFFAIPLIKDPKAVTEEDPENETAGKQKPLELCVCLVPELYTRGFGS
IADFLVQRLTLLRDKMSTDTAEDCLEYVGIEEEKGNGMNSLLGTFLKNLQGDGFEQIFQF
MLGSYVGWQGKEDVLRERLDLLAEKVKRLPKPKFAGEWSGHRMFLHGQLKSWSSNFFRLF
NETRELLESIKSDIQHATMLISYVEEKGGYHPQLLSQYRKLMEQLPALRTKVLDPEIEMT
HMSEAVRSYIMIHKSVAGFLPDLLESLDRDKDREFLLSIFPRIPKIDKKTKEIVAWELPG
EPEEGYLFTANNLFRNFLENPKHVPRFMAERIPEDWTRLRSAPVWFDGMVKQWQKVVNQL
VESPGALYQFNESFLRQRLQAMLTVYKRDLQTEKFLKLLADVCRPLVDFFGLGGNDIIFK
SCQDPRKQWQTVIPLSVPADVYTACEGLAIRLRETLGFEWKNLKGHEREDFLRLHQLLGN
LLFWIRDAKLVVKLEDWMNNPCVQEYVEARKAIDLPLEIFGFEVPIFLNGYLFSELRQLE
LLLRRKSVMTSYSVKTTGSPNRLFQLVYLPLNPSDPEKKNSNNFQERLDTPTGLSRRFLD
LTLDAFAGKLLTDPVTQELKTMAGFYDHLFGFKLPCKLAAMSNHPGSSSKMVVLAKPKKG
VASNIGFEPIPDPAHPVFRVRSSWPELKYLEGLLYLPEDTPLTIELAETSVSCQSVSSVA
FDLKNLTTILGRVGEFRVTADQPFKLTPIIPEKEESFIGKTYLGLDAGERSGVGFAIVTV
DGDGYEVQRLGVHEDTQLMALQQVASKSLKEPVFQPLRKGTFRQQERIRKSLRGCYWNFY
HALMIKYRAKVVHEESVGSSGLVGQWLRAFQKDLKKADVLPKKGGKNGVDKKKRESSAQD
TLWGGAFSKKEEQQIAFEVQAAGSSQFCLKCGWWFQLGMREVNRVQESGVVLDWNRSIVT
FLIESSGEKVYGFSPQQLEKGFRPDIETFKKMVRDFMRPPMFDRKGRPAAAYERFVLGRR
HRRYRFDKVFEERFGRSALFICPRVGCGNFDHSSEQSAVVLALIGYIADKEGMSGKKLVY
VRLAELMAEWKLKKLERSRVEEQSSAQ (SEQ ID NO: 5)

>CasY18
MKRIAKFRHDKPVKREAWSKGYRVHKNRIINKVTRSIKYPLVVKDEWKKRLIDDAAHDYRWLVG
PINYSDWCRDPNQYSILEFWIDFLCVGGVFQSSHSNICRLAIQLSGGSVFEQEWKDLSPFVRAN
LIQGIKPAEFIGFLTAEFRSSSNPKNFISKFFEGSNEDLESLTNEFASIVDFIKAKDISLLRKS
LPSCKKIAPNLWEKAVGSHSTNELLKLLTKYTRVMLVAEPSHSDRVFSQTVLQSNDQDDPELTG
PLPSHKVGKASYLFIPEFIREVNLDKISKLDLSAKSKLAVEQVKKLSELTSDFKQIENQSEAYF
GLSTSFNELSNFLGILIRTLRNAPEAILKDQIALCAPLDKDILKITLDWLCDRAQALPENPRFE
TNWAEYRSYLGGKIKSWFSNYENFFEIPQAASSQQNNNREKKLGNRSAIRALNLKKEAFEKARE
TFKGDKGTLEKIDLAYRLLGSISPEVLQCDEGLKLYQQFNDELLVLNETINQKFQDAKRDIKAK
KEKESFEKLQRNLSSPLPRIPEFFGERAKKGYQKARVSPKLARHLLECLNDWLARFAKVEESAF
SEKEFQRILDWLRTSDFLPVFIRKSKDPPSWLRYIARVATGKYYFWVSEYSRKRVQIIDKPIAQ
NPLKELISWFLLNKDAFSRDNELFKGLSSKMVTLARIMAGILRDRGEGLKELQAMTSKLDNIGL
LHPSFSVPVTDSLKDAAFYRAFFSELEGLLNIGRSRLIIERITLQSQQSKNKKTRRPLMPEPFI
NEDKEVFLAFPKFETKNKVKGTRVVYNSPDEVNWLLSPIRSSKGQLSFMFRCLSEDAKIMTTSG
GCSYIVEFKKLLEAQEEVLSIHDCDIIPRAFVSIPFTLERESEETKPDWKPNRFMGVDIGEYAV
AYCVIEKGTDSIEILDCGIVRNGAHRVLKEKVDRLKRRQRSMTFGAMDTSIAAARESLVGNYRN
RLHAIALKHGAKLVYEYEVSAFESGGNRIKKVYETLKKSDCTGETEADKNARKHIWGETNAVGD
QIGAGWTSQTCAKCGRSFGADLKAGNFGVAVPVPEKVEDSKGHYAYHEFPFEDGLKVRGFLKPN
KIISDQKELAKAVHAYMRPPLVALGKRKLPKNARYRRGNSSLFRCPFSDCGFTADADIQAAYNI
AVKQLYKPKKGYPKERKWQDFVILKPKEPSKLFDKQFYRPN (SEQ ID NO: 8)

```
                106     113       123       133        137    144
                 |       |         |         |          |      |
1. CasY1  EGSKSPSEKI---FEQIDFELKNKLDKEQFKDIILLNTGI---------RSSSNVRSL

2. CasY2  RGDKSIVDKFNASIKKKHADLYALVDIKALYDFL----------TSDARRGLKTEEEF
3. CasY3  --NETALQDL---FETLDDDLKHVLDRKKWCDFIKTGTPK----TNDQGRLKKQIKNL
4. CasY4  RGGS--------------YELTKTLKGSHLYDELQTDKVIKFLNKKEISRANGSLDKL
5. CasY5  SGEE--------------SVLRAALASSPFVDDINLAQAEKFL---AVSRRTGQ-DKL
6. CasY6  SGEE--------------SVLRAALASSPFVDDINLAQAEKFL---AVSRRTGQ-DKL
7. CasY7  NSDQ--VSPFRKVLEQSPFFLAGRLKVEPAERILSVE-------IRKIGKRENRVENY

                 154       164       174      181       191
                  |         |         |        |         |
1. CasY1  RGRFLKCFKEEFRDTEEVIACVDKWSKDLIVEG---KSILVSKQFLYWEEEFGI---

2. CasY2  -------FNSKRNTLFP--KFRKKDNKAVDLWVKKFIGLDNKDKLNFTKKFIGF---
3. CasY3  -------LKGNKREEIE--KTLNESDDELKEKI-NRIADVFAKNKSDKYTIEKT---
4. CasY4  KKDIIDCFKAEYRERHK--DQCNKLADDIKNAKKDAGASLGERQKKLFRDFFGT---
5. CasY5  GKRIGECFAEGRLEALGIKDRMREFVQAID------VAQTAGQRFAAKLKIFGT---
6. CasY6  GKRIGECFAEGRLEALGIKDRMREFVQAID------VAQTAGQRFAAKLKIFGT---
7. CasY7  AADVETCFIGQLSSDEK--QSIQKLANDIW------DSKDHEEQRMLKADFFATPLI

                 197 201      209       219        230          231
                  |   |        |         |          |            |
1. CasY1  -------KIFPHFKD--NHDLPKLTFFVEPSLEFSPHLPLANC-----------LER

2. CasY2  -------DPNPQIKY-------DHTFFFHQDINFDLERITTPKELISTYKKFLGKNKD
3. CasY3  -------D-KPNTEKYPRINDVQVAFFCHPDFEEITERDRTKT-LDLIINRF---NKR
4. CasY4  -------SEQSENDKPSFTNPLNLTCCLLPFDTVNNNRNRGE----VLFNKL---KEY
5. CasY5  -------SQMPEAKQ--WNNDSGLTVCILPDYYV-PEENRADQ-LVVLLRRL---REI
6. CasY6  -------SQMPEAKQ--WNNDSGLTVCILPDYYV-PEENRADQ-LVVLLRRL---REI
7. CasY7  KDPKAVTEEDPENETAGKQKPLELCVCLVPELYTRGFGSIAD----FLVQRL---TLL
```

```
              237    244    251                  261   265        275
              |      |      |                    |     |          |
1. CasY1  LKKFDISRES-----LLGLDN-NFSAFSNYFNE----LF--NLLSRGEIKKIVTAVLA

2. CasY2  LYGSDETTED-QLKMVLGFHN-NHGAFSKYFNA----SLEAFRGRDNSLVE---QIIN
3. CasY3  YEITENKKDD-KTSNRMALYSLNQGYIPRVLND----LFLFVKDNEDDFSQFLSDLEN
4. CasY4  AQKLDKNEGSLEMWEYIGIGN-SGTAFSNFLGE----GFL-GRLRENKITELKKAMMD
5. CasY5  AYCMGIEDEA--GFEHLGI---DPGALSNFSNGNPKRGFL-GRLLNNDIIALANNMSA
6. CasY6  AYCMGIEDEA--GFEHLGI---DPGALSNFSNGNPKRGFL-GRLLNNDIIALANNMSA
7. CasY7  RDKMSTDTAE-DCLEYVGIEEEKGNGVNSLLGT-----FL-KNLQGDGFEQIFQFMLG

                    285    292      302      310      320      330
                    |      |        |        |        |        |
1. CasY1  VSKSW---ENEPELEKRLHFLSEKAKLL--GYPKLTSSWADYRVIIGGKIKSWHSNY

2. CasY2  NSPYW--NSHRKELEKRIIFLQVQSKKI--KETELGKP-HEYLASFGGKFESWVSNY
3. CasY3  FFSFS--NEQIKIIKERLKKLKKYAEPIP-GKPQLADKWDDYASDFGGKLESWYSNR
4. CasY4  ITDAWRGQEQEEELEKRLRILAALTIKL--REPKFDNHWGGYRSDINGKLSSWLQNY
5. CasY5  MTPYW--EGRKGELIERLAWLKHRAEGLYLKEPHFGNSWADHRSRIFSRIAGWLSGC
6. CasY6  MTPYW--EGRKGELIERLAWLKHRAEGLYLKEPHFGNSWADHRSRIFSRIAGWLSGC
7. CasY7  SYVGW--QGKEDVLRERLDLLAEKVKRL--PKPKFAGEWSGHRMFLHGQLKSWSSNF

                    340      343       353       363       373
                    |        |         |         |         |
1. CasY1  TEQLIKVREDL--------KKHQIALDKLQEDLKKVVDSSLREQIEAQREALLPLLDTM

2. CasY2  LRQEEEMKRQLFGYEENKKGQKKFIVGNKQELDKIIRGTDEYEIKAISKETIGLTQKC
3. CasY3  IEKLKKIPESV--------SDLRNNLEKIRNVLKKQNNA-----------SKILELSQKI
4. CasY4  INQTVKIKEDL--------KGHKKDLKKAKEMINRFGESDTKE--EAVVSSLLESIEKI
5. CasY5  AGKLKIAKDQI--------SGVRTDLFLLKRLLDAVPQSAP--------SPDFIASISAL
6. CasY6  AGKLKIAKDQI--------SGVRTDLFLLKRLLDAVPQSAP--------SPDFIASISAL
7. CasY7  FRLFNETRELL--------ESIKSDIQHATMLISYVEEKGGYH------PQLLSQYRKI
```

FIG. 2D

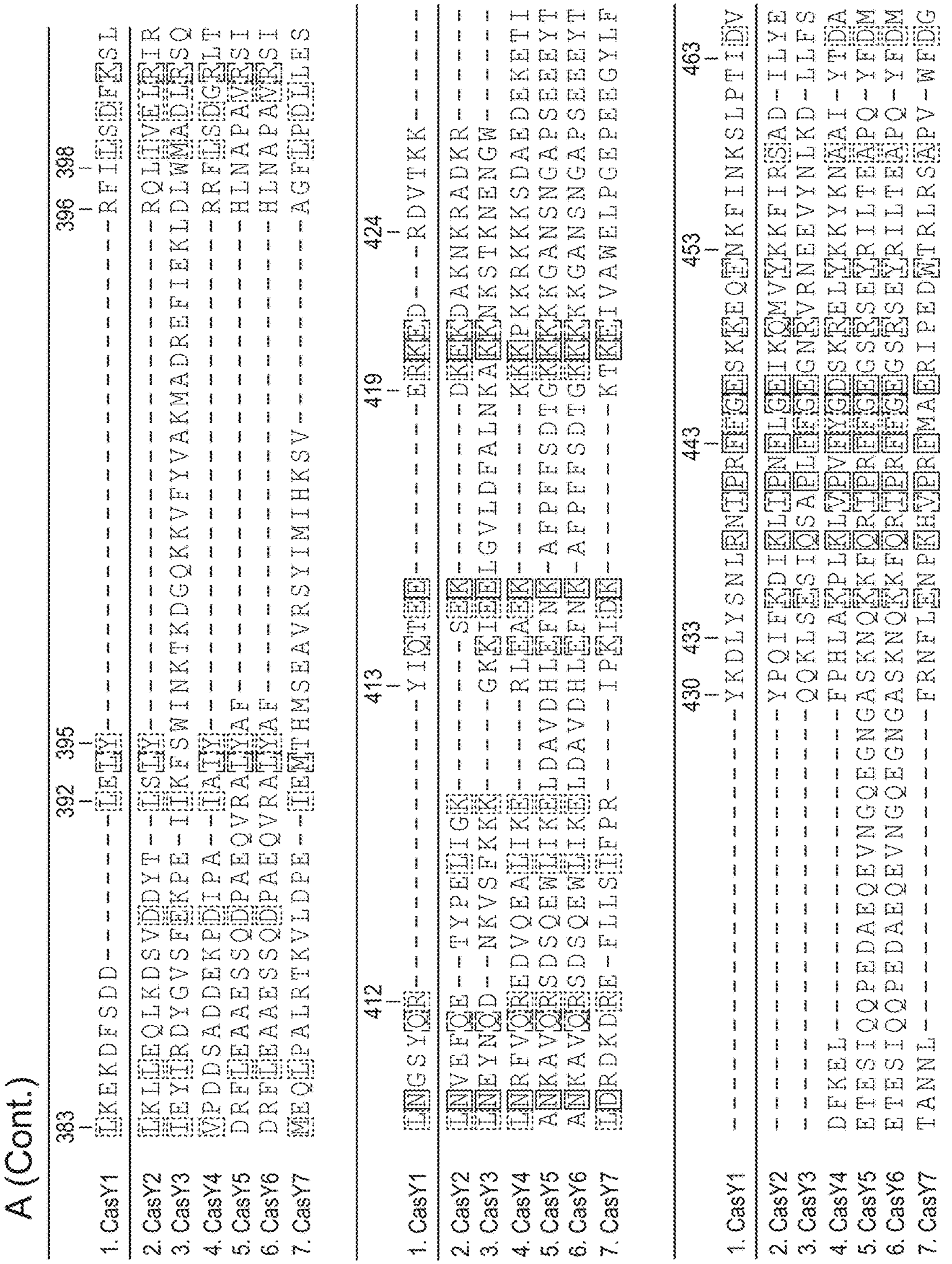

A (Cont.)

|       | 383                                                                 | 392 395 396 398 |
|-------|---------------------------------------------------------------------|-----------------|
| 1. CasY1 | LKEKDFSDD---------------------------------LELY-----RFILSDFKSL |
| 2. CasY2 | IKLIEQLKDSVDDYT--------------------------LSLY-----RQLIVELRIR |
| 3. CasY3 | IEYIRDYGVSFEKPE-IIKFSWINKTKDGQKKVFYVAKMADREFIEKLDLWMADLRSQ |
| 4. CasY4 | VPDDSADDEKPIDPA--------------------------IATY-----RRFLSDGRLT |
| 5. CasY5 | DRFEAAESSQDPAEQVRAFYAF--------------------------HLNAPAVRSI |
| 6. CasY6 | DRFEAAESSQDPAEQVRAFYAF--------------------------HLNAPAVRSI |
| 7. CasY7 | MEQIPALRTKVLDPE---IEMTHMSEAVRSYIMIHKSV-----AGFIPDLLES |

|       | 412 413 419 424 |
|-------|-----------------|
| 1. CasY1 | LNGSYQR--------YIQTEE-----ERKED--RDVTKK------- |
| 2. CasY2 | INVEFQE--TYPEILIGK-----SEK-----DKEK-DAKNKRADKR-- |
| 3. CasY3 | LNEYNQD--NKVSFKKK-----IEL-----KKK-NKSTKNENGW--- |
| 4. CasY4 | INRFVQREDVQEALIKE-----RLEAEK-----KKK-PKKRKKKSDAEDEKETI |
| 5. CasY5 | ANKAVQRSDSQEWLIKELDAVDHLFNK-AFPFFSDTGKKKGANSNGAPSEEEYT |
| 6. CasY6 | ANKAVQRSDSQEWLIKELDAVDHLFNK-AFPFFSDTGKKKGANSNGAPSEEEYT |
| 7. CasY7 | LDRDKDRE-FLLSIFPR-----IPKIDK-----KTKEIVAWELPGEPEEGYLF |

|       | 430 433 443 453 463 |
|-------|---------------------|
| 1. CasY1 | ------------------------------------------------ |
| 2. CasY2 | YKDLYSNLRNIERIEGESKEEQENKFINKSLPTIIDV |
| 3. CasY3 | YPQIFKDIKLIPNELGEIKQMVYKKFIRSAD-ILYE |
| 4. CasY4 | QQKLSESIQSABLEFGNRVRNEEVYNLKD-LLFS |
| 5. CasY5 | FPHLAKPLKLVPVFYGDSKRELYKKYKNAAI-YTIDA |
| 6. CasY6 | DFKEL-ETESIQQPEDAEQEVNGQEGNGASKNQKFQRTPREGSREYRILTEAPQ-YFDM |
| 7. CasY7 | ETESIQQPEDAEQEVNGQEGNGASKNQKFQRTPREGSREYRILTEAPQ-YFDM |
| | TANNL----FRNFLENPKHVPREMAERIPEDWTRLRSAPV-WFDG |

```
             473       483        490       497       507
1. CasY1     GLKILEDIRNALETVSVRK---PPSITEEYVTKQ---LEKLSRKYKINAFNS------
2. CasY2     GINFIDQIDKQITQNLLPC-FKNDKERIEFTEKQ---FETLRRKYYL--MNS------
3. CasY3     FIKNVENILMSSEAEDLKN--IKIEYKEDGAKKGNYVLNVLARFYAR--FNEDGYGGW
4. CasY4     LWKAVEKIYKSAFSSSLKNSFFDTDFDKDFFIKR---LQKIFSVYRR--FNT------
5. CasY5     FCNNMRAIFMQLESQPRKA----PRDFKCFLQNR---LQKLYKQTFLN-ARS------
6. CasY6     FCNNMRAIFMQLESQPRKA----PRDFKCFLQNR---LQKLYKQTFLN-ARS------
7. CasY7     MVKQWQKVVNQLVESPGAL----YQFNESFLRQR---LQAMLTVYKRD-LQT------

             512       523                522 525      535
1. CasY1     NRFKQITEQV-----------------LRKYNNGELPKISEVFYR---YPRESHVAIR
2. CasY2     SRFHHVIEGTINNRKLIEMKKRENSELKTFSDSKFVLSKLFLKKGKKYENEVYYTFY
3. CasY3     NKVKTVLENT---------AREAGTDFSKYGNNNNRNAGRFYLN----GREEQVFTL
4. CasY4     DKWKPIVKNS-----------------FAPYCDIVSLAENEVLYK----PKQSRSRKS
5. CasY5     NKCRALLESV-----------------LISWGEFYTYGANEKKFR----LRHEASERS
6. CasY6     NKCRALLESV-----------------LISWGEFYTYGANEKKFR----LRHEASERS
7. CasY7     EKFIKLLADV-----------------CRPLVDFFGLGGNDIIFKSCQDPRKQWQTVI

             550         551       561       571       577       587
1. CasY1     I-----------LPVKISNPRKDTSYLLDKYQISPDW----KNSNPGEVVDLIEIYKL
2. CasY2     INPKARDQRRIKIVLDINGNNSVGILQDLVQKLKPKWDDIIKKNDMGELIDAIEIEKV
3. CasY3     IKF---EK---------SITVEKITETVKLPSLLDEAYRDLVNENKNHKLRDVIQLSKT
4. CasY4     AAI---DKNRVRLPSTENIAKAGTATARELSVAGRDWKDLLKKEEHEEYIDLIELHKT
5. CasY5     SDP---D-----------YVVQQATETARRLFLFGFEW----RDCSAGERVDLVEIHKK
6. CasY6     SDP---D-----------YVVQQATETARRLFLFGFEW----RDCSAGERVDLVEIHKK
7. CasY7     P----------LSVPADVYTACEGTAT-RLRETLGFEW----KNLKGHEREDFLRLHQL
```

```
                597     607     615     625          630    640
1. CasY1  TLGWLLSCNKDFSMDFSSY--DLKLPPEAASLIKNF-----GSCLSGYYLSKMIFNCI

2. CasY2  RLGILIALYCEHKFKIKKELLSLDLFASAYQYLELE---DDPEELSGTNLGRFLQSLV
3. CasY3  IMALVLSHS-DKEKQTGG-------------------------------------NYI
4. CasY4  ATALLLAVT-ETQLDTSAL--DFVENGTVKDFMKTR---DGNLVLEGRFLEMFSQSIV
5. CasY5  ATSFLLAIT-QAEVSVGSY--NWLGNSTVSRYLSVA----GTDTLYGTQLEEFLNATV
6. CasY6  ATSFLLAIT-QAEVSVGSY--NWLGNSTVSRYLSVA----GTDTLYGTQLEEFLNATV
7. CasY7  LGNLLFWIR-DAKLVVKLE--DWMNNPCVQEYVEARKAIDLPLETFGFEVPIFLNGYL

                 650       660             678
1. CasY1  TSEIKGMITLYTRDKFVVRYVTQMIGSNQKFPLLC----------------------

2. CasY2  CSEIKGAINKISRTEYIERYTVQPMNTEKNYPLLI----------------------
3. CasY3  HSKLSGYNALISKRDFISRYSVQTTNGTCCKLAIG----------------------
4. CasY4  FSELRGLAGLMSRKEFITRSATQTMNGKQAELLYIPHEFQS------------AKIT
5. CasY5  LSQMRGLAIRLSSQELKDGFDVQLESSCCDNLQHLLVYRASRDLAA------CKRAT
6. CasY6  LSQMRGLAIRLSSQELKDGFDVQLESSCCDNLQHLLVYRASRDLAA------CKRAT
7. CasY7  FSELRQLELLLRRKSVMTSYSVKTTGSPNRLFQIVYLPLNPSDPEKKNSNNFQERLD

                                          679     687      697
1. CasY1  ------------------------------LVGEKQTK-NFSRNWGVLTEEKG---DL

2. CasY2  ------------------------------NKEGKATW---------HTAAKD---DL
3. CasY3  ------------------------------KGKSKKGN-EIDRYFYAFQFFKN---DD
4. CasY4  TPKEMSRAFLDLAPAEFATSLEPESLSEKSLLKLKQMR-YYPHYFGYELTRTGQGIDG
5. CasY5  CPAELDPKILVLPVGAFIASVMKMIERGDEPLAGAYLR-HRPHSFGWQTRVRGVA-EV
6. CasY6  CPAELDPKILVLPAGAFIASVMKMIERGDEPLAGAYLR-HRPHSFGWQTRVRGVA-EV
7. CasY7  TPTGLSRRFLDLTLDAFAGKL----LTDPVTQELKTMAGFYDHLFGFKLPCKLAAMSN
```

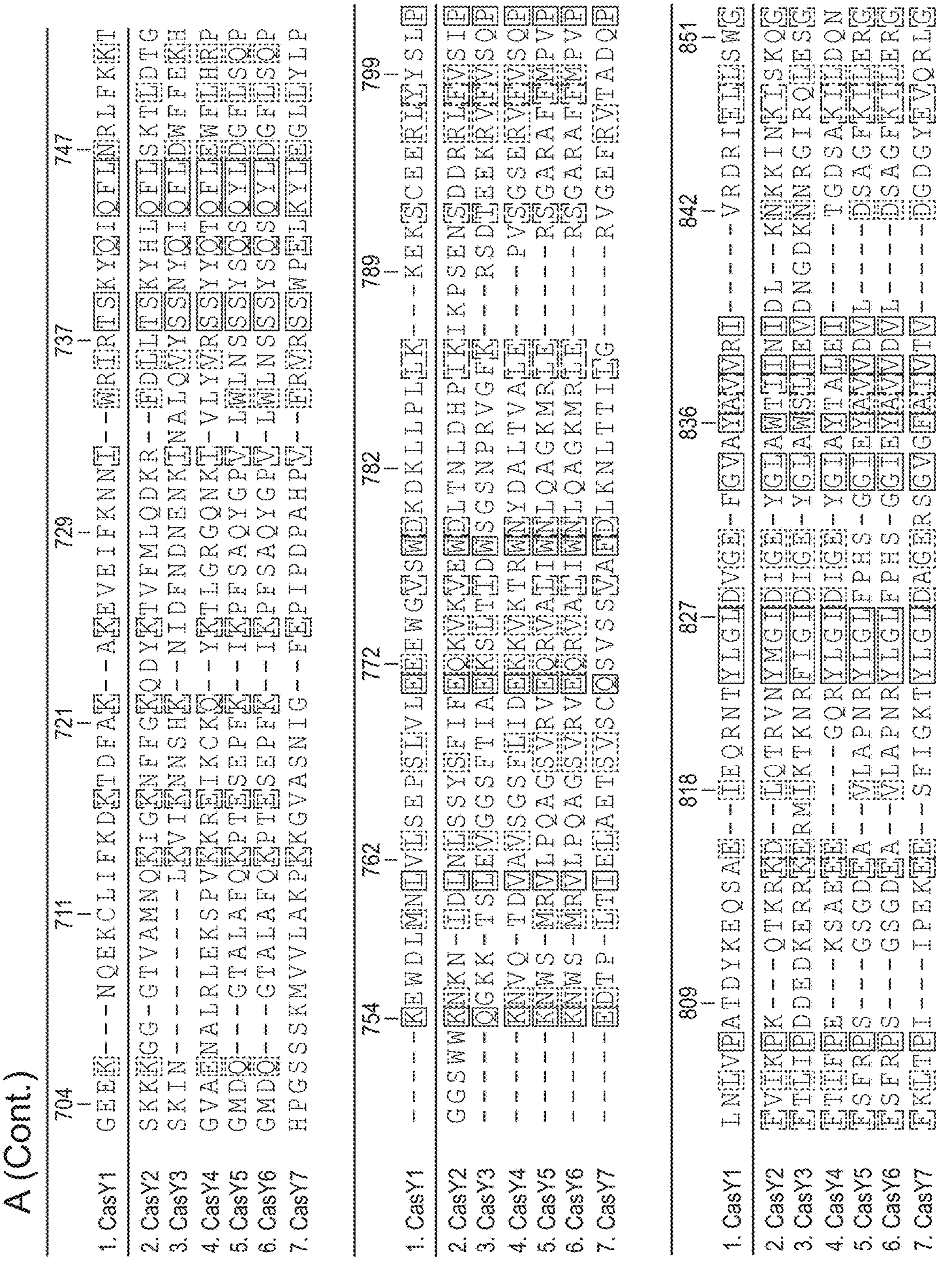

A (Cont.)

```
              704               711               721               729               737               747
               |                 |                 |                 |                 |                 |
1. CasY1    GEEK----NQEKCLIFKDKTDFAK--AKEVEIFKNNI--WRIRTSKYQIQFLNRLFKKT
2. CasY2    SKKKGG-GTVAMNQRIGKNFFGKQDYETVFMLQDKR--EDLLTSKYHLQFLISKTLDTG
3. CasY3    SKIN---LKVIKNNSHK--NIDFNDNENKINALQVYSSNYQIQFLDWFFEKH
4. CasY4    GVAENALRLEKSPVKKREIKCKQ--YKTLGRGQNKT--VLYVRSSYYQTQFLEWFLHRIP
5. CasY5    GMDQ---GTALAFQKPTESEPEK--IKPFSAQYGPV--LWLNSSYSQSQYLDGFLSQP
6. CasY6    GMDQ---GTALAFQKPTESEPEK--IKPFSAQYGPV--LWLNSSYSQSQYLDGFLSQP
7. CasY7    HPGSSSKMVVLAKPKKGVASNIG--FEPIPDPAHPV--ERVRSSMPELKYLEGLLYLP

              754               762               772               782               789               799
               |                 |                 |                 |                 |                 |
1. CasY1    ----KEWDLMN--VLSEPSLVIEEWGVSMDKLLPLK---KEKSCEERLYYSLP
2. CasY2    GGSWKN---LDNLSSYYSFIFEKVKVEWDLTNLDHPTKIKPSENSDDRRLEVISIP
3. CasY3    QGKK-TSLEWGGSFTIAEKSLTTDWSGSNPRVGFE---RSDLEEKRVEVVSQP
4. CasY4    KNVQ-IDVAVSGFLIDERKVKTRWNYDALTVALE---PVSGSERVEVVSQP
5. CasY5    KNWS---MRVLPQAGSVRVEQVATIWNLQAGKMRLE---RSGARAFEMPVP
6. CasY6    KNWS---MRVLPQAGSVRVEQVALIWNLQAGKMRLE---RSGARAFEMPVP
7. CasY7    EDTP-LTTELAETSVSCQSVSSVAFDLKNLTTIEG---RVGEFRVTADQP

              809               818               827               836               842               851
               |                 |                 |                 |                 |                 |
1. CasY1    LNLVPATDYKEQSAE--NEQRNTYLGLIDVGE--FGVAYAVVRL--VRDRIELLSWG
2. CasY2    EVIKPK--QTKRKD--LQTRVNYMGIDIGE--YGLAMTIDNDL--KNKKINKLSKQG
3. CasY3    ETLIDDEDKERRKER-MIKTKNRFIGLDIGE--YGLAMSLIEWDNGDKNNRGIRQLESG
4. CasY4    ETTFPE--KSAEEE--GQRYLGLDIGE--YGLAYTADEL--TGDSAKILDQN
5. CasY5    ESFRPS---GSGDEA--VLAPNRYLGLFPHS-GGLEHAVVDVL--DSAGFKILERG
6. CasY6    ESFRPS---GSGDEA--VLAPNRYLGLFPHS-GGLEHAVVDVL--DSAGFKILERG
7. CasY7    EKLTPI--IPEKEE--SFIGKTYLGLDAGERSVGFALITV--DGDGYEVQRLG
```

```
                861        870        876        886        896
1. CasY1   FLKDPALRKIRE-RVQDMK----KKQVMAVFSSSSTAVARVREMAIHSLRNQIHSIAL

2. CasY2   FTYEPLTHKVRD-YVATIK----DNQVRGTFGMPDTKLARLRENAITSLRNQVHDIAM
3. CasY3   FTTDNQQQVLKK-NVKSWR----QNQIRQTETSPDTKIARLRESLIGSYKNQLESLVV
4. CasY4   FTSDPQLKTLRE-EVKGLK----LDQRRGTFAMPSTKIARIRESLVHSLRNRIHHLAL
5. CasY5   TLAVNGFSQKRG-ERQEEAH--REKQRRGISDIGRKKPVQAEVDAANELHRKYTDVAT
6. CasY6   TLAVNGFSQKRG-ERQEEAH--REKQRRGISDIGRKKPVQAEVDAANELHRKYTDVAT
7. CasY7   VHEDTQLMALQQVASKSLKEPVFQPLRKGTE----RQQERIRKSLRGCYWNFYHALVI

           906        916        926        936          942   947
1. CasY1   AYKAKIIYEISISNFETGGNRMAKIYRSIKVSDVYR---------ESGADTLVSEMI

2. CasY2   RYDAKPVYEFEISNFETGSNKVKVIYDSVKRADIGRGQ------NNTEADNTEVNLV
3. CasY3   AKKANLSFEYEVSGFEVGGKRVAKTYDSIKRGSVRK-----------KDNNSQNDQS
4. CasY4   KHKAKIVYELEVSRFEEGKQKIKKVYATLKKADVYS----------EIDADKNLQTTV
5. CasY5   RLGCRIVVQWAPQPKPGTAPTAQTVYARAVRTEAPRS---------GNQEDHARMKSS
6. CasY6   RLGCRIVVQWAPQPKPGTAPTAQTVYARAVRTEAPRS---------GNQEDHARMKSS
7. CasY7   KYRAKVVHEESVGSSGLVGQWLRAFQKDLKKADVLPKKGGKNGVDKKRESSAQDTL

                        956        967        977        986        996
1. CasY1   WG----------KKNKQMGNHISSYATSYTCCNCAR-TPFELVIDNDKEYEKG----G

2. CasY2   WG----------KTSKQFGSQIGAYATSYICSFCGY-SPYYEFENSKSGDEEG----A
3. CasY3   WG----------KKGINEWSFETTAAGTSQFCTHCKR-WSSLAIVDIEEYELKD----Y
4. CasY4   WG-------------KLAVASEISASYTSQFCGACKKLWRAEMQVDETITT---------
5. CasY5   WGYTWGTYWEKRKPEDILGISTQVYWTGGIGESCP-------------------------
6. CasY6   WGYTWSTYWEKRKPEDILGISTQVYWTGGIGESCP-------------------------
7. CasY7   WG----GAFS-KKEEQQIAFEVQAACSSQFCLKCGW-WFQLGMREVNRVQESGVVLDW
```

FIG. 2I

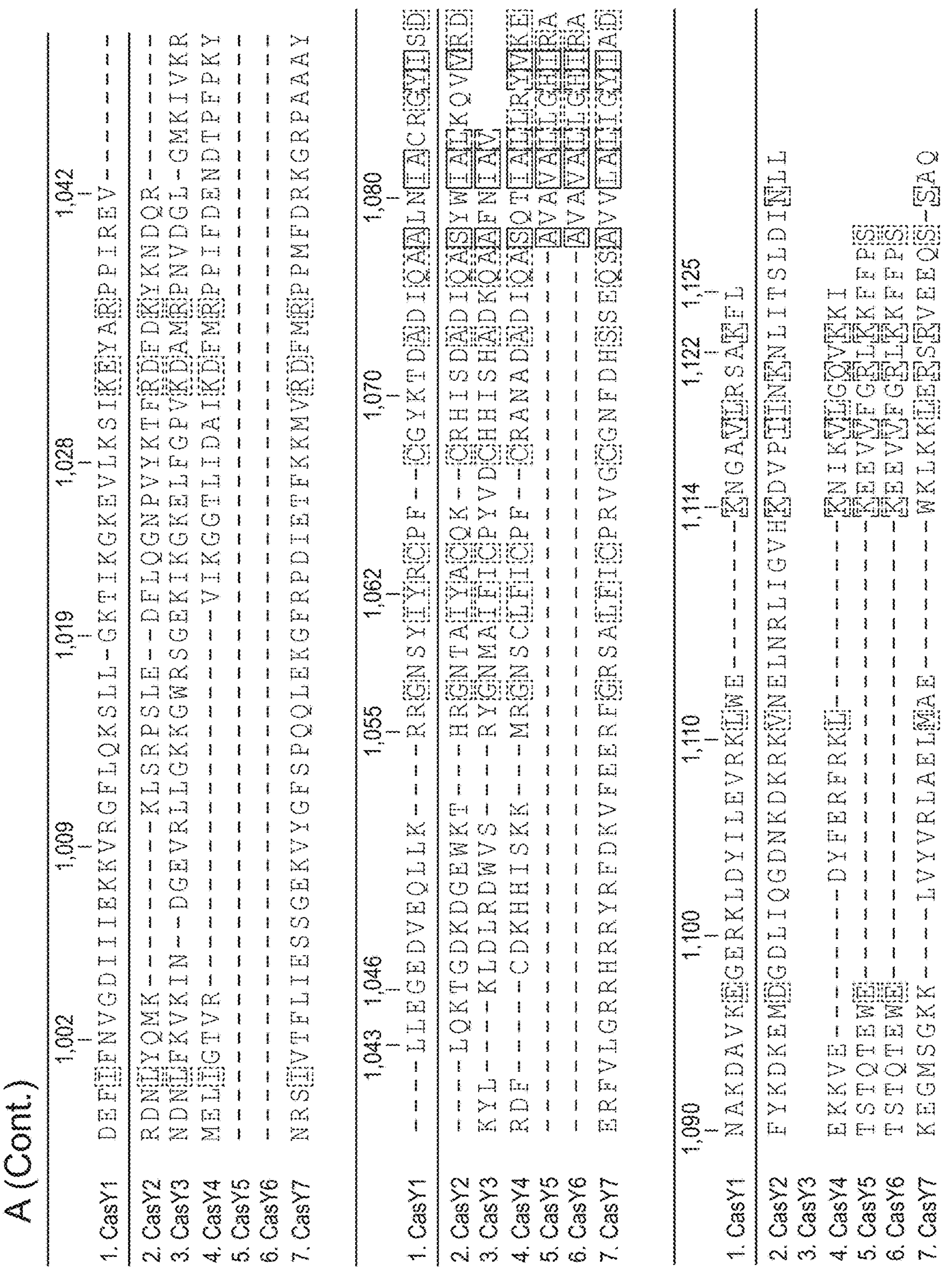

A (Cont.)

```
              1,002          1,009          1,019        1,028                           1,042
               |              |              |            |                               |
1.CasY1   DEFLENVGDIIIEKKVRGFLQKSLL-GKTIKGKEVLKSIKEYARPPIREV------
2.CasY2   RDNLYQMK-----------------KLSRPSLE--DFLQGNPVYKTFRDFDKYKNDQR-----
3.CasY3   NDNLFKVKIN------DGEVRLLGKKWRSGEKIKGKELFGPVKDAMRPNVDGL-GMKIVKR
4.CasY4   MELLGTVR-----------------------------------VIKGGTLIDAIKDFMRPPIFDENDTPFPKY
5.CasY5   
6.CasY6   
7.CasY7   NRSIVTFLIESSGEKVYGFSPQQLEKGFRPDIEFFKKMVRDFMRPPMFDRKGRPAAAY

          1,043 1,046         1,055         1,062                   1,070             1,080
           |    |              |             |                       |                 |
1.CasY1        -LLEGEDVEQLLK----RRGNSYIYRCPF---CGYKTDADIQAALNLACRGYILSD
2.CasY2   ----LQKTGDKDGEWKT-----HRGNTAITYACQK-----CRHISDADIQASYWALKQVVRD
3.CasY3   KYL-----KLDLRDWVS-----RYGNMAIFICPYVDCHHISHADKQAAFNLAV
4.CasY4   RDF-------CDKHHISKK---MRGNSCLFICPF----CRANADADIQASQTALLRYVKE
5.CasY5                                                              AVAVALLGHIRA
6.CasY6                                                              AVAVALLGHIRA
7.CasY7   ERFVLGRRHRRYRFDKVFEERFGRSALFICPRVGGGNFDHSSEQSAVLALIGYIAD

          1,090          1,100         1,110           1,114      1,122 1,125
           |              |             |               |          |    |
1.CasY1   NAKDAVKEGERKLDYILEVRKLWE---------ENGAVLRSAKFL
2.CasY2   FYKDKEMDGDLIQGDNKDKRKVNELNRLIGVHKDVPHINKNLITSLDINLL
3.CasY3   EKKVE---------DYFERFRKLI-----------KNIKVLIGVKKI
4.CasY4   TSTQTEWE-----------------------------KEEVVFGRLKKFFPS
5.CasY5   TSTQTEWE-----------------------------KEEVVFGRLKKFFPS
6.CasY6                                          KEEVVFGRLKKFFPS
7.CasY7   KEGMSGKK-----LVYVRLAELMAE---------WKLKKLERSVEEQSI-SAQ
```

FIG. 2J

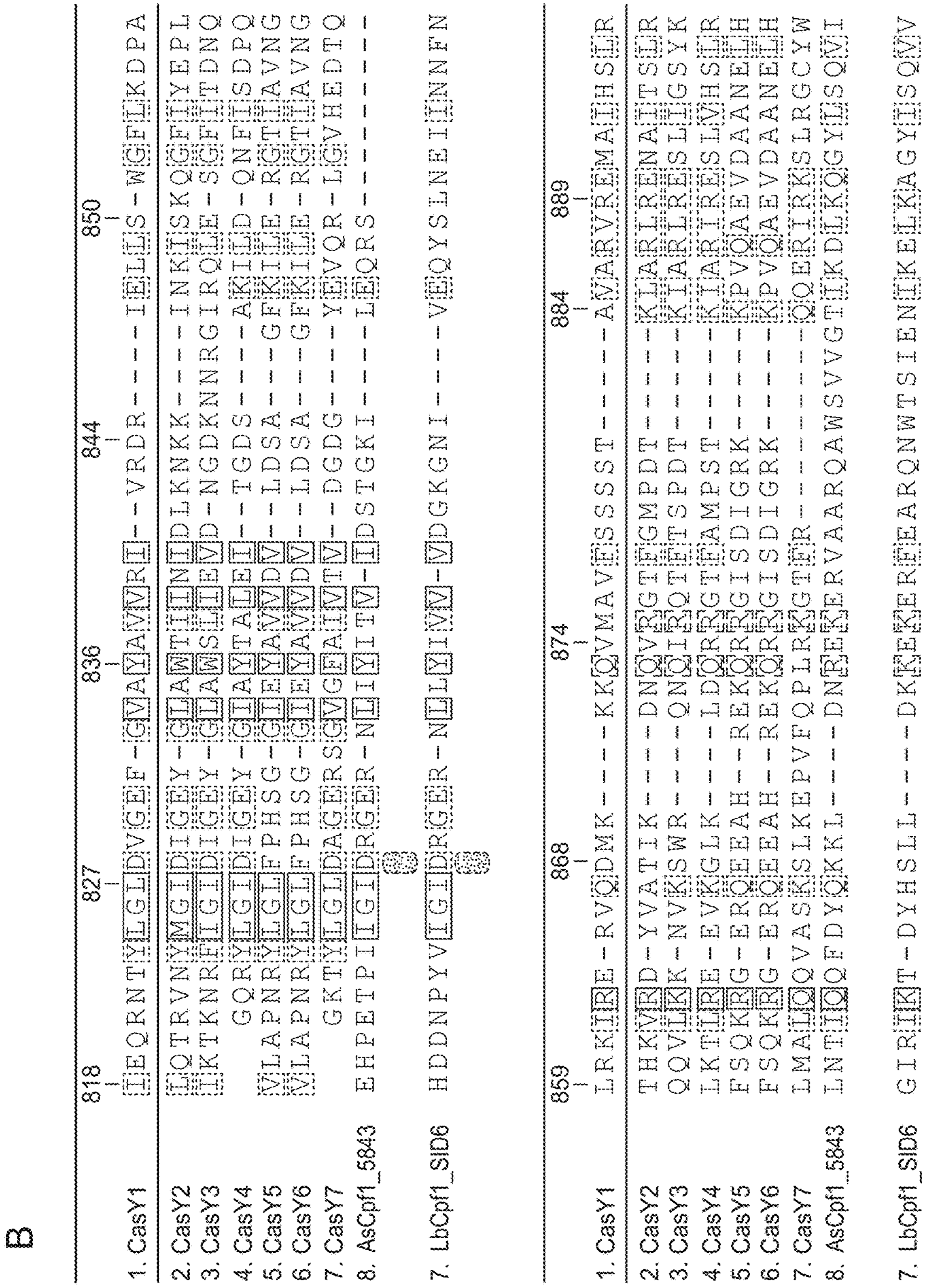

B

|   | 818 | 827 | 836 | 844 | 850 |
|---|---|---|---|---|---|
| 1. CasY1 | IEQRNTIY | LGLIDVGEF | GVAYAVRI | --VRDR-- | --IELIS-WGFLKDPA |
| 2. CasY2 | LQTRVNY | MGIDIGEY | GIAWTINID | LKNKK--- | INKISKQGFIYEPL |
| 3. CasY3 | IKTKNRF | IGIDIGEY | GIAWSLEVD | -NGDKNNRGIRQLE- | SGFITDNQ |
| 4. CasY4 | GQRYL | GIDIGEY | GIAYTALEL | --TGDS-- | -AKILD-QNFISDPQ |
| 5. CasY5 | VLAPNRI | LGIFPHSG | GIEYAVDV | --LDSA-- | -GFKILE-RGTAVNG |
| 6. CasY6 | VLAPNRI | LGIFPHSG | GIEYAVDV | --LDSA-- | -GFKILE-RGTAVNG |
| 7. CasY7 | GKTIY | LGIDAGERS | VGEAITV | --DGDG-- | -YEVQR-LGVHEDTQ |
| 8. AsCpf1_5843 | EHPETPI | IGIDRGER | NLIYITV | IDSTGKI- | -LEQRS-- |
| 7. LbCpf1_SID6 | HDDNPYV | IGIDRGER | NLIVIYV | -VDGKGNI | VEQYSLNEIINNFN |

|   | 859 | 868 | 874 | 884 | 889 |
|---|---|---|---|---|---|
| 1. CasY1 | LRKIRE-- | RVQDMK-- | --KKQVMAVESSST-- | --AVARVREMAIHSLR |
| 2. CasY2 | THKVRD- | YVATIK-- | DNQVRGTFGMPDT-- | KIARLRENAITSLLR |
| 3. CasY3 | QQVLKK- | NVKISWR- | QNQIRQTETSPDT-- | KIARLRESLIGSYK |
| 4. CasY4 | LKTIRE- | EVKGLK-- | LDQRRGTFAMPST-- | KIARTRESLVHSLR |
| 5. CasY5 | FSQKRG- | ERQEEAH- | REKQRRGISDIGRK- | KPVQAEVDAANELH |
| 6. CasY6 | FSQKRG- | ERQEEAH- | REKQRRGISDIGRK- | KPVQAEVDAANELH |
| 7. CasY7 | LMAILQ- | VASKSLKEPVFQPLRKGTFR | --QQERIRKSLRGCYW |
| 8. AsCpf1_5843 | LNTIQ-FDYQKKL-- | DNKERVAARQAWSVVGTIKDLKQGYLSQVI |
| 7. LbCpf1_SID6 | GIRIKT- | DYHSLL-- | --DKKEKEREEARQNWTSIENIKELKAGYISQVV |

|  | 899 | 909 | 919 | 928 | 937 |
|---|---|---|---|---|---|
| 1. CasY1 | NQIHS | ALAYKAKIIY | EISISNFET | GGNRM--AK | IYRSIKVSDVYR- |
| 2. CasY2 | NQVHD | AMRYDAKPVY | EFEISNFET | GSNKV---- | KVTYDSVKRADTGRG |
| 3. CasY3 | NQLES | MVAKKANTS | FEYEVSGFEV | GGKRV---- | AKIYDSIKRGSVRK |
| 4. CasY4 | NRIHH | ALKHKAKIIV | ELEVSRFEG | KQKH---- | KKVYATLKKADVYS |
| 5. CasY5 | RKIYTDV | ATRLGCRIVV | QWAPQPKPG | TAPTA---- | QTVYARAVRTEAPR |
| 6. CasY6 | RKIYTDV | ATRLGCRIVV | QWAPQPKPG | TAPTA---- | QTVLARAVRTEAPR |
| 7. CasY7 | NFYHAD | MIKYRAKVV | HEESVGSSGLVGQWL | G---- | RAFQKDLKKADVLPKKGG |
| 8. AsCpf1_5843 | HEIVD | MIHYQAVVVL | ENLNFGFKSKRTG | IAEKAVYQQFEKMLIDK-- |  |
| 7. LbCpf1_SID6 | HKICE | DVEKYDAVTA | LEDLNSGFKNSRVKV-EKQVYQKFEKMLIDK-- |  |  |

|  | 942 | 955 | 956 | 960 |
|---|---|---|---|---|
| 1. CasY1 | ---ESGA | DTLVSEMIWG | --KKN-KQMGNHISSY |  |
| 2. CasY2 | ---QNNTEA | DNTEVNLVWG | --KTS-KQFGSQLGAY |  |
| 3. CasY3 | ---KDNNS | QDQSWG | --KKGINEWSFETTAA |  |
| 4. CasY4 | ---EIDA | DKNLQTTVWG | --KLA--VASEISAS |  |
| 5. CasY5 | ---SGNQE | DHARMKSSWG | -TYWEKRKPEDILGISTQVY |  |
| 6. CasY6 | ---SGNQE | DHARMKSSWG | -TYWEKRKPEDILGISTQVY |  |
| 7. CasY7 | KNGVDKKKR | ESSAQDTLWG | -GAFSKEE-QQIAFEVQAA |  |
| 8. AsCpf1_5843 | LNCLVLKDYPAEKV | GVLNPYQLTDQFTSAKMGTQSGFLFYVPAP |  |  |
| 7. LbCpf1_SID6 | LNYMV | DKKSNPCAT | GGALKGYQITNKFESFKSMSTQNGFIFYIPAW |  |

```
                   970       980           994               995
                   |         |             |                 |
1. CasY1           ATSYTCCNCARTPFELVIDNDKEYEK----------------GGDEFIFN
2. CasY2           ATSYICSFCGYSPYYEFENSKSGDEE----------------GARDNLYQ
3. CasY3           GTSQFCTHCKRWSSLAIVDIEEYELK----------------DYNDNLFK
4. CasY4           YTSQFCGACKKLWRAEMQVDETITTQ-------------------ELIGT
5. CasY5           WTGGIGESCPAVAVALLGHIRATSTQ------------------------
6. CasY6           WTGGIGESCPAVAVALLGHIRATSTQ------------------------
7. CasY7           GSSQFCLKCGWWFQLGMREVNRVQESGVVL------------DWNRSIVT
8. AsCpf1_5843     YTSKIDPLTGFVDPFVWKTIKNHESRKHFLEGFDFLHY--DVKTGDFILH

7. LbCpf1_SID6     LTSKIDPSTGFVNLLKTKYTSIADSKK-FISSFDRIMYVPEEDLFEFALD

                   1,004                   1,005  1,012     1,016
                   |                       |      |         |
1. CasY1           VG----------------------DEKKVRGF------LQKSLLGKTIKG
2. CasY2           MKK-----------------------------------LSRPSLEDFLQG
3. CasY3           VKI---------------------NDGEVRLLGK-----KGWRSGEKIKG
4. CasY4           VRV--------------------------------------------IKG
5. CasY5           --------------------------------------------TEWEKE
6. CasY6           --------------------------------------------TEWEKE
7. CasY7           FLIE-------------------SSGEKVYGFSP-----QQLEKGFRPDI
8. AsCpf1_5843     FKMNRNLSFQRGLPGFMPAWDIVFEKNETQFDAKGTPFIAGKRIVPVIEN

7. LbCpf1_SID6     YK-----NFSRTDADYIKKWKLYSYGNRIRIFAA-----AKKNNVFAWEE
```

```
               1,026     1,036      1,042             1,043    1,052
1. CasY1       KEVLKSIKEYARPPI------REV-------------LLEGEDVEQL---
2. CasY2       NPVYKTFRDFDKYKN------DQR-------------LQKTGDKDGEWK-
3. CasY3       KELFGPVKDAMRPNV------DGLGMKIVKRKYLK---------------
4. CasY4       GTLIDAIKDFMRPPI-----FDENDTPFPKYRDFC-------DKHHISK-
5. CasY5       EVVFGRLKKFF-PS
6. CasY6       EVVFGRLKKFF-PS
7. CasY7       ETFKKMVRDFMRPPM-----FDRKGRPAAAYERFV--LGRRHRRYRFDKV
8. AsCpf1_5843 HRFTGRYRDLY-PANELIALLEEKGIVFRDGSNILPKLLENDDSHAIDTM

7. LbCpf1_SID6 VCLTSAYKELF-----------NKYGINYQQG-DIRALLCEQSDKAFYSSF

                              1,053   1,061          1,067
1. CasY1       --------------LKRRGNSYIYRCPF----------CGYKT----------
2. CasY2       ----------------THRGNTAIYACQK---------CRHIS----------
3. CasY3       --------LDLRDWVSRYGNMAIFICPYV--------DCHHIS----------
4. CasY4       ---------------KMRGNSCLFICPF----------CRANA----------
5. CasY5
6. CasY6
7. CasY7       FE-------------ERFGRSALFICPRV--------GCGNFD----------
8. AsCpf1_5843 VALIRSVLQMRNS-NAATGEDYINSPVRDLNGVCFDSRFQNPE----WPM

7. LbCpf1_SID6 MALMSLMLQMRNSITGRTDVDFLISPVKNSDGIFYDSRNYEAQENAILPK
```

```
                  1,072      1,083      1,093      1,103      1,113
1. CasY1          DADIQAALNIACRGYTSDNAKDAVKEGERKLDYILEVRKLWEKNGAV---
2. CasY2          DADIQASYWIALKQVVRDFYKDKEMDGDLIQGDNKDKRKVNELNRLIGVH
3. CasY3          HADKQAAFNIAV
4. CasY4          DADIQASQTIALLRYVKEEKK---------VEDYFERFRK-----------
5. CasY5
6. CasY6
7. CasY7          HSSEQSAVVLALIGYTADKEG---MSGK-KLVYVRLAELMAEWKLKK---
8. AsCpf1_5843    DADANGAYHIALKGQL--------------LLNHLKESKDLKLQN------
7. LbCpf1_SID6    NADANGAYNIARKVLW--------------AIGQFKKAEDEKLDKVKI---

                      1,119  1,125
1. CasY1          ----LRSAKFL
2. CasY2          KDVPIINKNLITSLDINLL
3. CasY3
4. CasY4          ----LKNIKVLG--QMKKI
5. CasY5
6. CasY6
7. CasY7          ----LERSRVEE--QSSAQ
8. AsCpf1_5843    ---GISNQDWLAYIQELRN
7. LbCpf1_SID6    ---AISNKEWLEYAQTSVK
```

A

| | Repeat |
|---|---|
| CasY1 | CTCCGAAAGTATCGGGGATAAAGGC |
| CasY2 | CACCGAAATTTGGAGAGGATAAGGC |
| CasY3 | CTCCGAATTATCGGGAGGATAAGGC |
| CasY4 | CCCCGAATATAGGGGACAAAAAGGC |
| CasY5 (and Y6) | GTCTAGACATACAGGTGGAAAGGTGAGAGTAAAGAC |

B

FIG. 16C
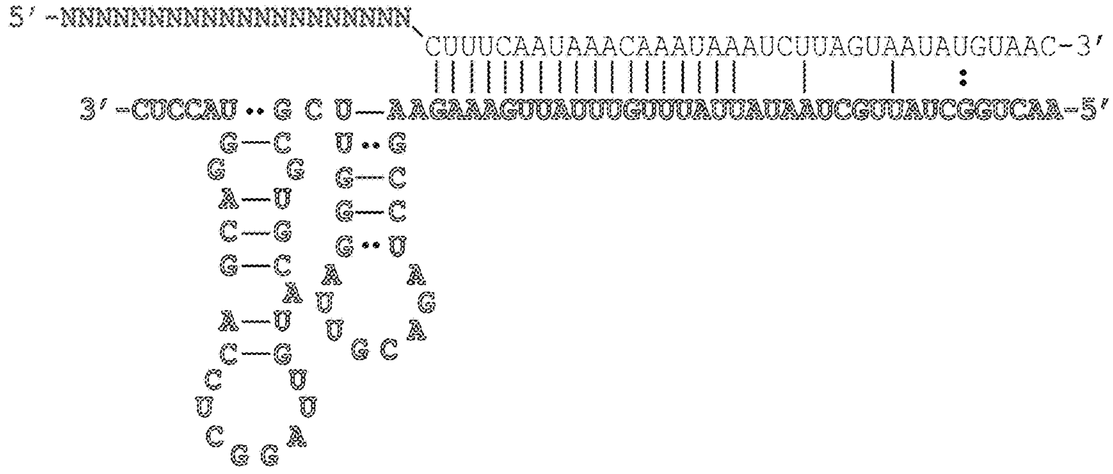
FIG. 16D
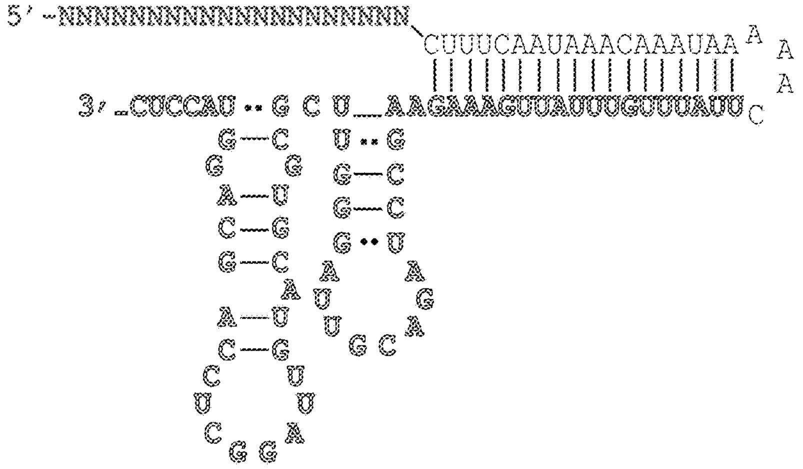
FIG. 16E
*In vivo E. coli* targeting assay
| Protein | Guide |
|---|---|
| AR1-Cas9<br>AR1-dCas9 | crRNA<br>sgRNA-69<br>sgRNA-104<br>sgRNA-179 |
| AR4-Cas9<br>AR4-dCas9 | crRNA<br>sgRNA-75<br>sgRNA-122 |

FIG. 21

*In vitro* cleavage conditions assayed for Cas9 from ARMAN-1

| Protein Purification | Buffer | Salt (mM) | Metal | Guide | Target | Temperature |
|---|---|---|---|---|---|---|
| AR1-Cas9 #1 | Tris<br>ph 7.5 | 300 | $Mg^{2+}$<br>$Mn^{2+}$<br>$Zn^{2+}$ | crRNA<br>cr:69<br>cr:69<br>cr:69 | dsDNA<br>ssDNA<br>DNA Bubble<br>ssRNA<br>dsDNA | 37 |
| AR1-Cas9 #1 | Tris<br>ph 7.5 | 100-500 | $Mg^{2+}$ | cr:69<br>cr:104<br>cr:179 | dsDNA | 37 |
| AR1-Cas9 #1 | Tris<br>ph 7.5 | 300 | $Mg^{2+}$<br>$Mn^{2+}$<br>$Zn^{2+}$ | cr:69<br>cr:104<br>cr:179 | dsDNA | 30-48 |
| AR1-Cas9 #1 | MOPS:<br>pH 6<br>pH 6.5<br>pH 7.0<br>pH 7.5 | 300 | $Mg^{2+}$ | cr:69<br>cr:104<br>cr:179 | dsDNA | 37 |
| AR1-Cas9 #1 | Citrate:<br>pH 5<br>pH 5.5<br>pH 6 | 300 | $Mg^{2+}$ | cr:69<br>cr:104<br>cr:179 | dsDNA | 37 |
| AR1-Cas9 #1 | Tris<br>ph 7.5 | 300 | $Mg^{2+}$<br>$Mn^{2+}$<br>$Zn^{2+}$ | cr:69<br>cr:104<br>cr:179 | plasmid | 37-50 |
| AR1-Cas9 #2 | Tris<br>ph 7.5 | 300 | $Mg^{2+}$<br>$Mn^{2+}$<br>$Zn^{2+}$ | cr:69<br>cr:104<br>cr:179 | dsDNA | 37 |
| AR1-Cas9 #3 | Tris<br>ph 7.5 | 300 | $Mg^{2+}$<br>$Mn^{2+}$<br>$Zn^{2+}$ | cr:69<br>cr:104<br>cr:179 | dsDNA | 37 |
| AR1-Cas9 #4 | Tris<br>ph 7.5 | 300 | $Mg^{2+}$<br>$Mn^{2+}$<br>$Zn^{2+}$ | cr:69<br>cr:104<br>cr:179 | dsDNA | 37 |
| AR1-Cas9 #5 | Tris<br>ph 7.5 | 300 | $Mg^{2+}$<br>$Mn^{2+}$<br>$Zn^{2+}$ | cr:69<br>cr:104<br>cr:179 | dsDNA | 37 |
| AR1-Cas9 #6 | Tris<br>ph 7.5 | 300 | $Mg^{2+}$<br>$Mn^{2+}$<br>$Zn^{2+}$ | cr:69<br>cr:104<br>cr:179 | ssDNA<br>dsDNA | 37 |
| AR4-Cas9 #1 | Tris<br>ph 7.5 | 300 | $Mg^{2+}$<br>$Mn^{2+}$<br>$Zn^{2+}$ | sgRNA-<br>122 | dsDNA | 37 |
| AR4-Cas9 #2 | Tris<br>ph 7.5 | 300 | $Mg^{2+}$<br>$Mn^{2+}$<br>$Zn^{2+}$ | sgRNA-<br>122 | dsDNA | 37 |
| AR4-Cas9 #3 | Tris<br>ph 7.5 | 300 | $Mg^{2+}$<br>$Mn^{2+}$<br>$Zn^{2+}$ | sgRNA-<br>122 | dsDNA | 37 |
| AR4-Cas9 #4 | Tris<br>ph 7.5 | 300 | $Mg^{2+}$<br>$Mn^{2+}$<br>$Zn^{2+}$ | sgRNA-<br>122 | dsDNA | 37 |

RNA-GUIDED NUCLEIC ACID MODIFYING ENZYMES AND METHODS OF USE THEREOF

CROSS-REFERENCE

This application is a national stage filing under 35 U.S.C. § 371 of PCT/US2017/054047, filed Sep. 28, 2017, which claims the benefit of U.S. Provisional Patent Application No. 62/402,849, filed Sep. 30, 2016, which applications are incorporated herein by reference in their entirety.

STATEMENT REGARDING FEDERALLY SPONSORED RESEARCH

This invention was made with government support under 1244557 awarded by the National Science Foundation and under DE-AC02-05CH11231 awarded by the U.S. Department of Energy. The government has certain rights in the invention.

INCORPORATION BY REFERENCE OF SEQUENCE LISTING PROVIDED AS A TEXT FILE

A Sequence Listing is provided herewith as a text file, "BERK-343WO_SeqList_ST25.txt" created on Sep. 28, 2017 and having a size of 244 KB. The contents of the text file are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has enabled their use as a versatile technology that is revolutionizing the field of genome manipulation.

Current CRISPR-Cas technologies are based on systems from cultured bacteria, leaving untapped the vast majority of organisms that have not been isolated. To date, only a few Class 2 CRISPR/Cas systems have been discovered. There is a need in the art for additional Class 2 CRISPR/Cas systems (e.g., Cas protein plus guide RNA combinations).

SUMMARY

The present disclosure provides RNA-guided endonuclease polypeptides, referred to herein as "CasY" polypeptides (also referred to as "CasY proteins"); nucleic acids encoding the CasY polypeptides; and modified host cells comprising the CasY polypeptides and/or nucleic acids encoding same. CasY polypeptides are useful in a variety of applications, which are provided.

The present disclosure provides guide RNAs (referred to herein as "CasY guide RNAs") that bind to and provide sequence specificity to the CasY proteins; nucleic acids encoding the CasY guide RNAs; and modified host cells comprising the CasY guide RNAs and/or nucleic acids encoding same. CasY guide RNAs are useful in a variety of applications, which are provided.

The present disclosure provides methods of identifying a CRISPR RNA-guided endonuclease.

BRIEF DESCRIPTION OF THE DRAWINGS

FIG. 1 depicts examples of naturally occurring CasY protein sequences.

NT, non-target). c, Plasmid interference by Deltaproteobacteria CasX. Experiments were conducted in triplicate and mean±s.d. is shown. d, PAM depletion assays for the Planctomycetes CasX locus expressed in *E. coli*. PAM sequences depleted greater than 30-fold compared to a control library were used to generate the WebLogo.

Figure 10:
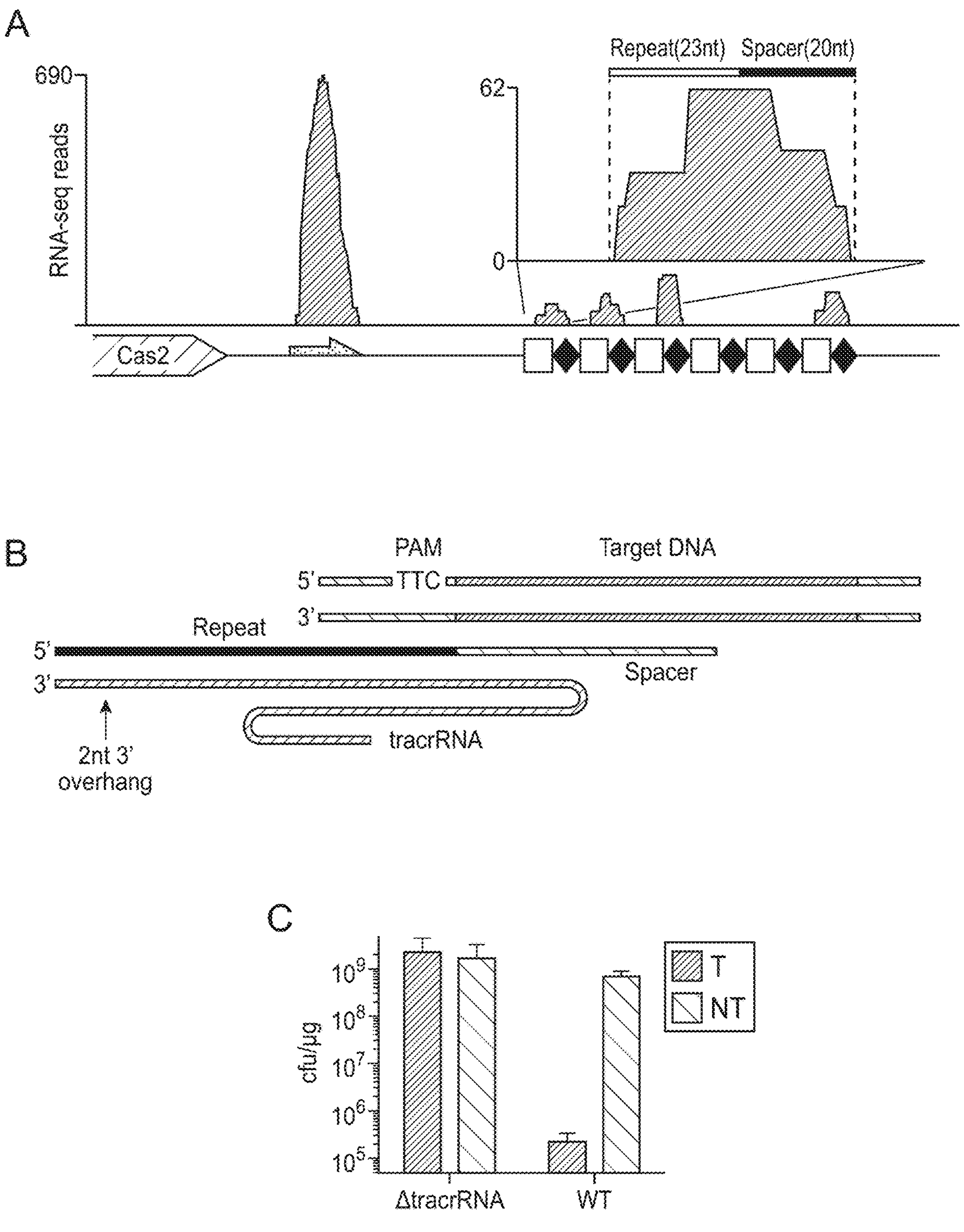

FIG. 10 (panels a-c) presents data showing CasX is a dual-guided CRISPR complex. a, Mapping of environmental RNA sequences (metatranscriptomic data) to the CasX CRISPR locus diagramed below (red arrow, putative tracrRNA; white boxes, repeat sequences; green diamonds, spacer sequences). Inset shows detailed view of the first repeat and spacer. b, Diagram of CasX double-stranded DNA interference. The site of RNA processing is indicated by black arrows. c, Results of plasmid interference assays with the putative tracrRNA knocked out of the CasX locus (T, target; NT, non-target). Experiments were conducted in triplicate and mean±s.d. is shown.

FIG. 11 (panels a-c) presents data showing expression of a CasY locus in *E. coli* is sufficient for DNA interference. a, Diagrams of CasY loci and neighboring proteins. b, WebLogo of 5' PAM sequences depleted greater than 3-fold by CasY relative to a control library. c, Plasmid interference by *E. coli* expressing CasY.1 and transformed with targets containing the indicated PAM. Experiments were conducted in triplicate and mean±s.d is shown.

Figure 12:
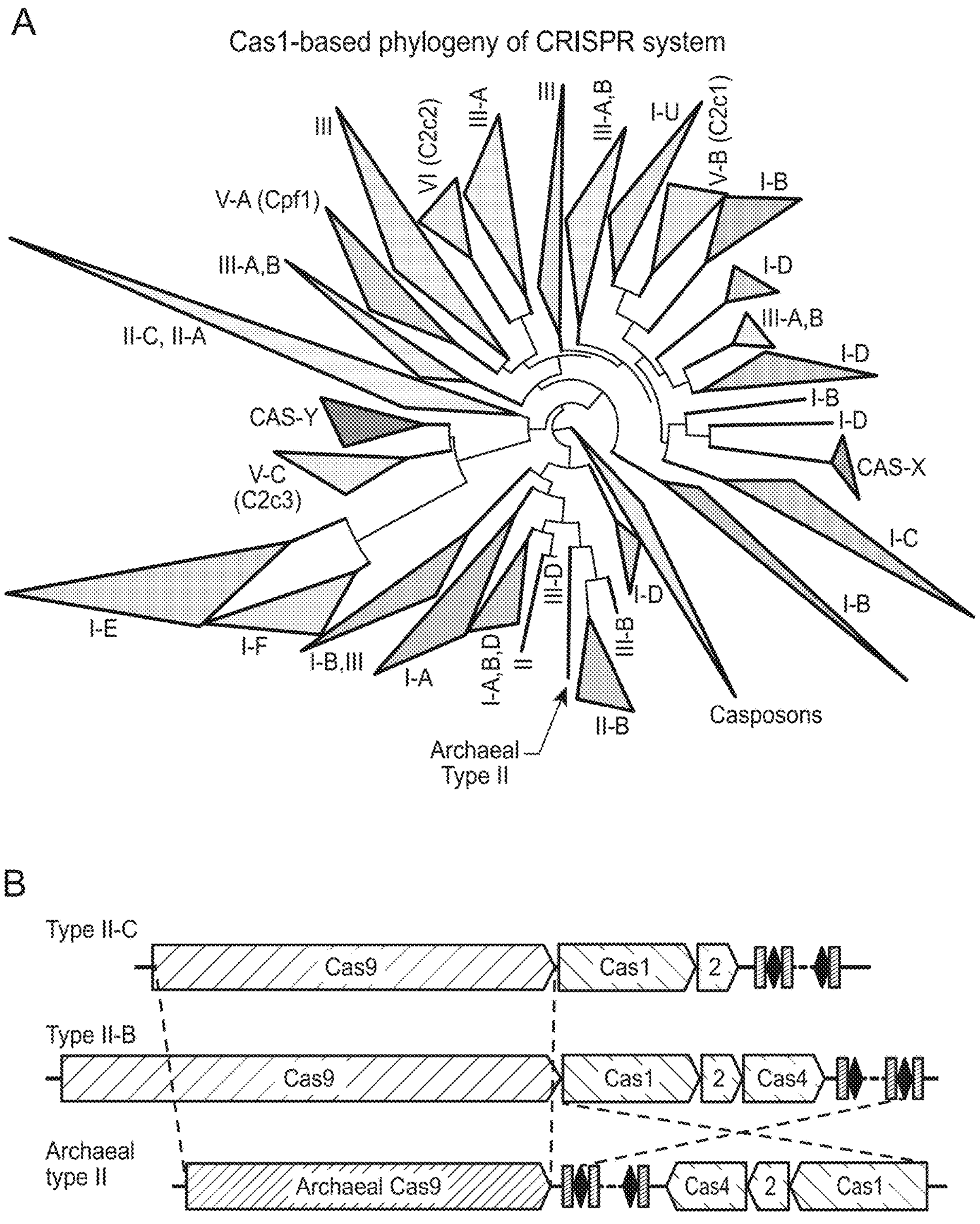
Figure 13A:
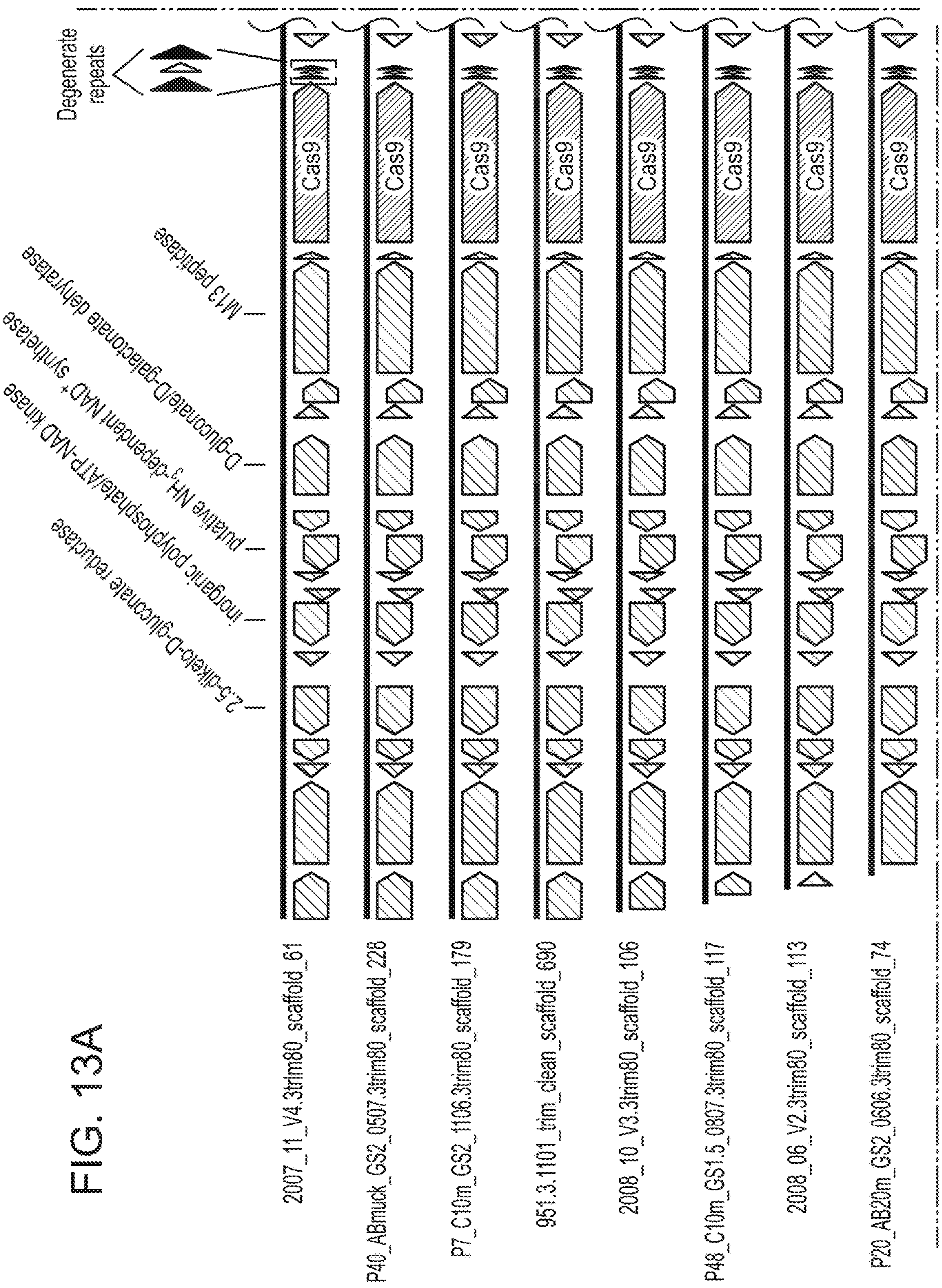
Figure 13B:
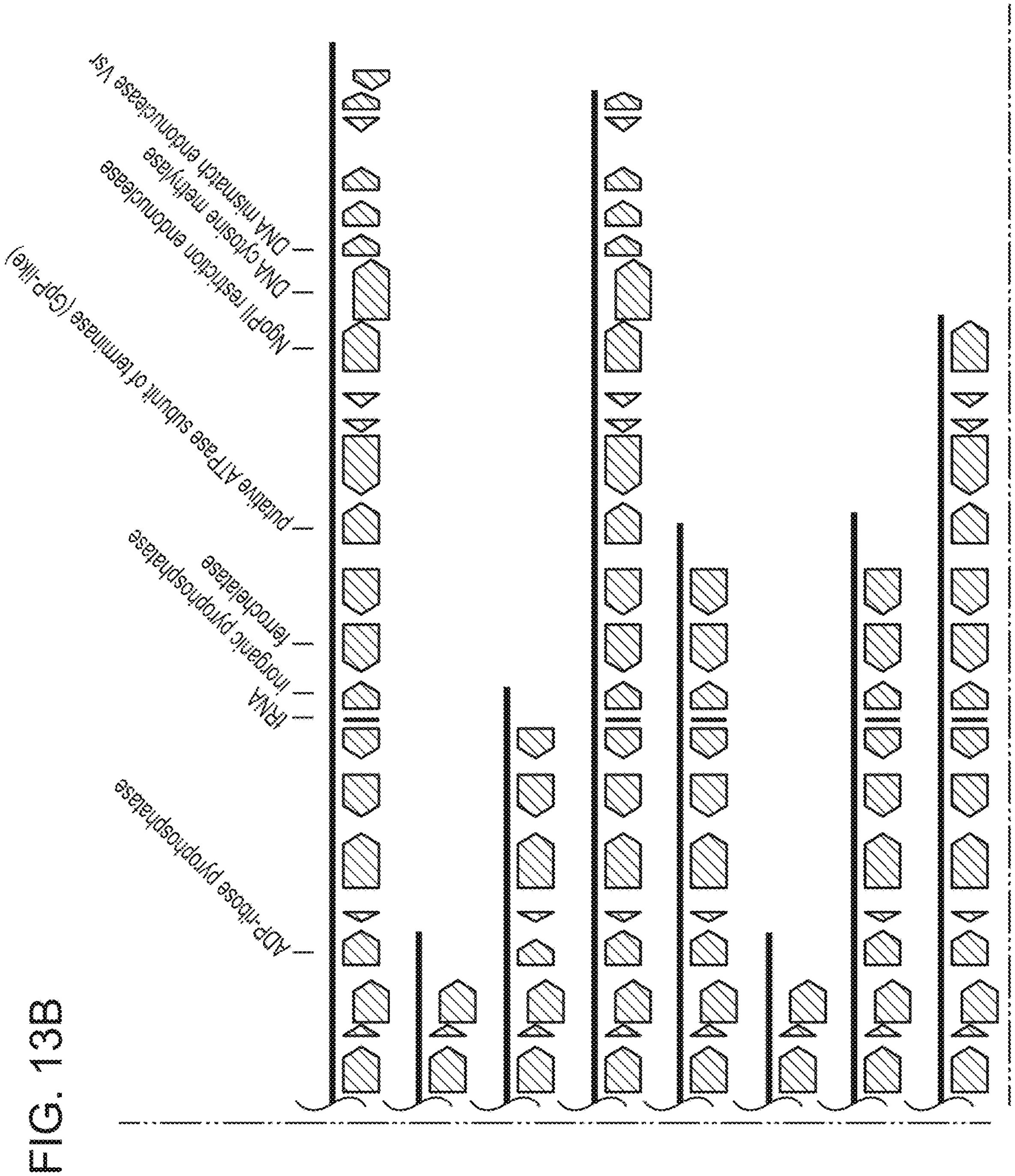
Figure 13C:
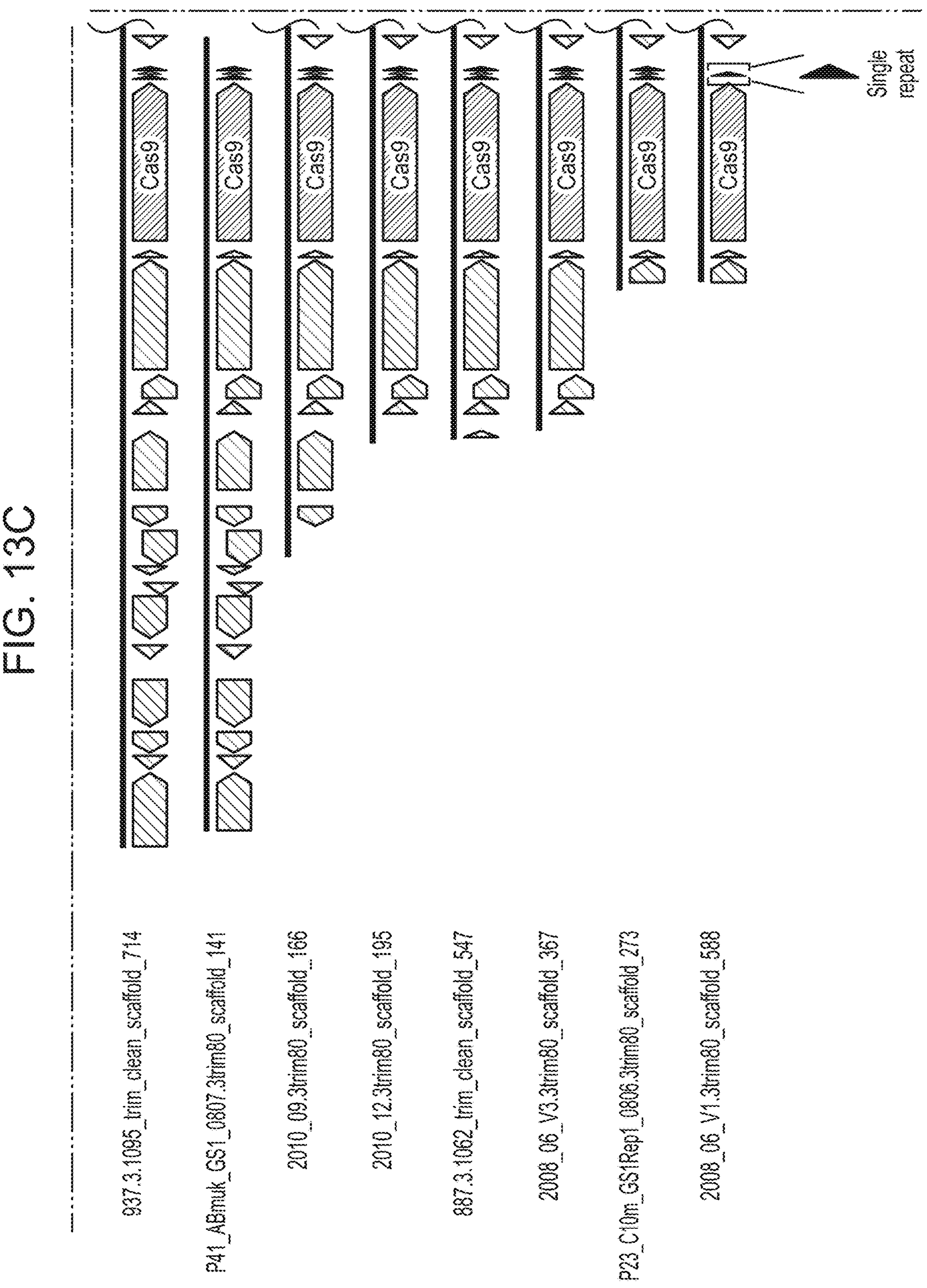
Figure 13D:
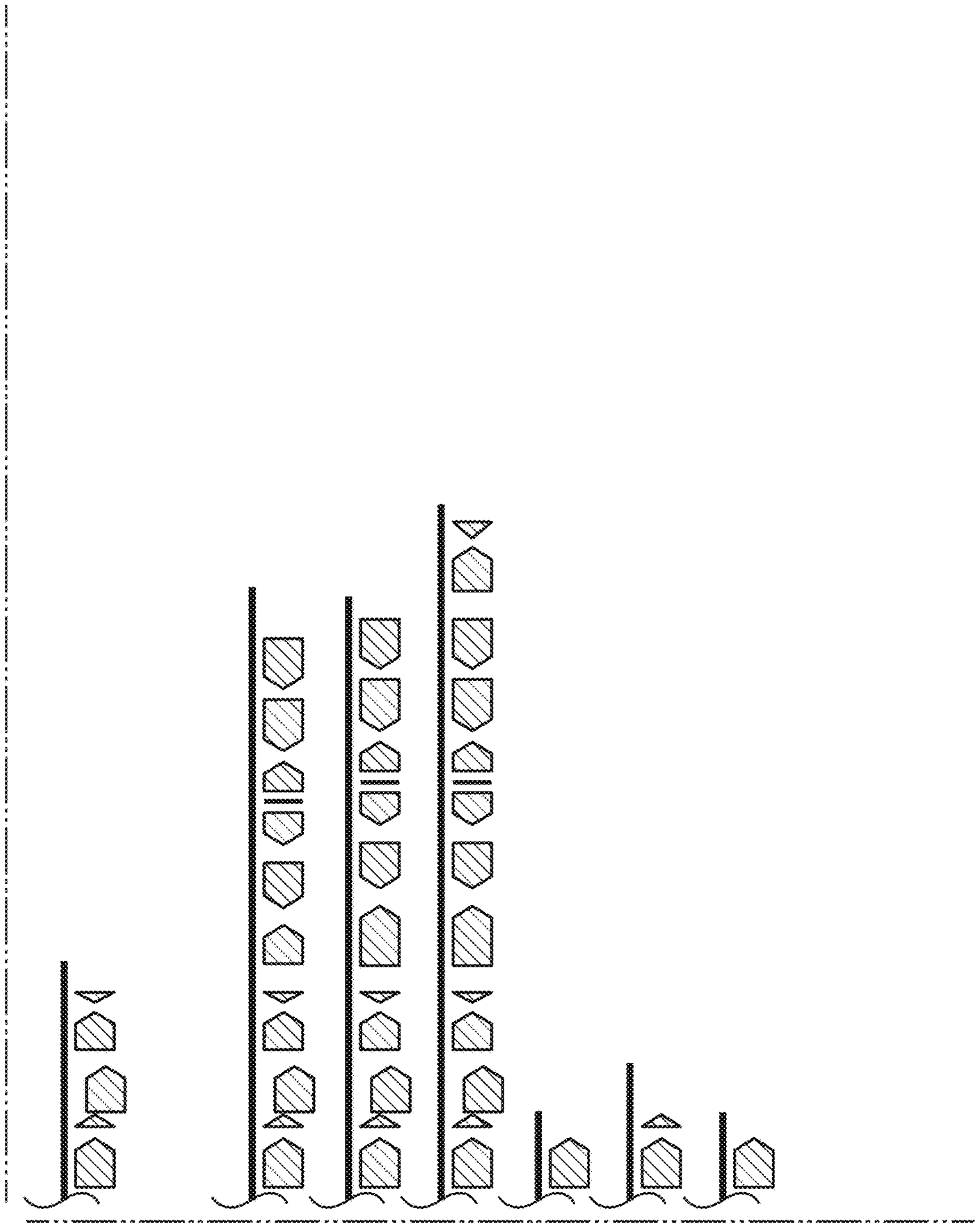
Figure 14A:
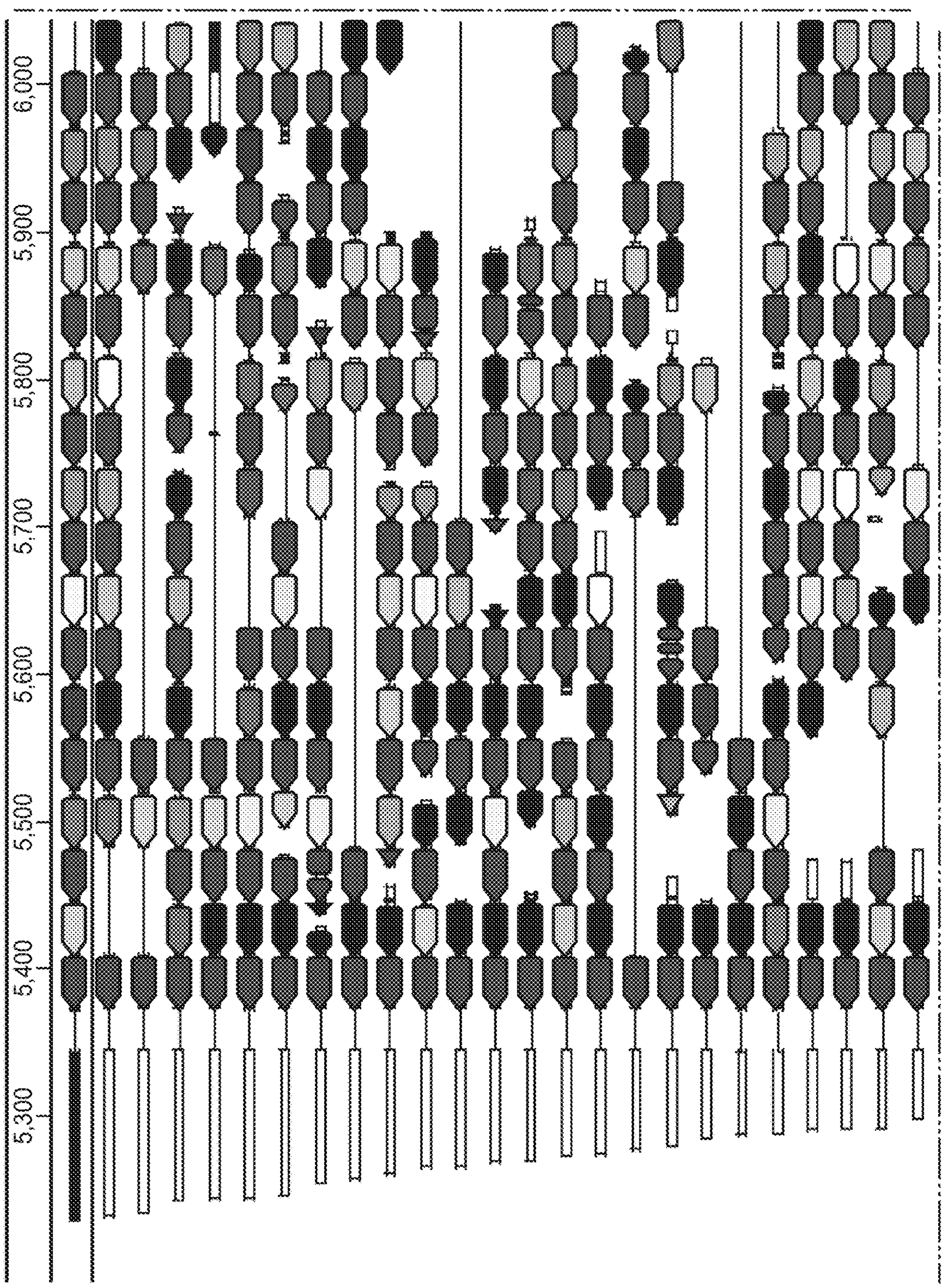
Figure 14B:
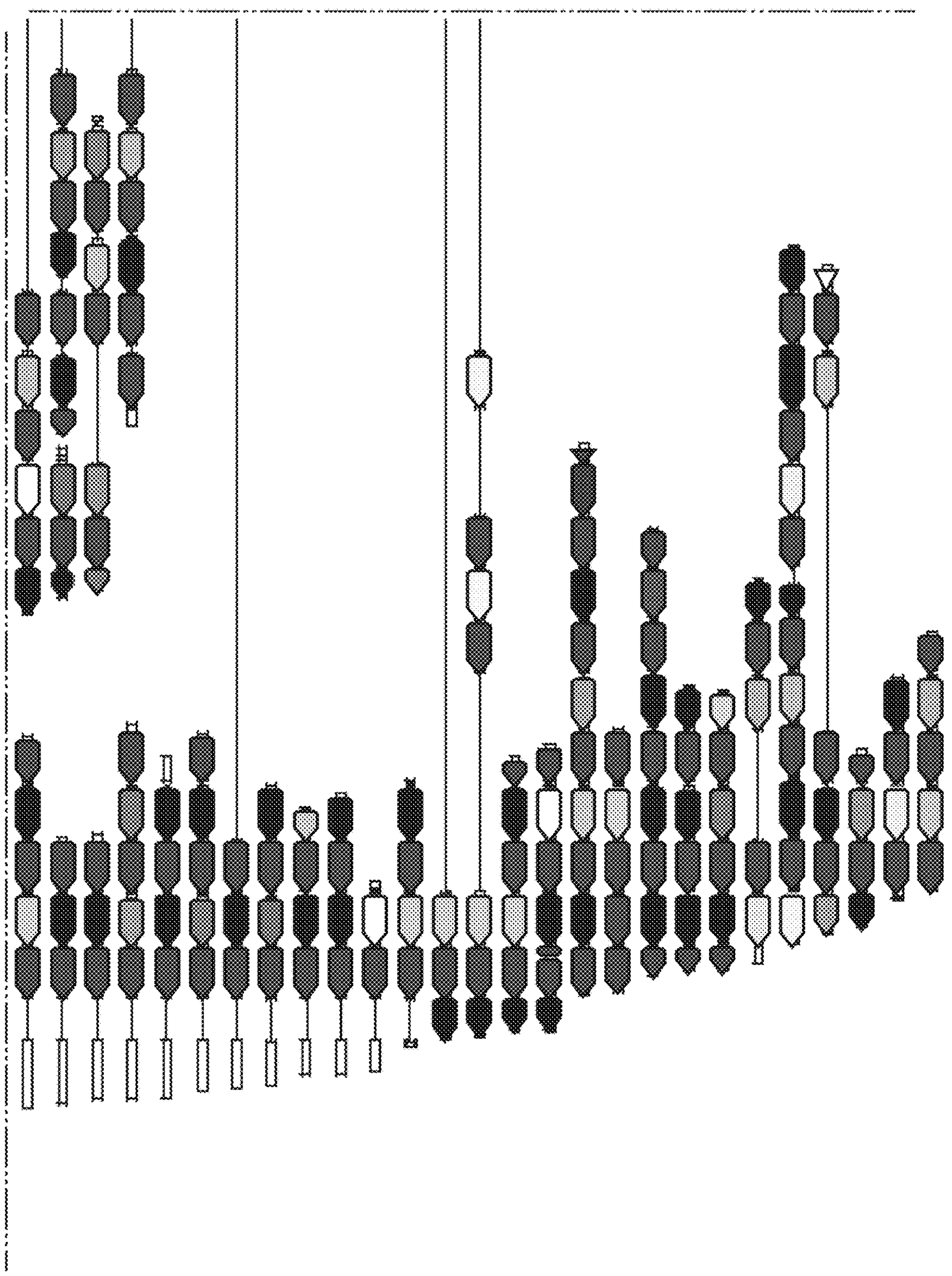
Figure 14C:
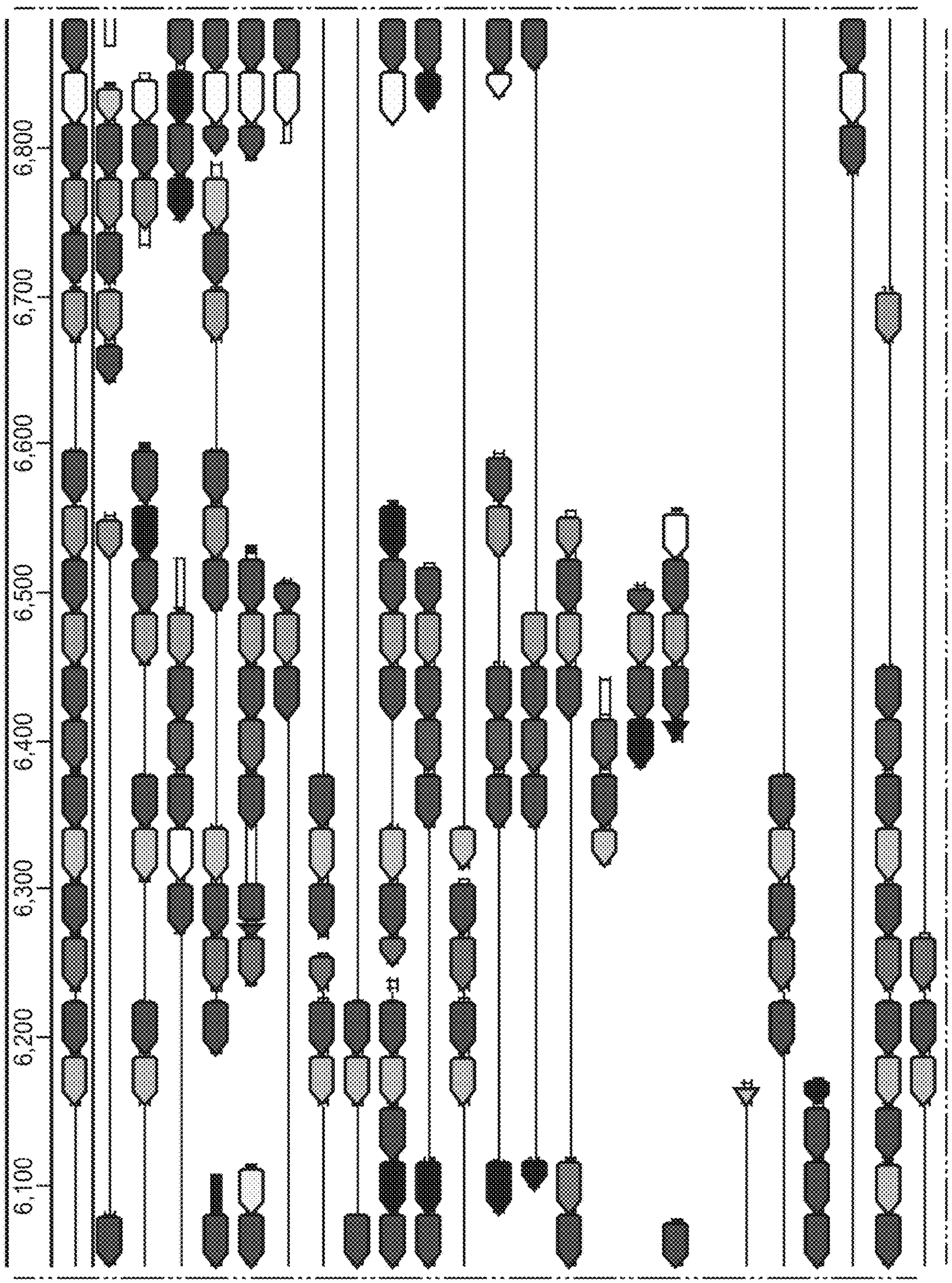
Figure 14D:
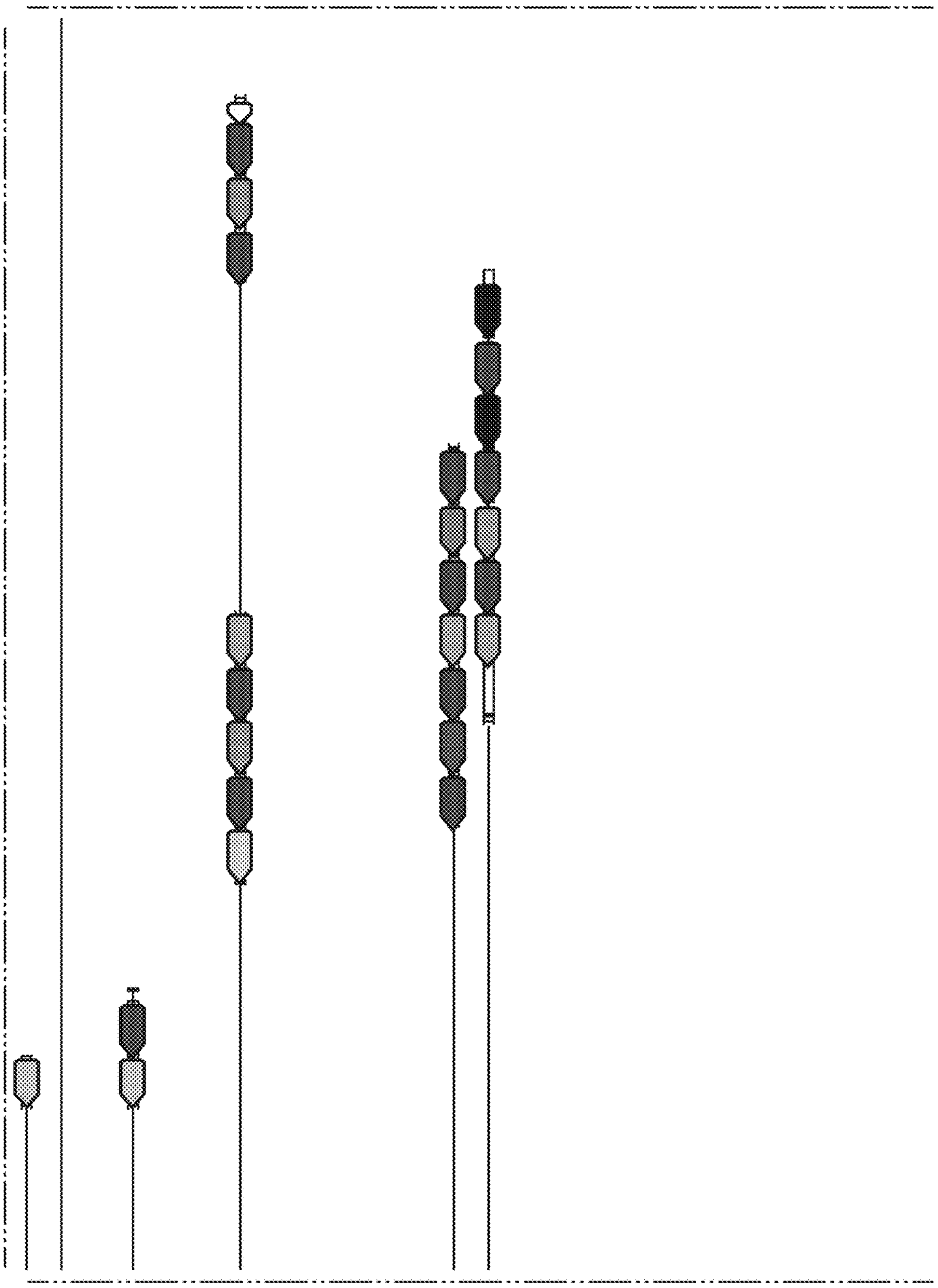
Figure 14E:
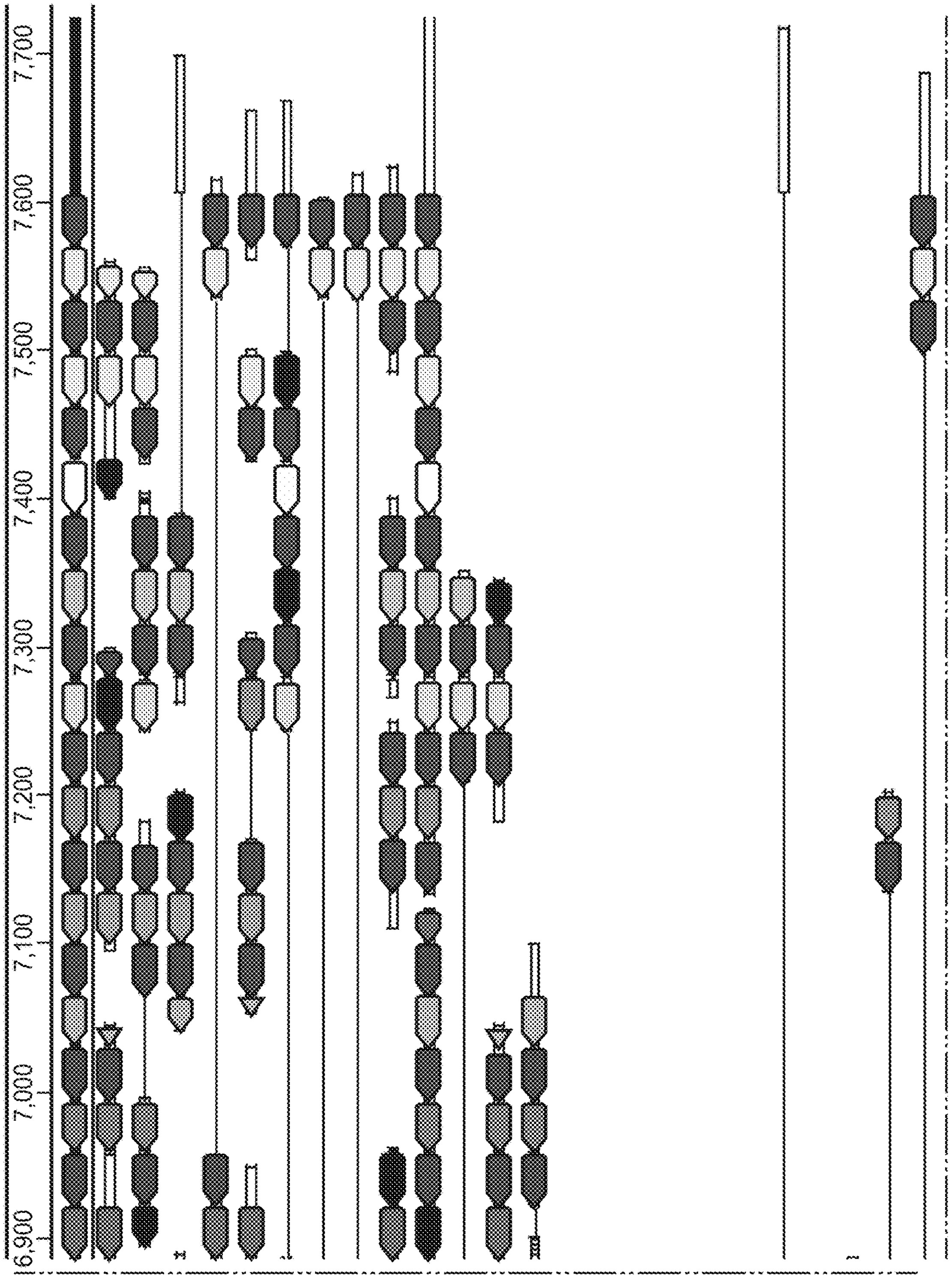
Figure 14F:
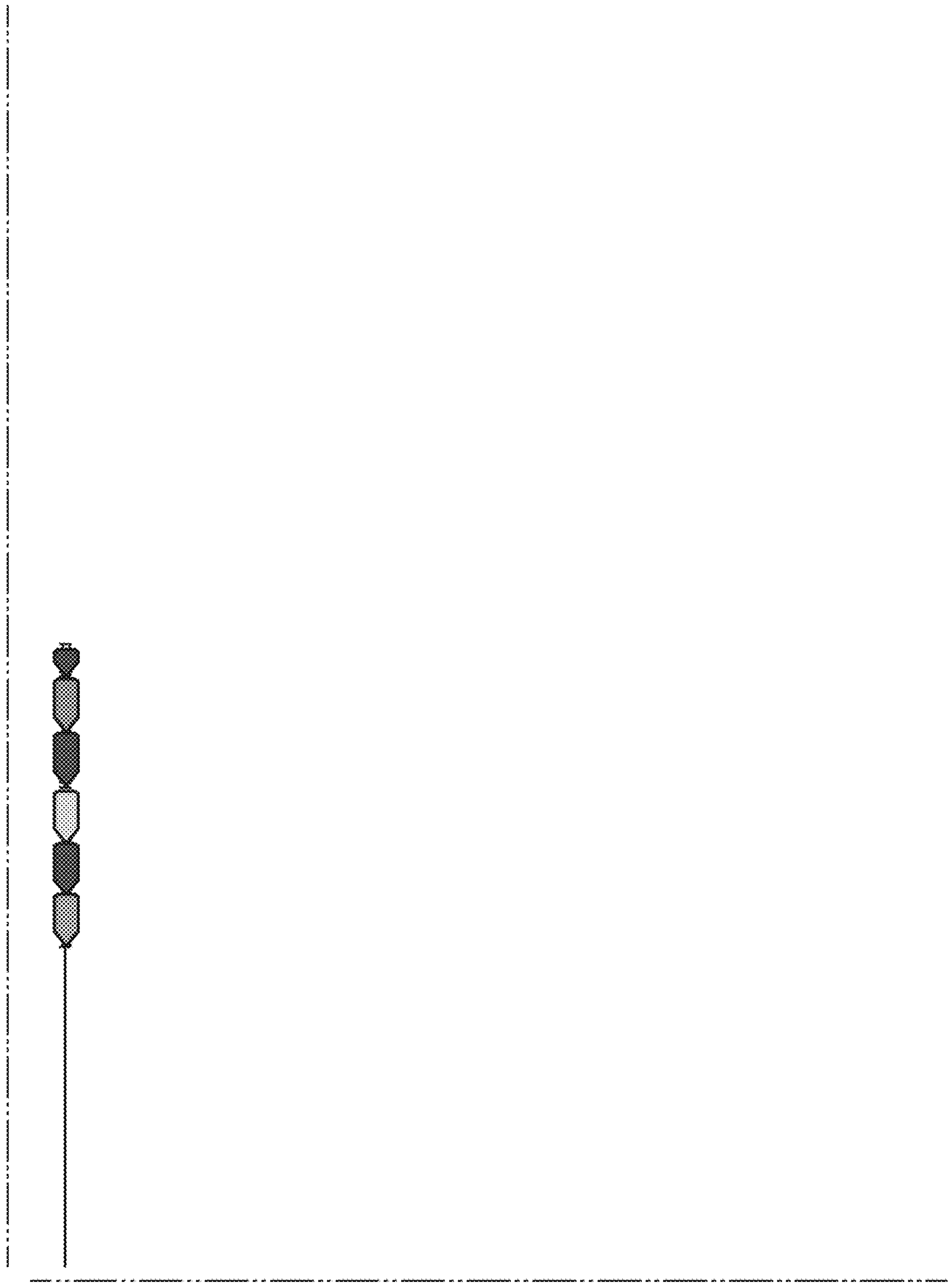

FIG. 12 (panels a-b) presents newly identified CRISPR-Cas in context of known systems. a, Simplified phylogenetic tree of the universal Cas1 protein. CRISPR types of known systems are noted on the wedges and branches; the newly described systems are in bold. Detailed Cas1 phylogeny is presented in Supplementary Data 2. b, Proposed evolutionary scenario that gave rise to the archaeal type II system as a result of a recombination between type II-B and type II-C loci.

FIG. 13 (panels a-d) shows that archaeal Cas9 from ARMAN-4 is found on numerous contigs with a degenerate CRISPR array. Cas9 from ARMAN-4 is highlighted in dark red on 16 different contigs. Proteins with putative domains or functions are labeled whereas hypothetical proteins are unlabeled. Fifteen of the contigs contain two degenerate direct repeats (one bp mismatch) and a single, conserved spacer. The remaining contig contains only one direct repeat. Unlike ARMAN-1, no additional Cas proteins are found adjacent to Cas9 in ARMAN-4.

FIG. 14 presents a full reconstruction of ARMAN-1 CRISPR arrays. Reconstruction of CRISPR arrays, that include reference assembled sequences, as well as array segments reconstructed from the short DNA reads. Green arrows indicate repeats and colored arrows indicate CRISPR spacers (identical spacers are colored the same whereas unique spacers are colored in black). In CRISPR systems, spacers are typically added unidirectionally, so the high variety of spacers on the left side is attributed to recent acquisition.

Figure 15:
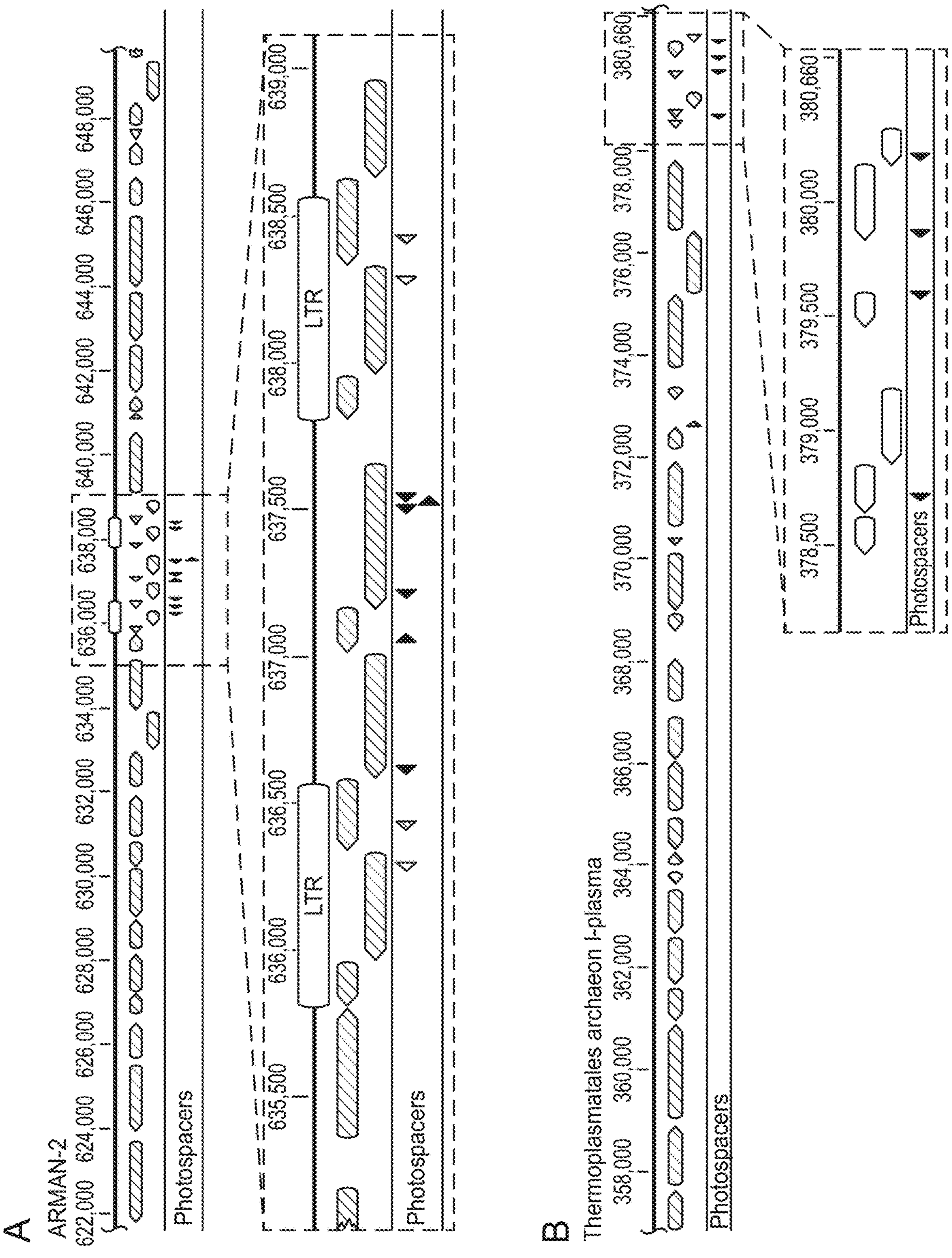

FIG. 15 (panels a-b) shows that ARMAN-1 spacers map to genomes of archaeal community members. a, Protospacers (red arrows) from ARMAN-1 map to the genome of ARMAN-2, a nanoarchaeon from the same environment. Six protospacers map uniquely to a portion of the genome flanked by two long-terminal repeats (LTRs), and two additional protospacers match perfectly within the LTRs (blue and green). This region is likely a transposon, suggesting the CRISPR-Cas system of ARMAN-1 plays a role in suppressing mobilization of this element. b, Protospacers also map to a Thermoplasmatales archaeon (I-plasma), another member of the Richmond Mine ecosystem that is found in the same samples as ARMAN organisms. The protospacers cluster within a region of the genome encoding short, hypothetical proteins, suggesting this might also represent a mobile element.

Figure 16A:
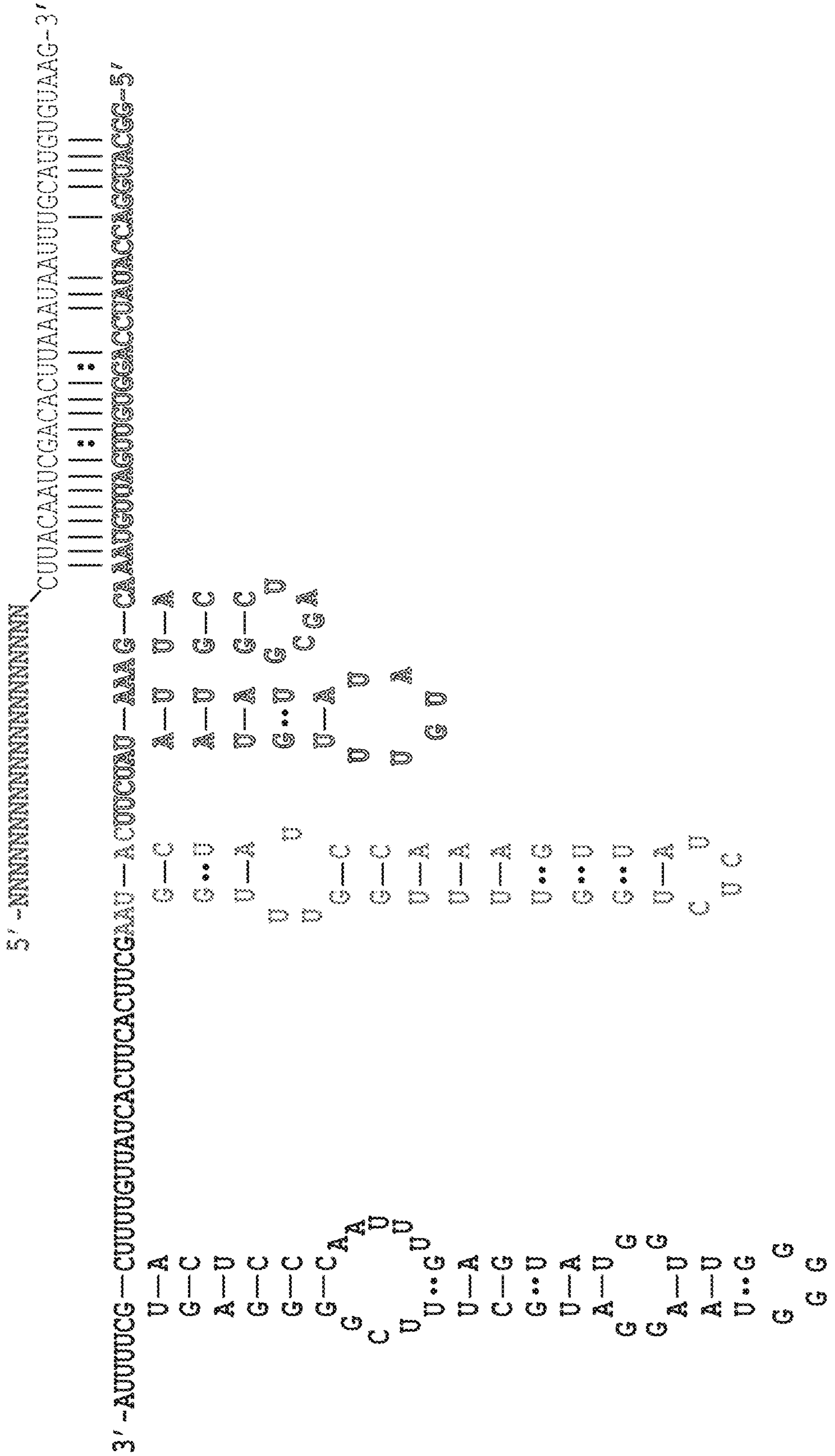
Figure 16B:
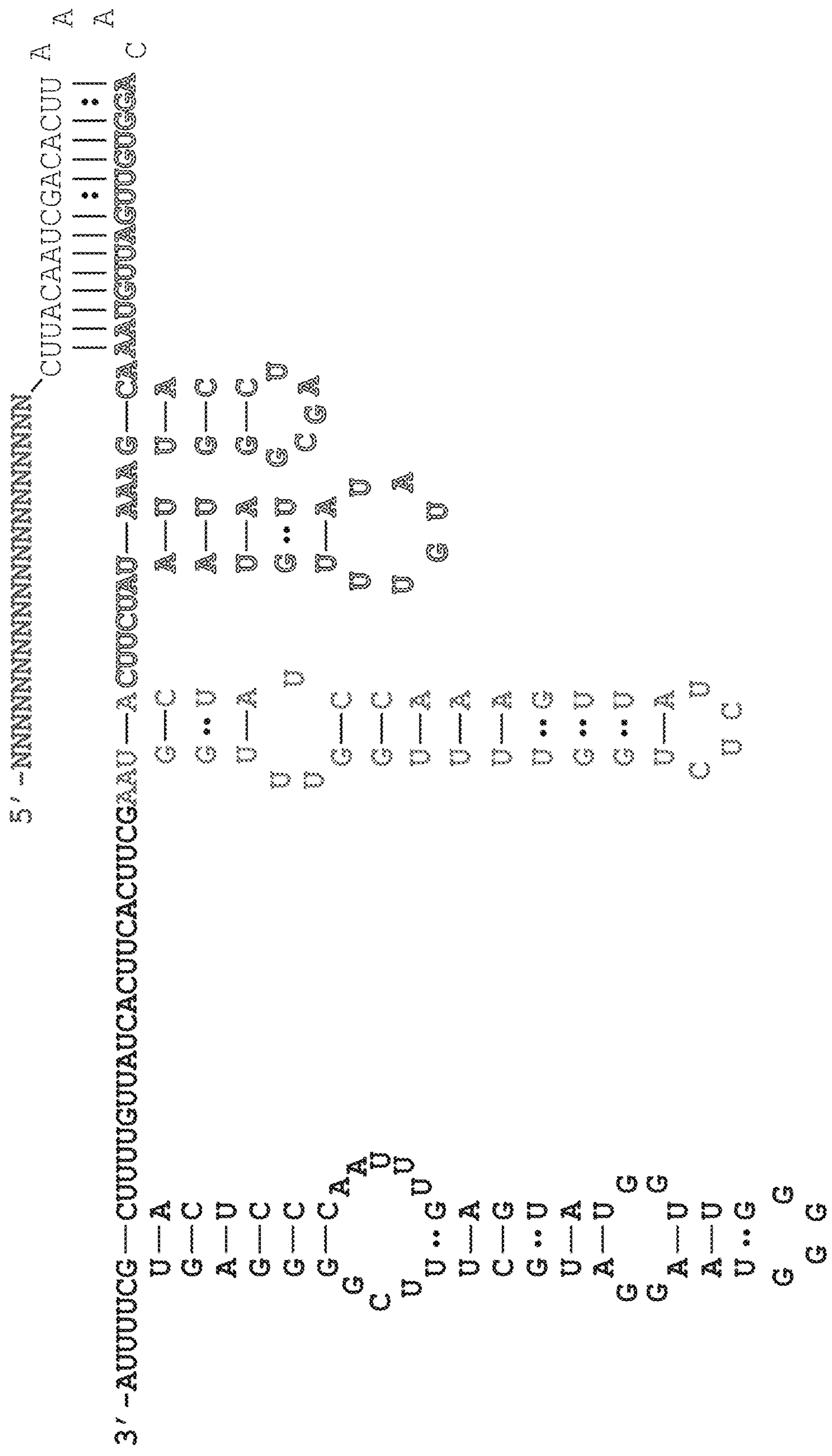

FIG. 16 (panels a-e) presents predicted secondary structure of ARMAN-1 crRNA and tracrRNA. a, The CRISPR repeat and tracrRNA anti-repeat are depicted in black whereas the spacer-derived sequence is shown as a series of green N's. No clear termination signal can be predicted from the locus, so three different tracrRNA lengths were tested based on their secondary structure—69, 104, and 179 in red, blue, and pink, respectively. b, Engineered single-guide RNA corresponding to dual-guide in a. c, Dual-guide for ARMAN-4 Cas9 with two different hairpins on 3' end of tracrRNA (75 and 122). d, Engineered single-guide RNA corresponding to dual-guide in c. e, Conditions tested in *E. coli* in vivo targeting assay. (Top to bottom: SEQ ID NOs:143-145, 140-142).

Figure 17:
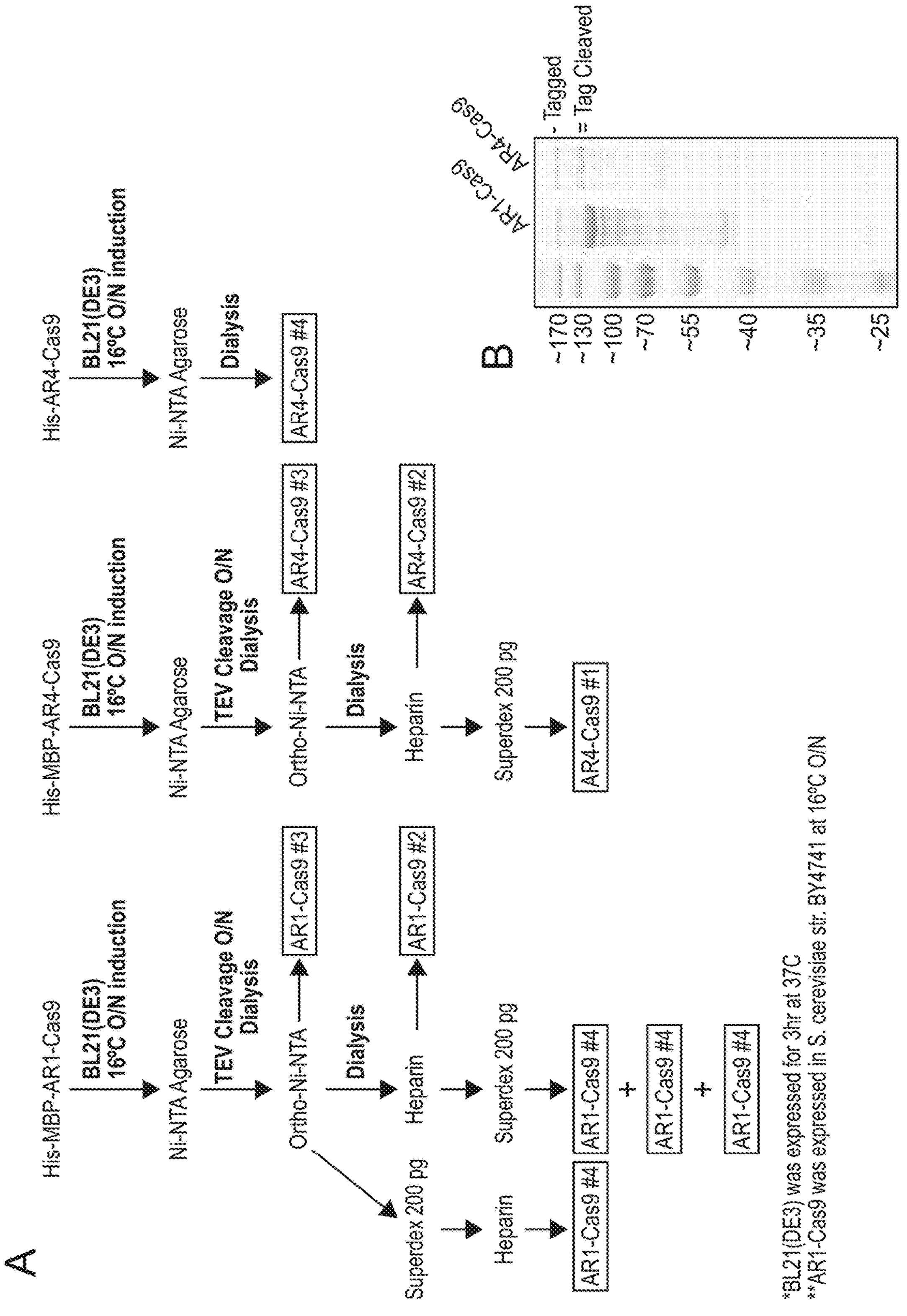

FIG. 17 (panels a-b) presents purification schema for in vitro biochemistry studies. a, ARMAN-1 (AR1) and ARMAN-4 (AR4) Cas9 were expressed and purified under a variety of conditions as outlined in the Supplementary Materials. Proteins outlined in blue boxes were tested for cleavage activity in vitro. b, Fractions of AR1-Cas9 and AR4-Cas9 purifications were separated on a 10% SDS-PAGE gel.

Figure 18:
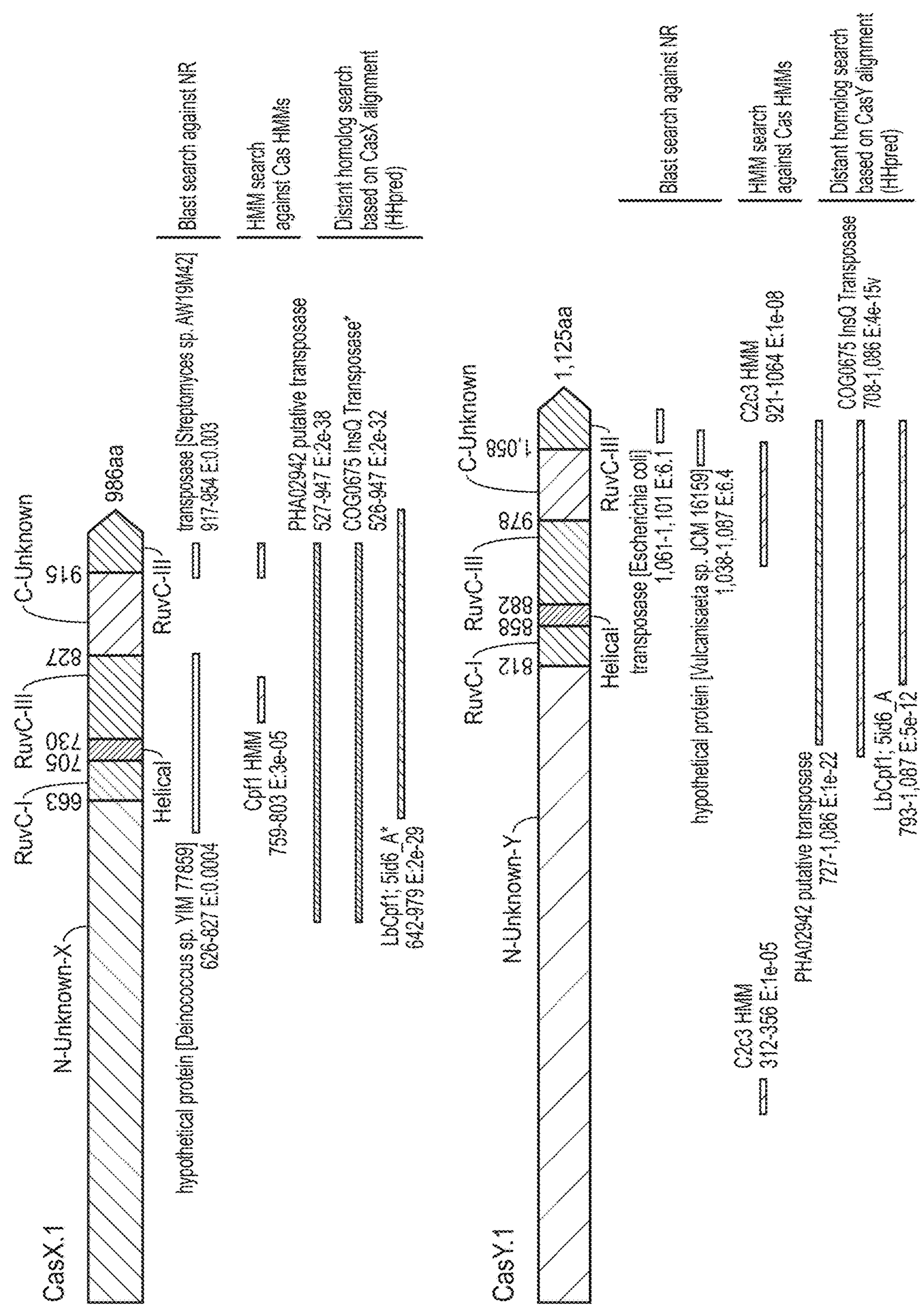
Figure 19A:
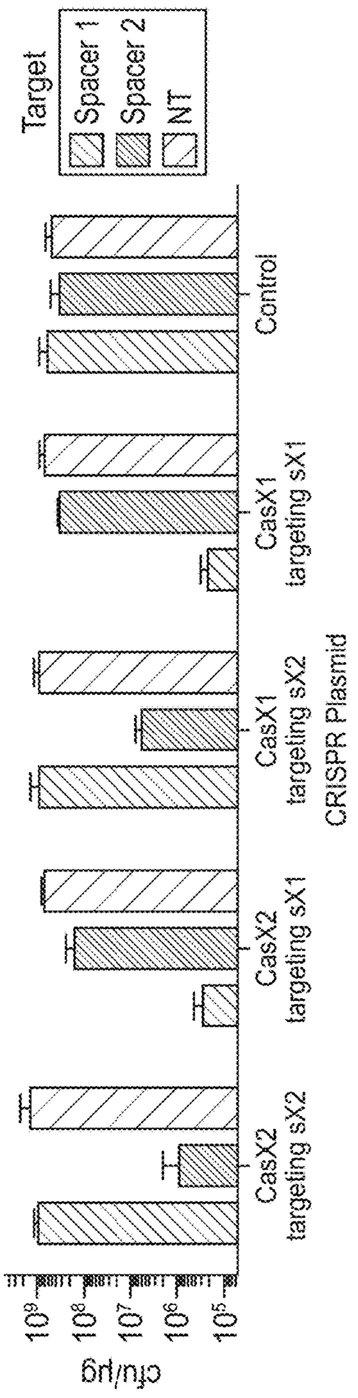
Figure 19B:
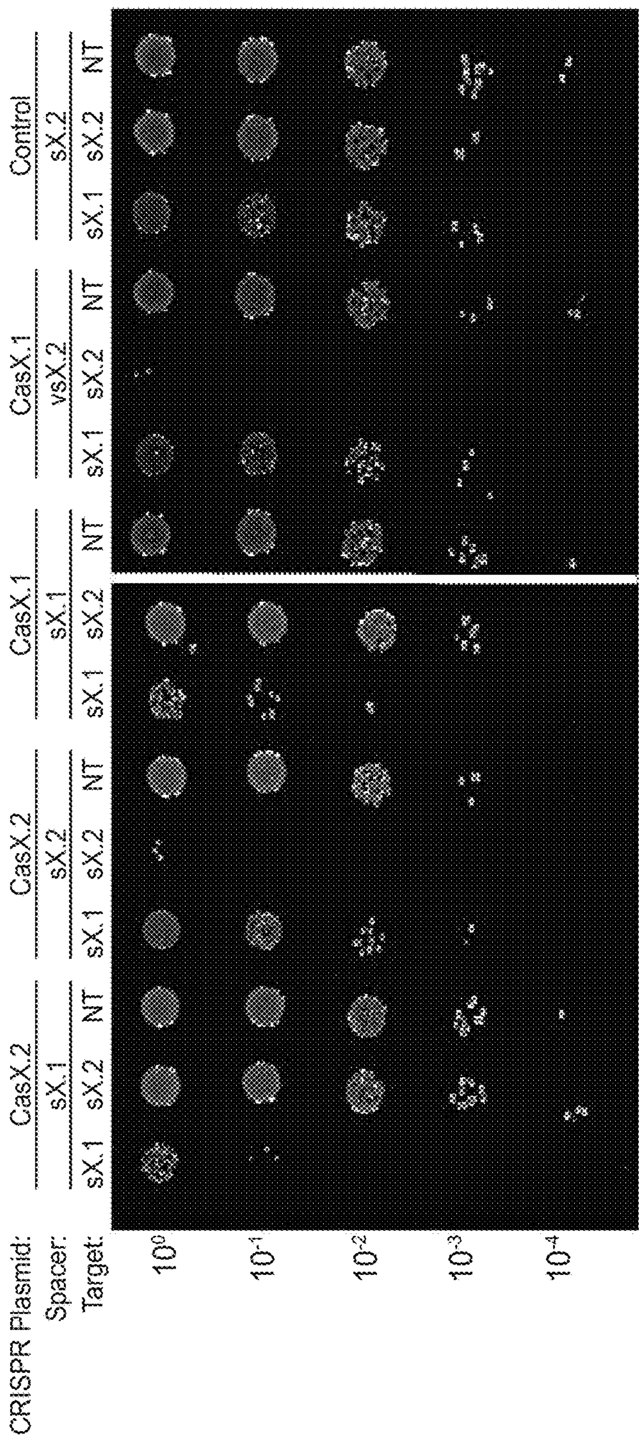
Figure 19C:
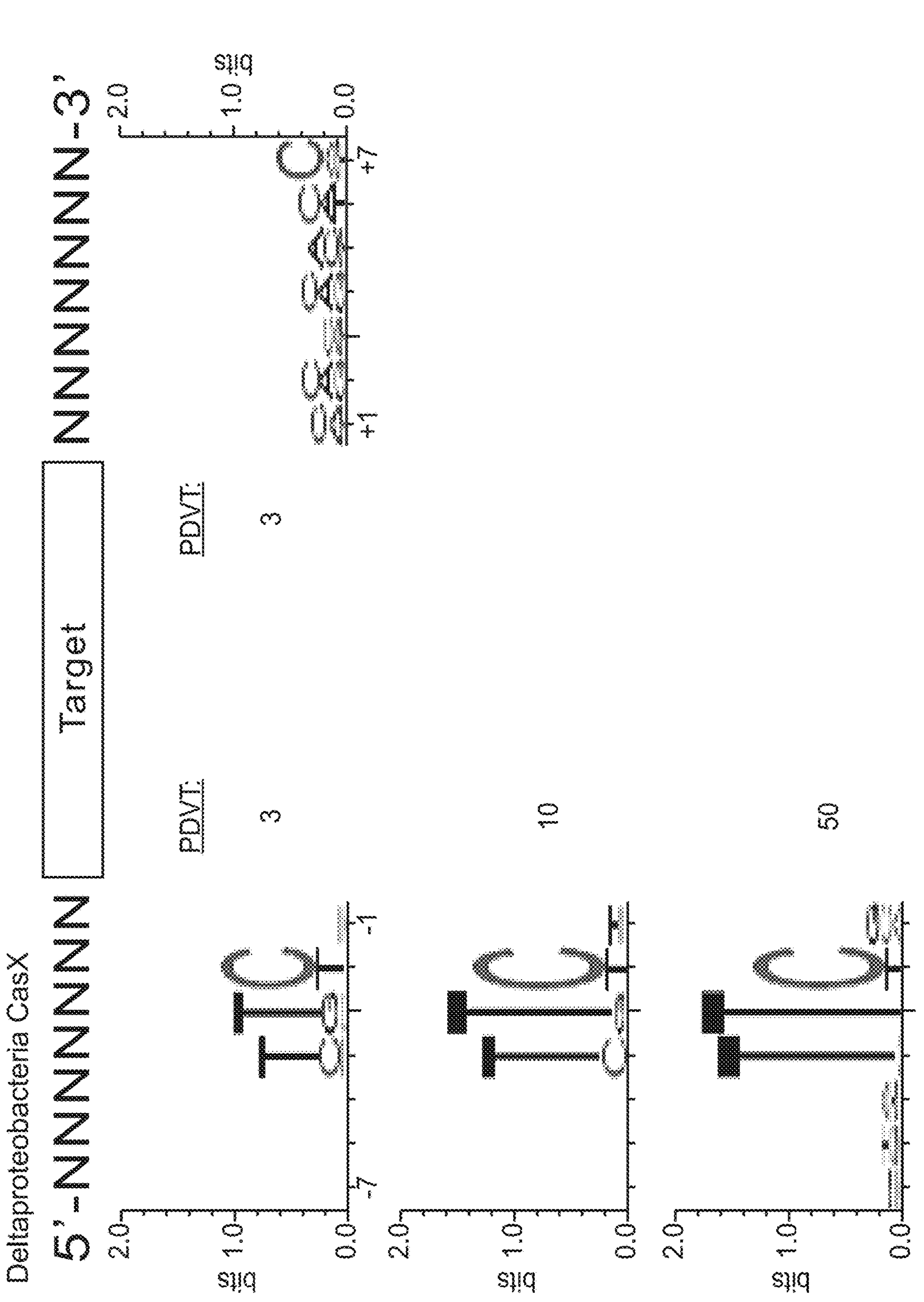
Figure 19D:
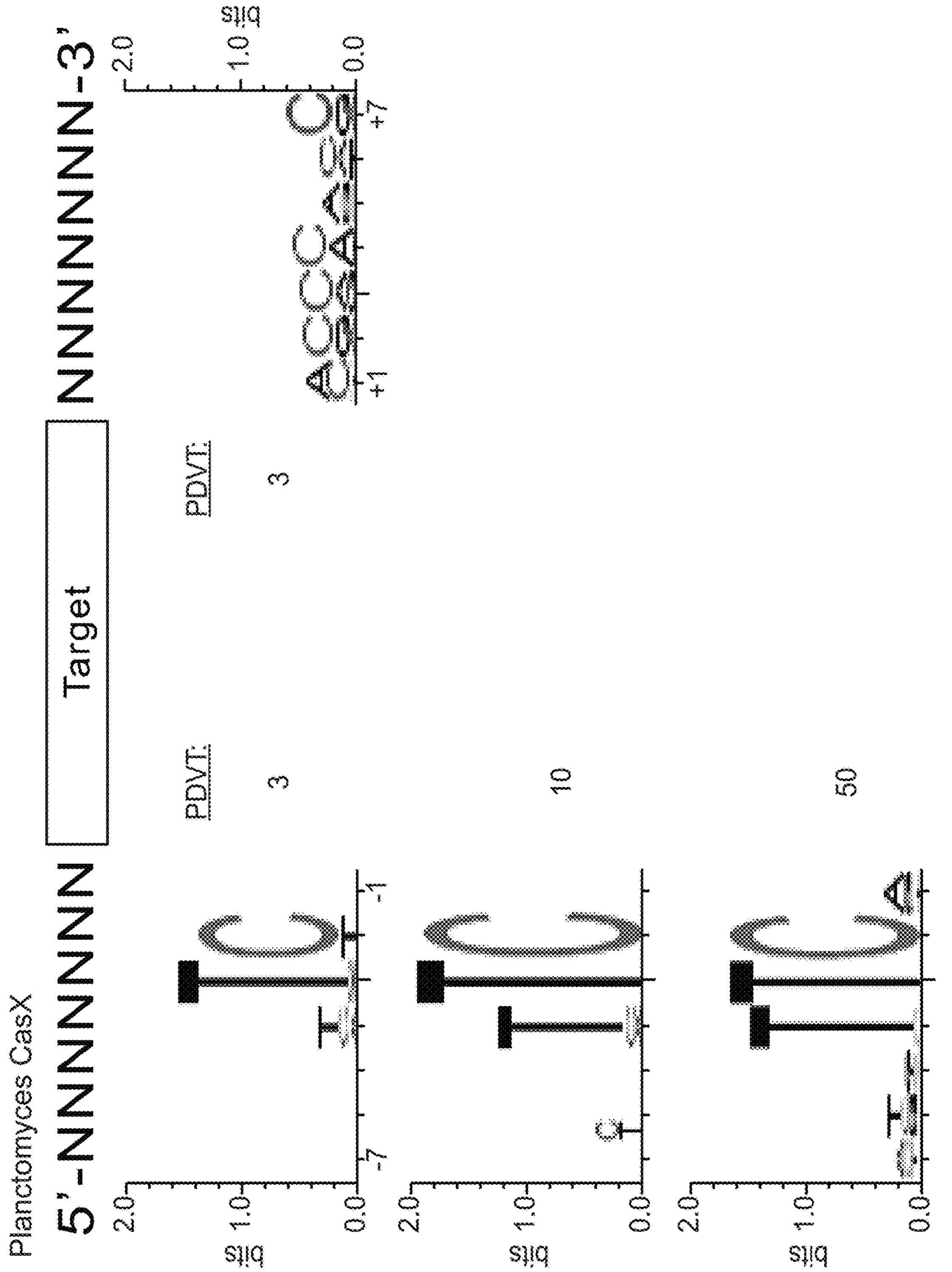

FIG. 18 presents newly identified CRISPR-Cas systems compared to known proteins. Similarity of CasX and CasY to known proteins based on the following searches: (1) Blast search against the non-redundant (NR) protein database of NCBI, (2) Hidden markov model (HMM) search against an HMM database of all known proteins and (3) distant homology search using HHpred[30].

FIG. 19 (panels a-d) presents data related to programed DNA interference by CasX. a, Plasmid interference assays for CasX2 (Planctomycetes) and CasX1 (Deltaproteobacteria), continued from FIG. 9, panel c (sX1, CasX spacer 1; sX2, CasX spacer 2; NT, non-target). Experiments were conducted in triplicate and mean±s.d. is shown. b, Serial dilution of *E. coli* expressing a CasX locus and transformed with the specified target, continued from FIG. 9, panel b. c, PAM depletion assays for the Deltaproteobacteria CasX and d, Planctomycetes CasX expressed in *E. coli*. PAM sequences depleted greater than the indicated PAM depletion value threshold (PDVT) compared to a control library were used to generate the WebLogo.

Figure 20:
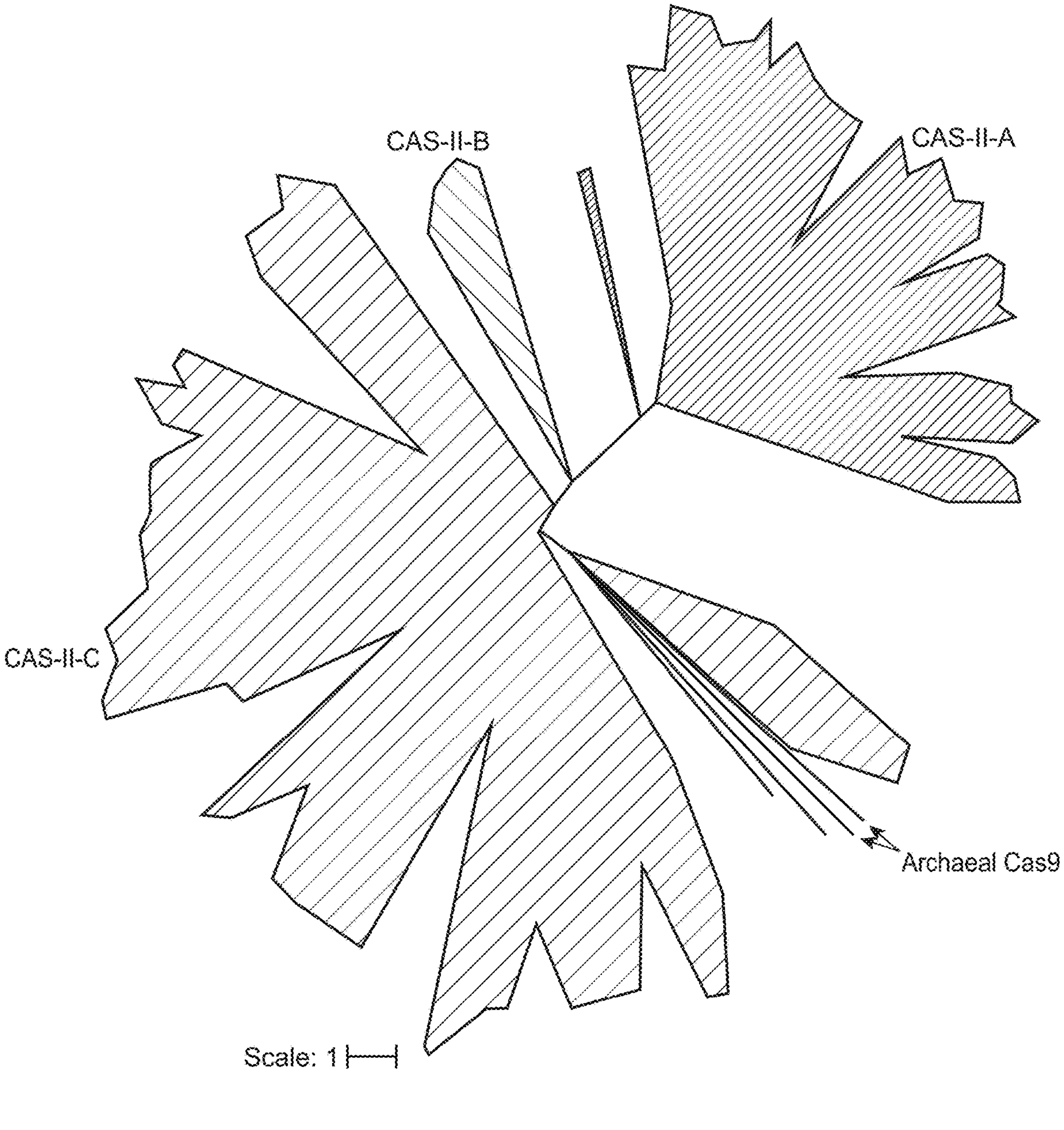

FIG. 20 presents an evolutionary tree of Cas9 homologs. Maximum-likelihood phylogenic tree of Cas9 proteins, showing the previously described systems colored based on their type: II-A in blue, II-B in green and II-C in purple. The Archaeal Cas9, cluster with type II-C CRISPR-Cas systems, together with two newly described bacterial Cas9 from uncultivated bacteria.

FIG. 21 presents a table of cleavage conditions assayed for Cas9 from ARMAN-1 and ARMAN-4.

DEFINITIONS

"Heterologous," as used herein, means a nucleotide or polypeptide sequence that is not found in the native nucleic acid or protein, respectively. For example, relative to a CasY polypeptide, a heterologous polypeptide comprises an amino acid sequence from a protein other than the CasY polypeptide. In some cases, a portion of a CasY protein from one species is fused to a portion of a CasY protein from a different species. The CasY sequence from each species could therefor be considered to be heterologous relative to one another. As another example, a CasY protein (e.g., a dCasY protein) can be fused to an active domain from a non-CasY protein (e.g., a histone deacetylase), and the sequence of the active domain could be considered a heterologous polypeptide (it is heterologous to the CasY protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasY polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided endonuclease polypeptides, referred to herein as "CasY" polypeptides (also referred to as "CasY proteins"); nucleic acids encoding the CasY polypeptides; and modified host cells comprising the CasY polypeptides and/or nucleic acids encoding same. CasY polypeptides are useful in a variety of applications, which are provided.

The present disclosure provides guide RNAs (referred to herein as "CasY guide RNAs") that bind to and provide sequence specificity to the CasY proteins; nucleic acids encoding the CasY guide RNAs; and modified host cells comprising the CasY guide RNAs and/or nucleic acids encoding same. CasY guide RNAs are useful in a variety of applications, which are provided.

The present disclosure provides methods of identifying a CRISPR RNA-guided endonuclease.

Compositions

CRISPR/CasY Proteins and Guide RNAs

A CRISPR/Cas endonuclease (e.g., a CasY protein) interacts with (binds to) a corresponding guide RNA (e.g., a CasY guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasY protein forms a complex with a CasY guide RNA and the guide RNA provides sequence specificity to the RNP complex via the guide sequence. The CasY protein of the complex provides the site-specific activity. In other words, the CasY protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasY polypeptide (and/or a nucleic acid encoding the CasY polypeptide) (e.g., where the CasY polypeptide can be a naturally existing protein, a nickase CasY protein, a dCasY protein, a chimeric CasY protein, etc.). The present disclosure provides compositions comprising a CasY guide RNA (and/or a nucleic acid encoding the CasY guide RNA). The present disclosure provides compositions comprising (a) a CasY polypeptide (and/or a nucleic acid encoding the CasY polypeptide) (e.g., where the CasY polypeptide can be a naturally existing protein, a nickase CasY protein, a dCasY protein, a chimeric CasY protein, etc.) and (b) a CasY guide RNA (and/or a nucleic acid encoding the CasY guide RNA). The present disclosure provides a nucleic acid/protein complex (RNP complex) comprising: (a) a CasY polypeptide of the present disclosure (e.g., where the CasY polypeptide can be a naturally existing protein, a nickase CasY protein, a dCasY protein, a chimeric CasY protein, etc.); and (b) a CasY guide RNA.

CasY Protein

A CasY polypeptide (this term is used interchangeably with the term "CasY protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasY protein includes a fusion partner with an activity, and in some cases the CasY protein provides nuclease activity). In some cases, the CasY protein is a naturally-occurring protein (e.g., naturally occurs in prokaryotic cells). In other cases, the CasY protein is not a naturally-occurring polypeptide (e.g., the CasY protein is a variant CasY protein, a chimeric protein, and the like).

Assays to determine whether given protein interacts with a CasY guide RNA can be any convenient binding assay that tests for binding between a protein and a nucleic acid. Suitable binding assays (e.g., gel shift assays) will be known to one of ordinary skill in the art (e.g., assays that include adding a CasY guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CasY protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring CasY guide RNA is a crRNA, where the crRNA includes (i) a guide sequence that hybridizes to a target sequence in the target DNA and (ii) a protein binding segment which includes a stem-loop (hairpin—dsRNA duplex) that binds to the CasY protein.

Figure 2A:
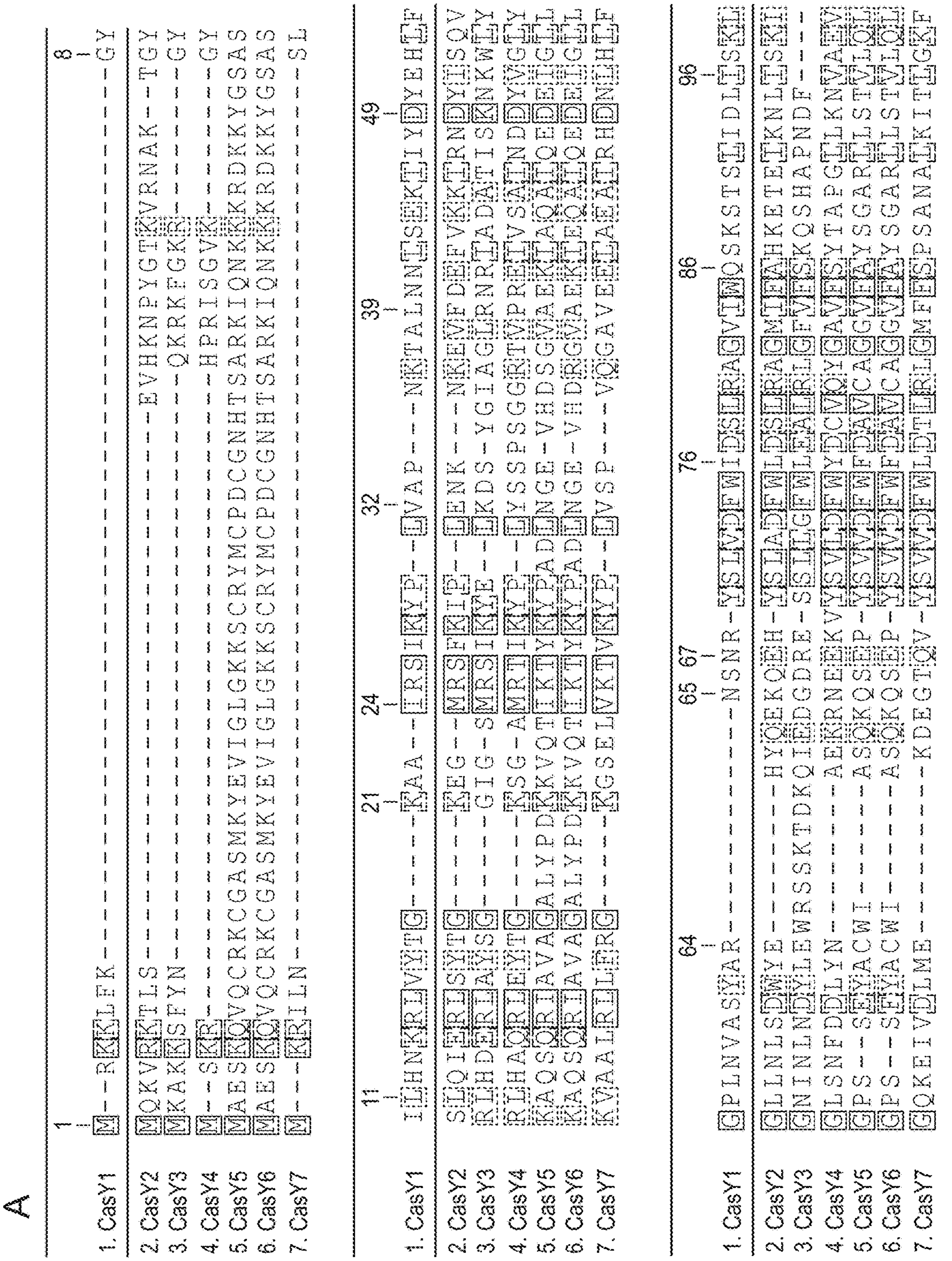
FIG. 2 (panels a-b)_depicts an alignment of naturally occurring CasY protein sequences. (Panel A: Top to Bottom, SEQ ID NOs:153-159; Panel B: SEQ ID NOs:146-152, 138-139).

In some embodiments, the CasY protein of the subject methods and/or compositions is (or is derived from) a naturally occurring (wild type) protein. Examples of naturally occurring CasY proteins are depicted in FIG. 1 and are set forth as SEQ ID NOs: 1-7. Examples of naturally occurring CasY proteins are depicted in FIG. 1 and are set forth as SEQ ID NOs: 1-8. An alignment of example naturally occurring CasY proteins is presented in FIG. 2 (the proteins are labeled as "Y1.", "Y2.", "Y3.", etc.). Partial DNA scaffolds of 7 naturally occurring CasY CRISPR loci (assembled from sequencing data) are set forth as SEQ ID NOs: 21-27. It is important to note that this newly discovered protein (CasY) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasY protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. It is also noted herein that bacteria harboring CasY CRISPR loci were present in environmental samples that were collected at low temperature (e.g., 10-17° C.). Thus, CasY is expected to be able to function well at low temperatures (e.g., 10-14° C., 10-17° C., 10-20° C.) (e.g., better than other Cas endoconucleases discovered to date).

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 1. In some cases, a CasY protein includes an amino acid sequence having the CasY protein sequence set forth as SEQ ID NO: 1. In some cases, a CasY protein includes an amino acid sequence having the CasY protein sequence set forth as SEQ ID NO: 1, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 2. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 2. In some cases, a CasY protein includes an amino acid sequence having the CasY protein sequence set forth as SEQ ID NO: 2. In some cases, a CasY protein includes an amino acid sequence having the CasY protein sequence set forth as SEQ ID NO: 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 3. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 3. In some cases, a CasY protein includes an amino acid sequence having the CasY protein sequence set forth as SEQ ID NO: 3. In some cases, a CasY protein includes an amino acid sequence having the CasY protein sequence set forth as SEQ ID NO: 3, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 4. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 4. In some cases, a CasY protein includes an amino acid sequence having the CasY protein sequence set forth as SEQ ID NO: 4. In some cases, a CasY protein includes an amino acid sequence having the CasY protein sequence set forth as SEQ ID NO: 4, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 5. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 5. In some cases, a CasY protein includes an amino acid sequence having the CasY protein sequence set forth as SEQ ID NO: 5. In some cases, a CasY protein includes an amino acid sequence having the CasY protein sequence set forth as SEQ ID NO: 5, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 6. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 6. In some cases, a CasY protein includes an amino acid sequence having the CasY protein sequence set forth as SEQ ID NO: 6. In some cases, a CasY protein includes an amino acid sequence having the CasY protein sequence set forth as SEQ ID NO: 6, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 7. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 7. In some cases, a CasY protein includes an amino acid sequence having the CasY protein sequence set forth as SEQ ID NO: 7. In some cases, a CasY protein includes an amino acid sequence having the CasY protein sequence set forth as SEQ ID NO: 7, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 8. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 8. In some cases, a CasY protein includes an amino acid sequence having the CasY protein sequence set forth as SEQ ID NO: 8. In some cases, a CasY protein includes an amino acid sequence having the CasY protein sequence set forth as SEQ ID NO: 8, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasY protein sequence set forth as SEQ ID NO: 9. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasY protein sequence set forth as SEQ ID NO: 9. In some cases, a CasY protein includes an amino acid sequence having 80% or more sequence identity (e.g., 85% or more, 90% or more, 95% or more, 97% or more, 98% or more, 99% or more, or 100% sequence identity) with the CasY protein sequence set forth as SEQ ID NO: 9. In some cases, a CasY protein includes an amino acid sequence having 90% or more sequence identity (e.g., 95% or more, 97% or more, 98% or more, 99% or more, or 100% sequence identity) with the CasY protein sequence set forth as SEQ ID NO: 9. In some cases, a CasY protein includes an amino acid sequence having the CasY protein sequence set forth as SEQ ID NO: 9. In some cases, a CasY protein includes an amino acid sequence having the CasY protein sequence set forth as SEQ ID NO: 9, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-4. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-4. In some cases, a CasY protein includes an amino acid sequence having the CasY protein sequence set forth in any one of SEQ ID NOs: 1-4. In some cases, a CasY protein includes an amino acid sequence having the CasY protein sequence set forth in any one of SEQ ID NOs: 1-4, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-5. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-5. In some cases, a CasY protein includes an amino acid sequence having the CasY protein sequence set forth in any one of SEQ ID NOs: 1-5. In some cases, a CasY protein includes an amino acid sequence having the CasY protein sequence set forth in any one of SEQ ID NOs: 1-5, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-7. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-7. In some cases, a CasY protein includes an amino acid sequence having the CasY protein sequence set forth in any one of SEQ ID NOs: 1-7. In some cases, a CasY protein includes an amino acid sequence having the CasY protein sequence set forth in any one of SEQ ID NOs: 1-7, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasY protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with any one of the CasY protein sequences set forth as SEQ ID NOs: 1-8. In some cases, a CasY protein includes an amino acid sequence having 90% or more sequence identity (e.g., 95% or more, 97% or more, 98% or more, 99% or more, or 100% sequence identity) with any one of the CasY protein sequences set forth as SEQ ID NOs: 1-8. In some cases, a CasY protein includes an amino acid sequence having the CasY protein sequence set forth in any one of SEQ ID NOs: 1-8. In some cases, a CasY protein includes an amino acid sequence having the CasY protein sequence set forth in any one of SEQ ID NOs: 1-8, with the exception that the sequence includes an amino acid substitution (e.g., 1, 2, or 3 amino acid substitutions) that reduces the naturally occurring catalytic activity of the protein (e.g., such as at amino acid positions described below).

CasY Protein Domains

Figure 3A:
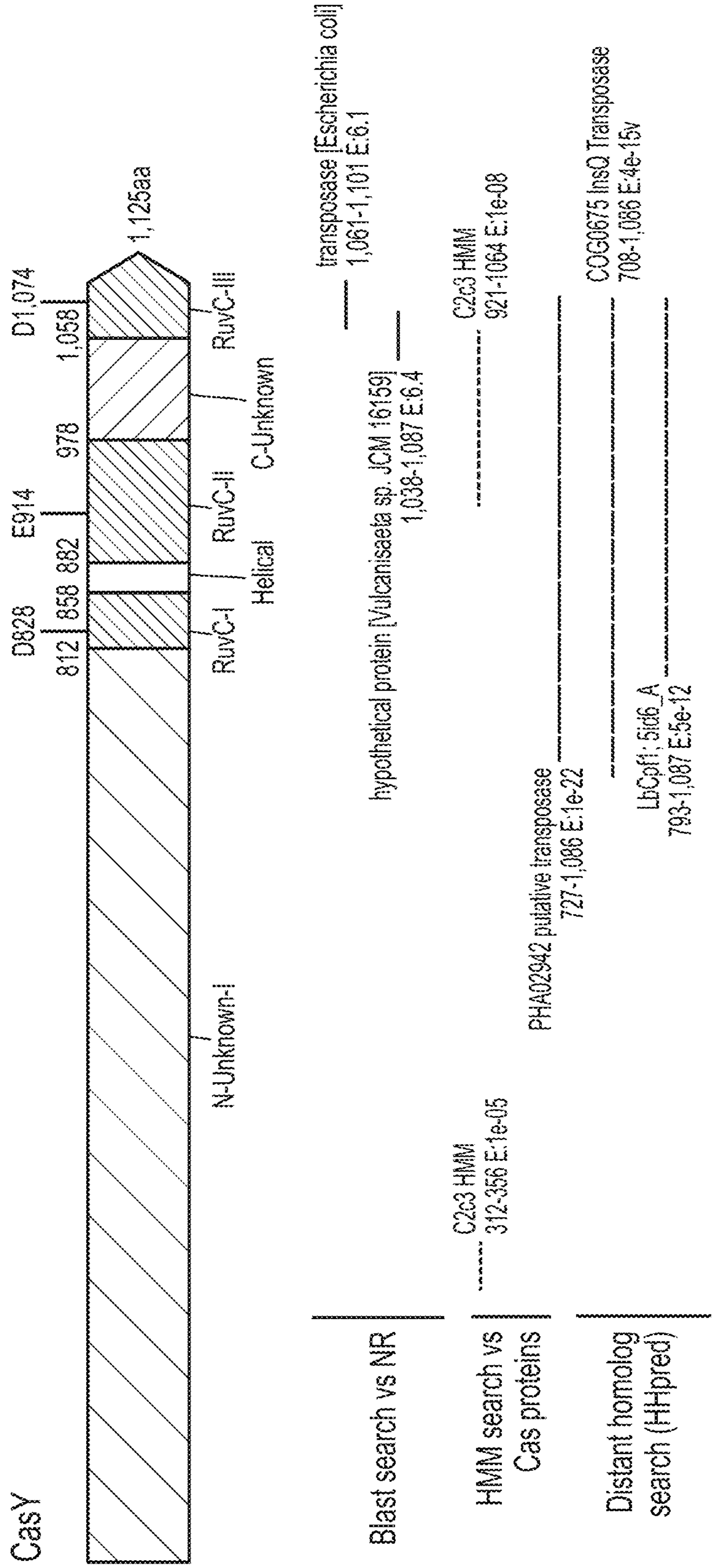
FIG. 3 (panels a-b) depicts a schematic domain representation for CasY. Also shown are results from various searches attempting to identify homologs of CasY. Also depicted are portions of the CasY-containing CRISPR loci there were identified.
Figure 3B:
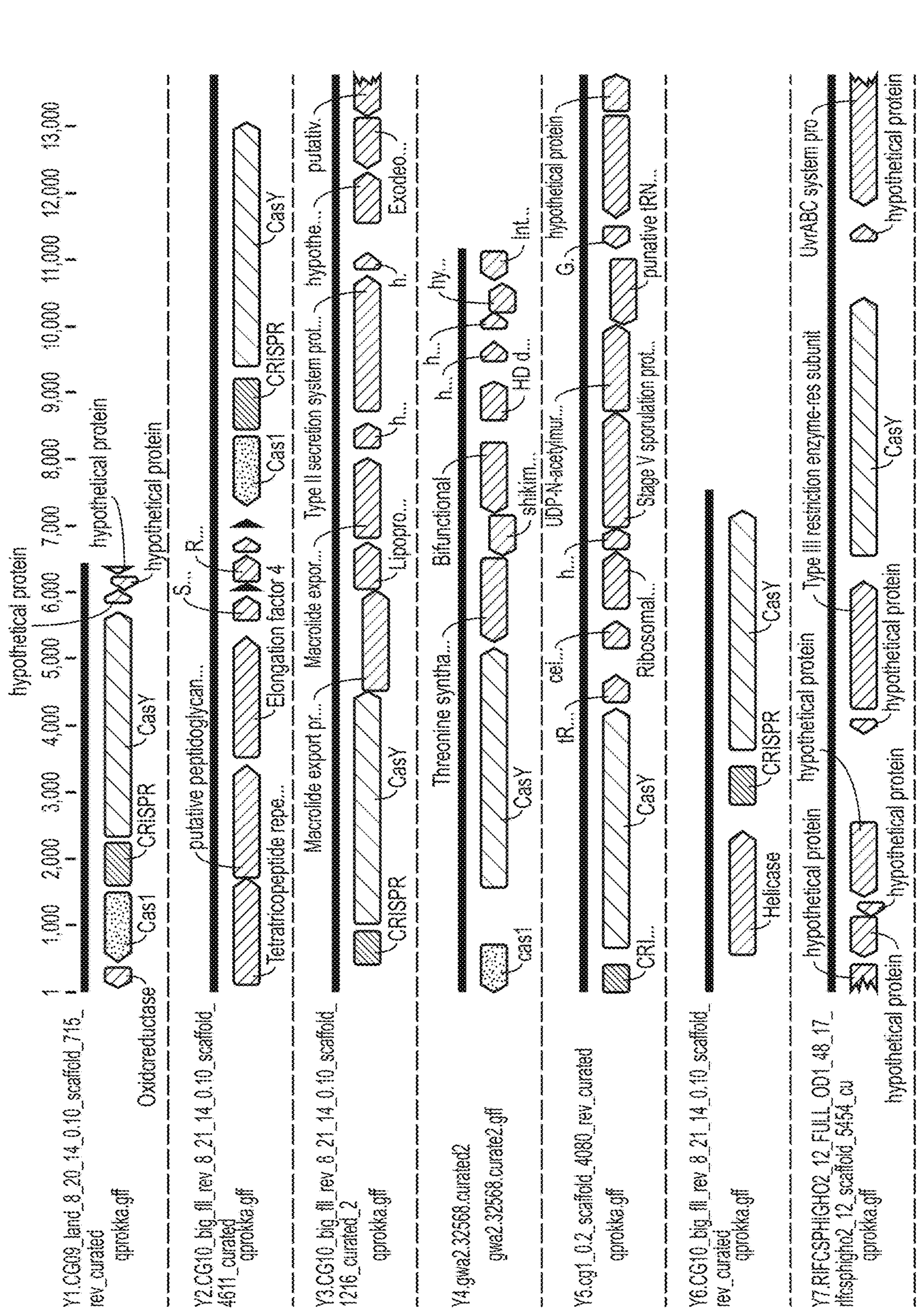

The domains of a CasY protein are depicted in FIG. 3. As can be seen in the schematic representation of FIG. 3 (amino acids are numbered based on the CasY1 protein (SEQ ID NO: 1)), a CasY protein includes an N-terminal domain roughly 800-1000 amino acids in length (e.g., about 815 for CasY1 and about 980 for CasY5), and a C-terminal domain that includes 3 partial RuvC domains (RuvC-I, RuvC-II, and RuvC-III, also referred to herein as subdomains) that are not contiguous with respect to the primary amino acid sequence of the CasY protein, but form a RuvC domain once the protein is produced and folds. Thus, in some cases, a CasY protein (of the subject compositions and/or methods) includes an amino acid sequence with an N-terminal domain (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids). In some cases, a CasY protein (of the subject compositions and/or methods) includes an amino acid sequence having a length (e.g., not including any fused heterologous sequence such as an NLS and/or a domain with a catalytic activity) in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids) that is N-terminal to a split Ruv C domain (e.g., 3 partial RuvC domains—RuvC-I, RuvC-II, and RuvC-III).

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth as SEQ ID NO: 1. In some cases, a CasY protein includes an amino acid sequence having amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-4. In some cases, a CasY protein includes a fragment of the amino acid sequence of any one of SEQ ID NOs: 1-4 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-5. In some cases, a CasY protein includes a fragment of the amino acid sequence of any one of SEQ ID NOs: 1-5 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-7. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-7. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-7. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-7. In some cases, a CasY protein includes a fragment of the amino acid sequence of any one of SEQ ID NOs: 1-7 that corresponds to amino acids 1-812 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of the CasY protein sequence set forth in any one of SEQ ID NOs: 1-8. In some cases, a CasY protein includes a fragment of the amino acid sequence of any one of SEQ ID NOs: 1-8 that corresponds to amino acids 1-812 of the CasY protein sequence set forth as SEQ ID NO: 1.

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some cases, a CasY protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasY protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes a split Ruv C domain (e.g., 3 partial RuvC domains—RuvC-I, RuvC-II, and RuvC-III). In some cases, a CasY protein includes an amino acid sequence corresponding to amino acids 1-812 of the CasY protein sequence set forth as SEQ ID NO: 1; and a second amino acid sequence, C-terminal to the first amino acid sequence, that includes a split Ruv C domain (e.g., 3 partial RuvC domains—RuvC-I, RuvC-II, and RuvC-III).

In some embodiments, the split RuvC domain of a CasY protein (of the subject compositions and/or methods) includes a region between the RuvC-II and RuvC-III subdomains that is larger than the RuvC-III subdomain. For example, in some cases, the ratio of the length of the region between the RuvC-II and RuvC-III subdomains over the length of the RuvC-III subdomain is 1.1 or greater (e.g., 1.2). In some cases, the ratio of the length of the region between the RuvC-II and RuvC-III subdomains over the length of the RuvC-III subdomain is greater than 1). In some cases, the ratio of the length of the region between the RuvC-II and RuvC-III subdomains over the length of the RuvC-III subdomain is greater than land between 1 and 1.5 (e.g., 1 and 1.4, 1 and 1.3, or 1 and 1.2).

In some embodiments (for a CasY protein of the subject compositions and/or methods), the ratio of the length of the RuvC-II subdomain over the length of the RuvC-III subdomain is 2 or less (e.g., 1.8 or less, 1.7 or less, 1.6 or less, 1.5 or less, or 1.4 or less). For example, in some cases, the ratio of the length of the RuvC-II subdomain over the length of the RuvC-III subdomain is 1.5 or less (e.g., 1.4 or less). In some embodiments, the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4).

In some cases (for a CasY protein of the subject compositions and/or methods), the ratio of the length of the region between the RuvC-II and RuvC-III subdomains over the length of the RuvC-III subdomain is greater than 1. In some cases, the ratio of the length of the region between the RuvC-II and RuvC-III subdomains over the length of the RuvC-III subdomain is greater than land between 1 and 1.3 (e.g., 1 and 1.2).

In some cases (for a CasY protein of the subject compositions and/or methods), the region between the RuvC-II and RuvC-III subdomains is at least 60 amino acids in length (e.g., at least 65, 68, or 70 amino acids in length). In some cases, the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids).

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-4; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-5; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-7; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 75% or more sequence identity (e.g., 80% or more, 85% or more, 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence having 85% or more sequence identity (e.g., 90% or more, 95% or more, 97% or more, 98% or more, 99% or more, or 100% sequence identity) with the N-terminal domain (e.g., the domain depicted as amino acids 1-812 for CasY1 in FIG. 3, panel a) of any one of the CasY protein sequences set forth as SEQ ID NOs: 1-8; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes a first amino acid sequence with an N-terminal domain (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence (C-terminal to the first) having a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.5 (e.g., 1 and 1.4, 1 and 1.3, 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.5 (e.g., 1 and 1.2); (ix) the region between the RuvC-II and RuvC-III subdomains is at least 60 amino acids in length (e.g., at least 65 or at least 70 amino acids in length); (x) the region between the RuvC-II and RuvC-III subdomains is at least 65 amino acids in length; (xi) the region between the RuvC-II and RuvC-III subdomains has a length in a range of from 60-110 amino acids (e.g., a range of from 60-105, 60-100, 60-95, 60-90, 65-110, 65-105, 65-100, 65-95, or 65-90 amino acids); or (xii) the region between the RuvC-II and RuvC-III subdomains has a length in a range of from 65-95 amino acids.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of the CasY protein sequence set forth as SEQ ID NO: 1. In some cases, a CasY protein includes an amino acid sequence having amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a fragment of the amino acid sequence of any one of the CasY protein sequences set forth as SEQ ID NOs: 1-4 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a fragment of the amino acid sequence of any one of the CasY protein sequences set forth as SEQ ID NOs: 1-5 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes a fragment of the amino acid sequence of any one of the CasY protein sequences set forth as SEQ ID NOs: 1-7 that corresponds to amino acids 812-1125 of the CasY protein sequence set forth as SEQ ID NO: 1.

In some cases, a CasY protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. For example, in some cases, a CasY protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes an amino acid sequence having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a fragment of the amino acid sequence of any one of the CasY protein sequences set forth as SEQ ID NOs: 1-8 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-4. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-4 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-5. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-5 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-7. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-7 that corresponds to amino acids 812-1125 of the CasY protein sequence set forth as SEQ ID NO: 1.

In some cases, a CasY protein (of the subject compositions and/or methods) includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. For example, in some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 812-1125 for CasY1 in FIG. 3, panel a) of any one of the CasY protein sequences set forth as SEQ ID NOs: 1-8. In some cases, a CasY protein includes a first amino acid sequence (an N-terminal domain) (e.g., not including any fused heterologous sequence such as an NLS and/or a domain with a catalytic activity) having a length in a range of from 750 to 1050 amino acids (e.g, from 750 to 1025, 750 to 1000, 750 to 950, 775 to 1050, 775 to 1025, 775 to 1000, 775 to 950, 800 to 1050, 800 to 1025, 800 to 1000, or 800 to 950 amino acids); and a second amino acid sequence, positioned C-terminal to the first amino acid sequence, having a fragment of the amino acid sequence of any one of the CasY protein sequences set forth as SEQ ID NOs: 1-8 that corresponds to amino acids 812-1125 of the CasY protein sequence set forth as SEQ ID NO: 1.

CasY Variants

A variant CasY protein has an amino acid sequence that is different by at least one amino acid (e.g., has a deletion, insertion, substitution, fusion) when compared to the amino acid sequence of the corresponding wild type CasY protein. A CasY protein that cleaves one strand but not the other of a double stranded target nucleic acid is referred to herein as a "nickase" (e.g., a "nickase CasY"). A CasY protein that has substantially no nuclease activity is referred to herein as a dead CasY protein ("dCasY") (with the caveat that nuclease activity can be provided by a heterologous polypeptide—a fusion partner—in the case of a chimeric CasY protein, which is described in more detail below). For any of the CasY variant proteins described herein (e.g., nickase CasY, dCasY, chimeric CasY), the CasY variant can include a CasY protein sequence with the same parameters described above (e.g., domains that are present, percent identity, and the like).

Variants—Catalytic Activity

In some cases, the CasY protein is a variant CasY protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasY protein is a catalytically 'dead' protein (has substantially no cleavage activity) and can be referred to as a 'dCasY.' In some cases, the variant CasY protein is a nickase (cleaves only one strand of a double stranded target nucleic acid, e.g., a double stranded target DNA). As described in more detail herein, in some cases, a CasY protein (in some case a CasY protein with wild type cleavage activity and in some cases a variant CasY with reduced cleavage activity, e.g., a dCasY or a nickase CasY) is fused (conjugated) to a heterologous polypeptide that has an activity of interest (e.g., a catalytic activity of interest) to form a fusion protein (a chimeric CasY protein).

Catalytic residues of CasY include D828, E914, D1074 when numbered according to CasY1 (SEQ ID NO: 1) (these residues are underlined in FIG. 1 for SEQ ID NO: 1). (see, e.g., the alignments of FIG. 2, panels a and b).

Thus, in some cases, the CasY protein has reduced activity and one or more of the above described amino acids (or one or more corresponding amino acids of any CasY protein) are mutated (e.g., substituted with an alanine). In some cases, the variant CasY protein is a catalytically 'dead' protein (is catalytically inactive) and is referred to as 'dCasY.' A dCasY protein can be fused to a fusion partner that provides an activity, and in some cases, the dCasY (e.g., one without a fusion partner that provides catalytic activity—but which can have an NLS when expressed in a eukaryotic cell) can bind to target DNA and can block RNA polymerase from translating from a target DNA. In some cases, the variant CasY protein is a nickase (cleaves only one strand of a double stranded target nucleic acid, e.g., a double stranded target DNA).

Variants—Chimeric CasY (i.e., Fusion Proteins)

As noted above, in some cases, a CasY protein (in some cases a CasY protein with wild type cleavage activity and in some cases a variant CasY with reduced cleavage activity, e.g., a dCasY or a nickase CasY) is fused (conjugated) to a heterologous polypeptide that has an activity of interest (e.g., a catalytic activity of interest) to form a fusion protein (a chimeric CasY protein). A heterologous polypeptide to which a CasY protein can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasY protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasY protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL acitvation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners are dihydrofolate reductase (DHFR) destabilization domain (e.g., to generate a chemically controllable chimeric CasY protein), and a chloroplast transit peptide. Suitable chloroplast transit peptides include, but are not limited to:

```
                                        (SEQ ID NO: 83)
MASMISSSAVTTVSRASRGQSAAMAPFGGLKSMTGFPVRKVNTDITSITS

NGGRVKCMQVWPPIGKKKFETLSYLPPLTRDSRA;

                                        (SEQ ID NO: 84)
MASMISSSAVTTVSRASRGQSAAMAPFGGLKSMTGFPVRKVNTDITSITS

NGGRVKS;

                                        (SEQ ID NO: 85)
MASSMLSSATMVASPAQATMVAPFNGLKSSAAFPATRKANNDITSITSNG

GRVNCMQVWPPIEKKKFETLSYLPDLTDSGGRVNC;

                                        (SEQ ID NO: 86)
MAQVSRICNGVQNPSLISNLSKSSQRKSPLSVSLKTQQHPRAYPISSSWG

LKKSGMTLIGSELRPLKVMSSVSTAC;

                                        (SEQ ID NO: 87)
MAQVSRICNGVWNPSLISNLSKSSQRKSPLSVSLKTQQHPRAYPISSSWG

LKKSGMTLIGSELRPLKVMSSVSTAC;

                                        (SEQ ID NO: 88)
MAQINNMAQGIQTLNPNSNFHKPQVPKSSSFLVFGSKKLKNSANSMLVLK

KDSIFMQLFCSFRISASVATAC;
```

-continued (SEQ ID NO: 89)
MAALVTSQLATSGTVLSVTDRFRRPGFQGLRPRNPADAALGMRTVGASAA

PKQSRKPHRFDRRCLSMVV;

(SEQ ID NO: 90)
MAALTTSQLATSATGFGIADRSAPSSLLRHGFQGLKPRSPAGGDATSLSV

TTSARATPKQQRSVQRGSRRFPSVVVC;

(SEQ ID NO: 91)
MASSVLSSAAVATRSNVAQANMVAPFTGLKSAASFPVSRKQNLDITSIAS

NGGRVQC;

(SEQ ID NO: 92)
MESLAATSVFAPSRVAVPAARALVRAGTVVPTRRTSSTSGTSGVKCSAAV

TPQASPVISRSAAAA;

and (SEQ ID NO: 93)
MGAAATSMQSLKFSNRLVPPSRRLSPVPNNVTCNNLPKSAAPVRTVKCCA

SSWNSTINGAAATTNGASAASS.

In some case, a CasY fusion polypeptide of the present disclosure comprises: a) a CasY polypeptide of the present disclosure; and b) a chloroplast transit peptide. Thus, for example, a CRISPR-CasY complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasY fusion polypeptide of the present disclosure can comprise: a) a CasY polypeptide of the present disclosure; and b) an endosomal escape peptide. In some cases, an endosomal escape polypeptide comprises the amino acid sequence GLFXALLXLLXSLWXLLLXA (SEQ ID NO:94), wherein each X is independently selected from lysine, histidine, and arginine. In some cases, an endosomal escape polypeptide comprises the amino acid sequence (SEQ ID NO: 95)
GLFHALLHLLHSLWHLLLHA.

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et., al., J Virol. 2006 February; 80(4):1939-48; Tan et al., Proc Natl Acad Sci U S A. 2003 Oct. 14; 100(21):11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20; 533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasY polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasY polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasY polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cώ-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Aby1, etc.).

Examples of various additional suitable heterologous polypeptide (or fragments thereof) for a subject chimeric CasY polypeptide include, but are not limited to those described in the following applications (which publications are related to other CRISPR endonucleases such as Cas9, but the described fusion partners can also be used with CasY instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasY fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) a nuclear localization signal (NLS) (e.g, in some cases 2 or more, 3 or more, 4 or more, or 5 or more NLSs). Thus, in some cases, a CasY polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasY protein (e.g., a wild type CasY protein, a variant CasY protein, a chimeric CasY protein, a dCasY protein, a chimeric CasY protein where the CasY portion has reduced nuclease activity—such as a dCasY protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 96); the NLS from nucleoplasmin (e.g., the nucleoplasmin bipartite NLS with the sequence KRPAATKKAGQAKKKK (SEQ ID NO: 97)); the c-myc NLS having the amino acid sequence PAAKRVKLD (SEQ ID NO: 98) or RQRRNELKRSP (SEQ ID NO: 99); the hRNPA1 M9 NLS having the sequence NQSSNFGPMKGGNFGGRSSGPYGGGGQYFAKPRNQGGY (SEQ ID NO: 100); the sequence RMRIZFKNKGKDTAELRRRRVEVSVELRKAKKDEQILKRRNV (SEQ ID NO: 101) of the IBB domain from importin-alpha; the sequences VSRKRPRP (SEQ ID NO: 102) and PPKKARED (SEQ ID NO: 103) of the myoma T protein; the sequence PQPKKKPL (SEQ ID NO: 104) of human p53; the sequence SALIKKKKKMAP (SEQ ID NO: 105) of mouse c-abl IV; the sequences DRLRR (SEQ ID NO: 106) and PKQKKRK (SEQ ID NO: 107) of the influenza virus NS1; the sequence RKLKKKIKKL (SEQ ID NO: 108) of the Hepatitis virus delta antigen; the sequence REKKKFLKRR (SEQ ID NO: 109) of the mouse Mx1 protein; the sequence KRKGDEVDGVDEVAKKKSKK (SEQ ID NO: 110) of the human poly(ADP-ribose) polymerase; and the sequence RKCLQAGMNLEARKTKK (SEQ ID NO: 111) of the steroid hormone receptors (human) glucocorticoid. In general, NLS (or multiple NLSs) are of sufficient strength to drive accumulation of the CasY protein in a detectable amount in the nucleus of a eukaryotic cell. Detection of accumulation in the nucleus may be performed by any suitable technique. For example, a detectable marker may be fused to the CasY protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a CasY fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type CasY to generate a fusino protein, or linked to a variant CasY protein such as a dCasY, nickase CasY, or chimeric CasY protein to generate a fusion protein). In some embodiments, a PTD is covalently linked to the carboxyl terminus of a polypeptide (e.g., linked to a wild type CasY to generate a fusino protein, or linked to a variant CasY protein such as a dCasY, nickase CasY, or chimeric CasY protein to generate a fusion protein). In some cases, the PTD is inserted interally in the CasY fusion polypeptide (i.e., is not at the N- or C-terminus of the CasY fusion polypeptide) at a suitable insertion site. In some cases, a subject CasY fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasY fusion polypeptide includes one or more NLSs (e.g., 2 or more, 3 or more, 4 or more, or 5 or more NLSs). In some embodiments, a PTD is covalently linked to a nucleic acid (e.g., a CasY guide nucleic acid, a polynucleotide encoding a CasY guide nucleic acid, a polynucleotide encoding a CasY fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:113); Transportan GWTLNSAGYLLGKINL- KALAALAKKIL (SEQ ID NO:114); KALAWEAKLAKALAKALAKHLAKALAKALKCEA (SEQ ID NO:115); and RQIKIWFQNRRMKWKK (SEQ ID NO:116). Exemplary PTDs include but are not limited to, YGRKKRRQRRR (SEQ ID NO:117), RKKRRQRRR (SEQ ID NO:118); an arginine homopolymer of from 3 arginine residues to 50 arginine residues; Exemplary PTD domain amino acid sequences include, but are not limited to, any of the following: YGRKKRRQRRR (SEQ ID NO:119); RKKRRQRR (SEQ ID NO:120); YARAAARQARA (SEQ ID NO:121); THRLPRRRRRR (SEQ ID NO:122); and GGRRARRRRRR (SEQ ID NO:123). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject CasY protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 124), $GGSGGS_n$ (SEQ ID NO: 125), and $GGGS_n$ (SEQ ID NO: 126), where n is an integer of at least one), glycine-alanine polymers, alanine-serine polymers. Exemplary linkers can comprise amino acid sequences including, but not limited to, GGSG (SEQ ID NO: 127), GGSGG (SEQ ID NO: 128), GSGSG (SEQ ID NO: 129), GSGGG (SEQ ID NO: 130), GGGSG (SEQ ID NO: 131), GSSSG (SEQ ID NO: 132), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasY polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, 0-glucuronidase, invertase, Xanthine Oxidase, firefly luciferase, glucose oxidase (GO), and the like.

Protospacer Adjacent Motif (PAM)

A CasY protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

Figure 5A:
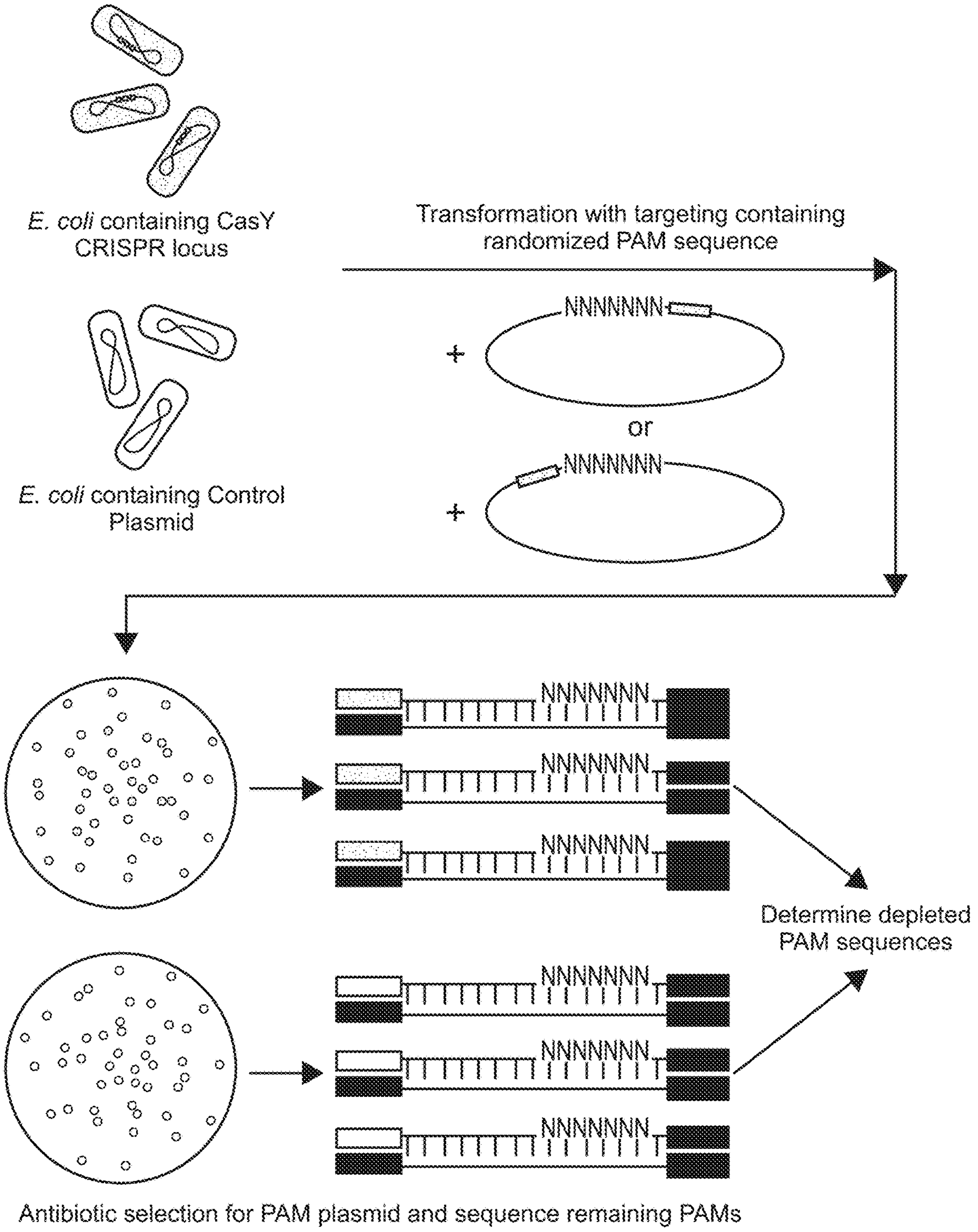
FIG. 5 (panels a-d) depicts experiments performed (PAM dependent plasmid interference by CasY) to determine a PAM sequence for CasY.
Figure 5B:
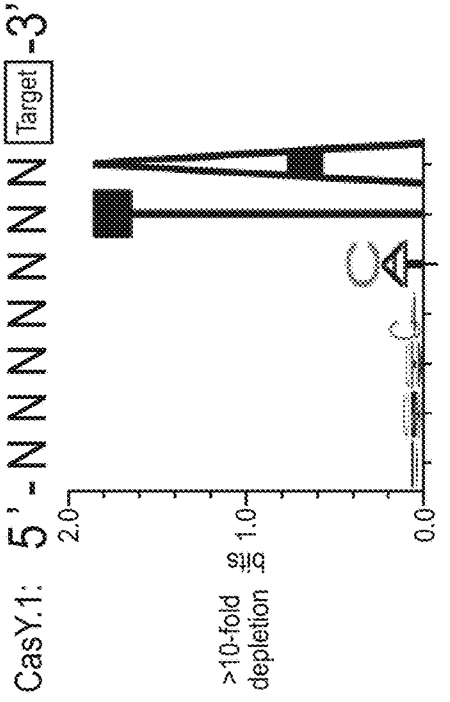
Figure 5C:
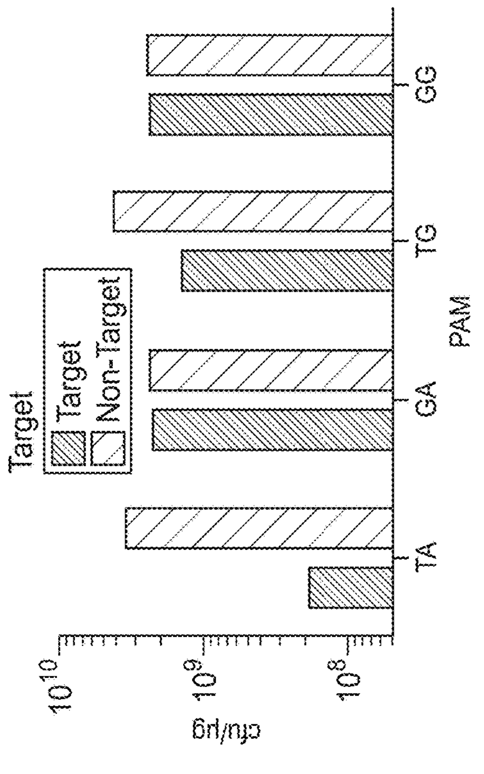
Figure 5D:
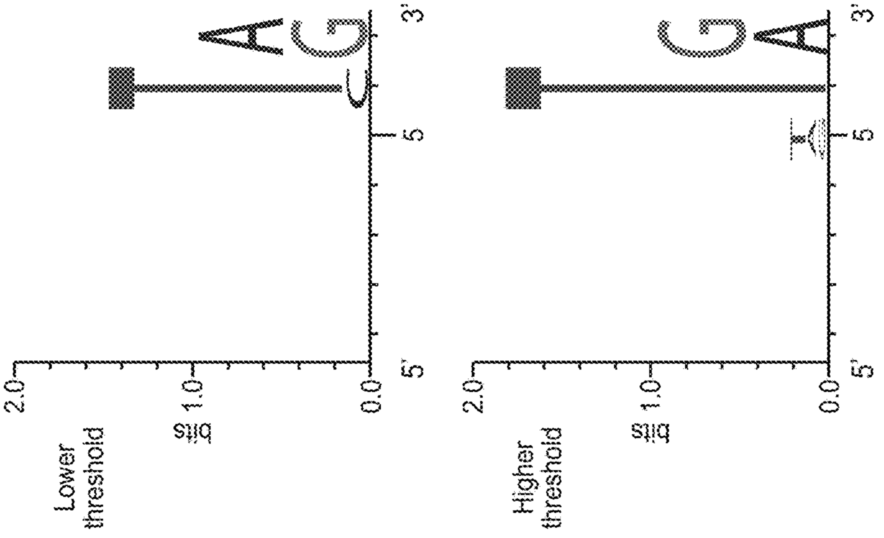

In some embodiments, the PAM for a CasY protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some embodiments (e.g., when CasY1 as described herein is used), the PAM sequence of the non-complementary strand is 5'-TA-3' (and in some cases XTA, where X is C, A, or T). As an example, see FIG. 5 and FIG. 7 (in which the PAM is TA, or CTA if you consider the PAM to be XTA where X is C, A, or T). In some embodiments (e.g., when CasY1 as described herein is used), the PAM sequence of the non-complementary strand is 5'-TA-3' (and in some cases HTA, where H is C, A, or T). As an example, see FIG. 5 and FIG. 7 (in which the PAM is TA, or CTA if the PAM is considered to be HTA where H is C, A, or T). In some cases (e.g., when CasY2 as described herein is used), the PAM sequence of the non-complementary strand is a 5'-YR-3' flanking sequence 5' of the target (where Y is a T or C and R is an A or G). In some cases (e.g., when CasY2 as described herein is used), the PAM sequence of the non-complementary strand is 5'-TR-3' (e.g., 5'-DTR-3') (where R is an A or G and D is an A, G, or T). As an example, see FIG. 5*d*.

In some cases, different CasY proteins (i.e., CasY proteins from various species) may be advantageous to use in the various provided methods in order to capitalize on various enzymatic characteristics of the different CasY proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasY proteins from different species may require different PAM sequences in the target DNA. Thus, for a particular CasY protein of choice, the PAM sequence requirement may be different than the 5'-TA-3' (or XTA, HTA) sequence described above. Various methods (including in silico and/or wet lab methods) for identification of the appropriate PAM sequence are known in the art and are routine, and any convenient method can be used. The TA (XTA, HTA) PAM sequence described herein was identified using a PAM depletion assay (e.g., see FIG. 5 of the working examples below).

CasY Guide RNA

A nucleic acid molecule that binds to a CasY protein, forming a ribonucleoprotein complex (RNP), and targets the complex to a specific location within a target nucleic acid (e.g., a target DNA) is referred to herein as a "CasY guide RNA" or simply as a "guide RNA." It is to be understood that in some cases, a hybrid DNA/RNA can be made such that a CasY guide RNA includes DNA bases in addition to RNA bases, but the term "CasY guide RNA" is still used to encompass such a molecule herein.

A CasY guide RNA can be said to include two segments, a targeting segment and a protein-binding segment. The targeting segment of a CasY guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasY polypeptide. The protein-binding segment of a subject CasY guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasY guide RNA (the guide sequence of the CasY guide RNA) and the target nucleic acid.

A CasY guide RNA and a CasY protein, e.g., a fusion CasY polypeptide, form a complex (e.g., bind via non-covalent interactions). The CasY guide RNA provides target specificity to the complex by including a targeting segment, which includes a guide sequence (a nucleotide sequence that is complementary to a sequence of a target nucleic acid). The CasY protein of the complex provides the site-specific activity (e.g., cleavage activity provided by the CasY protein and/or an activity provided by the fusion partner in the case of a chimeric CasY protein). In other words, the CasY protein is guided to a target nucleic acid sequence (e.g. a target sequence) by virtue of its association with the CasY guide RNA.

The "guide sequence" also referred to as the "targeting sequence" of a CasY guide RNA can be modified so that the CasY guide RNA can target a CasY protein (e.g., a naturally occurring CasY protein, a fusion CasY polypeptide (chimeric CasY), and the like) to any desired sequence of any desired target nucleic acid, with the exception (e.g., as described herein) that the PAM sequence can be taken into account. Thus, for example, a CasY guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

Guide Sequence of a CasY Guide RNA

A subject CasY guide RNA includes a guide sequence (i.e., a targeting sequence), which is a nucleotide sequence that is complementary to a sequence (a target site) in a target nucleic acid. In other words, the guide sequence of a CasY guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasY guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Protein-Binding Segment of a CasY Guide RNA

The protein-binding segment of a subject CasY guide RNA interacts with a CasY protein. The CasY guide RNA guides the bound CasY protein to a specific nucleotide sequence within target nucleic acid via the above mentioned guide sequence. The protein-binding segment of a CasY guide RNA comprises two stretches of nucleotides that are complementary to one another and hybridize to form a double stranded RNA duplex (dsRNA duplex). Thus, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject CasY guide RNA can include one or more (1, 2, 3, 4, 5, etc) mutations relative to a naturally occurring duplex region. For example, in some cases a base pair can be maintained while the nucleotides contributing to the base pair from each segment can be different. In some cases, the duplex region of a subject CasY guide RNA includes more paired bases, less paired bases, a smaller bulge, a larger bulge, fewer bulges, more bulges, or any convenient combination thereof, as compared to a naturally occurring duplex region (of a naturally occurring CasY guide RNA).

Examples of various Cas9 guide RNAs can be found in the art, and in some cases variations similar to those introduced into Cas9 guide RNAs can also be introduced into CasY guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

A CasY guide RNA comprises both the guide sequence and two stretches ("duplex-forming segments") of nucleotides that hybridize to form the dsRNA duplex of the protein-binding segment. The particular sequence of a given CasY guide RNA can be characteristic of the species in which the a crRNA is found. Examples of suitable CasY guide RNAs are provided herein.

Example Guide RNA Sequences

Figure 6:
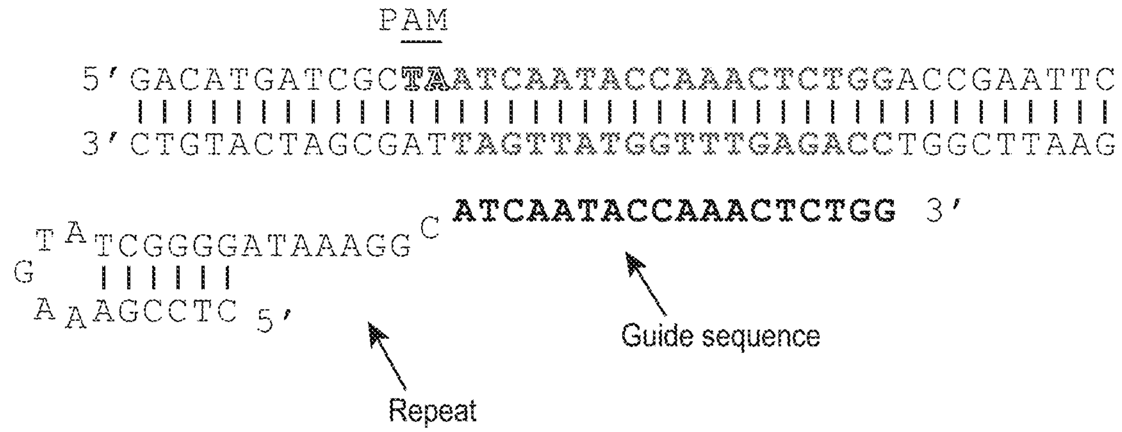
FIG. 6 (panels a-b) presents 'repeat' sequences of naturally occurring CasY guide RNAs, and an example CasY guide RNA hybridizing to target DNA. (Top to bottom, SEQ ID NOs:31-35; SEQ ID NOs:135-137).

The repeat sequences (non-guide sequence portion of example CasY guide RNAs) depicted in FIG. 6 (panels a and b) are from the natural locus for CasY1-Y5. In some cases, a subject CasY guide RNA comprises (e.g., in addition to a guide sequence) the crRNA sequence CTCCGAAAGTATCGGGGATAAAGGC (SEQ ID NO: 31) [RNA is CUCCGAAAGUAUCGGGGAUAAAGGC (SEQ ID NO: 11)] (e.g., see FIG. 6). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGAAAGTATCGGGGATAAAGGC (SEQ ID NO: 31) [RNA is CUCCGAAAGUAUCGGGGAUAAAGGC (SEQ ID NO: 11)]. In some cases, a subject CasY guide RNA comprises a nucleotide sequence having 90% or more identity (e.g., 93% or more, 95% or more, 97% or more, 98% or more, or 100% identity) with the crRNA sequence CTCCGAAAGTATCGGGGATAAAGGC (SEQ ID NO: 31) [RNA is CUCCGAAAGUAUCGGGGAUAAAGGC (SEQ ID NO: 11)].

In some cases, a subject CasY guide RNA comprises (e.g., in addition to a guide sequence) the crRNA sequence CACCGAAATTTGGAGAGGATAAGGC (SEQ ID NO: 32) [RNA is CACCGAAAUUUGGAGAGGAUAAGGC (SEQ ID NO: 12)] (e.g., see FIG. 6). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CACCGAAATTTGGAGAGGATAAGGC (SEQ ID NO: 32) [RNA is CACCGAAAUUUGGAGAGGAUAAGGC (SEQ ID NO: 12)]. In some cases, a subject CasY guide RNA comprises a nucleotide sequence having 90% or more identity (e.g., 93% or more, 95% or more, 97% or more, 98% or more, or 100% identity) with the crRNA sequence CACCGAAATTTGGAGAGGATAAGGC (SEQ ID NO: 32) [RNA is CACCGAAAUUUGGAGAGGAUAAGGC (SEQ ID NO: 12)].

In some cases, a subject CasY guide RNA comprises (e.g., in addition to a guide sequence) the crRNA sequence CTCCGAATTATCGGGAGGATAAGGC (SEQ ID NO: 33) [RNA is CUCCGAAUUAUCGGGAGGAUAAGGC (SEQ ID NO: 13)] (e.g., see FIG. 6). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGAATTATCGGGAGGATAAGGC (SEQ ID NO: 33) [RNA is CUCCGAAUUAUCGGGAGGAUAAGGC (SEQ ID NO: 13)]. In some cases, a subject CasY guide RNA comprises a nucleotide sequence having 90% or more identity (e.g., 93% or more, 95% or more, 97% or more, 98% or more, or 100% identity) with the crRNA sequence CTCCGAATTATCGGGAGGATAAGGC (SEQ ID NO: 33) [RNA is CUCCGAAUUAUCGGGAGGAUAAGGC (SEQ ID NO: 13)].

In some cases, a subject CasY guide RNA comprises (e.g., in addition to a guide sequence) the crRNA sequence CCCCGAATATAGGGGACAAAAAGGC (SEQ ID NO: 34) [RNA is CCCCGAAUAUAGGGGACAAAAAGGC (SEQ ID NO: 14)] (e.g., see FIG. 6). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CCCCGAATATAGGGGACAAAAAGGC (SEQ ID NO: 34) [RNA is CCCCGAAUAUAGGGGACAAAAAGGC (SEQ ID NO: 14)]. In some cases, a subject CasY guide RNA comprises a nucleotide sequence having 90% or more identity (e.g., 93% or more, 95% or more, 97% or more, 98% or more, or 100% identity) with the crRNA sequence CCCCGAATATAGGGGACAAAAAGGC (SEQ ID NO: 34) [RNA is CCCCGAAUAUAGGGGACAAAAAGGC (SEQ ID NO: 14)].

In some cases, a subject CasY guide RNA comprises (e.g., in addition to a guide sequence) the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)] (e.g., see FIG. 6). In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)]. In some cases, a subject CasY guide RNA comprises a nucleotide sequence having 90% or more identity (e.g., 93% or more, 95% or more, 97% or more, 98% or more, or 100% identity) with the crRNA sequence GTCTAGACATACAGGTGGAAAGGTGAGAGTAAAGAC (SEQ ID NO: 35) [RNA is GUCUAGACAUACAGGUGGAAAGGUGAGAGUAAAGAC (SEQ ID NO: 15)].

In some cases, a subject CasY guide RNA comprises (e.g., in addition to a guide sequence) the crRNA sequence set forth in any one of SEQ ID NOs: 11-15. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-15. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-15.

In some cases, a subject CasY guide RNA comprises (e.g., in addition to a guide sequence) the crRNA sequence set forth in any one of SEQ ID NOs: 11-14. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-14. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-14.

The repeat sequence (non-guide sequence portion of an example CasY guide RNA) from the natural locus for CasY18 is CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises (e.g., in addition to a guide sequence) the crRNA sequence CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises a nucleotide sequence having 80% or more identity (e.g., 85% or more, 90% or more, 93% or more, 95% or more, 97% or more, 98% or more, or 100% identity) with the crRNA sequence CTCCGTGAATACGTGGGGTAAAGGC (SEQ ID NO: 36) [RNA is CUCCGUGAAUACGUGGGGUAAAGGC (SEQ ID NO: 16)]. In some cases, a subject CasY guide RNA comprises a nucleotide sequence having 90% or more identity (e.g., 93% or more, 95% or more, 97% or more, 98% or more, or 100% identity) with the crRNA sequence CTCCGTGAATACGTGGGGTAAAGGC (SEQ ID NO: 36) [RNA is CUCCGUGAAUACGUGGGGUAAAGGC (SEQ ID NO: 16)].

In some cases, a subject CasY guide RNA comprises (e.g., in addition to a guide sequence) the crRNA sequence set forth in any one of SEQ ID NOs: 11-16. In some cases, a subject CasY guide RNA comprises (e.g., in addition to a guide sequence) a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-16. In some cases, a subject CasY guide RNA comprises a nucleotide sequence having 90% or more identity (e.g., 93% or more, 95% or more, 97% or more, 98% or more, or 100% identity) with the crRNA sequence set forth in any one of SEQ ID NOs: 11-16.

CasY Systems

The present disclosure provides a CasY system. A CasY system of the present disclosure can comprise: a) a CasY polypeptide of the present disclosure and a CasY guide RNA; b) a CasY polypeptide of the present disclosure, a CasY guide RNA, and a donor template nucleic acid; c) a CasY fusion polypeptide of the present disclosure and a CasY guide RNA; d) a CasY fusion polypeptide of the present disclosure, a CasY guide RNA, and a donor template nucleic acid; e) an mRNA encoding a CasY polypeptide of the present disclosure; and a CasY guide RNA; f) an mRNA encoding a CasY polypeptide of the present disclosure, a CasY guide RNA, and a donor template nucleic acid; g) an mRNA encoding a CasY fusion polypeptide of the present disclosure; and a CasY guide RNA; h) an mRNA encoding a CasY fusion polypeptide of the present disclosure, a CasY guide RNA, and a donor template nucleic acid; i) a recombinant expression vector comprising a nucleotide sequence encoding a CasY polypeptide of the present disclosure and a nucleotide sequence encoding a CasY guide RNA; j) a recombinant expression vector comprising a nucleotide sequence encoding a CasY polypeptide of the present disclosure, a nucleotide sequence encoding a CasY guide RNA, and a nucleotide sequence encoding a donor template nucleic acid; k) a recombinant expression vector comprising a nucleotide sequence encoding a CasY fusion polypeptide of the present disclosure and a nucleotide sequence encoding a CasY guide RNA; 1) a recombinant expression vector comprising a nucleotide sequence encoding a CasY fusion polypeptide of the present disclosure, a nucleotide sequence encoding a CasY guide RNA, and a nucleotide sequence encoding a donor template nucleic acid; m) a first recombinant expression vector comprising a nucleotide sequence encoding a CasY polypeptide of the present disclosure, and a second recombinant expression vector comprising a nucleotide sequence encoding a CasY guide RNA; n) a first recombinant expression vector comprising a nucleotide sequence encoding a CasY polypeptide of the present disclosure, and a second recombinant expression vector comprising a nucleotide sequence encoding a CasY guide RNA; and a donor template nucleic acid; o) a first recombinant expression vector comprising a nucleotide sequence encoding a CasY fusion polypeptide of the present disclosure, and a second recombinant expression vector comprising a nucleotide sequence encoding a CasY guide RNA; p) a first recombinant expression vector comprising a nucleotide sequence encoding a CasY fusion polypeptide of the present disclosure, and a second recombinant expression vector comprising a nucleotide sequence encoding a CasY guide RNA; and a donor template nucleic acid; q) a recombinant expression vector comprising a nucleotide sequence encoding a CasY polypeptide of the present disclosure, a nucleotide sequence encoding a first CasY guide RNA, and a nucleotide sequence encoding a second CasY guide RNA; or r) a recombinant expression vector comprising a nucleotide sequence encoding a CasY fusion polypeptide of the present disclosure, a nucleotide sequence encoding a first CasY guide RNA, and a nucleotide sequence encoding a second CasY guide RNA; or some variation of one of (a) through (r).

Nucleic Acids

The present disclosure provides one ore more nucleic acids comprising one or more of: a donor polynucleotide sequence, a nucleotide sequence encoding a CasY polypeptide (e.g., a wild type CasY protein, a nickase CasY protein, a dCasY protein, chimeric CasY protein, and the like), a CasY guide RNA, and a nucleotide sequence encoding a CasY guide RNA. The present disclosure provides a nucleic acid comprising a nucleotide sequence encoding a CasY fusion polypeptide. The present disclosure provides a recombinant expression vector that comprises a nucleotide sequence encoding a CasY polypeptide. The present disclosure provides a recombinant expression vector that comprises a nucleotide sequence encoding a CasY fusion polypeptide. The present disclosure provides a recombinant expression vector that comprises: a) a nucleotide sequence encoding a CasY polypeptide; and b) a nucleotide sequence encoding a CasY guide RNA(s). The present disclosure provides a recombinant expression vector that comprises: a) a nucleotide sequence encoding a CasY fusion polypeptide; and b) a nucleotide sequence encoding a CasY guide RNA(s). In some cases, the nucleotide sequence encoding the CasY protein and/or the nucleotide sequence encoding the CasY guide RNA is operably linked to a promoter that is operable in a cell type of choice (e.g., a prokarytoic cell, a eukaryotic cell, a plant cell, an animal cell, a mammalian cell, a primate cell, a rodent cell, a human cell, etc.).

In some cases, a nucleotide sequence encoding a CasY polypeptide of the present disclosure is codon optimized. This type of optimization can entail a mutation of a CasY-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasY-encoding nucleotide sequence could be used. As another non-limiting example, if the intended host cell were a mouse cell, then a mouse codon-optimized CasY-encoding nucleotide sequence could be generated. As another non-limiting example, if the intended host cell were a plant cell, then a plant codon-optimized CasY-encoding nucleotide sequence could be generated. As another non-limiting example, if the intended host cell were an insect cell, then an insect codon-optimized CasY-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasY guide RNA that hybridizes to a target sequence of the target locus of the targeted genome (e.g., operably linked to a promoter that is operable in a target cell such as a eukaryotic cell); and (iii) a nucleotide sequence encoding a CasY protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasY guide RNA that hybridizes to a target sequence of the target locus of the targeted genome (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasY guide RNA that hybridizes to a target sequence of the target locus of the targeted genome (e.g., operably linked to a promoter that is operable in a target cell such as a eukaryotic cell); and (ii) a nucleotide sequence encoding a CasY protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasY guide RNA is operably linked to a control element, e.g., a transcriptional control element, such as a promoter. In some embodiments, a nucleotide sequence encoding a CasY protein or a CasY fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EFla, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasY protein, thus resulting in a chimeric CasY polypeptide.

In some embodiments, a nucleotide sequence encoding a CasY guide RNA and/or a CasY fusion polypeptide is operably linked to an inducible promoter. In some embodiments, a nucleotide sequence encoding a CasY guide RNA and/or a CasY fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasY guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a CasY protein (e.g., a wild type CasY protein, a nickase CasY protein, a dCasY protein, a chimeric CasY protein and the like) is operably linked to a promoter operable in a eukaryotic cell (e.g., a CMV promoter, an EFla promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasY protein and/or a CasY guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasY protein can be provided as RNA. The RNA can be provided by direct chemical synthesis or may be transcribed in vitro from a DNA (e.g., encoding the CasY protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasY guide RNA; recombinant expression vectors encoding the CasY protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasY guide RNA and/or a CasY polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasY guide RNA and/or a CasY protein to a cell may include nucleic acid sequences that encode for selectable markers in the target cells, so as to identify cells that have taken up the CasY guide RNA and/or CasY protein.

A nucleic acid comprising a nucleotide sequence encoding a CasY polypeptide, or a CasY fusion polypeptide, is in some cases an RNA. Thus, a CasY fusion protein can be introduced into cells as RNA. Methods of introducing RNA into cells are known in the art and may include, for example, direct injection, transfection, or any other method used for the introduction of DNA. A CasY protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasY polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 133). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasY polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasY guide RNA, encoding a CasY fusion protein, etc.) and proteins (e.g., a CasY fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasY polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasY polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasY polypeptide, or a CasY fusion polypeptide, of the present disclosure is at least 80% pure, at least 85% pure, at least 90% pure, at least 95% pure, at least 98% pure, or at least 99% pure (e.g., free of contaminants, non-CasY proteins or other macromolecules, etc.).

To induce cleavage or any desired modification to a target nucleic acid (e.g., genomic DNA), or any desired modification to a polypeptide associated with target nucleic acid, the CasY guide RNA and/or the CasY polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasY guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasY guide RNA that does not change when the guide sequence is changed to hybrized to a desired target sequence (e.g., sequences that contribute to the CasY binding aspect of the guide RNA, e.g, the sequences that contribute to the dsRNA duplex(es) of the CasY guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasY guide RNA, except that the portion encoding the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasY guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasY guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular $—CH_2—NH—O—CH_2—$, $—CH_2—N(CH_3)—O—CH_2—$ (known as a methylene (methylimino) or MMI backbone), $—CH_2—O—N(CH_3)—CH_2—$, $—CH_2—N(CH_3)—N(CH_3)—CH_2—$ and $—O—N(CH_3)—CH_2—CH_2—$ (wherein the native phosphodiester internucleotide linkage is represented as $—O—P(=O)(OH)—O—CH_2—$). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH═$CH_2$), —O-allyl (—O—$CH_2$—CH═$CH_2$) and fluoro (F). 2'-sugar substituent groups may be in the arabino (up) position or ribo (down) position. A suitable 2'-arabino modification is 2'-F Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications*, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N. Y Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); atruncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO:113); Transportan GWTLNSAGYLLGKINLKALAALAKKIL SEQ ID NO:114); KALAWEAKLAKALAKALAKHLAKALAKALKCEA SEQ ID NO:115); and RQIKIWFQNRRMKWKK SEQ ID NO:116). Exemplary PTDs include but are not limited to, YGRKKRRQRRR SEQ ID NO:117), RKKRRQRRR SEQ ID NO:118); an arginine homopolymer of from 3 arginine residues to 50 arginine residues; Exemplary PTD domain amino acid sequences include, but are not limited to, any of the following: YGRKKRRQRRR SEQ ID NO:119); RKKRRQRR SEQ ID NO:120); YARAAARQARA SEQ ID NO:121); THRLPRRRRRR SEQ ID NO:122); and GGRRARRRRRR SEQ ID NO:123). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasY guide RNA (or a nucleic acid comprising a nucleotide sequence encoding same) and/or a CasY polypeptide of the present disclosure (or a nucleic acid comprising a nucleotide sequence encoding same) and/or a CasY fusion polypeptide of the present disclosure (or a nucleic acid that includes a nucleotide sequence encoding a CasY fusion polypeptide of the present disclosure) and/or a donor polynucleotide (donor template) can be introduced into a host cell by any of a variety of well-known methods.

Any of a variety of compounds and methods can be used to deliver to a target cell a CasY system of the present disclosure (e.g., where a CasY system comprises: a) a CasY polypeptide of the present disclosure and a CasY guide RNA; b) a CasY polypeptide of the present disclosure, a CasY guide RNA, and a donor template nucleic acid; c) a CasY fusion polypeptide of the present disclosure and a CasY guide RNA; d) a CasY fusion polypeptide of the present disclosure, a CasY guide RNA, and a donor template nucleic acid; e) an mRNA encoding a CasY polypeptide of the present disclosure; and a CasY guide RNA; f) an mRNA encoding a CasY polypeptide of the present disclosure, a CasY guide RNA, and a donor template nucleic acid; g) an mRNA encoding a CasY fusion polypeptide of the present disclosure; and a CasY guide RNA; h) an mRNA encoding a CasY fusion polypeptide of the present disclosure, a CasY guide RNA, and a donor template nucleic acid; i) a recombinant expression vector comprising a nucleotide sequence encoding a CasY polypeptide of the present disclosure and a nucleotide sequence encoding a CasY guide RNA; j) a recombinant expression vector comprising a nucleotide sequence encoding a CasY polypeptide of the present disclosure, a nucleotide sequence encoding a CasY guide RNA, and a nucleotide sequence encoding a donor template nucleic acid; k) a recombinant expression vector comprising a nucleotide sequence encoding a CasY fusion polypeptide of the present disclosure and a nucleotide sequence encoding a CasY guide RNA; l) a recombinant expression vector comprising a nucleotide sequence encoding a CasY fusion polypeptide of the present disclosure, a nucleotide sequence encoding a CasY guide RNA, and a nucleotide sequence encoding a donor template nucleic acid; m) a first recombinant expression vector comprising a nucleotide sequence encoding a CasY polypeptide of the present disclosure, and a second recombinant expression vector comprising a nucleotide sequence encoding a CasY guide RNA; n) a first recombinant expression vector comprising a nucleotide sequence encoding a CasY polypeptide of the present disclosure, and a second recombinant expression vector comprising a nucleotide sequence encoding a CasY guide RNA; and a donor template nucleic acid; o) a first recombinant expression vector comprising a nucleotide sequence encoding a CasY fusion polypeptide of the present disclosure, and a second recombinant expression vector comprising a nucleotide sequence encoding a CasY guide RNA; p) a first recombinant expression vector comprising a nucleotide sequence encoding a CasY fusion polypeptide of the present disclosure, and a second recombinant expression vector comprising a nucleotide sequence encoding a CasY guide RNA; and a donor template nucleic acid; q) a recombinant expression vector comprising a nucleotide sequence encoding a CasY polypeptide of the present disclosure, a nucleotide sequence encoding a first CasY guide RNA, and a nucleotide sequence encoding a second CasY guide RNA; or r) a recombinant expression vector comprising a nucleotide sequence encoding a CasY fusion polypeptide of the present disclosure, a nucleotide sequence encoding a first CasY guide RNA, and a nucleotide sequence encoding a second CasY guide RNA; or some variation of one of (a) through (r). As a non-limiting example, a CasY system of the present disclosure can be combined with a lipid. As another non-limiting example, a CasY system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like.

In some cases, a CasY polypeptide of the present disclosure is provided as a nucleic acid (e.g., an mRNA, a DNA, a plasmid, an expression vector, a viral vector, etc.) that encodes the CasY polypeptide. In some cases, the CasY polypeptide of the present disclosure is provided directly as a protein (e.g., without an associated guide RNA or with an associate guide RNA, i.e., as a ribonucleoprotein complex). A CasY polypeptide of the present disclosure can be introduced into a cell (provided to the cell) by any convenient method; such methods are known to those of ordinary skill in the art. As an illustrative example, a CasY polypeptide of the present disclosure can be injected directly into a cell (e.g., with or without a CasY guide RNA or nucleic acid encoding a CasY guide RNA, and with or without a donor polynucleotide). As another example, a preformed complex of a CasY polypeptide of the present disclosure and a CasY guide RNA (an RNP) can be introduced into a cell (e.g, eukaryotic cell) (e.g., via injection, via nucleofection; via a protein transduction domain (PTD) conjugated to one or more components, e.g., conjugated to the CasY protein, conjugated to a guide RNA, conjugated to a CasY polypeptide of the present disclosure and a guide RNA; etc.).

In some cases, a CasY fusion polypeptide (e.g., dCasY fused to a fusion partner, nickase CasY fused to a fusion partner, etc.) of the present disclosure is provided as a nucleic acid (e.g., an mRNA, a DNA, a plasmid, an expression vector, a viral vector, etc.) that encodes the CasY fusion polypeptide. In some cases, the CasY fusion polypeptide of the present disclosure is provided directly as a protein (e.g., without an associated guide RNA or with an associate guide RNA, i.e., as a ribonucleoprotein complex). A CasY fusion polypeptide of the present disclosure can be introduced into a cell (provided to the cell) by any convenient method; such methods are known to those of ordinary skill in the art. As an illustrative example, a CasY fusion polypeptide of the present disclosure can be injected directly into a cell (e.g., with or without nucleic acid encoding a CasY guide RNA and with or without a donor polynucleotide). As another example, a preformed complex of a CasY fusion polypeptide of the present disclosure and a CasY guide RNA (an RNP) can be introduced into a cell (e.g., via injection, via nucleofection; via a protein transduction domain (PTD) conjugated to one or more components, e.g., conjugated to the CasY fusion protein, conjugated to a guide RNA, conjugated to a CasY fusion polypeptide of the present disclosure and a guide RNA; etc.).

In some cases, a nucleic acid (e.g., a CasY guide RNA; a nucleic acid comprising a nucleotide sequence encoding a CasY polypeptide of the present disclosure; etc.) is delivered to a cell (e.g., a target host cell) and/or a polypeptide (e.g., a CasY polypeptide; a CasY fusion polypeptide) in a particle, or associated with a particle. In some cases, a CasY system of the present disclosure is delivered to a cell in a particle, or associated with a particle. The terms "particle" and nanoparticle" can be used interchangeable, as appropriate. A recombinant expression vector comprising a nucleotide sequence encoding a CasY polypeptide of the present disclosure and/or a CasY guide RNA, an mRNA comprising a nucleotide sequence encoding a CasY polypeptide of the present disclosure, and guide RNA may be delivered simultaneously using particles or lipid envelopes; for instance, a CasY polypeptide and a CasY guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasY polypepide and a CasY guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasY polypeptide of the present disclosure (or an mRNA comprising a nucleotide sequence encoding a CasY polypeptide of the present disclosure; or a recombinant expression vector comprising a nucleotide sequence encoding a CasY polypeptide of the present disclosure) and/or CasY guide RNA (or a nucleic acid such as one or more expression vectors encoding the CasY guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a CasY polypeptide of the present disclosure, a CasY fusion polypeptide of the present disclosure, an RNP of the present disclosure, a nucleic acid of the present disclosure, or a CasY system of the present disclosure (e.g., where a CasY system comprises: a) a CasY polypeptide of the present disclosure and a CasY guide RNA; b) a CasY polypeptide of the present disclosure, a CasY guide RNA, and a donor template nucleic acid; c) a CasY fusion polypeptide of the present disclosure and a CasY guide RNA; d) a CasY fusion polypeptide of the present disclosure, a CasY guide RNA, and a donor template nucleic acid; e) an mRNA encoding a CasY polypeptide of the present disclosure; and a CasY guide RNA; f) an mRNA encoding a CasY polypeptide of the present disclosure, a CasY guide RNA, and a donor template nucleic acid; g) an mRNA encoding a CasY fusion polypeptide of the present disclosure; and a CasY guide RNA; h) an mRNA encoding a CasY fusion polypeptide of the present disclosure, a CasY guide RNA, and a donor template nucleic acid; i) a recombinant expression vector comprising a nucleotide sequence encoding a CasY polypeptide of the present disclosure and a nucleotide sequence encoding a CasY guide RNA; j) a recombinant expression vector comprising a nucleotide sequence encoding a CasY polypeptide of the present disclosure, a nucleotide sequence encoding a CasY guide RNA, and a nucleotide sequence encoding a donor template nucleic acid; k) a recombinant expression vector comprising a nucleotide sequence encoding a CasY fusion polypeptide of the present disclosure and a nucleotide sequence encoding a CasY guide RNA; l) a recombinant expression vector comprising a nucleotide sequence encoding a CasY fusion polypeptide of the present disclosure, a nucleotide sequence encoding a CasY guide RNA, and a nucleotide sequence encoding a donor template nucleic acid; m) a first recombinant expression vector comprising a nucleotide sequence encoding a CasY polypeptide of the present disclosure, and a second recombinant expression vector comprising a nucleotide sequence encoding a CasY guide RNA; n) a first recombinant expression vector comprising a nucleotide sequence encoding a CasY polypeptide of the present disclosure, and a second recombinant expression vector comprising a nucleotide sequence encoding a CasY guide RNA; and a donor template nucleic acid; o) a first recombinant expression vector comprising a nucleotide sequence encoding a CasY fusion polypeptide of the present disclosure, and a second recombinant expression vector comprising a nucleotide sequence encoding a CasY guide RNA; p) a first recombinant expression vector comprising a nucleotide sequence encoding a CasY fusion polypeptide of the present disclosure, and a second recombinant expression vector comprising a nucleotide sequence encoding a CasY guide RNA; and a donor template nucleic acid; q) a recombinant expression vector comprising a nucleotide sequence encoding a CasY polypeptide of the present disclosure, a nucleotide sequence encoding a first CasY guide RNA, and a nucleotide sequence encoding a second CasY guide RNA; or r) a recombinant expression vector comprising a nucleotide sequence encoding a CasY fusion polypeptide of the present disclosure, a nucleotide sequence encoding a first CasY guide RNA, and a nucleotide sequence encoding a second CasY guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell.

In some cases, lipid nanoparticles (LNPs) are used to deliver a CasY polypeptide of the present disclosure, a CasY fusion polypeptide of the present disclosure, an RNP of the present disclosure, a nucleic acid of the present disclosure, or a CasY system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a CasY guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of from 25 nm to 200 nm. In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of 100 nm or less In some cases, nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell have a diameter of from 35 nm to 60 nm.

Nanoparticles suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell. A prototype nanoparticle of semi-solid nature is the liposome.

In some cases, an exosome is used to deliver a CasY polypeptide of the present disclosure, a CasY fusion polypeptide of the present disclosure, an RNP of the present disclosure, a nucleic acid of the present disclosure, or a CasY system of the present disclosure, to a target cell. Exosomes are endogenous nano-vesicles that transport RNAs and proteins, and which can deliver RNA to the brain and other target organs.

In some cases, a liposome is used to deliver a CasY polypeptide of the present disclosure, a CasY fusion polypeptide of the present disclosure, an RNP of the present disclosure, a nucleic acid of the present disclosure, or a CasY system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+-0.0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a CasY system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a CasY system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A CasY system of the present disclosure, or a component thereof, may be delivered encapsulated in PLGA microspheres such as that further described in US published applications 20130252281 and 20130245107 and 20130244279.

Supercharged proteins can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a CasY polypeptide of the present disclosure, a CasY fusion polypeptide of the present disclosure, an RNP of the present disclosure, a nucleic acid of the present disclosure, or a CasY system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a CasY polypeptide of the present disclosure, a CasY fusion polypeptide of the present disclosure, an RNP of the present disclosure, a nucleic acid of the present disclosure (e.g., a CasY guide RNA, a nucleic acid encoding a CasY guide RNA, a nucleic acid encoding CasY polypeptide, a donor template, and the like), or a CasY system of the present disclosure, to a target cell (e.g., a target cell in vivo, where the target cell is a target cell in circulation, a target cell in a tissue, a target cell in an organ, etc.). An implantable device suitable for use in delivering a CasY polypeptide of the present disclosure, a CasY fusion polypeptide of the present disclosure, an RNP of the present disclosure, a nucleic acid of the present disclosure, or a CasY system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasY polypeptide, the CasY fusion polypeptide, the RNP, or the CasY system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear—auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intraocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasY polypeptide of the present disclosure and/or a nucleic acid comprising a nucleotide sequence encoding a CasY polypeptide of the present disclosure. The present disclosure provides a modified cell comprising a CasY polypeptide of the present disclosure, where the modified cell is a cell that does not normally comprise a CasY polypeptide of the present disclosure. The present disclosure provides a modified cell (e.g., a genetically modified cell) comprising nucleic acid comprising a nucleotide sequence encoding a CasY polypeptide of the present disclosure. The present disclosure provides a genetically modified cell that is genetically modified with an mRNA comprising a nucleotide sequence encoding a CasY polypeptide of the present disclosure. The present disclosure provides a genetically modified cell that is genetically modified with a recombinant expression vector comprising a nucleotide sequence encoding a CasY polypeptide of the present disclosure. The present disclosure provides a genetically modified cell that is genetically modified with a recombinant expression vector comprising: a) a nucleotide sequence encoding a CasY polypeptide of the present disclosure; and b) a nucleotide sequence encoding a CasY guide RNA of the present disclosure. The present disclosure provides a genetically modified cell that is genetically modified with a recombinant expression vector comprising: a) a nucleotide sequence encoding a CasY polypeptide of the present disclosure; b) a nucleotide sequence encoding a CasY guide RNA of the present disclosure; and c) a nucleotide sequence encoding a donor template.

A cell that serves as a recipient for a CasY polypeptide of the present disclosure and/or a nucleic acid comprising a nucleotide sequence encoding a CasY polypeptide of the present disclosure and/or a CasY guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasY polypeptide of the present disclosure and/or a nucleic acid comprising a nucleotide sequence encoding a CasY polypeptide of the present disclosure and/or a CasY guide RNA of the present disclosure is referred to as a "host cell" or a "target cell." A host cell or a target cell can be a recipient of a CasY system of the present disclosure. A host cell or a target cell can be a recipient of a CasY RNP of the present disclosure. A host cell or a target cell can be a recipient of a single component of a CasY system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasY system of the present disclosure, or a component of a CasY system of the present disclosure.

A kit of the present disclosure can comprise: a) a CasY polypeptide of the present disclosure and a CasY guide RNA; b) a CasY polypeptide of the present disclosure, a CasY guide RNA, and a donor template nucleic acid; c) a CasY fusion polypeptide of the present disclosure and a CasY guide RNA; d) a CasY fusion polypeptide of the present disclosure, a CasY guide RNA, and a donor template nucleic acid; e) an mRNA encoding a CasY polypeptide of the present disclosure; and a CasY guide RNA; f) an mRNA encoding a CasY polypeptide of the present disclosure, a CasY guide RNA, and a donor template nucleic acid; g) an mRNA encoding a CasY fusion polypeptide of the present disclosure; and a CasY guide RNA; h) an mRNA encoding a CasY fusion polypeptide of the present disclosure, a CasY guide RNA, and a donor template nucleic acid; i) a recombinant expression vector comprising a nucleotide sequence encoding a CasY polypeptide of the present disclosure and a nucleotide sequence encoding a CasY guide RNA; j) a recombinant expression vector comprising a nucleotide sequence encoding a CasY polypeptide of the present disclosure, a nucleotide sequence encoding a CasY guide RNA, and a nucleotide sequence encoding a donor template nucleic acid; k) a recombinant expression vector comprising a nucleotide sequence encoding a CasY fusion polypeptide of the present disclosure and a nucleotide sequence encoding a CasY guide RNA; l) a recombinant expression vector comprising a nucleotide sequence encoding a CasY fusion polypeptide of the present disclosure, a nucleotide sequence encoding a CasY guide RNA, and a nucleotide sequence encoding a donor template nucleic acid; m) a first recombinant expression vector comprising a nucleotide sequence encoding a CasY polypeptide of the present disclosure, and a second recombinant expression vector comprising a nucleotide sequence encoding a CasY guide RNA; n) a first recombinant expression vector comprising a nucleotide sequence encoding a CasY polypeptide of the present disclosure, and a second recombinant expression vector comprising a nucleotide sequence encoding a CasY guide RNA; and a donor template nucleic acid; o) a first recombinant expression vector comprising a nucleotide sequence encoding a CasY fusion polypeptide of the present disclosure, and a second recombinant expression vector comprising a nucleotide sequence encoding a CasY guide RNA; p) a first recombinant expression vector comprising a nucleotide sequence encoding a CasY fusion polypeptide of the present disclosure, and a second recombinant expression vector comprising a nucleotide sequence encoding a CasY guide RNA; and a donor template nucleic acid; q) a recombinant expression vector comprising a nucleotide sequence encoding a CasY polypeptide of the present disclosure, a nucleotide sequence encoding a first CasY guide RNA, and a nucleotide sequence encoding a second CasY guide RNA; or r) a recombinant expression vector comprising a nucleotide sequence encoding a CasY fusion polypeptide of the present disclosure, a nucleotide sequence encoding a first CasY guide RNA, and a nucleotide sequence encoding a second CasY guide RNA; or some variation of one of (a) through (r).

A kit of the present disclosure can comprise: a) a component, as described above, of a CasY system of the present disclosure, or can comprise a CasY system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasY guide RNA; and the like. A kit of the present disclosure can comprise: a) a component, as described above, of a CasY system of the present disclosure, or can comprise a CasY system of the present disclosure; and b) a therapeutic agent.

A kit of the present disclosure can comprise a recombinant expression vector comprising: a) an insertion site for inserting a nucleic acid comprising a nucleotide sequence encoding a portion of a CasY guide RNA that hybridizes to a target nucleotide sequence in a target nucleic acid; and b) a nucleotide sequence encoding the CasY-binding portion of a CasY guide RNA. A kit of the present disclosure can comprise a recombinant expression vector comprising: a) an insertion site for inserting a nucleic acid comprising a nucleotide sequence encoding a portion of a CasY guide RNA that hybridizes to a target nucleotide sequence in a target nucleic acid; b) a nucleotide sequence encoding the CasY-binding portion of a CasY guide RNA; and c) a nucleotide sequence encoding a CasY polypeptide of the present disclosure.

Utility

A CasY polypeptide of the present disclosure, or a CasY fusion polypeptide of the present disclosure, finds use in a variety of methods (e.g., in combination with a CasY guide RNA and in some cases further in combination with a donor template). For example, a CasY polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasY polypeptide of the present disclosure; and b) one or more (e.g., two) CasY guide RNAs. In some cases, a method of the present disclosure for modifying a target nucleic acid comprises contacting the target nucleic acid with: a) a CasY polypeptide of the present disclosure; b) a CasY guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasY polypeptide includes binding of the CasY polypeptide to a particular region in a target nucleic acid (by virtue of being targeted there by an associated CasY guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasY polypeptide or with a CasY fusion polypeptide, etc., encompass all methods for contacting the target nucleic acid. For example, a CasY polypeptide can be provided to a cell as protein, RNA (encoding the CasY polypeptide), or DNA (encoding the CasY polypeptide); while a CasY guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasY polypeptide; in the form of a protein for a CasY fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasY polypeptide or a CasY fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a CasY locus, e.g., a nucleic acid comprising a nucleotide sequence encoding a CasY polypeptide as well as nucleotide sequences of about 1 kilobase (kb) to 5 kb in length surrounding the CasY-encoding nucleotide sequence from a cell (e.g., in some cases a cell that in its natural state (the state in which it occurs in nature) comprises a CasY locus) comprising a CasY locus, where the target cell does not normally (in its natural state) comprise a CasY locus. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a CasY locus, e.g., a nucleic acid obtained from a source cell (e.g., in some cases a cell that in its natural state (the state in which it occurs in nature) comprises a CasY locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a CasY polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a CasY locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a CasY polypeptide of the present disclosure, or with a CasY fusion polypeptide of the present disclosure. In some cases, abmethod of the present disclosure for modifying a target nucleic acid comprises contacting a target nucleic acid with a CasY polypeptide and a CasY guide RNA. In some cases, a method of the present disclosure for modifying a target nucleic acid comprises contacting a target nucleic acid with a CasY polypeptide, a first CasY guide RNA, and a second CasY guide RNA In some cases, a method of the present disclosure for modifying a target nucleic acid comprises contacting a target nucleic acid with a CasY polypeptide of the present disclosure and a CasY guide RNA and a donor DNA template.

Target Nucleic Acids and Target Cells of Interest

A CasY polypeptide of the present disclosure, or a CasY fusion polypeptide of the present disclosure, when bound to a CasY guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasY guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to geneically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasY protein (and/or nucleic acid encoding the protein such as DNA and/or RNA), and/or CasY guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata*, Myriapodia, Hexipodia, Arachnida, *Insecta*, Archaeognatha, *Thysanura*, Palaeoptera, Ephemeroptera, *Odonata, Anisoptera, Zygoptera*, Neoptera, Exopterygota, *Plecoptera*, Embioptera, *Orthoptera, Zoraptera, Dermaptera, Dictyoptera, Notoptera*, Grylloblattidae, Mantophasmatidae, Phasmatodea, *Blattaria, Isoptera*, Mantodea, Parapneuroptera, Psocoptera, Thysanoptera, Phthiraptera, *Hemiptera*, Endopterygota or Holometabola, *Hymenoptera, Coleoptera*, Strepsiptera, Raphidioptera, *Megaloptera, Neuroptera*, Mecoptera, *Siphonaptera, Diptera, Trichoptera*, or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas9 guide RNA (or a nucleic acid comprising a nucleotide sequence encoding same), and/or a Cas9 fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: 50169-409X(12)00283-9. doi: 10.1016/j.addr.2012.09.023), and the like. Any or all of the components can be introduced into a cell as a composition (e.g., including any convenient combination of: a a CasY polypeptide, a CasY guide RNA, a donor polynucleotide, etc.) using known methods, e.g., such as nucleofection.

Donor Polynucleotide (Donor Template)

Guided by a CasY guide RNA, a CasY protein in some cases generates site-specific double strand breaks (DSBs) or single strand breaks (SSBs) (e.g., when the CasY protein is a nickase variant) within double-stranded DNA (dsDNA) target nucleic acids, which are repaired either by nonhomologous end joining (NHEJ) or homology-directed recombination (HDR).

In some cases, contacting a target DNA (with a CasY protein and a CasY guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, CasY guide RNA (or DNA encoding same) and a CasY protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasY guide RNA and CasY protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasY protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair ot a non disease-causing base pair). In some embodiments, the donor sequence comprises a nonhomologous sequence flanked by two regions of homology, such that homology-directed repair between the target DNA region and the two flanking sequences results in insertion of the nonhomologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasY guide RNA and/or a CasY fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasY polypeptide of the present disclosure; a nucleic acid comprising a nucleotide sequence encoding a CasY fusion polypeptide of the present disclosure; etc.), is used as a transgene to generate a transgenic non-human organism that produces a CasY polypeptide, or a CasY fusion polypeptide, of the present disclosure. The present disclosure provides a transgenic-non-human organism comprising a nucleotide sequence encoding a CasY polypeptide, or a CasY fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasY polypeptide or a CasY fusion polypeptide. In some embodiments, the genome of the transgenic non-human animal comprises a nucleotide sequence encoding a CasY polypeptide, or a CasY fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasY polypeptide, or a CasY fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasY polypeptide of the present disclosure; a nucleic acid comprising a nucleotide sequence encoding a CasY fusion polypeptide of the present disclosure; etc.), is used as a transgene to generate a transgenic plant that produces a CasY polypeptide, or a CasY fusion polypeptide, of the present disclosure. The present disclosure provides a transgenic plant comprising a nucleotide sequence encoding a CasY polypeptide, or a CasY fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasY polypeptide, or a CasY fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasY polypeptide, or a CasY fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasY polypeptide, or a CasY fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Methods of Identifying a Crispr RNA-Guided Endonuclease

Provided are methods of identifying a CRISPR RNA-guided endonuclease. For example, in some embodiments, such a method includes a step of detecting in a plurality of metagenomic nucleotide sequences, a nucleotide sequence encoding a Cas1 polypeptide. Cas1 proteins are known in the art and are present in the vicinity of CRISPR loci of Class 2 CRISPR systems, those CRISPR systems that include a single effector protein that functions as an endonuclease and does not require interaction with a complex of proteins in order to function properly. While the Cas 1 protein itself is involved in acquisition of new target sequences into the CRISPR locus, and thus is not the desired effector protein for identification by this method, the presence of a Cas1 protein in the vicinity of a CRISPR locus is an indication that at least one of the other Cas proteins present near the locus may be an effector protein (an RNA-guided endonuclease).

As used herein, the term "metagenomics" means the parallel analysis of nucleic acids recovered from multiple microorganisms (e.g., bacteria, archaea, etc.) in a sample, e.g., an environmental sample such as a sample that contains an unknown quantity of prokaryotes (bacteria/archaea) and may contain prokaryotes that have never before discovered and/or characterized. Nucleic acids can be recovered from such a sample by any convenient method, and generally the nucleic acids are recovered together from the entire sample such that prior to analysis it is unknown from which microorganism any given nucleic acid molecule originated. In some embodiments, the sample contains an unknown mixture and/or quantity of microorganisms. The nucleic acids can then be sequenced to generate a plurality of metagenomic sequences. In some cases, a subject method of identifying a CRISPR RNA-guided endonuclease includes a step of isolating a sample (e.g., an environmental sample). In some cases, a subject method of identifying a CRISPR RNA-guided endonuclease includes a step of isolating nucleic acids from the sample and/or assaying the sample to generated a plurality of metagenomic nucleotide sequences from the sample.

Once a Cas1 protein is identified, a subject method of identifying a CRISPR RNA-guided endonuclease can include a step of detecting a CRISPR array (a repeat-spacer-repeat array) in the vicinity of the Cas1-encoding nucleotide sequence. The method can then include a step of cloning (e.g., from a nucleic acid sample from which the plurality of metagenomic nucleotide sequences was derived) a CRISPR locus comprising the detected CRISPR array, into an expression vector to generate a recombinant CRISPR locus expression vector. The CRISPR locus can then be tested for function by assaying the recombinant CRISPR locus expression vector for the ability to cleave a target nucleic acid. Any convenient assay can be used. In some embodiments the assaying step includes introducing the recombinant CRISPR locus expression vector and a target nucleic into a cell, e.g., a heterologous host cell such as an *E. coli* cell. For example, refer to the PAM depletion assays of the working examples below (FIG. 5). In some cases, the step of assaying includes introducing into a population of host cells (e.g., *E. coli* cells) a plasmid library wherein each plasmid of the library has 4 to 10 (e.g., 5 to 10, 5 to 8, 6 to 10, 6 to 8, 5, 6, 7, 8,) nucleotides randomized 5' and/or 3' of a target sequence. The host cells can already contain the recombinant CRISPR locus expression vector to be tested, or the recombinant CRISPR locus expression vector can be introduced after the library. Only test CRISPR loci that are functional, and therefore include a functional CRISPR RNA-guided endonuclease, will result in the ability to cleave plasmids that have the target sequence. The reason for included the randomized sequences 5' and 3' of the target sequence is that one might not know the PAM sequence required for the desired endonuclease at the outset of the experiment.

If the expression vector can cleave a target nucleic acid (e.g., one with an appropriate target sequence and PAM, such as a target sequence that matches as least one spacer of the CRISPR array), then the CRISPR locus comprises a nucleotide sequence encoding a candidate CRISPR RNA-guided endonuclease. Thus, one can then identify an open reading frame from the CRISPR locus that encodes a CRISPR RNA-guided endonuclease. In some cases, it is desirable to identify a previously unknown CRISPR RNA-guided endonuclease, and thus in some cases, the identified polypeptide that has less than 20% amino acid sequence identity (e.g., less than 15%, less than 10%, less than 5% amino acid sequence identity) to the amino acid sequence of a known CRISPR RNA-guided endonuclease polypeptide.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure, numbered 1-123 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspects

1. A composition comprising:

a) a CasY polypeptide, or a nucleic acid molecule encoding the CasY polypeptide; and b) a CasY guide RNA, or one or more DNA molecules encoding the CasY guide RNA.

2. The composition of 1, wherein the CasY polypeptide comprises an amino acid sequence having 50% or more identity to the amino acid sequence set forth in SEQ ID NO:1 or SEQ ID NO:2 (or the amino acid sequence set forth in any one of SEQ ID NOs:1-8).

3. The composition of 1 or 2, wherein the CasY guide RNA comprises a nucleotide sequence having 80% or more identity with the crRNA sequence set forth in any one of SEQ ID NOs: 11-15.

4. The composition of 1 or 2, wherein the CasY polypeptide is fused to an NLS sequence.

5. The composition of any one of 1-4, wherein the composition comprises a lipid.

6. The composition of any one of 1-4, wherein a) and b) are within a liposome.

7. The composition of any one of 1-4, wherein a) and b) are within a particle.

8. The composition of any one of 1-7, comprising one or more of: a buffer, a nuclease inhibitor, and a protease inhibitor.

9. The composition of any one of 1-8, wherein the CasY polypeptide comprises an amino acid sequence having 85% or more identity to the amino acid sequence set forth in SEQ ID NO:1 or SEQ ID NO:2 (or the amino acid sequence set forth in any one of SEQ ID NOs:1-8).

10. The composition of any one of 1-9, wherein the CasY polypeptide is a nickase that can cleave only one strand of a double-stranded target nucleic acid molecule.

11. The composition of any one of 1-9, wherein the CasY polypeptide is a catalytically inactive CasY Polypeptide (dCasY).

12. The composition of 10 or 11, wherein the CasY polypeptide comprises one or more mutations at a position corresponding to those selected from: D672, E769, and D935 of SEQ ID NO: 1.

13. The composition of any one of 1-12, further comprising a DNA donor template.

14. A CasY fusion polypeptide comprising: a CasY polypeptide fused to a heterologous polypeptide.

15. The CasY fusion polypeptide of 14, wherein the CasY polypeptide comprises an amino acid sequence having 50% or more identity to the amino acid sequence set forth in SEQ ID NO:1 or SEQ ID NO:2 (or the amino acid sequence set forth in any one of SEQ ID NOs:1-8).

16. The CasY fusion polypeptide of 14, wherein the CasY polypeptide comprises an amino acid sequence having 85% or more identity to the amino acid sequence set forth in SEQ ID NO:1 or SEQ ID NO:2 (or the amino acid sequence set forth in any one of SEQ ID NOs:1-8).

17. The CasY fusion polypeptide of any one of 14-16, wherein the CasY polypeptide is a nickase that can cleave only one strand of a double-stranded target nucleic acid molecule.

18. The CasY fusion polypeptide of any one of 14-17, wherein the CasY polypeptide is a catalytically inactive CasY Polypeptide (dCasY).

19. The CasY fusion polypeptide of 17 or 18, wherein the CasY polypeptide comprises one or more mutations at a position corresponding to those selected from: D672, E769, and D935 of SEQ ID NO: 1.

20. The CasY fusion polypeptide of any one of 14-19, wherein the heterologous polypeptide is fused to the N-terminus and/or the C-terminus of the CasY polypeptide.

21. The CasY fusion polypeptide of any one of 14-20, comprising an NLS.

22. The CasY fusion polypeptide of any one of 14-21, wherein the heterologous polypeptide is a targeting polypeptide that provides for binding to a cell surface moiety on a target cell or target cell type.

23. The CasY fusion polypeptide of any one of 14-21, wherein the heterologous polypeptide exhibits an enzymatic activity that modifies target DNA.

24. The CasY fusion polypeptide of 23, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

25. The CasY fusion polypeptide of 24, wherein the heterologous polypeptide exhibits an one or more enzymatic activities selected from: nuclease activity, methyltransferase activity, demethylase activity, deamination activity, depurination activity, integrase activity, transposase activity, and recombinase activity.

26. The CasY fusion polypeptide of any one of 14-21, wherein the heterologous polypeptide exhibits an enzymatic activity that modifies a target polypeptide associated with a target nucleic acid.

27. The CasY fusion polypeptide of 26, wherein the heterologous polypeptide exhibits histone modification activity.

28. The CasY fusion polypeptide of 26 or 27, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-Glena transferase) and deglycosylation activity.

29. The CasY fusion polypeptide of 28, wherein the heterologous polypeptide exhibits an one or more enzymatic activities selected from: methyltransferase activity, demethylase activity, acetyltransferase activity, and deacetylase activity.

30. The CasY fusion polypeptide of any one of 14-21, wherein the heterologous polypeptide is an endosomal escape polypeptide.

31. The CasY fusion polypeptide of 30, wherein the endosomal escape polypeptide comprises an amino acid sequence selected from: GLFXALLXLLXSLWXLLLXA (SEQ ID NO:94), and GLFHALLHLLHSLWHLLLHA (SEQ ID NO:95), wherein each X is independently selected from lysine, histidine, and arginine.

32. The CasY fusion polypeptide of any one of 14-21, wherein the heterologous polypeptide is a chloroplast transit peptide.

33. The CasY fusion polypeptide of 32, wherein the chloroplast transit peptide comprises an amino acid sequence selected from

```
(SEQ ID NO: 83)
MASMISSSAVTTVSRASRGQSAAMAPFGGLKSMTGFPVRKVNTDITSITS

NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS

NGGRVKS;
```

-continued (SEQ ID NO: 85)
MASSMLSSATMVASPAQATMVAPFNGLKSSAAFPATRKANNDITSITSNG

GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG

LKKSGMTLIGSELRPLKVMSSVSTAC;

(SEQ ID NO: 87)
MAQVSRICNGVWNPSLISNLSKSSQRKSPLSVSLKTQQHPRAYPISSSWG

LKKSGMTLIGSELRPLKVMSSVSTAC;

(SEQ ID NO: 88)
MAQINNMAQGIQTLNPNSNFHKPQVPKSSSFLVFGSKKLKNSANSMLVLK

KDSIFMQLFCSFRISASVATAC;

(SEQ ID NO: 89)
MAALVTSQLATSGTVLSVTDRFRRPGFQGLRPRNPADAALGMRTVGASAA

PKQSRKPHRFDRRCLSMVV;

(SEQ ID NO: 90)
MAALTTSQLATSATGFGIADRSAPSSLLRHGFQGLKPRSPAGGDATSLSV

TTSARATPKQQRSVQRGSRRFPSVVVC;

(SEQ ID NO: 91)
MASSVLSSAAVATRSNVAQANMVAPFTGLKSAASFPVSRKQNLDITSIAS

NGGRVQC;

(SEQ ID NO: 92)
MESLAATSVFAPSRVAVPAARALVRAGTVVPTRRTSSTSGTSGVKCSAAV

TPQASPVISRSAAAA;
and (SEQ ID NO: 93)
MGAAATSMQSLKFSNRLVPPSRRLSPVPNNVTCNNLPKSAAPVRTVKCCA

SSWNSTINGAAATTNGASAASS.

34. The CasY fusion polypeptide of any one of 14-21, wherein the heterologous polypeptide is protein that increases or decreases transcription.

35. The CasY fusion polypeptide of 34, wherein the heterologous polypeptide is a transcriptional repressor domain.

36. The CasY fusion polypeptide of 34, wherein the heterologous polypeptide is a transcriptional activation domain.

37. The CasY fusion polypeptide of any one of 14-21, wherein the heterologous polypeptide is a protein biding domain.

38. A nucleic acid molecule encoding the CasY fusion polypeptide of any one of 14-37.

39. The nucleic acid molecule of 38, wherein the nucleotide sequence encoding the CasY fusion polypeptide is operably linked to a promoter.

40. The nucleic acid molecule of 39, wherein the promoter is functional in a eukaryotic cell.

41. The nucleic acid molecule of 40, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

42. The nucleic acid molecule of any one of 39-41, wherein the promoter is one or more of: a constitutive promoter, an inducible promoter, a cell type-specific promoter, and a tissue-specific promoter.

43. The nucleic acid molecule of any one of 38-42, wherein the DNA molecule is a recombinant expression vector.

44. The nucleic acid molecule of 43, wherein the recombinant expression vector is a recombinant adenoassociated viral vector, a recombinant retroviral vector, or a recombinant lentiviral vector.

45. The nucleic acid molecule of 39, wherein the promoter is functional in a prokaryotic cell.

46. The nucleic acid molecule of 38, wherein the nucleic acid molecule is an mRNA.

47. One or more nucleic molecules encoding:

(a) a CasY guide RNA; and (b) a CasY polypeptide.

48. The one or more nucleic acid molecules of 47, wherein the CasY polypeptide comprises an amino acid sequence having 50% or more identity to the amino acid sequence set forth in SEQ ID NO:1 or SEQ ID NO:2 (or the amino acid sequence set forth in any one of SEQ ID NOs:1-8).

49. The one or more nucleic acid molecules of 47, wherein the CasY polypeptide comprises an amino acid sequence having 85% or more identity to the amino acid sequence set forth in SEQ ID NO:1 or SEQ ID NO:2 (or the amino acid sequence set forth in any one of SEQ ID NOs:1-8).

50. The one or more nucleic acid molecules of any one of 47-49, wherein the CasY guide RNA comprises a nucleotide sequence having 80% or more identity with the crRNA sequence set forth in any one of SEQ ID NOs: 11-15.

51. The one or more nucleic acid molecules of any one of 47-50, wherein the CasY polypeptide is fused to an NLS sequence.

52. The one or more nucleic acid molecules of any one of 47-51, wherein said one or more nucleic acid molecules comprises a nucleotide sequence encoding the CasY guide RNA that is operably linked to a promoter.

53. The one or more nucleic acid molecules of any one of 47-52, wherein said one or more nucleic acid molecules comprises a nucleotide sequence encoding the CasY polypeptide that is operably linked to a promoter.

54. The one or more nucleic acid molecules of 52 or 53, wherein the promoter operably linked to the nucleotide sequence encoding the CasY guide RNA, and/or the promoter operably linked to the nucleotide sequence encoding the CasY polypeptide, is functional in a eukaryotic cell.

55. The one or more nucleic acid molecules of 54, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

56. The one or more nucleic acid molecules of any one of 53-55, wherein the promoter is one or more of: a constitutive promoter, an inducible promoter, a cell type-specific promoter, and a tissue-specific promoter.

57. The one or more nucleic acid molecules of any one of 47-56, wherein the one or more nucleic acid molecules is one or more recombinant expression vectors.

58. The one or more nucleic acid molecules of 57, wherein the one or more recombinant expression vectors are selected from: one or more adenoassociated viral vectors, one or more recombinant retroviral vectors, or one or more recombinant lentiviral vectors.

59. The one or more nucleic acid molecules of 53, wherein the promoter is functional in a prokaryotic cell.

60. A eukaryotic cell comprising one or more of:

a) a CasY polypeptide, or a nucleic acid molecule encoding the CasY polypeptide, b) a CasY fusion polypeptide, or a nucleic acid molecule encoding the CasY fusion polypeptide, and c) a CasY guide RNA, or a nucleic acid molecule encoding the CasY guide RNA.

61. The eukaryotic cell of 60, comprising the nucleic acid molecule encoding the CasY polypeptide, wherein said nucleic acid molecule is integrated into the genomic DNA of the cell.

62. The eukaryotic cell of 60 or 61, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

63. A cell comprising a CasY fusion polypeptide, or a nucleic acid molecule encoding the CasY fusion polypeptide.

64. The cell of 63, wherein the cell is a prokaryotic cell.

65. The cell of 63 or 64, comprising the nucleic acid molecule encoding the CasY fusion polypeptide, wherein said nucleic acid molecule is integrated into the genomic DNA of the cell.

66. A method of modifying a target nucleic acid, the method comprising contacting the target nucleic acid with:

a) a CasY polypeptide; and b) a CasY guide RNA comprising a guide sequence that hybridizes to a target sequence of the target nucleic acid, wherein said contacting results in modification of the target nucleic acid by the CasY polypeptide.

67. The method of 66, wherein said modification is cleavage of the target nucleic acid.

68. The method of 66 or 67, wherein the target nucleic acid is selected from: double stranded DNA, single stranded DNA, RNA, genomic DNA, and extrachromosomal DNA.

69. The method of any of 66-68, wherein said contacting takes place in vitro outside of a cell.

70. The method of any of 66-68, wherein said contacting takes place inside of a cell in culture.

71. The method of any of 66-68, wherein said contacting takes place inside of a cell in vivo.

72. The method of 70 or 71, wherein the cell is a eukaryotic cell.

73. The method of 72, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

74. The method of 70 or 71, wherein the cell is a prokaryotic cell.

75. The method of any one of 66-74, wherein said contacting results in genome editing.

76. The method of any one of 66-75, wherein said contacting comprises: introducing into a cell: (a) the CasY polypeptide, or a nucleic acid molecule encoding the CasY polypeptide, and (b) the CasY guide RNA, or a nucleic acid molecule encoding the CasY guide RNA.

77. The method of 76, wherein said contacting further comprises: introducing a DNA donor template into the cell.

78. The method of any one of 66-77, wherein the CasY guide RNA comprises a nucleotide sequence having 80% or more identity with the crRNA sequence set forth in any one of SEQ ID NOs: 11-15.

79. The method of any one of 66-78, wherein the CasY polypeptide is fused to an NLS sequence.

80. A method of modulating transcription from a target DNA, modifying a target nucleic acid, or modifying a protein associated with a target nucleic acid, the method comprising contacting the target nucleic acid with:

a) a CasY fusion polypeptide comprising a CasY polypeptide fused to a heterologous polypeptide; and b) a CasY guide RNA comprising a guide sequence that hybridizes to a target sequence of the target nucleic acid.

81. The method of 80, wherein the CasY guide RNA comprises a nucleotide sequence having 80% or more identity with the crRNA sequence set forth in any one of SEQ ID NOs: 11-15.

82. The method of 80 or 81, wherein the CasY fusion polypeptide comprises an NLS sequence.

83. The method of any of 80-82, wherein said modification is not cleavage of the target nucleic acid.

84. The method of any of 80-83, wherein the target nucleic acid is selected from: double stranded DNA, single stranded DNA, RNA, genomic DNA, and extrachromosomal DNA.

85. The method of any of 80-84, wherein said contacting takes place in vitro outside of a cell.

86. The method of any of 80-84, wherein said contacting takes place inside of a cell in culture.

87. The method of any of 80-84, wherein said contacting takes place inside of a cell in vivo.

88. The method of 86 or 87, wherein the cell is a eukaryotic cell.

89. The method of 88, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

90. The method of 86 or 87, wherein the cell is a prokaryotic cell.

91. The method of any one of 80-90, wherein said contacting comprises: introducing into a cell: (a) the CasY fusion polypeptide, or a nucleic acid molecule encoding the CasY fusion polypeptide, and (b) the CasY guide RNA, or a nucleic acid molecule encoding the CasY guide RNA.

92. The method of any one of 80-91, wherein the CasY polypeptide is a catalytically inactive CasY Polypeptide (dCasY).

93. The method of any one of 80-92, wherein the CasY polypeptide comprises one or more mutations at a position corresponding to those selected from: D672, E769, and D935 of SEQ ID NO: 1.

94. The method of any one of 80-93, wherein the heterologous polypeptide exhibits an enzymatic activity that modifies target DNA.

95. The method of 94, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

96. The method of 95, wherein the heterologous polypeptide exhibits an one or more enzymatic activities selected from: nuclease activity, methyltransferase activity, demethylase activity, deamination activity, depurination activity, integrase activity, transposase activity, and recombinase activity.

97. The method of any one of 80-93, wherein the heterologous polypeptide exhibits an enzymatic activity that modifies a target polypeptide associated with a target nucleic acid.

98. The method of 97, wherein the heterologous polypeptide exhibits histone modification activity.

99. The method of 97 or 98, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

100. The method of 99, wherein the heterologous polypeptide exhibits an one or more enzymatic activities selected from: methyltransferase activity, demethylase activity, acetyltransferase activity, and deacetylase activity.

101. The method of any one of 80-93, wherein the heterologous polypeptide is protein that increases or decreases transcription.

102. The method of 101, wherein the heterologous polypeptide is a transcriptional repressor domain.

103. The method of 101, wherein the heterologous polypeptide is a transcriptional activation domain.

104. The method of any one of 80-93, wherein the heterologous polypeptide is a protein biding domain.

105. A transgenic, multicellular, non-human organism whose genome comprises a transgene comprising a nucleotide sequence encoding one or more of:

a) a CasY polypeptide, b) a CasY fusion polypeptide, and c) a CasY guide RNA.

106. The transgenic, multicellular, non-human organism of 105, wherein the CasY polypeptide comprises an amino acid sequence having 50% or more amino acid sequence identity to the amino acid sequence set forth in SEQ ID NO:1 or SEQ ID NO:2 (or the amino acid sequence set forth in any one of SEQ ID NOs:1-8).

107. The transgenic, multicellular, non-human organism of 105, wherein the CasY polypeptide comprises an amino acid sequence having 85% or more amino acid sequence identity to the amino acid sequence set forth in SEQ ID NO:1 or SEQ ID NO:2 (or the amino acid sequence set forth in any one of SEQ ID NOs:1-8).

108. The transgenic, multicellular, non-human organism of any one of 105-107, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

109. A system comprising:

a) a CasY polypeptide and a CasY guide RNA;

b) a CasY polypeptide, a CasY guide RNA, and a DNA donor template;

c) a CasY fusion polypeptide and a CasY guide RNA;

d) a CasY fusion polypeptide, a CasY guide RNA, and a DNA donor template;

e) an mRNA encoding a CasY polypeptide, and a CasY guide RNA;

f) an mRNA encoding a CasY polypeptide; a CasY guide RNA, and a DNA donor template;

g) an mRNA encoding a CasY fusion polypeptide, and a CasY guide RNA;

h) an mRNA encoding a CasY fusion polypeptide, a CasY guide RNA, and a DNA donor template;

i) one or more recombinant expression vectors comprising: i) a nucleotide sequence encoding a CasY polypeptide; and ii) a nucleotide sequence encoding a CasY guide RNA;

j) one or more recombinant expression vectors comprising: i) a nucleotide sequence encoding a CasY polypeptide; ii) a nucleotide sequence encoding a CasY guide RNA; and iii) a DNA donor template;

k) one or more recombinant expression vectors comprising: i) a nucleotide sequence encoding a CasY fusion polypeptide; and ii) a nucleotide sequence encoding a CasY guide RNA; and l) one or more recombinant expression vectors comprising: i) a nucleotide sequence encoding a CasY fusion polypeptide; ii) a nucleotide sequence encoding a CasY guide RNA; and a DNA donor template.

110. The CasY system of 109, wherein the CasY polypeptide comprises an amino acid sequence having 50% or more amino acid sequence identity to the amino acid sequence set forth in SEQ ID NO:1 or SEQ ID NO:2 (or the amino acid sequence set forth in any one of SEQ ID NOs:1-8).

111. The CasY system of 109, wherein the CasY polypeptide comprises an amino acid sequence having 85% or more amino acid sequence identity to the amino acid sequence set forth in SEQ ID NO:1 or SEQ ID NO:2 (or the amino acid sequence set forth in any one of SEQ ID NOs:1-8).

112. The CasY system of any of 109-111, wherein the donor template nucleic acid has a length of from 8 nucleotides to 1000 nucleotides.

113. The CasY system of any of 109-111, wherein the donor template nucleic acid has a length of from 25 nucleotides to 500 nucleotides.

114. A kit comprising the CasY system of any one of 109-113.

115. The kit of 114, wherein the components of the kit are in the same container.

116. The kit of 114, wherein the components of the kit are in separate containers.

117. A sterile container comprising the CasY system of any one of 109-116.

118. The sterile container of 117, wherein the container is a syringe.

119. An implantable device comprising the CasY system of any one of 109-116.

120. The implantable device of 119, wherein the CasY system is within a matrix.

121. The implantable device of 119, wherein the CasY system is in a reservoir.

122. A method of identifying a CRISPR RNA-guided endonuclease, the method comprising:

detecting, in a plurality of metagenomic nucleotide sequences, a nucleotide sequence encoding a Cas1 polypeptide;

detecting a CRISPR array in the vicinity of the Cas1-encoding nucleotide sequence;

cloning, from a nucleic acid sample from which the plurality of metagenomic nucleotide sequences was derived, a CRISPR locus comprising the detected CRISPR array, into an expression vector to generate a recombinant CRISPR locus expression vector;

assaying the recombinant CRISPR locus expression vector for the ability to cleave a target nucleic acid, wherein a CRISPR locus that has the ability to cleave a target nucleic acid comprises a nucleotide sequence encoding a CRISPR RNA-guided endonuclease. identifying, in the CRISPR locus, an open reading frame encoding a polypeptide that has less than 20% amino acid sequence identity to the amino acid sequence of a known CRISPR RNA-guided endonuclease polypeptide.

123. The method of 122, wherein said assaying comprises introducing the recombinant CRISPR locus expression vector and a target nucleic into a cell.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

The work described herein includes an analysis of metagenomic samples of microbial communities from groundwater, sediments, and acid mine drainage. New Class 2 CRISPR-Cas systems were identified that are not represented among cultured organisms.

FIG. 3. CasY domains and similarity searches. (panel a) Schematic domain representation for CasY inferred from distant homolog alignments with AcCpf1, using HHpred. Conserved catalytic residues are marked by red bars above the proteins. CasY contains a RuvC split domain in the C-terminal region (RuvC-I, RuvC-II, and RuvC-III), and a large novel N-terminal domain. Below the schematic are displayed top hits based on the following searches: (1) BLAST search against all the proteins in NCBI (NR database, including model and environmental proteins). (2) Profile hidden markov model (HMM) search based on models built using all the Cas proteins described in Makarova et al. Nat Rev Microbiol. 2015 November; 13(11):722-36, and Shmakov et al. Mol Cell. 2015 Nov. 5; 60(3):385-97). (3) Distant homolog search based on HHpred. Hits are color-coded based on their significance, and the hit range and E-value is provided. Notably, CasY had only local hits. The 812 N-terminal amino acid of CasY had only one very minor partial hit. Combined, these finding indicate CasY is a new Cas protein. (panel b) Different CasY-contaning CRISPR loci scaffolds were constructed from sequence data.

Example 2

Figure 4A:
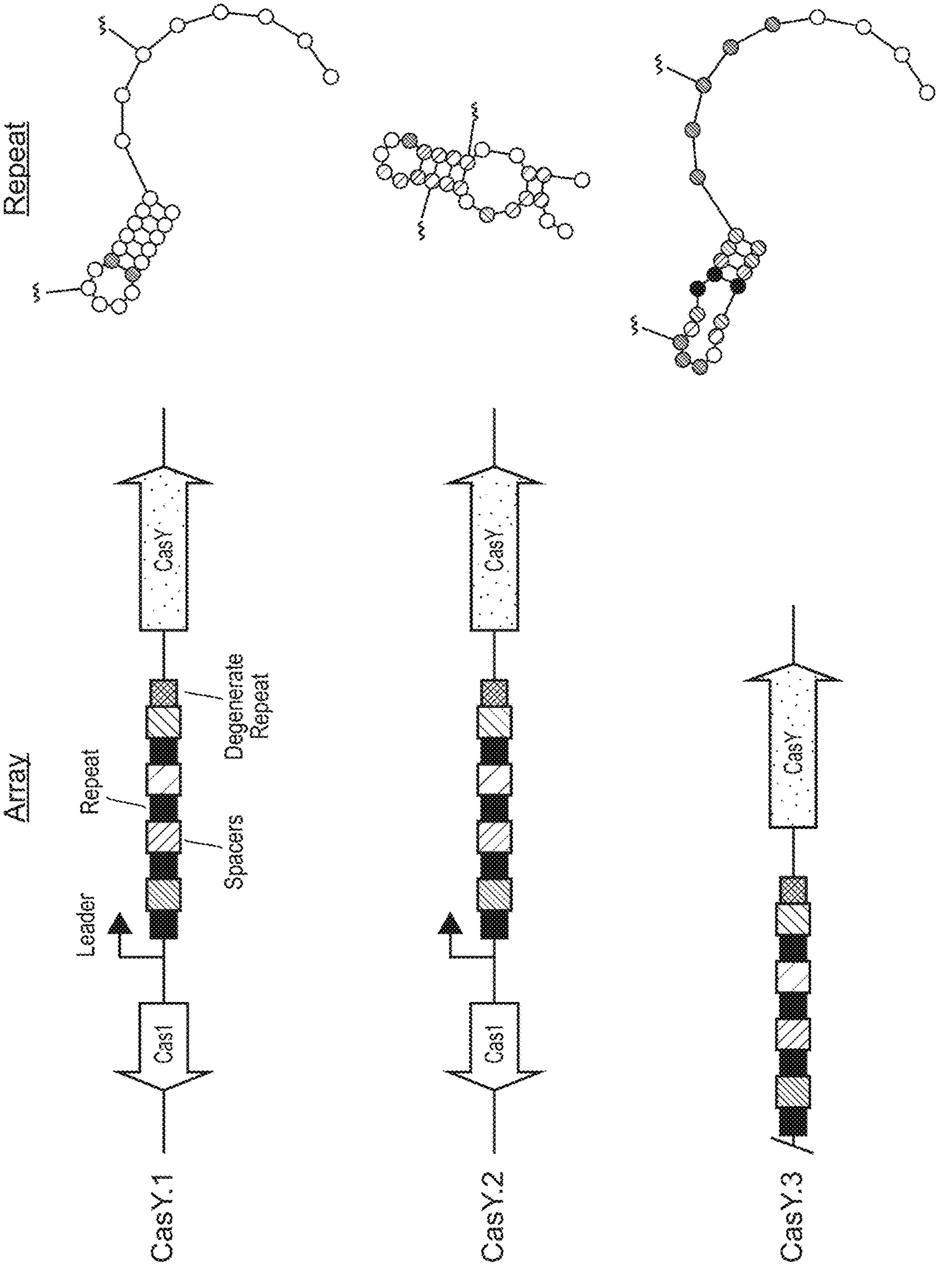
FIG. 4 depicts a schematic diagram of CasY and C2c3 loci. Interference proteins are shown in green, acquisition proteins in red. Repeats folded using RNA structure are shown to the right revealing a strong hairpin at the 5' end, suggesting self processing of the CRISPR array by CasY.
Figure 4B:
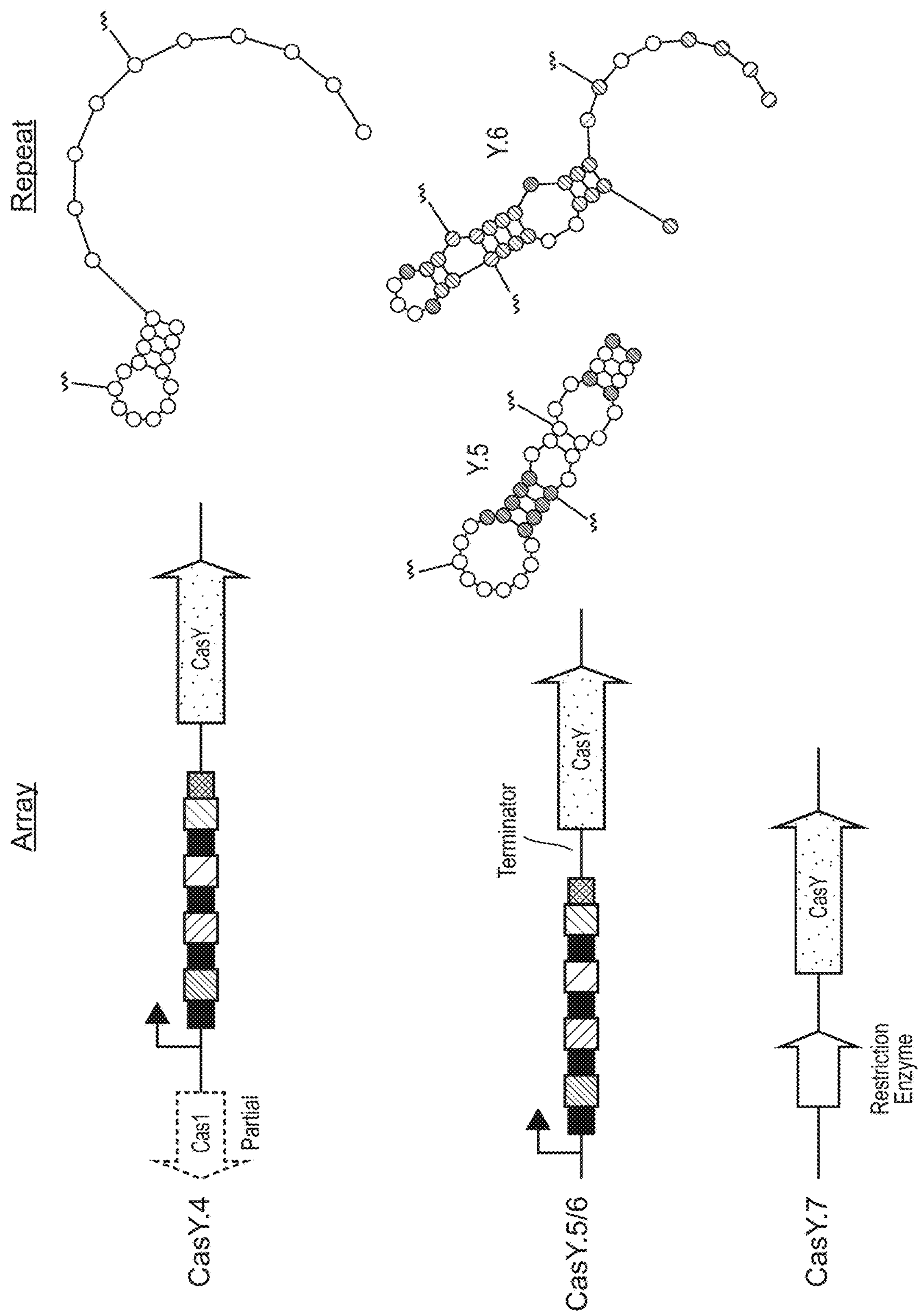
Figure 4C:
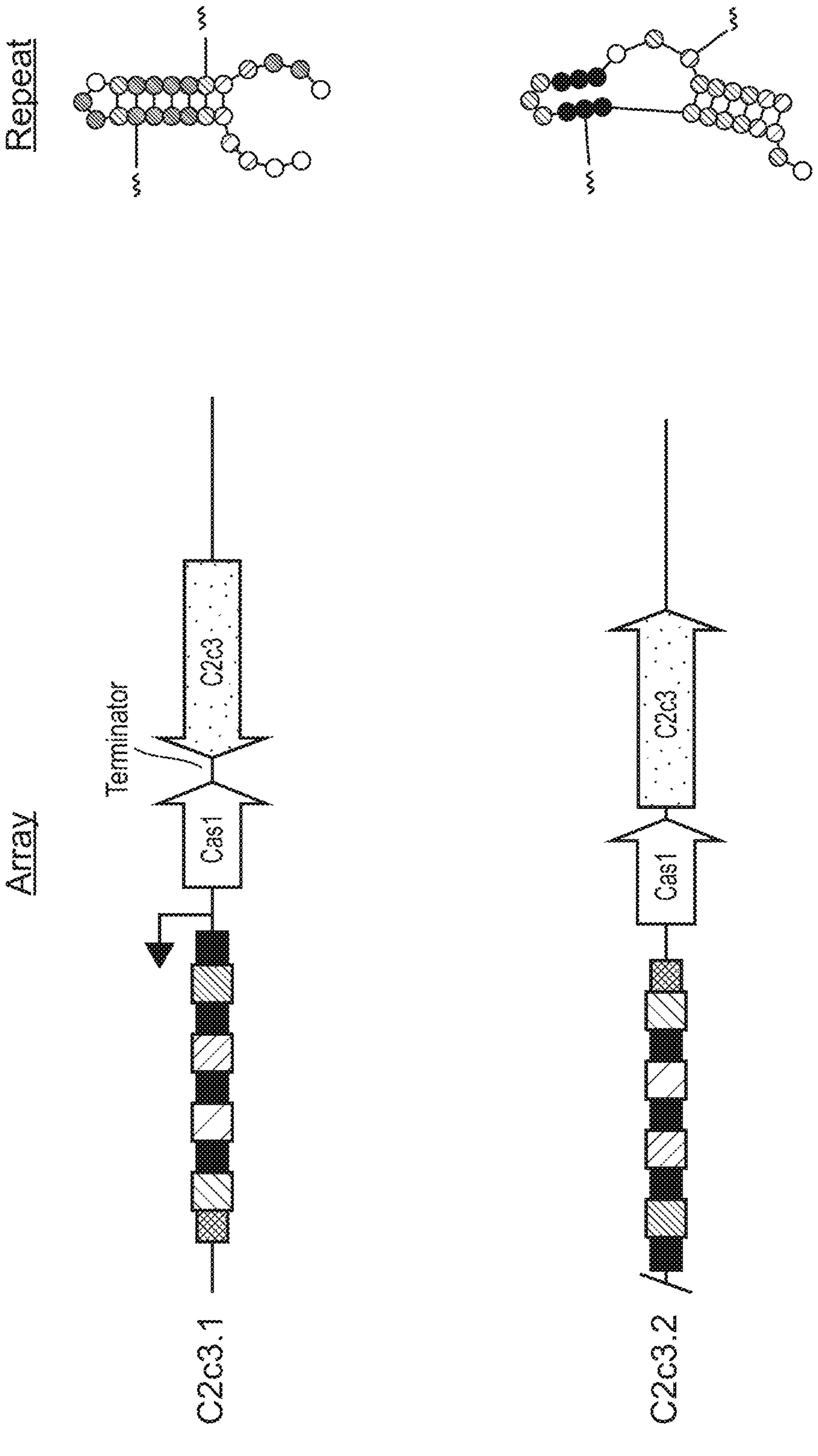

FIG. 4. Schematic diagram of Diagram of CasY and C2c3 loci. Interference proteins are shown in green, acquisition proteins in red. Repeats folded using RNA structure are shown to the right revealing a strong hairpin at the 5' end, suggesting self processing of the CRISPR array by CasY.

FIG. 5 (panels a-d) PAM dependent plasmid interference by CasY. (panel a) PAM depletion assays were conducted with CasY. *E. coli* containing the CasY CRISPR locus were transformed with a plasmid library with 7 nucleotides randomized 5' or 3' of the target sequence. The target plasmid was selected for and transformants were pooled. The randomized region was amplified and prepared for deep sequencing. Depleted sequences were identified and used to generate a PAM logo. (panel b) the generated PAM logo for CasY.1 showed a strong preference for sequences containing a 5'-TA-3' flanking sequence 5' of the target. A 3' PAM was not detected. (panel c) Four different PAMs were assayed directly to verify the PAM determined from the PAM depletion assay. (panel d) the generated PAM logos for CasY.2 showed a preference for sequences containing 5'-YR-3' and/or 5'-TR-3' (e.g., 5'-DTR-3') (lower threshold and higher threshold, respectively) flanking sequence 5' of the target (where Y is a T or C; R is an A or G; and D is an A, G, or T). A 3' PAM was not detected.

FIG. 6. (panel a) 'repeat' sequences from naturally occurring CasY guide RNAs (For CasY loci Y1-Y6). (panel b) Diagram of CasY RNA guided DNA cleavage. CasY protein binds to a crRNA (the CasY guide RNA) in the repeat region (black, repeat; red, spacer). Base pairing of the guide sequence of the guide RNA to the target sequence (blue) containing the correct protospacer adjacent motif (PAM) results in double stranded cleavage of the target DNA.

Example 3: New CRISPR-Cas Systems from Uncultivated Microbes

CRISPR-Cas adaptive immune systems have revolutionized genome engineering by providing programmable enzymes capable of site-specific DNA cleavage. However, current CRISPR-Cas technologies are based solely on systems from cultured bacteria, leaving untapped the vast majority of enzymes from organisms that have not been isolated. The data provide herein show, using cultivation-independent genome-resolved metagenomics, identification of new CRISPR-Cas systems, including the first reported Cas9 in the archaeal domain of life. This divergent Cas9 enzyme was found in little-studied nanoarchaea as part of an active CRISPR-Cas system. In bacteria, two previously unknown systems were discovered, CRISPR-CasX and CRISPR-CasY, which are among the most streamlined systems yet identified. Notably, all required functional components were identified by metagenomics, which allowed validation of robust RNA-guided DNA interference activity in *E. coli*. The data herein show that interrogation of environmental microbial communities combined with experiments in living cells allows access to an unprecedented diversity of genomes whose content will expand the repertoire of microbe-based biotechnologies.

Results

Figure 7:
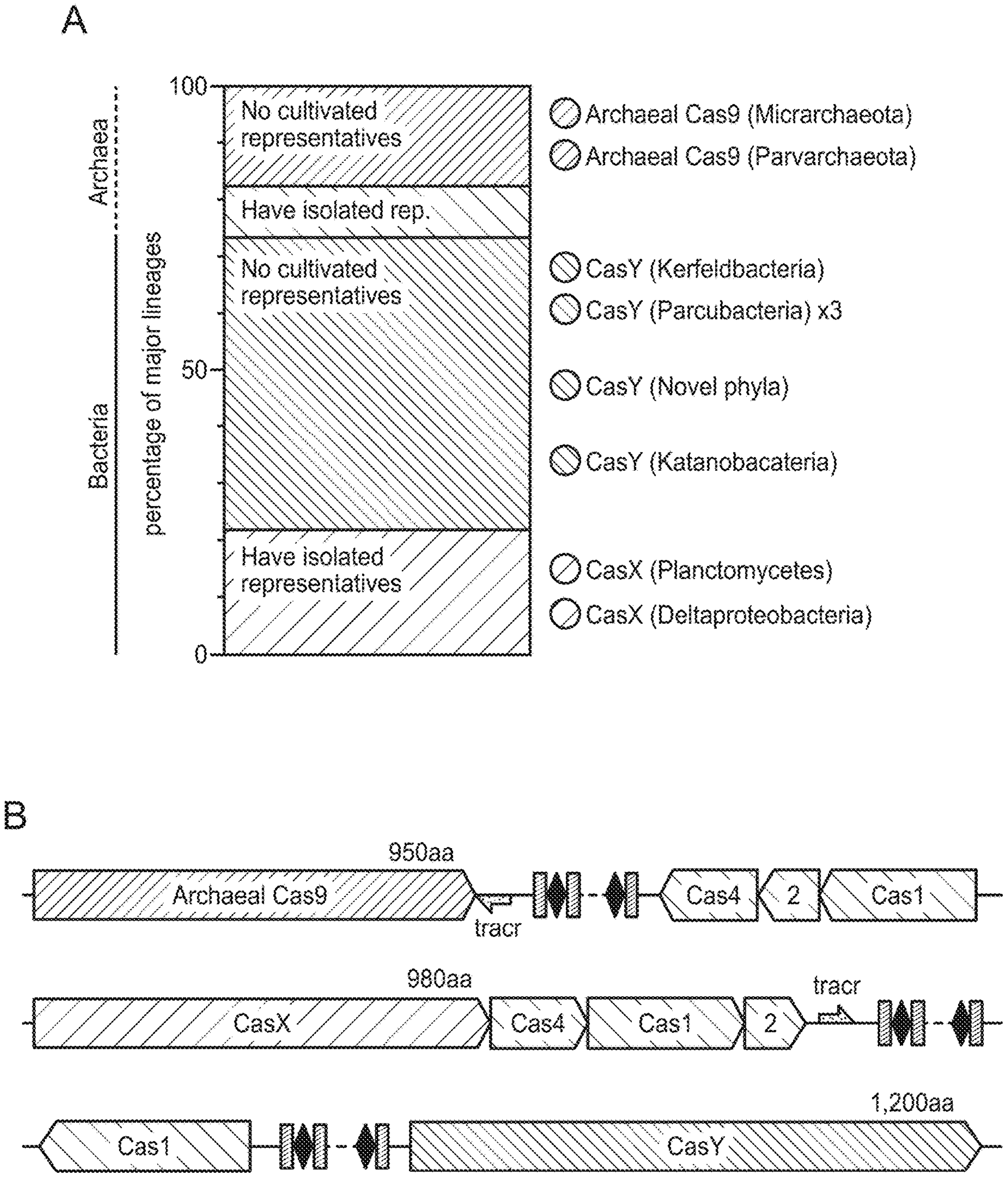
FIG. 7 (panels a-b) presents novel identified CRISPR-Cas systems from uncultivated organisms. a, Ratio of major lineages with and without isolated representatives in all bacteria and archaea, based on data of Hug et al.[32]. The results highlight the massive scale of as yet little investigated biology in these domains. Archaeal Cas9 and the novel CRISPR-CasY were found exclusively in lineages with no isolated representatives. b, Locus organization of the newly discovered CRISPR-Cas systems.

Terabase-scale metagenomic datasets from groundwater, sediment, and acid mine drainage microbial communities were analyzed, seeking class 2 CRISPR-Cas systems that are not represented among cultured organisms. The first Cas9 proteins in domain Archaea were identified and two new CRISPR-Cas systems were discovered, CRISPR-CasX and CRISPR-CasY, in uncultivated bacteria (FIG. 7). Notably, both the archaeal Cas9 and CasY were encoded exclusively in the genomes of organisms from lineages with no known isolated representatives.

First Identification of Archaeal Cas9

One of the hallmarks of CRISPR-Cas9 was its presumed presence only in the bacterial domain. It was therefore surprising to discover Cas9 proteins encoded in genomes of the nanoarchaea ARMAN-1 (*Candidatus* Micrarchaeum *acidiphilum* ARMAN-1) and ARMAN-4 (Candidatus *Parvarchaeum acidiphilum* ARMAN-4) in acid-mine drainage (AMD) metagenomic datasets. These findings expand the occurrence of Cas9-containing CRISPR systems to another domain of life.

The ARMAN-4 cas9 gene was found in 16 different samples in the same genomic context, but with no other adjacent cas genes (despite being centrally located in several DNA sequence contigs >25 kbp), and with only one adjacent CRISPR repeat-spacer unit (FIG. 13). The lack of a typical CRISPR array and cas1, which encodes the universal CRISPR integrase, points to a system with no capacity to acquire new spacers. No target could be identified for the spacer sequence, but given the conservation of the locus in samples collected over several years, its function in a "single-target" CRISPR-Cas system cannot be ruled out at this time.

Figure 8A:
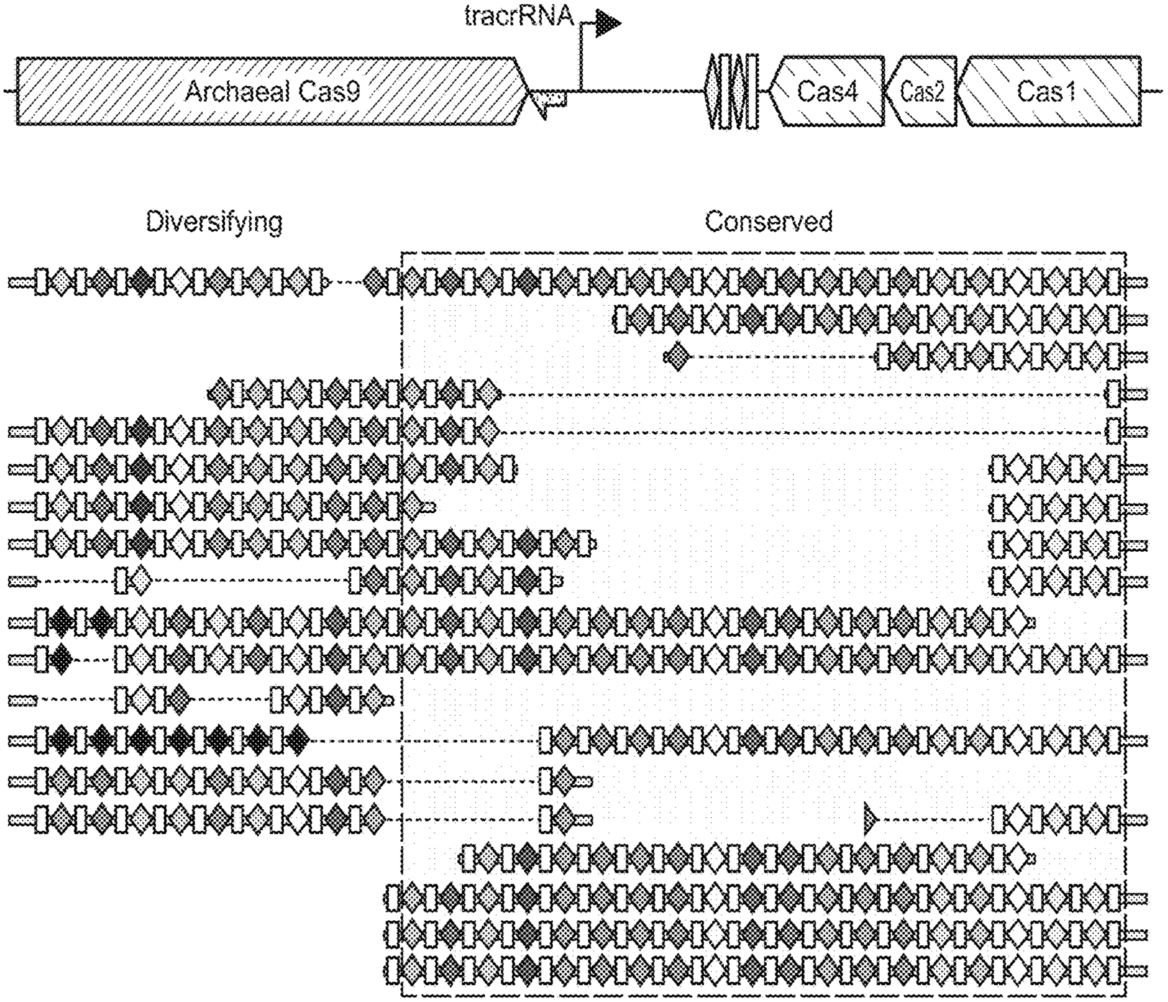
FIG. 8 (panels a-b) presents ARMAN-1 CRISPR array diversity and identification of the ARMAN-1 Cas9 PAM sequence. a, CRISPR arrays reconstructed from 15 different AMD samples. White boxes indicate repeats and colored diamonds indicate spacers (identical spacers are similarly colored; unique spacers are in black). The conserved region of the array is highlighted (on the right). The diversity of recently acquired spacers (on the left) indicates the system is active. An analysis that also includes CRISPR fragments from the read data is presented in FIG. 14. b, A single putative viral contig reconstructed from AMD metagenomic data contains 56 protospacers (red vertical bars) from the ARMAN-1 CRISPR arrays. c, Sequence analysis revealed a conserved 'NGG' PAM motif downstream of the protospacers on the non-target strand.

Conversely, the CRISPR-Cas locus in ARMAN-1, recovered from 15 different samples, includes large CRISPR arrays adjacent to cas1, cas2, cas4 and cas9 genes. Numerous alternative ARMAN-1 CRISPR arrays with a largely conserved end (likely comprised of the oldest spacers) and a variable region into which many distinct spacers have been incorporated were reconstructed (FIG. 8*a* and FIG. 14). Based on this hypervariability in spacer content, these data show that the ARMAN-1 CRISPR-Cas9 system is active in the sampled populations.

Figure 8B:
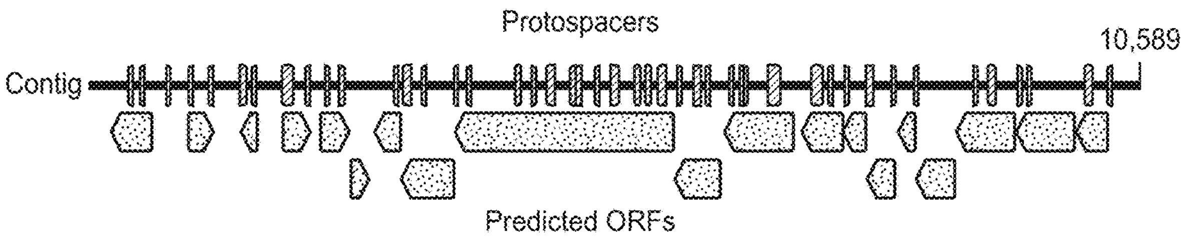

Remarkably, 56 of the putative spacer targets (protospacers) of the ARMAN-1 CRISPR-Cas9 system were located on a single 10 kbp genome fragment that is likely an ARMAN-1 virus, given that it encodes a high density of short hypothetical proteins (FIG. 8*b*). Indeed, cryo-electron tomographic reconstructions often identified viral particles attached to ARMAN cells. ARMAN-1 protospacers also derived from a putative transposon within the genome of ARMAN-2 (another nanoarchaeon) and a putative mobile element in the genomes of Thermoplasmatales archaea, including that of I-plasma from the same ecosystem (FIG. 15). Direct cytoplasmic "bridges" were observed between ARMAN and Thermoplasmatales cells, implying a close relationship between them. The ARMAN-1 CRISPR-Cas9 may thus defend against transposon propagation between these organisms, a role that is reminiscent of piRNA-mediated defense against transposition in the eukaryotic germ line.

Figure 8C:
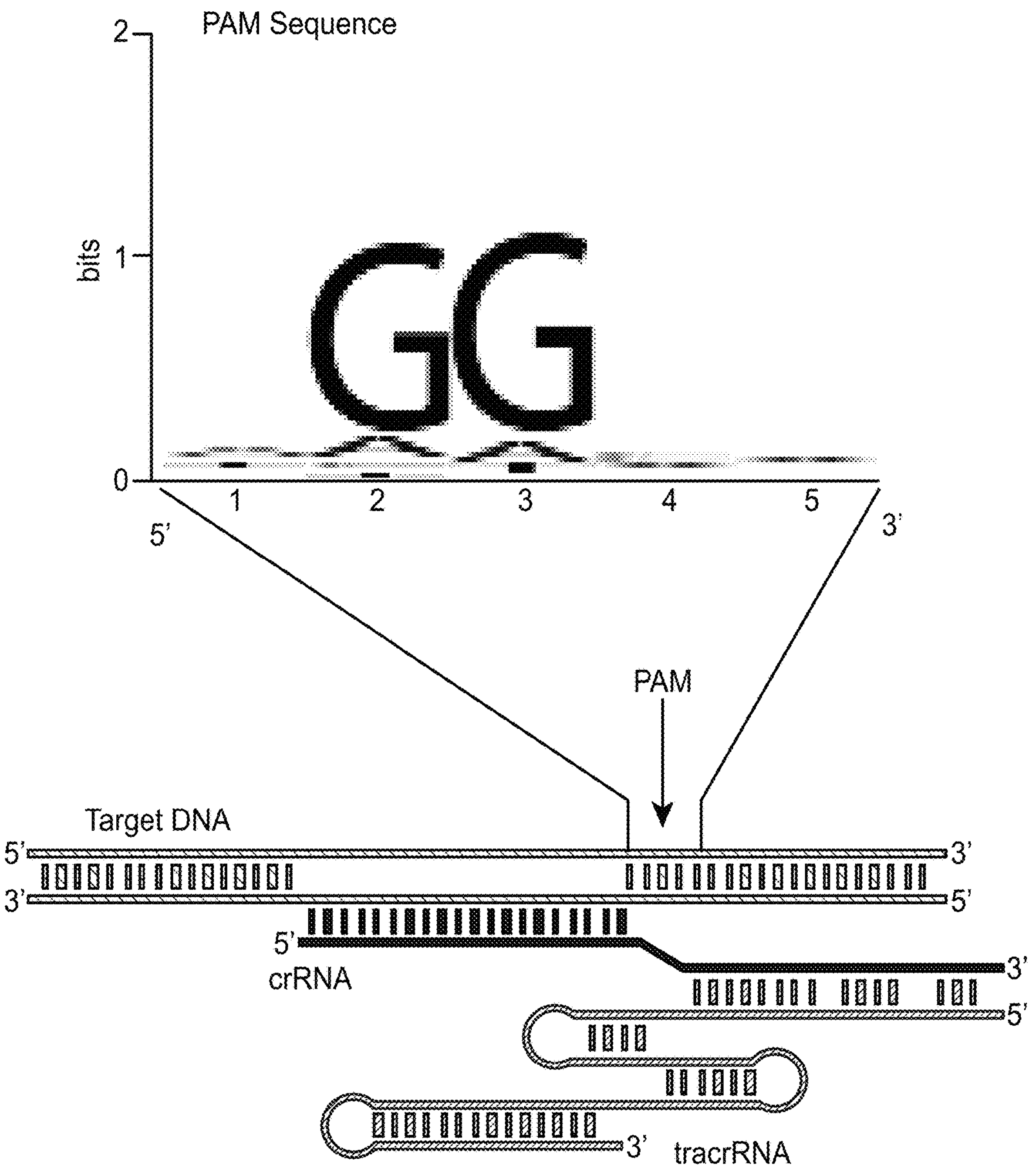

Active DNA-targeting CRISPR-Cas systems use 2 to 4 bp protospacer-adjacent motifs (PAMs) located next to target sequences for self versus non-self discrimination. Examining sequences adjacent to the genomic target sequences indeed revealed a strong 'NGG' PAM preference in ARMAN-1 (FIG. 8*c*). Cas9 also employs two separate transcripts, CRISPR RNA (crRNA) and trans-activating CRISPR RNA (tracrRNA), for RNA-guided DNA cleavage. A putative tracrRNA was identified in the vicinity of both ARMAN-1 and ARMAN-4 CRISPR-Cas9 systems (FIG. 16). Previously, it was suggested that type II CRISPR systems were absent in archaea due to a lack of the host factor, RNase III, responsible for crRNA-tracrRNA guide complex maturation. Notably, no RNase III homologs have been identified in the ARMAN-1 genome (estimated to be 95% complete) and no internal promoters are predicted for the CRISPR array, suggesting an as-yet undetermined mechanism of guide RNA production. Biochemical experiments to test cleavage activity of ARMAN-1 and ARMAN-4 Cas9 proteins purified from both *E. coli* and yeast and in vivo *E. coli* targeting assays did not reveal any detectable activity (see FIG. 21 and FIG. 17).

CRISPR-CasX is a New Dual-RNA-Guided CRISPR System

In addition to Cas9, only three families of class 2 Cas effector proteins have been discovered and experimentally validated: Cpf1, C2c1, and C2c2. Another gene, c2c3, which was identified only on small DNA fragments, has been suggested to also encode such a protein family. A new type of class 2 CRISPR-Cas system was found in the genomes of two bacteria recovered repeatedly from groundwater and sediment samples. The high conservation of this system in two organisms belonging to different phyla, Deltaproteobacteria and Planctomycetes, suggests a recent cross-phyla transfer. This newly described system includes Cas1, Cas2, Cas4 and an uncharacterized ~980 aa protein, referred to herein as CasX. The CRISPR arrays associated with each CasX had highly similar repeats of 37 base pairs, spacers of 33-34 base pairs, and a putative tracrRNA between the Cas operon and the CRISPR array (FIG. 7*b*). BLAST searches revealed only weak similarity (e-value $>1=10^{-4}$) to transposases, with similarity restricted to specific regions of the CasX C-terminus. Distant homology detection and protein modeling identified a RuvC domain near the CasX C-terminal end, with organization reminiscent of that found in type V CRISPR-Cas systems (FIG. 18). The rest of the CasX protein (630 N-terminal amino acids) showed no detectable similarity to any known protein, suggesting this is a novel class 2 effector. The combination of tracrRNA and separate Cas1, Cas2 and Cas4 proteins is unique among type V systems. Further, CasX is considerably smaller than any known type V proteins: 980 aa compared to a typical size of larger than 1,200 aa for Cpf1, C2c1 and C2c3.

Figure 9B:
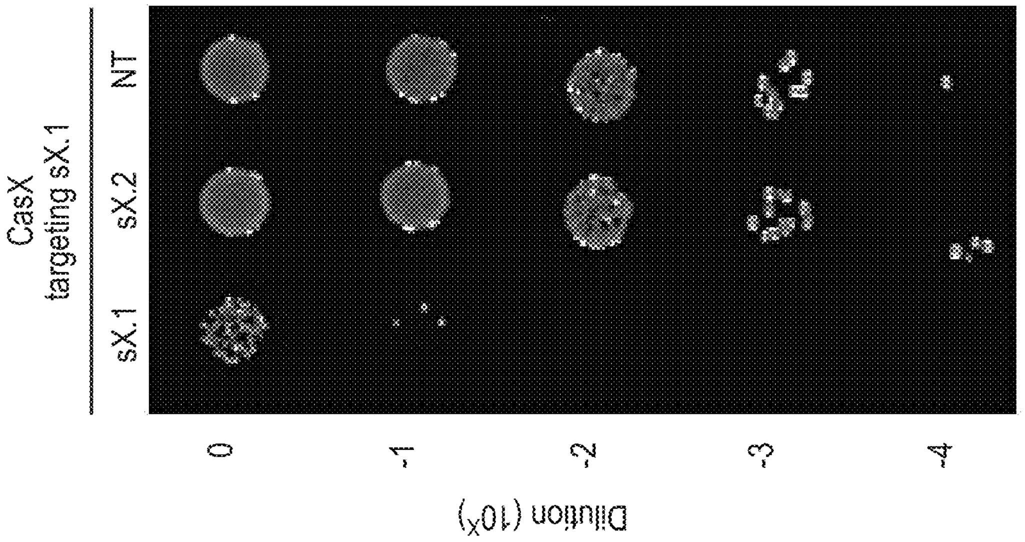
FIG. 9 (panels a-d) presents data showing that CasX mediates programmable DNA interference in *E. coli*. a, Diagram of CasX plasmid interference assays. *E. coli* expressing a minimal CasX locus is transformed with a plasmid containing a spacer matching the sequence in the CRISPR array (target) or plasmid containing a non-matching spacer (non-target). After being transformed, cultures are plated and colony forming units (cfu) quantified. b, Serial dilution of *E. coli* expressing the Planctomycetes CasX locus targeting spacer 1 (sX.1) and transformed with the specified target (sX1, CasX spacer 1; sX2, CasX spacer 2.
Figure 9A:
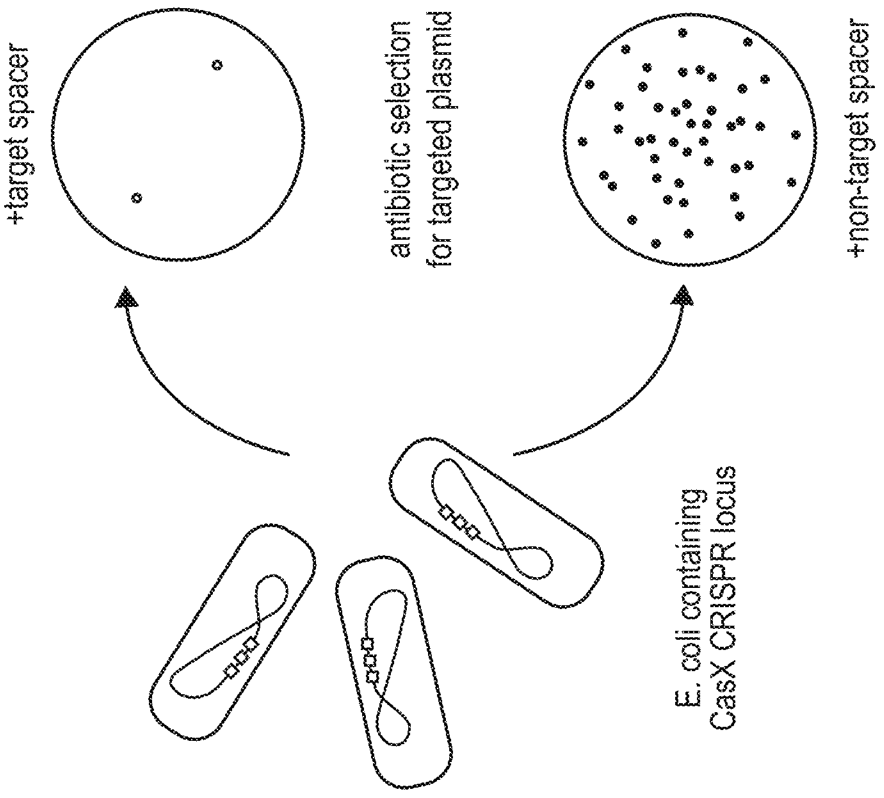
Figure 9C:
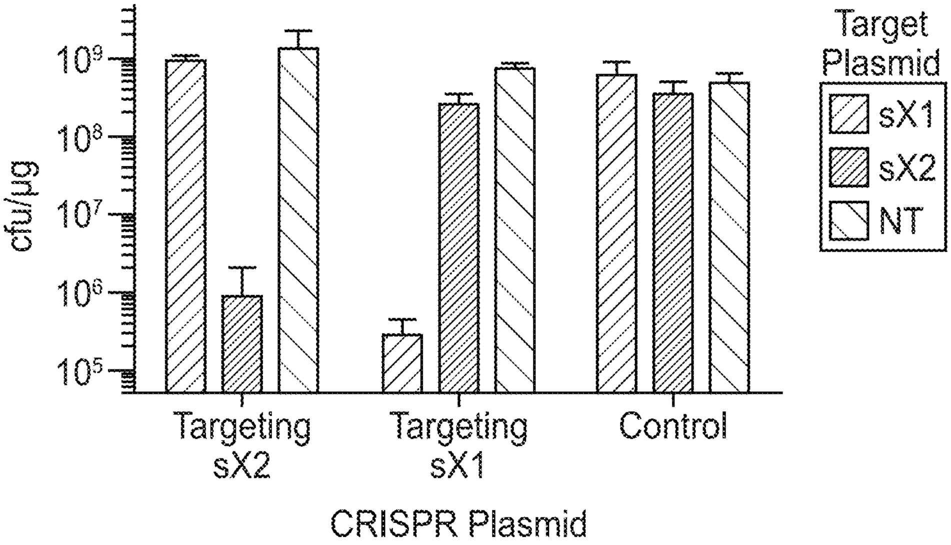
Figure 9D:
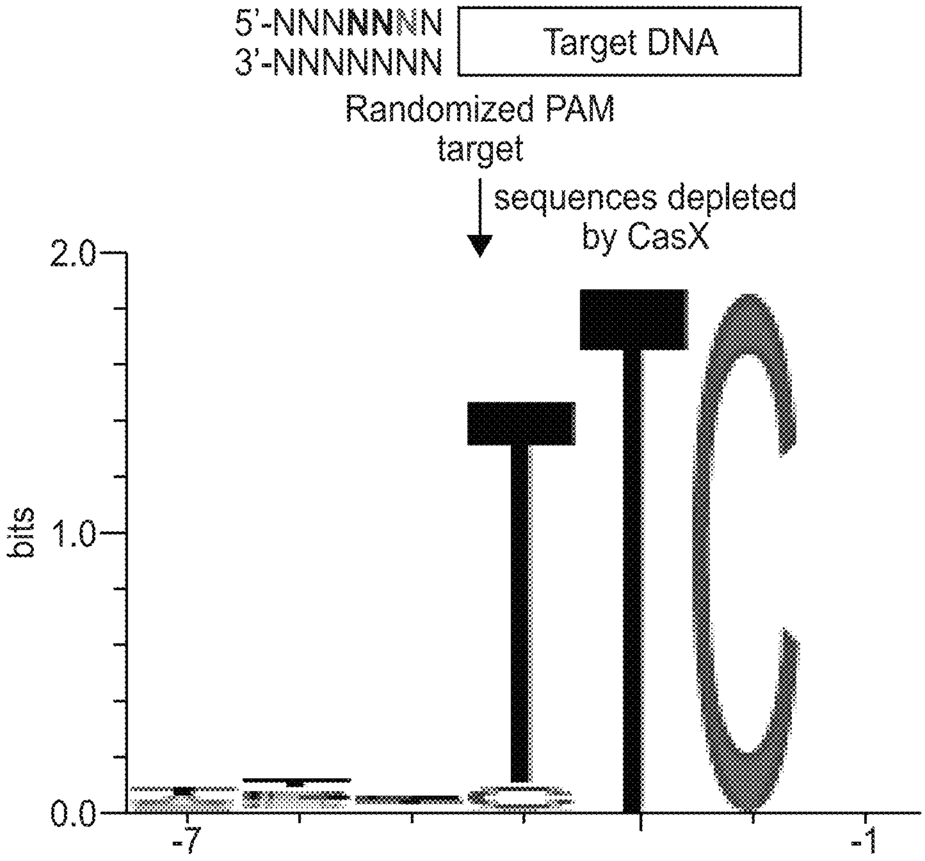

It was next wondered whether, despite its small size and non-canonical locus content, CasX would be capable of RNA-guided DNA targeting analogous to Cas9 and Cpf1 enzymes. To test this possibility, a plasmid encoding a minimal CRISPR-CasX locus including casX, a short repeat-spacer array and intervening noncoding regions was synthesized. When expressed in *E. coli*, this minimal locus blocked transformation by a plasmid bearing a target sequence identified by metagenomic analysis (FIG. 9*a-c*, FIG. 19). Furthermore, interference with transformation occurred only when the spacer sequence in the mini-locus matched the protospacer sequence in the plasmid target. To identify a PAM sequence for CasX, the transformation assay was repeated in *E. coli* using a plasmid containing either a 5' or 3' randomized sequence adjacent to the target site. This analysis revealed a stringent preference for the sequence 'TTCN' located immediately 5' of the protospacer sequence (FIG. 9*d*). No 3' PAM preference was observed (FIG. 19). Consistent with this finding, 'TTCA' was the sequence found upstream of the putative Deltaproteobacteria CRISPR-CasX protospacer that was identified in the environmental samples. Notably, both CRISPR-CasX loci share the same PAM sequence, in line with their high degree of CasX protein homology.

Examples of both single-RNA and dual-RNA guided systems exist among type V CRISPR loci. Environmental meta-transcriptomic data was used to determine whether CasX requires a tracrRNA for DNA targeting activity. This analysis revealed a non-coding RNA transcript with a sequence complementary to the CRISPR repeat encoded between the Cas2 open reading frame and the CRISPR array (FIG. 10*a*). Transcriptomic mapping further suggests that the CRISPR RNA (crRNA) is processed to include 22 nts of the repeat and 20 nts of the adjacent spacer, similar to the crRNA processing that occurs in CRISPR-Cas9 systems (FIG. 10*a*). Furthermore, a 2-nt 3' overhang was identified, consistem with RNase III-mediated processing of the crRNA-tracrRNA duplex (FIG. 10*b*). To determine the dependence of CasX activity on the putative tracrRNA, this region was deleted from the minimal CRISPR-CasX locus described above, and repeated the plasmid interference assays. Deletion of the putative tracrRNA-encoding sequence from the CasX plasmid abolished the robust transformation interference observed in its presence (FIG. 10*c*). Together, these results establish CasX as a new functional DNA-targeting, dual-RNA guided CRISPR enzyme.

CRISPR-CasY, a System Found Exclusively in Bacterial Lineages Lacking Isolates

Figure 11A:
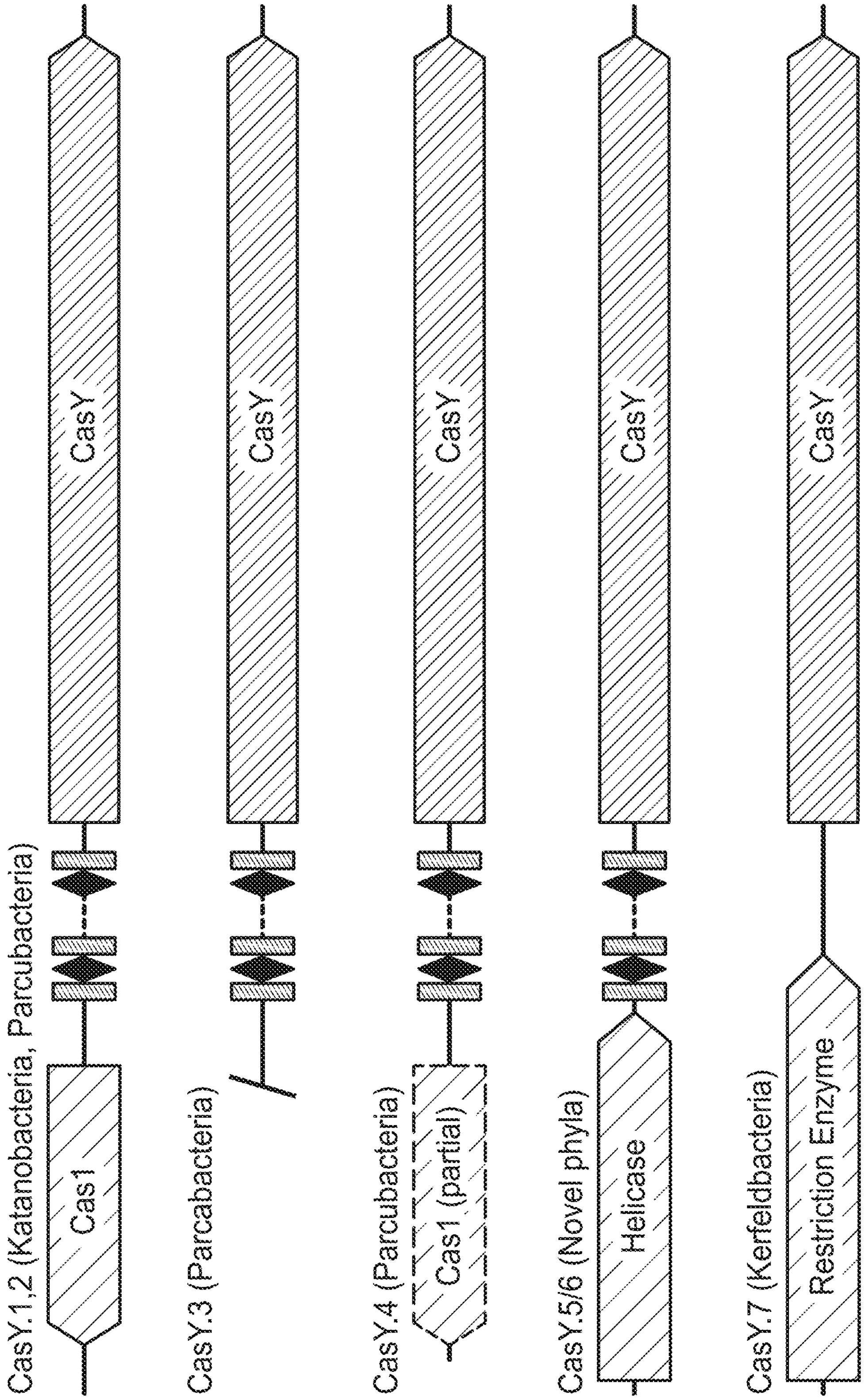

Another new class 2 Cas protein encoded in the genomes of certain candidate phyla radiation (CPR) bacteria was identified. These bacteria typically have small cell sizes (based on cryo-TEM data and enrichment via filtration), very small genomes and a limited biosynthetic capacity, indicating they are most likely symbionts. The new ~1,200 aa Cas protein, referred to herein as CasY, appears to be part of a minimal CRISPR-Cas system that includes, at most, Cas1 and a CRISPR array (FIG. 11*a*). Most of the CRISPR arrays have unusually short spacers of 17-19 nts, but one system, which lacks Cas1 (CasY.5), has longer spacers (27-29 nts). The six examples of CasY proteins identified had no significant sequence similarity to any protein in public databases. A sensitive search using profile models (HMMs) built from published Cas proteins[3,4] indicated that four of the six CasY proteins had local similarities (e-values $4\times10^{-11}$-$3\times10^{-18}$) to C2c3 in the C-terminal region overlapping the RuvC domains and a small region (~45 aa) of the N-terminus (see FIG. 18). C2c3 are putative type V Cas effectors that were identified on short contigs with no taxonomic affiliation, and have not been validated experimentally. Like CasY, the C2c3 were found next to arrays with short spacers and Cas1, but with no other Cas proteins. Notably, two of the CasY proteins identified in the current study had no significant similarity to C2c3, despite sharing significant sequence similarity (best Blast hits: e-values $6\times10^{-85}$, $7\times10^{75}$) with the other CasY proteins.

Figure 11B:
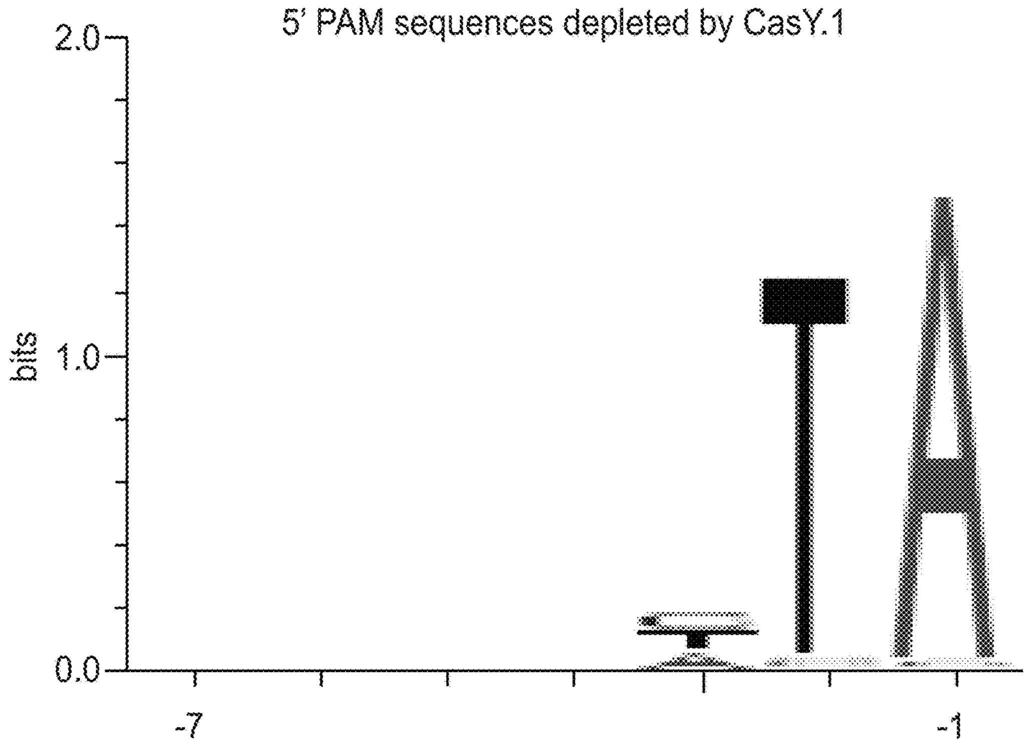
Figure 11C:
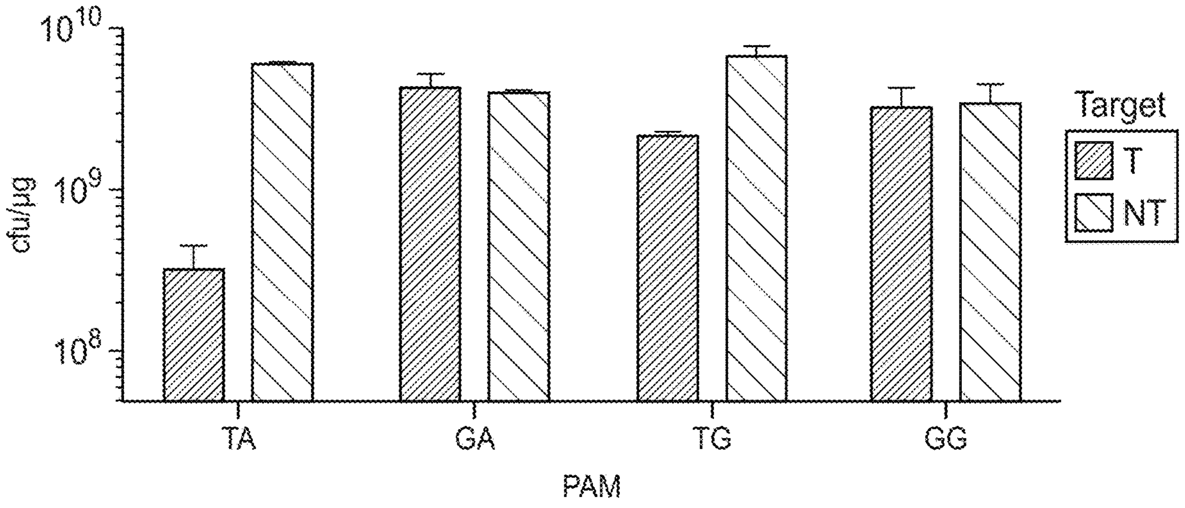

Given the low homology of CRISPR-CasY to any experimentally validated CRISPR loci, it was next wondered whether this system confers RNA-guided DNA interference, but due to the short spacer length reliable information did not exist about a possible PAM motif that might be required for such activity. To work around this, the entire CRISPR-CasY.1 locus was synthesized with a shortened CRISPR array and introduced into *E. coli* on a plasmid vector. These cells were then challenged in a transformation assay using a target plasmid with a sequence matching a spacer sequence in the array and containing an adjacent randomized 5' or 3' region to identify a possible PAM. Analysis of transformants revealed depletion of sequences containing a 5' TA directly adjacent to the targeted sequence (FIG. 11*b*). Using this identified PAM sequence, the CasY.1 locus was tested against plasmids containing a single PAM. Plasmid interference was demonstrated only in the presence of a target containing the identified 5' TA PAM sequence (FIG. 11*c*). Thus, these data show that CRISPR-CasY has DNA interference activity.

Discussion

New class 2 CRISPR-Cas adaptive immune systems in genomes from uncultivated bacteria and archaea were identified and characterized. Evolutionary analysis of Cas1 (FIG. 12*a*), which is universal to active CRISPR loci, suggested that the archaeal Cas9 system described here does not clearly fall into any existing type II subtype. The Cas1 phylogeny (as well as the existence of cas4) clustered it together with type II-B systems, yet the sequence of Cas9 was more similar to type II-C proteins (FIG. 20). Thus, the archaeal type II system may have arisen as a fusion of type II-C and II-B systems (FIG. 12*b*). Likewise, Cas1 phylogenetic analyses indicated that the Cas1 from the CRISPR-CasX system is distant from any other known type V system. Type V systems have been suggested to be the result of the fusion of a transposon with the adaptation module (Cas1-Cas2) from an ancestral type I system. It is therefore hypothesized that the CRISPR-CasX system emerged following a fusion event different from those that gave rise to the previously described type V systems. Strikingly, both CRISPR-CasY and the putative C2c3 systems seem to lack Cas2, a protein thought to be essential for integrating DNA into the CRISPR locus. Given that all CRISPR-Cas systems are thought be descendants of an ancestral type I system that contained both Cas1 and Cas2, CRISPR-CasY and C2c3 systems may either have different ancestry than the rest of the CRISPR-Cas systems, or alternatively, Cas2 might have been lost during their evolutionary history.

The discovery described herein of Cas9 in archaea and two previously unknown CRISPR-Cas systems in bacteria used extensive DNA and RNA sequence datasets obtained from complex natural microbial communities. In the case of CasX and CasY, genome context was critical to prediction of functions that would not have been evident from unassembled sequence information. Further, the identification of a putative tracrRNA as well as targeted viral sequences uncovered through analysis of the metagenomic data guided functional testing. Interestingly, some of the most compact CRISPR-Cas loci identified to date were discovered in organisms with very small genomes. A consequence of small genome size is that these organisms likely depend on other community members for basic metabolic requirements, and thus they have remained largely outside the scope of traditional cultivation-based methods. The limited number of proteins that are required for interference make these minimal systems especially valuable for the development of new genome editing tools. Importantly, it is shown herein that metagenomic discoveries related to CRISPR-Cas systems are not restricted to in silico observations, but can be introduced into an experimental setting where their function can be tested. Given that virtually all environments where life exists can now be probed by genome-resolved metagenomic methods, it is anticipated that the combined computational-experimental approach described herein will greatly expand the diversity of known CRISPR-Cas systems, providing new technologies for biological research and clinical applications.

Methods

Metagenomics and Metatranscriptomics

Metagenomic samples from three different sites were analyzed: (1) Acid mine drainage (AMD) samples collected between 2006 and 2010 from the Richmond Mine, Iron Mountain, Calif. (2) Groundwater and sediment samples collected between 2007 and 2013 from the Rifle Integrated Field Research (IFRC) site, adjacent to the Colorado River near Rifle, Colo. (3) Groundwater collected in 2009 and 2014 from Crystal Geyser, a cold, $CO_2$-driven geyser on the Colorado Plateau in Utah.

For the AMD data, DNA extraction methods and short read sequencing were reported by Denef and Banfield (2012) and Miller et al. (2011). For the Rifle data, DNA and RNA extraction, as well as sequencing, assembly, and genomic reconstructed were described by Anantharaman et al. (2016) and Brown et al. (2015). For samples from Crystal Geyser, methods follow those described by Probst et al (2016) and Emerson et al. (2015). Briefly, DNA was extracted from samples using the PowerSoil DNA Isolation Kit (MoBio Laboratories Inc., Carlsbad, Calif., USA). RNA was extracted from 0.2 m filters collected from six 2011 Rifle groundwater samples, as described by Brown et al. (2015). DNA was sequenced on Illumina HiSeq2000 platform, and Metatranscriptomic cDNA on 5500XL SOLiD platform. For the newly reported Crystal Geyser data and reanalysis of the AMD data, sequences were assembled using IDBA-UD. DNA and RNA (cDNA) read-mapping used to determine sequencing coverage and gene expression, respectively, was performed using Bowtie2. Open reading frames (ORFs) were predicted on assembled scaffolds using Prodigal. Scaffolds from the Crystal Geyser dataset were binned on the basis of differential coverage abundance patterns using a combination of ABAWACA, ABAWACA2 (https:(double forward slash)github.com/CK7) Maxbin2, and tetranucleotide frequency using Emergent Self-Organizing Maps (ESOM). Genomes were manually curated using % GC content, taxonomic affiliation, and genome completeness. Scaffolding errors were corrected using ra2.py (https:(double forward slash)github.com/christophertbrown).

CRISPR-Cas Computation Analysis

The assembled contigs from the various samples were scanned for known Cas proteins using Hidden Markov Model (HMMs) profiles, which were built using the HMMer suite, based on alignments from Makarova et al. and Shmakov et al. CRISPR arrays were identified using a local version of the CrisprFinder software. Loci that contained both Cas1 and a CRISPR array were further analyzed if one of the ten ORFs adjacent to the cas1 gene encoded for an uncharacterized protein larger than 800 aa, and no known cas interference genes were identified on the same contig. These large proteins were further analyzed as potential class 2 Cas effectors. The potential effectors were clustered to protein families based on sequence similarities using MCL. These protein families were expanded by building HMMs representing each of these families, and using them to search the metagenomic datasets for similar Cas proteins. To make sure that the protein families are indeed new, known homologs were searched using BLAST against NCBI's non-redundant (nr) and metagenomic (env_nr) protein databases, as well as HMM searches against the UniProt KnowledegeBase. Only proteins with no full-length hits (>25% of the protein's length) were considered novel proteins. Distant homology searches of the putative Cas proteins were performed using HHpred from the HH-suite. High scoring HHpred hits were used to infer domain architecture based on comparison to resolved crystal structures, and secondary structure that was predicted by JPred4. The HMM database, including the newly discovered Cas proteins are available in Supplementary Data 1.

Spacer sequences were determined from the assembled data using CrisprFinder. CRASS was used to locate additional spacers in short DNA reads of the relevant samples. Spacer targets (protospacers) were then identified by BLAST searches (using "-task blastn-short") against the relevant metagenomic assemblies for hits with <1 mismatch to spacers. Hits belonging to contigs that contained an associated repeat were filtered out (to avoid identifying CRISPR arrays as protospacers). Protospacer adjacent motifs (PAMs) were identified by aligning regions flanking the protospacers and visualized using WebLogo. RNA structures were predicted using mFold. CRISPR array diversity was analyzed by manually aligning spacers, repeats and flanking sequences from the assembled data. Manual alignments and contig visualizations were performed with Geneious 9.1.

For the phylogenetic analyses of Cas1 and Cas9 proteins of the newly identified systems were used along with the proteins from Makarova et al. and Shmakov et al. A non-redundant set was compiled by clustering together proteins with >90% identity using CD-HIT. Alignments were produced with MAFFT, and maximum-likelihood phylogenies were constructed using RAxML with PROTGAMMALG as the substitution model and 100 bootstrap samplings. Cas1 tree were rooted using the branch leading to casposons. Trees were visualized using FigTree 1.4.1 (http:(double forward slash)tree.bio.ed.ac.uk/sofward/figtree/).

Generation of Heterologous Plasmids

Metagenomic contigs were made into minimal CRISPR interference plasmids by removing proteins associated with acquisition for CasX and reducing the size of the CRISPR array for both CasX and CasY. The minimal locus was synthesized as Gblocks (Integrated DNA Technology) and assembled using Gibson Assembly.

PAM Depletion Assay

PAM depletion assays were conducted as previously described with modification.

Plasmid libraries containing randomized PAM sequences were assembled by annealing a DNA oligonucleotide containing a target with a 7 nt randomized PAM region with a primer and extended with Klenow Fragment (NEB). The double stranded DNA was digested with EcoRI and NcoI and ligated into a pUC19 backbone. The ligated library was transformed into DH5a and $>10^8$ cells were harvested and the plasmids extracted and purified. 200 ng of the pooled library was transformed into electrocompetent *E. coli* harboring a CRISPR locus or a control plasmid with no locus. The transformed cells were plated on selective media containing carbenicillin (100 mg $L^{-1}$) and chloramphenicol (30 mg $L^{-1}$) for 30 hours at 25° C. Plasmid DNA was extracted and the PAM sequence was amplified with adapters for Illumina sequencing. The 7 nt PAM region was extracted and PAM frequencies calculated for each 7 nt sequence. PAM sequences depleted above the specified threshold were used to generate a WebLogo.

Plasmid Interference

Putative targets identified from metagenomic sequence analysis or PAM depletion assays were cloned into a pUC19 plasmid. 10 ng of target plasmid were transformed into electrocompetent *E. coli* (NEB Stable) containing the CRISPR loci plasmid. Cells were recovered for 2 hrs at 25° C. and an appropriate dilution was plated on selective media. Plates were incubated at 25° C. and colony forming units were counted. All plasmid interference experiments were performed in triplicate and electrocompetent cells were prepared independently for each replicate.

ARMAN-Cas9 Protein Expression and Purification

Expression constructs for Cas9 from ARMAN-1 (AR1) and ARMAN-4 (AR4) were assembled from gBlocks (Integrated DNA Technologies) that were codon-optimized for *E. coli*. The assembled genes were cloned into a pET-based expression vector as an N-terminal $His_6$-MBP or $His_6$ fusion protein. Expression vectors were transformed into BL21 (DE3) *E. coli* cells and grown in LB broth at 37° C. For protein expression, cells were induced during mid-log phase with 0.4 mM IPTG (isopropyl β-D-1-thiogalactopyranoside) and incubated overnight at 16° C. All subsequent steps were conducted at 4° C. Cell pellets were resuspended in lysis buffer (50 mM Tris-HCl pH 8, 500 mM NaCl, 1 mM TCEP, 10 mM Imidazole) 0.5% Triton X-100 and supplemented with Complete protease inhibitor mixture (Roche) before lysis by sonication. Lysate was clarified by centrifugation at 15000 g for 40 min and applied to Superflow Ni-NTA agarose (Qiagen) in batch. The resin was washed with extensively with Wash Buffer A (50 mM Tris-HCl pH 8, 500 mM NaCl, 1 mM TCEP, 10 mM Imidazole) followed by 5 column volumes of Wash Buffer B (50 mM Tris-HCl pH 8, 1M NaCl, 1 mM TCEP, 10 mM Imidazole). Protein was eluted off of Ni-NTA resin with Elution Buffer (50 mM Tris-HCl pH 8, 500 mM NaCl, 1 mM TCEP, 300 mM Imidazole). The $His_6$-MBP tag was removed by TEV protease during overnight dialysis against Wash Buffer A. Cleaved Cas9 was removed from the affinity tag through a second Ni-NTA agarose column. The protein was dialyzed into IEX Buffer A (50 mM Tris-HCl pH 7.5, 300 mM NaCl, 1 mM TCEP, 5% glycerol) before application to a 5 mL Heparin HiTrap column (GE Life Sciences). Cas9 was eluted over a linear NaCl (0.3-1.5 M) gradient. Fractions were pooled and concentrated with a 30 kDa spin concentrator (Thermo Fisher). When applicable, Cas9 was further purified via size-exclusion chromatography on an Superdex 200 pg column (GE Life Sciences) and stored in IEX Buffer A for subsequent cleavage assays. For yeast expression, AR1-Cas9 was cloned into a Gall/10 His6-MBP TEV Ura *S. cerevisiae* expression vector (Addgene plasmid #48305). The vector was transformed into a BY4741 URA3 strain and cultures were grown in MEDIA at 30° C. At an OD600 of ~0.6, protein expression was induced with 2% w/v galactose and incubated overnight at 16° C. Protein purification was performed as above.

RNA In Vitro Transcription and Oligonucleotide Purification

In vitro transcription reactions were performed as previously described[65] using synthetic DNA templates containing a T7 promoter sequence. All in vitro transcribed guide RNAs and target RNAs or DNAs were purified via denaturing PAGE. Double-stranded target RNAs and DNAs were hybridized in 20 mM Tris HCl pH 7.5 and 100 mM NaCl by incubation at 95° C. for 1 min, followed by slow-cooling to room temperature. Hybrids were purified by native PAGE.

In Vitro Cleavage Assays

Purified DNA and RNA oligonucleotides were radiolabeled using T4 polynucleotide kinase (NEB) and [γ-32P] ATP (Perkin-Elmer) in 1×PNK buffer for 30 min at 37° C. PNK was heat inactivated at 65° C. for 20 min and free ATP was removed from the labeling reactions using illustra Microspin G-25 columns (GE Life Sciences). CrRNA and tracrRNAs were mixed in equimolar quantities in 1× refolding buffer (50 mM Tris HCl pH 7.5, 300 mM NaCl, 1 mM TCEP, 5% glycerol) and incubated at 70° C. for 5 min and then slow-cooled to room temperature. The reactions were supplemented to 1 mM final metal concentration and subsequently heated at 50° C. for 5 min. After slow-cooling to room temperature, refolded guides were placed on ice. Unless noted for buffer, salt concentration, Cas9 was reconstituted with an equimolar amount of guide in 1× cleavage buffer (50 mM Tris HCl pH 7.5, 300 mM NaCl, 1 mM TCEP, 5% glycerol, 5 mM divalent metal) at 37° C. for 10 min. Cleavage reactions were conducted in 1× cleavage buffer with a 10× excess of Cas9-guide complex over radiolabeled target at 37° C. or the indicated temperature. Reactions were quenched in an equal volume of gel loading buffer supplemented with 50 mM EDTA. Cleavage products were resolved on 10% denaturing PAGE and visualized by phosphorimaging.

In Vivo *E. coli* Interference Assays

*E. coli* transformation assays for AR1- and AR4-Cas9 were conducted as previously published[66]. Briefly, *E. coli* transformed with guide RNAs were made electrocompetent. Cells were then transformed with 9 fmol of plasmid encoding wild-type or catalytically inactive Cas9 (dCas9). A dilution series of recovered cells was plated on LB plates with selective antibiotics. Colonies were counted after 16 hr at 37° C.

TABLE 1

Details regarding the organisms and genomic location in which the CRISPR-Cas system were identified, as well as information on the number and average length of reconstructed spacers, and repeats length (NA, not available). ARMAN-1 spacers were reconstructed from 16 samples.

| Taxonomic group | Cas effector | NCBI Accession | Coordinates | Repeat length | # spacers | Spacers avg. length |
|---|---|---|---|---|---|---|
| ARMAN-1 | Cas9 | MOEG01000017 | 1827 . . . 7130 | 36 | 271 | 34.5 |
| ARMAN-4 | Cas9 | KY040241 | 11779 . . . 14900 | 36 | 1 | 36 |
| Deltaproteobacteria | CasX | MGPG01000094 | 4319 . . . 9866 | 37 | 5 | 33.6 |
| Planctomycetes | CasX | MHYZ01000150 | 1 . . . 5586 | 37 | 7 | 32.3 |
| *Candidatus* Katanobacteria | CasY.1 | MOEH01000029 | 459 . . . 5716 | 26 | 14 | 17.1 |
| *Candidatus* Vogelbacteria | CasY.2 | MOEJ01000028 | 7322 . . . 13087 | 26 | 18 | 17.3 |
| *Candidatus* Vogelbacteria | CasY.3 | MOEK01000006 | 1 . . . 4657 | 26 | 12 | 17.3 |
| *Candidatus* Parcubacteria | CasY.4 | KY040242 | 1 . . . 5193 | 25 | 13 | 18.4 |
| *Candidatus* Komeilibacteria | CasY.5 | MOEI01000022 | 2802 . . . 7242 | 36 | 8 | 26 |
| *Candidatus* Kerfeldbacteria | CasY.6 | MHKD01000036 | 11503 . . . 15366 | NA | NA | NA |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising:

a) a CasY fusion polypeptide, or a nucleic acid molecule encoding the CasY fusion polypeptide, wherein the CasY fusion polypeptide comprises a CasY polypeptide fused to a heterologous polypeptide, and wherein the CasY polypeptide comprises an amino acid sequence having 50% or more identity to the amino acid sequence set forth in SEQ ID NO:1 or SEQ ID NO:2; and b) a CasY guide RNA, or one or more DNA molecules encoding the CasY guide RNA.

2. The composition of claim 1, wherein the CasY polypeptide comprises an amino acid sequence having 80% or more identity to the amino acid sequence set forth in SEQ ID NO:1 or SEQ ID NO:2.

3. The composition of claim 1, wherein the heterologous polypeptide is a nuclear localization signal.

4. The composition of claim 1, comprising one or more of: a buffer, a nuclease inhibitor, a lipid, and a protease inhibitor.

5. The composition of claim 1, wherein the CasY polypeptide is a catalytically inactive CasY Polypeptide (dCasY).

6. The composition of claim 5, wherein the CasY polypeptide comprises one or more mutations at a position corresponding to those selected from: D828, E914, and D1074 of SEQ ID NO: 1.

7. The composition of claim 1, further comprising a DNA donor template.

8. A CasY fusion polypeptide comprising: a CasY polypeptide fused to a heterologous polypeptide, wherein the CasY polypeptide comprises an amino acid sequence having 50% or more identity to the amino acid sequence set forth in SEQ ID NO:1 or SEQ ID NO:2.

9. The CasY fusion polypeptide of claim 8, wherein the CasY polypeptide comprises an amino acid sequence having 59% 80% or more identity to the amino acid sequence set forth in SEQ ID NO:1 or SEQ ID NO:2.

10. The CasY fusion polypeptide of claim 8, wherein the CasY polypeptide is a catalytically inactive CasY Polypeptide (dCasY).

11. The CasY fusion polypeptide of claim 10, wherein the CasY polypeptide comprises one or more mutations at a position corresponding to those selected from: D828, E914, and D1074 of SEQ ID NO: 1.

12. The CasY fusion polypeptide of claim 8, wherein the heterologous polypeptide is a targeting polypeptide that provides for binding to a cell surface moiety on a target cell or target cell type.

13. The CasY fusion polypeptide of claim 8, wherein the heterologous polypeptide exhibits an enzymatic activity that modifies target DNA.

14. The CasY fusion polypeptide of claim 8, wherein the heterologous polypeptide exhibits an enzymatic activity that modifies a target polypeptide associated with a target nucleic acid.

15. The CasY fusion polypeptide of claim 8, wherein the heterologous polypeptide is an endosomal escape polypeptide.

16. The CasY fusion polypeptide of claim 8, wherein the heterologous polypeptide is a protein that increases or decreases transcription.

17. A nucleic acid comprising a nucleotide sequence encoding a CasY fusion polypeptide, wherein the CasY fusion polypeptide comprises a CasY polypeptide fused to a heterologous polypeptide, wherein the CasY polypeptide comprises an amino acid sequence having 50% or more identity to the amino acid sequence set forth in SEQ ID NO:1 or SEQ ID NO:2.

18. One or more nucleic acid molecules encoding:

(a) a CasY guide RNA; and (b) a CasY fusion polypeptide, wherein the CasY fusion polypeptide comprises a CasY polypeptide fused to a heterologous polypeptide, and wherein the CasY polypeptide comprises an amino acid sequence having 50% or more identity to the amino acid sequence set forth in SEQ ID NO:1 or SEQ ID NO:2.

19. The one or more nucleic acid molecules of claim 18, wherein the CasY polypeptide comprises an amino acid sequence having 80% or more identity to the amino acid sequence set forth in SEQ ID NO:1 or SEQ ID NO:2.

20. A eukaryotic cell comprising one or more of:

a) a CasY polypeptide, or a nucleic acid molecule encoding the CasY polypeptide, wherein the CasY polypeptide comprises an amino acid sequence having 50% or more identity to the amino acid sequence set forth in SEQ ID NO:1 or SEQ ID NO:2;

b) a CasY fusion polypeptide, or a nucleic acid molecule encoding the CasY fusion polypeptide, wherein the CasY fusion polypeptide comprises a CasY polypeptide fused to a heterologous polypeptide, and wherein the CasY polypeptide comprises an amino acid sequence having 50% or more identity to the amino acid sequence set forth in SEQ ID NO:1 or SEQ ID NO:2; and c) a CasY guide RNA, or a nucleic acid molecule encoding the CasY guide RNA.

21. A cell comprising a CasY fusion polypeptide, or a nucleic acid molecule encoding the CasY fusion polypeptide, wherein the CasY fusion polypeptide comprises a CasY polypeptide fused to a heterologous polypeptide, and wherein the CasY polypeptide comprises an amino acid sequence having 50% or more identity to the amino acid sequence set forth in SEQ ID NO:1 or SEQ ID NO:2.

22. A method of modifying a target nucleic acid, the method comprising contacting the target nucleic acid with:

a) a CasY polypeptide, wherein the CasY polypeptide comprises an amino acid sequence having 50% or more identity to the amino acid sequence set forth in SEQ ID NO:1 or SEQ ID NO:2; and b) a CasY guide RNA comprising a guide sequence that hybridizes to a target sequence of the target nucleic acid, wherein the target nucleic acid is double-stranded DNA, and wherein said contacting results in modification of the target nucleic acid by the CasY polypeptide.

23. The method of claim 22, wherein said modification is cleavage of the target nucleic acid.

24. The method of claim 22, wherein the target nucleic acid is genomic DNA or extrachromosomal DNA.

25. The method of claim 22, wherein said contacting takes place in vitro outside of a cell.

26. The method of claim 22, wherein said contacting takes place inside of a cell in vivo.

27. The method of claim 26, wherein the cell is a eukaryotic cell.

28. A method of modulating transcription from a target DNA, modifying a target nucleic acid, or modifying a protein associated with a target nucleic acid, the method comprising contacting the target nucleic acid with:

a) a CasY fusion polypeptide comprising a CasY polypeptide fused to a heterologous polypeptide, wherein the CasY polypeptide comprises an amino acid sequence having 50% or more identity to the amino acid sequence set forth in SEO ID NO: 1 or SEO ID NO:2; and b) a CasY guide RNA comprising a guide sequence that hybridizes to a target sequence of the target nucleic acid, wherein the target nucleic acid is double-stranded DNA.

* * * * *

UNITED STATES PATENT AND TRADEMARK OFFICE

CERTIFICATE OF CORRECTION

PATENT NO. : 11,371,062 B2
APPLICATION NO. : 16/335630
DATED : June 28, 2022
INVENTOR(S) : Jennifer A. Doudna et al.

It is certified that error appears in the above-identified patent and that said Letters Patent is hereby corrected as shown below:

In the Specification

In Column 23, Lines 13, 33 and 61, please delete the word "land" and replace it with -- 1 and --;

In Column 24, Lines 10, 41 and 56, please delete the word "land" and replace it with -- 1 and --;

In Column 25, Lines 18, 34 and 64, please delete the word "land" and replace it with -- 1 and --;

In Column 26, Lines 13, 43 and 58, please delete the word "land" and replace it with -- 1 and --;

In Column 27, Lines 20, 36 and 66, please delete the word "land" and replace it with -- 1 and --;

In Column 28, Lines 15, 45 and 60, please delete the word "land" and replace it with -- 1 and --;

In Column 29, Lines 22 and 38, please delete word the "land" and replace it with -- 1 and --;

In Column 30, Lines 1, 17, 47 and 62, please delete word the "land" and replace it with -- 1 and --;

In Column 31, Lines 24 and 40, please delete word the "land" and replace it with -- 1 and --;

In Column 32, Lines 3 and 18, please delete word the "land" and replace it with -- 1 and --;

In Column 46, Line 33, please delete "Pill/Aby1" and replace it with -- Pil1/Aby1 --;

In Column 61, Line 6, please delete "EFla" and replace it with -- EF1α --;

In Column 104, Line 34, please delete word the "O-Glena" and replace it with -- GlcNAc --;

In Column 114, Line 66, please delete word the "consistem" and replace it with -- consistent --;

Signed and Sealed this
Fourteenth Day of February, 2023

Katherine Kelly Vidal

Katherine Kelly Vidal
*Director of the United States Patent and Trademark Office*

In Column 118, Line 28, please delete "DH5a" and replace it with -- DH5α --;

In the Claims

In Column 364, Claim 28, Line 54, please delete both "SEO" and replace them with -- SEQ --.

SEQUENCE LISTING

<160> NUMBER OF SEQ ID NOS: 159

<210> SEQ ID NO 1
<211> LENGTH: 1125
<212> TYPE: PRT
<213> ORGANISM: Unknown
<220> FEATURE:
<223> OTHER INFORMATION: Synthetic sequence

<400> SEQUENCE: 1

Met Arg Lys Lys Leu Phe Lys Gly Tyr Ile Leu His Asn Lys Arg Leu
1 5 10 15

Val Tyr Thr Gly Lys Ala Ala Ile Arg Ser Ile Lys Tyr Pro Leu Val
20 25 30

Ala Pro Asn Lys Thr Ala Leu Asn Asn Leu Ser Glu Lys Ile Ile Tyr
35 40 45

Asp Tyr Glu His Leu Phe Gly Pro Leu Asn Val Ala Ser Tyr Ala Arg
50 55 60

Asn Ser Asn Arg Tyr Ser Leu Val Asp Phe Trp Ile Asp Ser Leu Arg
65 70 75 80

Ala Gly Val Ile Trp Gln Ser Lys Ser Thr Ser Leu Ile Asp Leu Ile
85 90 95

Ser Lys Leu Glu Gly Ser Lys Ser Pro Ser Glu Lys Ile Phe Glu Gln
100 105 110

Ile Asp Phe Glu Leu Lys Asn Lys Leu Asp Lys Glu Gln Phe Lys Asp
115 120 125

Ile Ile Leu Leu Asn Thr Gly Ile Arg Ser Ser Ser Asn Val Arg Ser
130 135 140

Leu Arg Gly Arg Phe Leu Lys Cys Phe Lys Glu Glu Phe Arg Asp Thr
145 150 155 160

Glu Glu Val Ile Ala Cys Val Asp Lys Trp Ser Lys Asp Leu Ile Val
165 170 175

Glu Gly Lys Ser Ile Leu Val Ser Lys Gln Phe Leu Tyr Trp Glu Glu
180 185 190

Glu Phe Gly Ile Lys Ile Phe Pro His Phe Lys Asp Asn His Asp Leu
195 200 205

Pro Lys Leu Thr Phe Phe Val Glu Pro Ser Leu Glu Phe Ser Pro His
210 215 220

Leu Pro Leu Ala Asn Cys Leu Glu Arg Leu Lys Lys Phe Asp Ile Ser
225 230 235 240

Arg Glu Ser Leu Leu Gly Leu Asp Asn Asn Phe Ser Ala Phe Ser Asn
245 250 255

Tyr Phe Asn Glu Leu Phe Asn Leu Leu Ser Arg Gly Glu Ile Lys Lys
260 265 270

Ile Val Thr Ala Val Leu Ala Val Ser Lys Ser Trp Glu Asn Glu Pro
275 280 285

Glu Leu Glu Lys Arg Leu His Phe Leu Ser Glu Lys Ala Lys Leu Leu
290 295 300

Gly Tyr Pro Lys Leu Thr Ser Ser Trp Ala Asp Tyr Arg Met Ile Ile
305 310 315 320

Gly Gly Lys Ile Lys Ser Trp His Ser Asn Tyr Thr Glu Gln Leu Ile
325 330 335

Lys Val Arg Glu Asp Leu Lys Lys His Gln Ile Ala Leu Asp Lys Leu
340 345 350

Gln Glu Asp Leu Lys Lys Val Val Asp Ser Ser Leu Arg Glu Gln Ile

```
        355                 360                 365

Glu Ala Gln Arg Glu Ala Leu Leu Pro Leu Leu Asp Thr Met Leu Lys
    370                 375                 380

Glu Lys Asp Phe Ser Asp Asp Leu Glu Leu Tyr Arg Phe Ile Leu Ser
385                 390                 395                 400

Asp Phe Lys Ser Leu Leu Asn Gly Ser Tyr Gln Arg Tyr Ile Gln Thr
                405                 410                 415

Glu Glu Glu Arg Lys Glu Asp Arg Asp Val Thr Lys Lys Tyr Lys Asp
            420                 425                 430

Leu Tyr Ser Asn Leu Arg Asn Ile Pro Arg Phe Phe Gly Glu Ser Lys
        435                 440                 445

Lys Glu Gln Phe Asn Lys Phe Ile Asn Lys Ser Leu Pro Thr Ile Asp
    450                 455                 460

Val Gly Leu Lys Ile Leu Glu Asp Ile Arg Asn Ala Leu Glu Thr Val
465                 470                 475                 480

Ser Val Arg Lys Pro Pro Ser Ile Thr Glu Glu Tyr Val Thr Lys Gln
                485                 490                 495

Leu Glu Lys Leu Ser Arg Lys Tyr Lys Ile Asn Ala Phe Asn Ser Asn
            500                 505                 510

Arg Phe Lys Gln Ile Thr Glu Gln Val Leu Arg Lys Tyr Asn Asn Gly
        515                 520                 525

Glu Leu Pro Lys Ile Ser Glu Val Phe Tyr Arg Tyr Pro Arg Glu Ser
    530                 535                 540

His Val Ala Ile Arg Ile Leu Pro Val Lys Ile Ser Asn Pro Arg Lys
545                 550                 555                 560

Asp Ile Ser Tyr Leu Leu Asp Lys Tyr Gln Ile Ser Pro Asp Trp Lys
                565                 570                 575

Asn Ser Asn Pro Gly Glu Val Val Asp Leu Ile Glu Ile Tyr Lys Leu
            580                 585                 590

Thr Leu Gly Trp Leu Leu Ser Cys Asn Lys Asp Phe Ser Met Asp Phe
        595                 600                 605

Ser Ser Tyr Asp Leu Lys Leu Phe Pro Glu Ala Ala Ser Leu Ile Lys
    610                 615                 620

Asn Phe Gly Ser Cys Leu Ser Gly Tyr Tyr Leu Ser Lys Met Ile Phe
625                 630                 635                 640

Asn Cys Ile Thr Ser Glu Ile Lys Gly Met Ile Thr Leu Tyr Thr Arg
                645                 650                 655

Asp Lys Phe Val Val Arg Tyr Val Thr Gln Met Ile Gly Ser Asn Gln
            660                 665                 670

Lys Phe Pro Leu Leu Cys Leu Val Gly Glu Lys Gln Thr Lys Asn Phe
        675                 680                 685

Ser Arg Asn Trp Gly Val Leu Ile Glu Glu Lys Gly Asp Leu Gly Glu
    690                 695                 700

Glu Lys Asn Gln Glu Lys Cys Leu Ile Phe Lys Asp Lys Thr Asp Phe
705                 710                 715                 720

Ala Lys Ala Lys Glu Val Glu Ile Phe Lys Asn Asn Ile Trp Arg Ile
                725                 730                 735

Arg Thr Ser Lys Tyr Gln Ile Gln Phe Leu Asn Arg Leu Phe Lys Lys
            740                 745                 750

Thr Lys Glu Trp Asp Leu Met Asn Leu Val Leu Ser Glu Pro Ser Leu
        755                 760                 765

Val Leu Glu Glu Glu Trp Gly Val Ser Trp Asp Lys Asp Lys Leu Leu
    770                 775                 780
```

Pro Leu Leu Lys Lys Glu Lys Ser Cys Glu Glu Arg Leu Tyr Tyr Ser
785 790 795 800

Leu Pro Leu Asn Leu Val Pro Ala Thr Asp Tyr Lys Glu Gln Ser Ala
805 810 815

Glu Ile Glu Gln Arg Asn Thr Tyr Leu Gly Leu Asp Val Gly Glu Phe
820 825 830

Gly Val Ala Tyr Ala Val Val Arg Ile Val Arg Asp Arg Ile Glu Leu
835 840 845

Leu Ser Trp Gly Phe Leu Lys Asp Pro Ala Leu Arg Lys Ile Arg Glu
850 855 860

Arg Val Gln Asp Met Lys Lys Lys Gln Val Met Ala Val Phe Ser Ser
865 870 875 880

Ser Ser Thr Ala Val Ala Arg Val Arg Glu Met Ala Ile His Ser Leu
885 890 895

Arg Asn Gln Ile His Ser Ile Ala Leu Ala Tyr Lys Ala Lys Ile Ile
900 905 910

Tyr Glu Ile Ser Ile Ser Asn Phe Glu Thr Gly Gly Asn Arg Met Ala
915 920 925

Lys Ile Tyr Arg Ser Ile Lys Val Ser Asp Val Tyr Arg Glu Ser Gly
930 935 940

Ala Asp Thr Leu Val Ser Glu Met Ile Trp Gly Lys Lys Asn Lys Gln
945 950 955 960

Met Gly Asn His Ile Ser Ser Tyr Ala Thr Ser Tyr Thr Cys Cys Asn
965 970 975

Cys Ala Arg Thr Pro Phe Glu Leu Val Ile Asp Asn Asp Lys Glu Tyr
980 985 990

Glu Lys Gly Gly Asp Glu Phe Ile Phe Asn Val Gly Asp Glu Lys Lys
995 1000 1005

Val Arg Gly Phe Leu Gln Lys Ser Leu Leu Gly Lys Thr Ile Lys
1010 1015 1020

Gly Lys Glu Val Leu Lys Ser Ile Lys Glu Tyr Ala Arg Pro Pro
1025 1030 1035

Ile Arg Glu Val Leu Leu Glu Gly Glu Asp Val Glu Gln Leu Leu
1040 1045 1050

Lys Arg Arg Gly Asn Ser Tyr Ile Tyr Arg Cys Pro Phe Cys Gly
1055 1060 1065

Tyr Lys Thr Asp Ala Asp Ile Gln Ala Ala Leu Asn Ile Ala Cys
1070 1075 1080

Arg Gly Tyr Ile Ser Asp Asn Ala Lys Asp Ala Val Lys Glu Gly
1085 1090 1095

Glu Arg Lys Leu Asp Tyr Ile Leu Glu Val Arg Lys Leu Trp Glu
1100 1105 1110

Lys Asn Gly Ala Val Leu Arg Ser Ala Lys Phe Leu
1115 1120 1125

<210> SEQ ID NO 2
<211> LENGTH: 1226
<212> TYPE: PRT
<213> ORGANISM: Unknown
<220> FEATURE:
<223> OTHER INFORMATION: Synthetic sequence

<400> SEQUENCE: 2

Met Gln Lys Val Arg Lys Thr Leu Ser Glu Val His Lys Asn Pro Tyr
1 5 10 15

-continued

```
Gly Thr Lys Val Arg Asn Ala Lys Thr Gly Tyr Ser Leu Gln Ile Glu
            20                  25                  30

Arg Leu Ser Tyr Thr Gly Lys Glu Gly Met Arg Ser Phe Lys Ile Pro
        35                  40                  45

Leu Glu Asn Lys Asn Lys Glu Val Phe Asp Glu Phe Val Lys Lys Ile
    50                  55                  60

Arg Asn Asp Tyr Ile Ser Gln Val Gly Leu Leu Asn Leu Ser Asp Trp
65                  70                  75                  80

Tyr Glu His Tyr Gln Glu Lys Gln Glu His Tyr Ser Leu Ala Asp Phe
                85                  90                  95

Trp Leu Asp Ser Leu Arg Ala Gly Val Ile Phe Ala His Lys Glu Thr
            100                 105                 110

Glu Ile Lys Asn Leu Ile Ser Lys Ile Arg Gly Asp Lys Ser Ile Val
        115                 120                 125

Asp Lys Phe Asn Ala Ser Ile Lys Lys Lys His Ala Asp Leu Tyr Ala
    130                 135                 140

Leu Val Asp Ile Lys Ala Leu Tyr Asp Phe Leu Thr Ser Asp Ala Arg
145                 150                 155                 160

Arg Gly Leu Lys Thr Glu Glu Glu Phe Phe Asn Ser Lys Arg Asn Thr
                165                 170                 175

Leu Phe Pro Lys Phe Arg Lys Lys Asp Asn Lys Ala Val Asp Leu Trp
            180                 185                 190

Val Lys Lys Phe Ile Gly Leu Asp Asn Lys Asp Lys Leu Asn Phe Thr
        195                 200                 205

Lys Lys Phe Ile Gly Phe Asp Pro Asn Pro Gln Ile Lys Tyr Asp His
    210                 215                 220

Thr Phe Phe Phe His Gln Asp Ile Asn Phe Asp Leu Glu Arg Ile Thr
225                 230                 235                 240

Thr Pro Lys Glu Leu Ile Ser Thr Tyr Lys Lys Phe Leu Gly Lys Asn
                245                 250                 255

Lys Asp Leu Tyr Gly Ser Asp Glu Thr Thr Glu Asp Gln Leu Lys Met
            260                 265                 270

Val Leu Gly Phe His Asn Asn His Gly Ala Phe Ser Lys Tyr Phe Asn
        275                 280                 285

Ala Ser Leu Glu Ala Phe Arg Gly Arg Asp Asn Ser Leu Val Glu Gln
    290                 295                 300

Ile Ile Asn Asn Ser Pro Tyr Trp Asn Ser His Arg Lys Glu Leu Glu
305                 310                 315                 320

Lys Arg Ile Ile Phe Leu Gln Val Gln Ser Lys Lys Ile Lys Glu Thr
                325                 330                 335

Glu Leu Gly Lys Pro His Glu Tyr Leu Ala Ser Phe Gly Gly Lys Phe
            340                 345                 350

Glu Ser Trp Val Ser Asn Tyr Leu Arg Gln Glu Glu Glu Val Lys Arg
        355                 360                 365

Gln Leu Phe Gly Tyr Glu Glu Asn Lys Lys Gly Gln Lys Lys Phe Ile
    370                 375                 380

Val Gly Asn Lys Gln Glu Leu Asp Lys Ile Ile Arg Gly Thr Asp Glu
385                 390                 395                 400

Tyr Glu Ile Lys Ala Ile Ser Lys Glu Thr Ile Gly Leu Thr Gln Lys
                405                 410                 415

Cys Leu Lys Leu Leu Glu Gln Leu Lys Asp Ser Val Asp Asp Tyr Thr
            420                 425                 430
```

-continued

```
Leu Ser Leu Tyr Arg Gln Leu Ile Val Glu Leu Arg Ile Arg Leu Asn
        435                 440                 445

Val Glu Phe Gln Glu Thr Tyr Pro Glu Leu Ile Gly Lys Ser Glu Lys
    450                 455                 460

Asp Lys Glu Lys Asp Ala Lys Asn Lys Arg Ala Asp Lys Arg Tyr Pro
465                 470                 475                 480

Gln Ile Phe Lys Asp Ile Lys Leu Ile Pro Asn Phe Leu Gly Glu Thr
                485                 490                 495

Lys Gln Met Val Tyr Lys Lys Phe Ile Arg Ser Ala Asp Ile Leu Tyr
            500                 505                 510

Glu Gly Ile Asn Phe Ile Asp Gln Ile Asp Lys Gln Ile Thr Gln Asn
        515                 520                 525

Leu Leu Pro Cys Phe Lys Asn Asp Lys Glu Arg Ile Glu Phe Thr Glu
    530                 535                 540

Lys Gln Phe Glu Thr Leu Arg Arg Lys Tyr Tyr Leu Met Asn Ser Ser
545                 550                 555                 560

Arg Phe His His Val Ile Glu Gly Ile Ile Asn Asn Arg Lys Leu Ile
                565                 570                 575

Glu Met Lys Lys Arg Glu Asn Ser Glu Leu Lys Thr Phe Ser Asp Ser
            580                 585                 590

Lys Phe Val Leu Ser Lys Leu Phe Leu Lys Lys Gly Lys Lys Tyr Glu
        595                 600                 605

Asn Glu Val Tyr Tyr Thr Phe Tyr Ile Asn Pro Lys Ala Arg Asp Gln
    610                 615                 620

Arg Arg Ile Lys Ile Val Leu Asp Ile Asn Gly Asn Asn Ser Val Gly
625                 630                 635                 640

Ile Leu Gln Asp Leu Val Gln Lys Leu Lys Pro Lys Trp Asp Asp Ile
                645                 650                 655

Ile Lys Lys Asn Asp Met Gly Glu Leu Ile Asp Ala Ile Glu Ile Glu
            660                 665                 670

Lys Val Arg Leu Gly Ile Leu Ile Ala Leu Tyr Cys Glu His Lys Phe
        675                 680                 685

Lys Ile Lys Lys Glu Leu Leu Ser Leu Asp Leu Phe Ala Ser Ala Tyr
    690                 695                 700

Gln Tyr Leu Glu Leu Glu Asp Asp Pro Glu Glu Leu Ser Gly Thr Asn
705                 710                 715                 720

Leu Gly Arg Phe Leu Gln Ser Leu Val Cys Ser Glu Ile Lys Gly Ala
                725                 730                 735

Ile Asn Lys Ile Ser Arg Thr Glu Tyr Ile Glu Arg Tyr Thr Val Gln
            740                 745                 750

Pro Met Asn Thr Glu Lys Asn Tyr Pro Leu Leu Ile Asn Lys Glu Gly
        755                 760                 765

Lys Ala Thr Trp His Ile Ala Ala Lys Asp Asp Leu Ser Lys Lys Lys
    770                 775                 780

Gly Gly Gly Thr Val Ala Met Asn Gln Lys Ile Gly Lys Asn Phe Phe
785                 790                 795                 800

Gly Lys Gln Asp Tyr Lys Thr Val Phe Met Leu Gln Asp Lys Arg Phe
                805                 810                 815

Asp Leu Leu Thr Ser Lys Tyr His Leu Gln Phe Leu Ser Lys Thr Leu
            820                 825                 830

Asp Thr Gly Gly Gly Ser Trp Trp Lys Asn Lys Asn Ile Asp Leu Asn
        835                 840                 845

Leu Ser Ser Tyr Ser Phe Ile Phe Glu Gln Lys Val Lys Val Glu Trp
```

-continued

```
    850                 855                 860

Asp Leu Thr Asn Leu Asp His Pro Ile Lys Ile Lys Pro Ser Glu Asn
865                 870                 875                 880

Ser Asp Asp Arg Arg Leu Phe Val Ser Ile Pro Phe Val Ile Lys Pro
                885                 890                 895

Lys Gln Thr Lys Arg Lys Asp Leu Gln Thr Arg Val Asn Tyr Met Gly
            900                 905                 910

Ile Asp Ile Gly Glu Tyr Gly Leu Ala Trp Thr Ile Ile Asn Ile Asp
        915                 920                 925

Leu Lys Asn Lys Lys Ile Asn Lys Ile Ser Lys Gln Gly Phe Ile Tyr
    930                 935                 940

Glu Pro Leu Thr His Lys Val Arg Asp Tyr Val Ala Thr Ile Lys Asp
945                 950                 955                 960

Asn Gln Val Arg Gly Thr Phe Gly Met Pro Asp Thr Lys Leu Ala Arg
                965                 970                 975

Leu Arg Glu Asn Ala Ile Thr Ser Leu Arg Asn Gln Val His Asp Ile
            980                 985                 990

Ala Met Arg Tyr Asp Ala Lys Pro  Val Tyr Glu Phe Glu  Ile Ser Asn
        995                 1000                1005

Phe Glu  Thr Gly Ser Asn Lys  Val Lys Val Ile Tyr  Asp Ser Val
    1010                1015                1020

Lys Arg  Ala Asp Ile Gly Arg  Gly Gln Asn Asn Thr  Glu Ala Asp
    1025                1030                1035

Asn Thr  Glu Val Asn Leu Val  Trp Gly Lys Thr Ser  Lys Gln Phe
    1040                1045                1050

Gly Ser  Gln Ile Gly Ala Tyr  Ala Thr Ser Tyr Ile  Cys Ser Phe
    1055                1060                1065

Cys Gly  Tyr Ser Pro Tyr Tyr  Glu Phe Glu Asn Ser  Lys Ser Gly
    1070                1075                1080

Asp Glu  Glu Gly Ala Arg Asp  Asn Leu Tyr Gln Met  Lys Lys Leu
    1085                1090                1095

Ser Arg  Pro Ser Leu Glu Asp  Phe Leu Gln Gly Asn  Pro Val Tyr
    1100                1105                1110

Lys Thr  Phe Arg Asp Phe Asp  Lys Tyr Lys Asn Asp  Gln Arg Leu
    1115                1120                1125

Gln Lys  Thr Gly Asp Lys Asp  Gly Glu Trp Lys Thr  His Arg Gly
    1130                1135                1140

Asn Thr  Ala Ile Tyr Ala Cys  Gln Lys Cys Arg His  Ile Ser Asp
    1145                1150                1155

Ala Asp  Ile Gln Ala Ser Tyr  Trp Ile Ala Leu Lys  Gln Val Val
    1160                1165                1170

Arg Asp  Phe Tyr Lys Asp Lys  Glu Met Asp Gly Asp  Leu Ile Gln
    1175                1180                1185

Gly Asp  Asn Lys Asp Lys Arg  Lys Val Asn Glu Leu  Asn Arg Leu
    1190                1195                1200

Ile Gly  Val His Lys Asp Val  Pro Ile Ile Asn Lys  Asn Leu Ile
    1205                1210                1215

Thr Ser  Leu Asp Ile Asn Leu  Leu
    1220                1225


<210> SEQ ID NO 3
<211> LENGTH: 1160
<212> TYPE: PRT
<213> ORGANISM: Unknown
```

<220> FEATURE:
<223> OTHER INFORMATION: Synthetic sequence

<400> SEQUENCE: 3

```
Met Lys Ala Lys Lys Ser Phe Tyr Asn Gln Lys Arg Lys Phe Gly Lys
1               5                   10                  15

Arg Gly Tyr Arg Leu His Asp Glu Arg Ile Ala Tyr Ser Gly Gly Ile
            20                  25                  30

Gly Ser Met Arg Ser Ile Lys Tyr Glu Leu Lys Asp Ser Tyr Gly Ile
        35                  40                  45

Ala Gly Leu Arg Asn Arg Ile Ala Asp Ala Thr Ile Ser Asp Asn Lys
    50                  55                  60

Trp Leu Tyr Gly Asn Ile Asn Leu Asn Asp Tyr Leu Glu Trp Arg Ser
65                  70                  75                  80

Ser Lys Thr Asp Lys Gln Ile Glu Asp Gly Asp Arg Glu Ser Ser Leu
                85                  90                  95

Leu Gly Phe Trp Leu Glu Ala Leu Arg Leu Gly Phe Val Phe Ser Lys
            100                 105                 110

Gln Ser His Ala Pro Asn Asp Phe Asn Glu Thr Ala Leu Gln Asp Leu
        115                 120                 125

Phe Glu Thr Leu Asp Asp Asp Leu Lys His Val Leu Asp Arg Lys Lys
    130                 135                 140

Trp Cys Asp Phe Ile Lys Ile Gly Thr Pro Lys Thr Asn Asp Gln Gly
145                 150                 155                 160

Arg Leu Lys Lys Gln Ile Lys Asn Leu Leu Lys Gly Asn Lys Arg Glu
                165                 170                 175

Glu Ile Glu Lys Thr Leu Asn Glu Ser Asp Asp Glu Leu Lys Glu Lys
            180                 185                 190

Ile Asn Arg Ile Ala Asp Val Phe Ala Lys Asn Lys Ser Asp Lys Tyr
        195                 200                 205

Thr Ile Phe Lys Leu Asp Lys Pro Asn Thr Glu Lys Tyr Pro Arg Ile
    210                 215                 220

Asn Asp Val Gln Val Ala Phe Phe Cys His Pro Asp Phe Glu Glu Ile
225                 230                 235                 240

Thr Glu Arg Asp Arg Thr Lys Thr Leu Asp Leu Ile Ile Asn Arg Phe
                245                 250                 255

Asn Lys Arg Tyr Glu Ile Thr Glu Asn Lys Lys Asp Asp Lys Thr Ser
            260                 265                 270

Asn Arg Met Ala Leu Tyr Ser Leu Asn Gln Gly Tyr Ile Pro Arg Val
        275                 280                 285

Leu Asn Asp Leu Phe Leu Phe Val Lys Asp Asn Glu Asp Asp Phe Ser
    290                 295                 300

Gln Phe Leu Ser Asp Leu Glu Asn Phe Phe Ser Phe Ser Asn Glu Gln
305                 310                 315                 320

Ile Lys Ile Ile Lys Glu Arg Leu Lys Lys Leu Lys Lys Tyr Ala Glu
                325                 330                 335

Pro Ile Pro Gly Lys Pro Gln Leu Ala Asp Lys Trp Asp Asp Tyr Ala
            340                 345                 350

Ser Asp Phe Gly Gly Lys Leu Glu Ser Trp Tyr Ser Asn Arg Ile Glu
        355                 360                 365

Lys Leu Lys Lys Ile Pro Glu Ser Val Ser Asp Leu Arg Asn Asn Leu
    370                 375                 380

Glu Lys Ile Arg Asn Val Leu Lys Lys Gln Asn Asn Ala Ser Lys Ile
385                 390                 395                 400
```

```
Leu Glu Leu Ser Gln Lys Ile Ile Glu Tyr Ile Arg Asp Tyr Gly Val
                405                 410                 415

Ser Phe Glu Lys Pro Glu Ile Ile Lys Phe Ser Trp Ile Asn Lys Thr
            420                 425                 430

Lys Asp Gly Gln Lys Lys Val Phe Tyr Val Ala Lys Met Ala Asp Arg
        435                 440                 445

Glu Phe Ile Glu Lys Leu Asp Leu Trp Met Ala Asp Leu Arg Ser Gln
    450                 455                 460

Leu Asn Glu Tyr Asn Gln Asp Asn Lys Val Ser Phe Lys Lys Lys Gly
465                 470                 475                 480

Lys Lys Ile Glu Glu Leu Gly Val Leu Asp Phe Ala Leu Asn Lys Ala
                485                 490                 495

Lys Lys Asn Lys Ser Thr Lys Asn Glu Asn Gly Trp Gln Gln Lys Leu
            500                 505                 510

Ser Glu Ser Ile Gln Ser Ala Pro Leu Phe Phe Gly Glu Gly Asn Arg
        515                 520                 525

Val Arg Asn Glu Glu Val Tyr Asn Leu Lys Asp Leu Leu Phe Ser Glu
    530                 535                 540

Ile Lys Asn Val Glu Asn Ile Leu Met Ser Ser Glu Ala Glu Asp Leu
545                 550                 555                 560

Lys Asn Ile Lys Ile Glu Tyr Lys Glu Asp Gly Ala Lys Lys Gly Asn
                565                 570                 575

Tyr Val Leu Asn Val Leu Ala Arg Phe Tyr Ala Arg Phe Asn Glu Asp
            580                 585                 590

Gly Tyr Gly Gly Trp Asn Lys Val Lys Thr Val Leu Glu Asn Ile Ala
        595                 600                 605

Arg Glu Ala Gly Thr Asp Phe Ser Lys Tyr Gly Asn Asn Asn Asn Arg
    610                 615                 620

Asn Ala Gly Arg Phe Tyr Leu Asn Gly Arg Glu Arg Gln Val Phe Thr
625                 630                 635                 640

Leu Ile Lys Phe Glu Lys Ser Ile Thr Val Glu Lys Ile Leu Glu Leu
                645                 650                 655

Val Lys Leu Pro Ser Leu Leu Asp Glu Ala Tyr Arg Asp Leu Val Asn
            660                 665                 670

Glu Asn Lys Asn His Lys Leu Arg Asp Val Ile Gln Leu Ser Lys Thr
        675                 680                 685

Ile Met Ala Leu Val Leu Ser His Ser Asp Lys Glu Lys Gln Ile Gly
    690                 695                 700

Gly Asn Tyr Ile His Ser Lys Leu Ser Gly Tyr Asn Ala Leu Ile Ser
705                 710                 715                 720

Lys Arg Asp Phe Ile Ser Arg Tyr Ser Val Gln Thr Thr Asn Gly Thr
                725                 730                 735

Gln Cys Lys Leu Ala Ile Gly Lys Gly Lys Ser Lys Lys Gly Asn Glu
            740                 745                 750

Ile Asp Arg Tyr Phe Tyr Ala Phe Gln Phe Phe Lys Asn Asp Asp Ser
        755                 760                 765

Lys Ile Asn Leu Lys Val Ile Lys Asn Asn Ser His Lys Asn Ile Asp
    770                 775                 780

Phe Asn Asp Asn Glu Asn Lys Ile Asn Ala Leu Gln Val Tyr Ser Ser
785                 790                 795                 800

Asn Tyr Gln Ile Gln Phe Leu Asp Trp Phe Phe Glu Lys His Gln Gly
                805                 810                 815
```

```
Lys Lys Thr Ser Leu Glu Val Gly Gly Ser Phe Thr Ile Ala Glu Lys
            820                 825                 830

Ser Leu Thr Ile Asp Trp Ser Gly Ser Asn Pro Arg Val Gly Phe Lys
        835                 840                 845

Arg Ser Asp Thr Glu Glu Lys Arg Val Phe Val Ser Gln Pro Phe Thr
    850                 855                 860

Leu Ile Pro Asp Asp Glu Asp Lys Glu Arg Arg Lys Glu Arg Met Ile
865                 870                 875                 880

Lys Thr Lys Asn Arg Phe Ile Gly Ile Asp Ile Gly Glu Tyr Gly Leu
                885                 890                 895

Ala Trp Ser Leu Ile Glu Val Asp Asn Gly Asp Lys Asn Asn Arg Gly
            900                 905                 910

Ile Arg Gln Leu Glu Ser Gly Phe Ile Thr Asp Asn Gln Gln Gln Val
        915                 920                 925

Leu Lys Lys Asn Val Lys Ser Trp Arg Gln Asn Gln Ile Arg Gln Thr
    930                 935                 940

Phe Thr Ser Pro Asp Thr Lys Ile Ala Arg Leu Arg Glu Ser Leu Ile
945                 950                 955                 960

Gly Ser Tyr Lys Asn Gln Leu Glu Ser Leu Met Val Ala Lys Lys Ala
                965                 970                 975

Asn Leu Ser Phe Glu Tyr Glu Val Ser Gly Phe Glu Val Gly Gly Lys
            980                 985                 990

Arg Val Ala Lys Ile Tyr Asp Ser  Ile Lys Arg Gly Ser  Val Arg Lys
        995                 1000                1005

Lys Asp  Asn Asn Ser Gln Asn  Asp Gln Ser Trp Gly  Lys Lys Gly
    1010                1015                1020

Ile Asn  Glu Trp Ser Phe Glu  Thr Thr Ala Ala Gly  Thr Ser Gln
    1025                1030                1035

Phe Cys  Thr His Cys Lys Arg  Trp Ser Ser Leu Ala  Ile Val Asp
    1040                1045                1050

Ile Glu  Glu Tyr Glu Leu Lys  Asp Tyr Asn Asp Asn  Leu Phe Lys
    1055                1060                1065

Val Lys  Ile Asn Asp Gly Glu  Val Arg Leu Leu Gly  Lys Lys Gly
    1070                1075                1080

Trp Arg  Ser Gly Glu Lys Ile  Lys Gly Lys Glu Leu  Phe Gly Pro
    1085                1090                1095

Val Lys  Asp Ala Met Arg Pro  Asn Val Asp Gly Leu  Gly Met Lys
    1100                1105                1110

Ile Val  Lys Arg Lys Tyr Leu  Lys Leu Asp Leu Arg  Asp Trp Val
    1115                1120                1125

Ser Arg  Tyr Gly Asn Met Ala  Ile Phe Ile Cys Pro  Tyr Val Asp
    1130                1135                1140

Cys His  His Ile Ser His Ala  Asp Lys Gln Ala Ala  Phe Asn Ile
    1145                1150                1155

Ala Val
    1160
```

<210> SEQ ID NO 4
<211> LENGTH: 1210
<212> TYPE: PRT
<213> ORGANISM: Unknown
<220> FEATURE:
<223> OTHER INFORMATION: Synthetic sequence

<400> SEQUENCE: 4

```
Met Ser Lys Arg His Pro Arg Ile Ser Gly Val Lys Gly Tyr Arg Leu
1               5                   10                  15

His Ala Gln Arg Leu Glu Tyr Thr Gly Lys Ser Gly Ala Met Arg Thr
            20                  25                  30

Ile Lys Tyr Pro Leu Tyr Ser Ser Pro Ser Gly Gly Arg Thr Val Pro
        35                  40                  45

Arg Glu Ile Val Ser Ala Ile Asn Asp Asp Tyr Val Gly Leu Tyr Gly
    50                  55                  60

Leu Ser Asn Phe Asp Asp Leu Tyr Asn Ala Glu Lys Arg Asn Glu Glu
65                  70                  75                  80

Lys Val Tyr Ser Val Leu Asp Phe Trp Tyr Asp Cys Val Gln Tyr Gly
                85                  90                  95

Ala Val Phe Ser Tyr Thr Ala Pro Gly Leu Leu Lys Asn Val Ala Glu
            100                 105                 110

Val Arg Gly Gly Ser Tyr Glu Leu Thr Lys Thr Leu Lys Gly Ser His
        115                 120                 125

Leu Tyr Asp Glu Leu Gln Ile Asp Lys Val Ile Lys Phe Leu Asn Lys
    130                 135                 140

Lys Glu Ile Ser Arg Ala Asn Gly Ser Leu Asp Lys Leu Lys Lys Asp
145                 150                 155                 160

Ile Ile Asp Cys Phe Lys Ala Glu Tyr Arg Glu Arg His Lys Asp Gln
                165                 170                 175

Cys Asn Lys Leu Ala Asp Asp Ile Lys Asn Ala Lys Lys Asp Ala Gly
            180                 185                 190

Ala Ser Leu Gly Glu Arg Gln Lys Lys Leu Phe Arg Asp Phe Phe Gly
        195                 200                 205

Ile Ser Glu Gln Ser Glu Asn Asp Lys Pro Ser Phe Thr Asn Pro Leu
    210                 215                 220

Asn Leu Thr Cys Cys Leu Leu Pro Phe Asp Thr Val Asn Asn Asn Arg
225                 230                 235                 240

Asn Arg Gly Glu Val Leu Phe Asn Lys Leu Lys Glu Tyr Ala Gln Lys
                245                 250                 255

Leu Asp Lys Asn Glu Gly Ser Leu Glu Met Trp Glu Tyr Ile Gly Ile
            260                 265                 270

Gly Asn Ser Gly Thr Ala Phe Ser Asn Phe Leu Gly Glu Gly Phe Leu
        275                 280                 285

Gly Arg Leu Arg Glu Asn Lys Ile Thr Glu Leu Lys Lys Ala Met Met
    290                 295                 300

Asp Ile Thr Asp Ala Trp Arg Gly Gln Glu Gln Glu Glu Glu Leu Glu
305                 310                 315                 320

Lys Arg Leu Arg Ile Leu Ala Ala Leu Thr Ile Lys Leu Arg Glu Pro
                325                 330                 335

Lys Phe Asp Asn His Trp Gly Gly Tyr Arg Ser Asp Ile Asn Gly Lys
            340                 345                 350

Leu Ser Ser Trp Leu Gln Asn Tyr Ile Asn Gln Thr Val Lys Ile Lys
        355                 360                 365

Glu Asp Leu Lys Gly His Lys Lys Asp Leu Lys Lys Ala Lys Glu Met
    370                 375                 380

Ile Asn Arg Phe Gly Glu Ser Asp Thr Lys Glu Glu Ala Val Val Ser
385                 390                 395                 400

Ser Leu Leu Glu Ser Ile Glu Lys Ile Val Pro Asp Asp Ser Ala Asp
                405                 410                 415

Asp Glu Lys Pro Asp Ile Pro Ala Ile Ala Ile Tyr Arg Arg Phe Leu
```

-continued

```
            420                 425                 430

Ser Asp Gly Arg Leu Thr Leu Asn Arg Phe Val Gln Arg Glu Asp Val
        435                 440                 445

Gln Glu Ala Leu Ile Lys Glu Arg Leu Glu Ala Glu Lys Lys Lys Lys
    450                 455                 460

Pro Lys Lys Arg Lys Lys Lys Ser Asp Ala Glu Asp Glu Lys Glu Thr
465                 470                 475                 480

Ile Asp Phe Lys Glu Leu Phe Pro His Leu Ala Lys Pro Leu Lys Leu
                485                 490                 495

Val Pro Asn Phe Tyr Gly Asp Ser Lys Arg Glu Leu Tyr Lys Lys Tyr
            500                 505                 510

Lys Asn Ala Ala Ile Tyr Thr Asp Ala Leu Trp Lys Ala Val Glu Lys
        515                 520                 525

Ile Tyr Lys Ser Ala Phe Ser Ser Ser Leu Lys Asn Ser Phe Phe Asp
    530                 535                 540

Thr Asp Phe Asp Lys Asp Phe Phe Ile Lys Arg Leu Gln Lys Ile Phe
545                 550                 555                 560

Ser Val Tyr Arg Arg Phe Asn Thr Asp Lys Trp Lys Pro Ile Val Lys
                565                 570                 575

Asn Ser Phe Ala Pro Tyr Cys Asp Ile Val Ser Leu Ala Glu Asn Glu
            580                 585                 590

Val Leu Tyr Lys Pro Lys Gln Ser Arg Ser Arg Lys Ser Ala Ala Ile
        595                 600                 605

Asp Lys Asn Arg Val Arg Leu Pro Ser Thr Glu Asn Ile Ala Lys Ala
    610                 615                 620

Gly Ile Ala Leu Ala Arg Glu Leu Ser Val Ala Gly Phe Asp Trp Lys
625                 630                 635                 640

Asp Leu Leu Lys Lys Glu Glu His Glu Glu Tyr Ile Asp Leu Ile Glu
                645                 650                 655

Leu His Lys Thr Ala Leu Ala Leu Leu Leu Ala Val Thr Glu Thr Gln
            660                 665                 670

Leu Asp Ile Ser Ala Leu Asp Phe Val Glu Asn Gly Thr Val Lys Asp
        675                 680                 685

Phe Met Lys Thr Arg Asp Gly Asn Leu Val Leu Glu Gly Arg Phe Leu
    690                 695                 700

Glu Met Phe Ser Gln Ser Ile Val Phe Ser Glu Leu Arg Gly Leu Ala
705                 710                 715                 720

Gly Leu Met Ser Arg Lys Glu Phe Ile Thr Arg Ser Ala Ile Gln Thr
                725                 730                 735

Met Asn Gly Lys Gln Ala Glu Leu Leu Tyr Ile Pro His Glu Phe Gln
            740                 745                 750

Ser Ala Lys Ile Thr Thr Pro Lys Glu Met Ser Arg Ala Phe Leu Asp
        755                 760                 765

Leu Ala Pro Ala Glu Phe Ala Thr Ser Leu Glu Pro Glu Ser Leu Ser
    770                 775                 780

Glu Lys Ser Leu Leu Lys Leu Lys Gln Met Arg Tyr Tyr Pro His Tyr
785                 790                 795                 800

Phe Gly Tyr Glu Leu Thr Arg Thr Gly Gln Gly Ile Asp Gly Gly Val
                805                 810                 815

Ala Glu Asn Ala Leu Arg Leu Glu Lys Ser Pro Val Lys Lys Arg Glu
            820                 825                 830

Ile Lys Cys Lys Gln Tyr Lys Thr Leu Gly Arg Gly Gln Asn Lys Ile
        835                 840                 845
```

-continued

```
Val Leu Tyr Val Arg Ser Ser Tyr Tyr Gln Thr Gln Phe Leu Glu Trp
    850                 855                 860

Phe Leu His Arg Pro Lys Asn Val Gln Thr Asp Val Ala Val Ser Gly
865                 870                 875                 880

Ser Phe Leu Ile Asp Glu Lys Lys Val Lys Thr Arg Trp Asn Tyr Asp
                885                 890                 895

Ala Leu Thr Val Ala Leu Glu Pro Val Ser Gly Ser Glu Arg Val Phe
            900                 905                 910

Val Ser Gln Pro Phe Thr Ile Phe Pro Glu Lys Ser Ala Glu Glu Glu
        915                 920                 925

Gly Gln Arg Tyr Leu Gly Ile Asp Ile Gly Glu Tyr Gly Ile Ala Tyr
    930                 935                 940

Thr Ala Leu Glu Ile Thr Gly Asp Ser Ala Lys Ile Leu Asp Gln Asn
945                 950                 955                 960

Phe Ile Ser Asp Pro Gln Leu Lys Thr Leu Arg Glu Glu Val Lys Gly
                965                 970                 975

Leu Lys Leu Asp Gln Arg Arg Gly Thr Phe Ala Met Pro Ser Thr Lys
            980                 985                 990

Ile Ala Arg Ile Arg Glu Ser Leu  Val His Ser Leu Arg  Asn Arg Ile
        995                 1000                 1005

His His  Leu Ala Leu Lys His  Lys Ala Lys Ile Val  Tyr Glu Leu
    1010                 1015                 1020

Glu Val  Ser Arg Phe Glu Glu  Gly Lys Gln Lys Ile  Lys Lys Val
    1025                 1030                 1035

Tyr Ala  Thr Leu Lys Lys Ala  Asp Val Tyr Ser Glu  Ile Asp Ala
    1040                 1045                 1050

Asp Lys  Asn Leu Gln Thr Thr  Val Trp Gly Lys Leu  Ala Val Ala
    1055                 1060                 1065

Ser Glu  Ile Ser Ala Ser Tyr  Thr Ser Gln Phe Cys  Gly Ala Cys
    1070                 1075                 1080

Lys Lys  Leu Trp Arg Ala Glu  Met Gln Val Asp Glu  Thr Ile Thr
    1085                 1090                 1095

Thr Gln  Glu Leu Ile Gly Thr  Val Arg Val Ile Lys  Gly Gly Thr
    1100                 1105                 1110

Leu Ile  Asp Ala Ile Lys Asp  Phe Met Arg Pro Pro  Ile Phe Asp
    1115                 1120                 1125

Glu Asn  Asp Thr Pro Phe Pro  Lys Tyr Arg Asp Phe  Cys Asp Lys
    1130                 1135                 1140

His His  Ile Ser Lys Lys Met  Arg Gly Asn Ser Cys  Leu Phe Ile
    1145                 1150                 1155

Cys Pro  Phe Cys Arg Ala Asn  Ala Asp Ala Asp Ile  Gln Ala Ser
    1160                 1165                 1170

Gln Thr  Ile Ala Leu Leu Arg  Tyr Val Lys Glu Glu  Lys Lys Val
    1175                 1180                 1185

Glu Asp  Tyr Phe Glu Arg Phe  Arg Lys Leu Lys Asn  Ile Lys Val
    1190                 1195                 1200

Leu Gly  Gln Met Lys Lys Ile
    1205                 1210
```

<210> SEQ ID NO 5
<211> LENGTH: 1287
<212> TYPE: PRT
<213> ORGANISM: Unknown
<220> FEATURE:

<223> OTHER INFORMATION: Synthetic sequence

<400> SEQUENCE: 5

```
Met Lys Arg Ile Leu Asn Ser Leu Lys Val Ala Ala Leu Arg Leu Leu
1               5                   10                  15

Phe Arg Gly Lys Gly Ser Glu Leu Val Lys Thr Val Lys Tyr Pro Leu
            20                  25                  30

Val Ser Pro Val Gln Gly Ala Val Glu Glu Leu Ala Glu Ala Ile Arg
        35                  40                  45

His Asp Asn Leu His Leu Phe Gly Gln Lys Glu Ile Val Asp Leu Met
    50                  55                  60

Glu Lys Asp Glu Gly Thr Gln Val Tyr Ser Val Val Asp Phe Trp Leu
65                  70                  75                  80

Asp Thr Leu Arg Leu Gly Met Phe Phe Ser Pro Ser Ala Asn Ala Leu
                85                  90                  95

Lys Ile Thr Leu Gly Lys Phe Asn Ser Asp Gln Val Ser Pro Phe Arg
            100                 105                 110

Lys Val Leu Glu Gln Ser Pro Phe Phe Leu Ala Gly Arg Leu Lys Val
        115                 120                 125

Glu Pro Ala Glu Arg Ile Leu Ser Val Glu Ile Arg Lys Ile Gly Lys
    130                 135                 140

Arg Glu Asn Arg Val Glu Asn Tyr Ala Ala Asp Val Glu Thr Cys Phe
145                 150                 155                 160

Ile Gly Gln Leu Ser Ser Asp Glu Lys Gln Ser Ile Gln Lys Leu Ala
                165                 170                 175

Asn Asp Ile Trp Asp Ser Lys Asp His Glu Glu Gln Arg Met Leu Lys
            180                 185                 190

Ala Asp Phe Phe Ala Ile Pro Leu Ile Lys Asp Pro Lys Ala Val Thr
        195                 200                 205

Glu Glu Asp Pro Glu Asn Glu Thr Ala Gly Lys Gln Lys Pro Leu Glu
    210                 215                 220

Leu Cys Val Cys Leu Val Pro Glu Leu Tyr Thr Arg Gly Phe Gly Ser
225                 230                 235                 240

Ile Ala Asp Phe Leu Val Gln Arg Leu Thr Leu Leu Arg Asp Lys Met
                245                 250                 255

Ser Thr Asp Thr Ala Glu Asp Cys Leu Glu Tyr Val Gly Ile Glu Glu
            260                 265                 270

Glu Lys Gly Asn Gly Met Asn Ser Leu Leu Gly Thr Phe Leu Lys Asn
        275                 280                 285

Leu Gln Gly Asp Gly Phe Glu Gln Ile Phe Gln Phe Met Leu Gly Ser
    290                 295                 300

Tyr Val Gly Trp Gln Gly Lys Glu Asp Val Leu Arg Glu Arg Leu Asp
305                 310                 315                 320

Leu Leu Ala Glu Lys Val Lys Arg Leu Pro Lys Pro Lys Phe Ala Gly
                325                 330                 335

Glu Trp Ser Gly His Arg Met Phe Leu His Gly Gln Leu Lys Ser Trp
            340                 345                 350

Ser Ser Asn Phe Phe Arg Leu Phe Asn Glu Thr Arg Glu Leu Leu Glu
        355                 360                 365

Ser Ile Lys Ser Asp Ile Gln His Ala Thr Met Leu Ile Ser Tyr Val
    370                 375                 380

Glu Glu Lys Gly Gly Tyr His Pro Gln Leu Leu Ser Gln Tyr Arg Lys
385                 390                 395                 400
```

```
Leu Met Glu Gln Leu Pro Ala Leu Arg Thr Lys Val Leu Asp Pro Glu
                405                 410                 415

Ile Glu Met Thr His Met Ser Glu Ala Val Arg Ser Tyr Ile Met Ile
            420                 425                 430

His Lys Ser Val Ala Gly Phe Leu Pro Asp Leu Leu Glu Ser Leu Asp
        435                 440                 445

Arg Asp Lys Asp Arg Glu Phe Leu Leu Ser Ile Phe Pro Arg Ile Pro
    450                 455                 460

Lys Ile Asp Lys Lys Thr Lys Glu Ile Val Ala Trp Glu Leu Pro Gly
465                 470                 475                 480

Glu Pro Glu Glu Gly Tyr Leu Phe Thr Ala Asn Asn Leu Phe Arg Asn
                485                 490                 495

Phe Leu Glu Asn Pro Lys His Val Pro Arg Phe Met Ala Glu Arg Ile
            500                 505                 510

Pro Glu Asp Trp Thr Arg Leu Arg Ser Ala Pro Val Trp Phe Asp Gly
        515                 520                 525

Met Val Lys Gln Trp Gln Lys Val Val Asn Gln Leu Val Glu Ser Pro
    530                 535                 540

Gly Ala Leu Tyr Gln Phe Asn Glu Ser Phe Leu Arg Gln Arg Leu Gln
545                 550                 555                 560

Ala Met Leu Thr Val Tyr Lys Arg Asp Leu Gln Thr Glu Lys Phe Leu
                565                 570                 575

Lys Leu Leu Ala Asp Val Cys Arg Pro Leu Val Asp Phe Phe Gly Leu
            580                 585                 590

Gly Gly Asn Asp Ile Ile Phe Lys Ser Cys Gln Asp Pro Arg Lys Gln
        595                 600                 605

Trp Gln Thr Val Ile Pro Leu Ser Val Pro Ala Asp Val Tyr Thr Ala
    610                 615                 620

Cys Glu Gly Leu Ala Ile Arg Leu Arg Glu Thr Leu Gly Phe Glu Trp
625                 630                 635                 640

Lys Asn Leu Lys Gly His Glu Arg Glu Asp Phe Leu Arg Leu His Gln
                645                 650                 655

Leu Leu Gly Asn Leu Leu Phe Trp Ile Arg Asp Ala Lys Leu Val Val
            660                 665                 670

Lys Leu Glu Asp Trp Met Asn Asn Pro Cys Val Gln Glu Tyr Val Glu
        675                 680                 685

Ala Arg Lys Ala Ile Asp Leu Pro Leu Glu Ile Phe Gly Phe Glu Val
    690                 695                 700

Pro Ile Phe Leu Asn Gly Tyr Leu Phe Ser Glu Leu Arg Gln Leu Glu
705                 710                 715                 720

Leu Leu Leu Arg Arg Lys Ser Val Met Thr Ser Tyr Ser Val Lys Thr
                725                 730                 735

Thr Gly Ser Pro Asn Arg Leu Phe Gln Leu Val Tyr Leu Pro Leu Asn
            740                 745                 750

Pro Ser Asp Pro Glu Lys Lys Asn Ser Asn Asn Phe Gln Glu Arg Leu
        755                 760                 765

Asp Thr Pro Thr Gly Leu Ser Arg Arg Phe Leu Asp Leu Thr Leu Asp
    770                 775                 780

Ala Phe Ala Gly Lys Leu Leu Thr Asp Pro Val Thr Gln Glu Leu Lys
785                 790                 795                 800

Thr Met Ala Gly Phe Tyr Asp His Leu Phe Gly Phe Lys Leu Pro Cys
                805                 810                 815

Lys Leu Ala Ala Met Ser Asn His Pro Gly Ser Ser Ser Lys Met Val
```

-continued

```
            820                 825                 830

Val Leu Ala Lys Pro Lys Lys Gly Val Ala Ser Asn Ile Gly Phe Glu
        835                 840                 845

Pro Ile Pro Asp Pro Ala His Pro Val Phe Arg Val Arg Ser Ser Trp
    850                 855                 860

Pro Glu Leu Lys Tyr Leu Glu Gly Leu Leu Tyr Leu Pro Glu Asp Thr
865                 870                 875                 880

Pro Leu Thr Ile Glu Leu Ala Glu Thr Ser Val Ser Cys Gln Ser Val
                885                 890                 895

Ser Ser Val Ala Phe Asp Leu Lys Asn Leu Thr Thr Ile Leu Gly Arg
            900                 905                 910

Val Gly Glu Phe Arg Val Thr Ala Asp Gln Pro Phe Lys Leu Thr Pro
        915                 920                 925

Ile Ile Pro Glu Lys Glu Glu Ser Phe Ile Gly Lys Thr Tyr Leu Gly
    930                 935                 940

Leu Asp Ala Gly Glu Arg Ser Gly Val Gly Phe Ala Ile Val Thr Val
945                 950                 955                 960

Asp Gly Asp Gly Tyr Glu Val Gln Arg Leu Gly Val His Glu Asp Thr
                965                 970                 975

Gln Leu Met Ala Leu Gln Gln Val Ala Ser Lys Ser Leu Lys Glu Pro
            980                 985                 990

Val Phe Gln Pro Leu Arg Lys Gly  Thr Phe Arg Gln Gln  Glu Arg Ile
        995                 1000                1005

Arg Lys  Ser Leu Arg Gly Cys  Tyr Trp Asn Phe Tyr  His Ala Leu
    1010                 1015                 1020

Met Ile  Lys Tyr Arg Ala Lys  Val Val His Glu Glu  Ser Val Gly
    1025                 1030                 1035

Ser Ser  Gly Leu Val Gly Gln  Trp Leu Arg Ala Phe  Gln Lys Asp
    1040                 1045                 1050

Leu Lys  Lys Ala Asp Val Leu  Pro Lys Lys Gly Gly  Lys Asn Gly
    1055                 1060                 1065

Val Asp  Lys Lys Lys Arg Glu  Ser Ser Ala Gln Asp  Thr Leu Trp
    1070                 1075                 1080

Gly Gly  Ala Phe Ser Lys Lys  Glu Glu Gln Gln Ile  Ala Phe Glu
    1085                 1090                 1095

Val Gln  Ala Ala Gly Ser Ser  Gln Phe Cys Leu Lys  Cys Gly Trp
    1100                 1105                 1110

Trp Phe  Gln Leu Gly Met Arg  Glu Val Asn Arg Val  Gln Glu Ser
    1115                 1120                 1125

Gly Val  Val Leu Asp Trp Asn  Arg Ser Ile Val Thr  Phe Leu Ile
    1130                 1135                 1140

Glu Ser  Ser Gly Glu Lys Val  Tyr Gly Phe Ser Pro  Gln Gln Leu
    1145                 1150                 1155

Glu Lys  Gly Phe Arg Pro Asp  Ile Glu Thr Phe Lys  Lys Met Val
    1160                 1165                 1170

Arg Asp  Phe Met Arg Pro Pro  Met Phe Asp Arg Lys  Gly Arg Pro
    1175                 1180                 1185

Ala Ala  Ala Tyr Glu Arg Phe  Val Leu Gly Arg Arg  His Arg Arg
    1190                 1195                 1200

Tyr Arg  Phe Asp Lys Val Phe  Glu Glu Arg Phe Gly  Arg Ser Ala
    1205                 1210                 1215

Leu Phe  Ile Cys Pro Arg Val  Gly Cys Gly Asn Phe  Asp His Ser
    1220                 1225                 1230
```

```
Ser Glu  Gln Ser Ala Val Val  Leu Ala Leu Ile Gly  Tyr Ile Ala
    1235                 1240                 1245

Asp Lys  Glu Gly Met Ser Gly  Lys Lys Leu Val Tyr  Val Arg Leu
    1250                 1255                 1260

Ala Glu  Leu Met Ala Glu Trp  Lys Leu Lys Lys Leu  Glu Arg Ser
    1265                 1270                 1275

Arg Val  Glu Glu Gln Ser Ser  Ala Gln
    1280                 1285
```

<210> SEQ ID NO 6
<211> LENGTH: 1192
<212> TYPE: PRT
<213> ORGANISM: Unknown
<220> FEATURE:
<223> OTHER INFORMATION: Synthetic sequence

<400> SEQUENCE: 6

```
Met Ala Glu Ser Lys Gln Met Gln Cys Arg Lys Cys Gly Ala Ser Met
1               5                   10                  15

Lys Tyr Glu Val Ile Gly Leu Gly Lys Lys Ser Cys Arg Tyr Met Cys
            20                  25                  30

Pro Asp Cys Gly Asn His Thr Ser Ala Arg Lys Ile Gln Asn Lys Lys
        35                  40                  45

Lys Arg Asp Lys Lys Tyr Gly Ser Ala Ser Lys Ala Gln Ser Gln Arg
    50                  55                  60

Ile Ala Val Ala Gly Ala Leu Tyr Pro Asp Lys Lys Val Gln Thr Ile
65                  70                  75                  80

Lys Thr Tyr Lys Tyr Pro Ala Asp Leu Asn Gly Glu Val His Asp Ser
                85                  90                  95

Gly Val Ala Glu Lys Ile Ala Gln Ala Ile Gln Glu Asp Glu Ile Gly
            100                 105                 110

Leu Leu Gly Pro Ser Ser Glu Tyr Ala Cys Trp Ile Ala Ser Gln Lys
        115                 120                 125

Gln Ser Glu Pro Tyr Ser Val Val Asp Phe Trp Phe Asp Ala Val Cys
    130                 135                 140

Ala Gly Gly Val Phe Ala Tyr Ser Gly Ala Arg Leu Leu Ser Thr Val
145                 150                 155                 160

Leu Gln Leu Ser Gly Glu Glu Ser Val Leu Arg Ala Ala Leu Ala Ser
                165                 170                 175

Ser Pro Phe Val Asp Asp Ile Asn Leu Ala Gln Ala Glu Lys Phe Leu
            180                 185                 190

Ala Val Ser Arg Arg Thr Gly Gln Asp Lys Leu Gly Lys Arg Ile Gly
        195                 200                 205

Glu Cys Phe Ala Glu Gly Arg Leu Glu Ala Leu Gly Ile Lys Asp Arg
    210                 215                 220

Met Arg Glu Phe Val Gln Ala Ile Asp Val Ala Gln Thr Ala Gly Gln
225                 230                 235                 240

Arg Phe Ala Ala Lys Leu Lys Ile Phe Gly Ile Ser Gln Met Pro Glu
                245                 250                 255

Ala Lys Gln Trp Asn Asn Asp Ser Gly Leu Thr Val Cys Ile Leu Pro
            260                 265                 270

Asp Tyr Tyr Val Pro Glu Glu Asn Arg Ala Asp Gln Leu Val Val Leu
        275                 280                 285

Leu Arg Arg Leu Arg Glu Ile Ala Tyr Cys Met Gly Ile Glu Asp Glu
    290                 295                 300
```

-continued

```
Ala Gly Phe Glu His Leu Gly Ile Asp Pro Gly Ala Leu Ser Asn Phe
305                 310                 315                 320

Ser Asn Gly Asn Pro Lys Arg Gly Phe Leu Gly Arg Leu Leu Asn Asn
                325                 330                 335

Asp Ile Ile Ala Leu Ala Asn Asn Met Ser Ala Met Thr Pro Tyr Trp
            340                 345                 350

Glu Gly Arg Lys Gly Glu Leu Ile Glu Arg Leu Ala Trp Leu Lys His
        355                 360                 365

Arg Ala Glu Gly Leu Tyr Leu Lys Glu Pro His Phe Gly Asn Ser Trp
    370                 375                 380

Ala Asp His Arg Ser Arg Ile Phe Ser Arg Ile Ala Gly Trp Leu Ser
385                 390                 395                 400

Gly Cys Ala Gly Lys Leu Lys Ile Ala Lys Asp Gln Ile Ser Gly Val
                405                 410                 415

Arg Thr Asp Leu Phe Leu Leu Lys Arg Leu Leu Asp Ala Val Pro Gln
            420                 425                 430

Ser Ala Pro Ser Pro Asp Phe Ile Ala Ser Ile Ser Ala Leu Asp Arg
        435                 440                 445

Phe Leu Glu Ala Ala Glu Ser Ser Gln Asp Pro Ala Glu Gln Val Arg
    450                 455                 460

Ala Leu Tyr Ala Phe His Leu Asn Ala Pro Ala Val Arg Ser Ile Ala
465                 470                 475                 480

Asn Lys Ala Val Gln Arg Ser Asp Ser Gln Glu Trp Leu Ile Lys Glu
                485                 490                 495

Leu Asp Ala Val Asp His Leu Glu Phe Asn Lys Ala Phe Pro Phe Phe
            500                 505                 510

Ser Asp Thr Gly Lys Lys Lys Lys Lys Gly Ala Asn Ser Asn Gly Ala
        515                 520                 525

Pro Ser Glu Glu Glu Tyr Thr Glu Thr Glu Ser Ile Gln Gln Pro Glu
    530                 535                 540

Asp Ala Glu Gln Glu Val Asn Gly Gln Glu Gly Asn Gly Ala Ser Lys
545                 550                 555                 560

Asn Gln Lys Lys Phe Gln Arg Ile Pro Arg Phe Phe Gly Glu Gly Ser
                565                 570                 575

Arg Ser Glu Tyr Arg Ile Leu Thr Glu Ala Pro Gln Tyr Phe Asp Met
            580                 585                 590

Phe Cys Asn Asn Met Arg Ala Ile Phe Met Gln Leu Glu Ser Gln Pro
        595                 600                 605

Arg Lys Ala Pro Arg Asp Phe Lys Cys Phe Leu Gln Asn Arg Leu Gln
    610                 615                 620

Lys Leu Tyr Lys Gln Thr Phe Leu Asn Ala Arg Ser Asn Lys Cys Arg
625                 630                 635                 640

Ala Leu Leu Glu Ser Val Leu Ile Ser Trp Gly Glu Phe Tyr Thr Tyr
                645                 650                 655

Gly Ala Asn Glu Lys Lys Phe Arg Leu Arg His Glu Ala Ser Glu Arg
            660                 665                 670

Ser Ser Asp Pro Asp Tyr Val Val Gln Gln Ala Leu Glu Ile Ala Arg
        675                 680                 685

Arg Leu Phe Leu Phe Gly Phe Glu Trp Arg Asp Cys Ser Ala Gly Glu
    690                 695                 700

Arg Val Asp Leu Val Glu Ile His Lys Lys Ala Ile Ser Phe Leu Leu
705                 710                 715                 720
```

-continued

```
Ala Ile Thr Gln Ala Glu Val Ser Val Gly Ser Tyr Asn Trp Leu Gly
                725                 730                 735

Asn Ser Thr Val Ser Arg Tyr Leu Ser Val Ala Gly Thr Asp Thr Leu
            740                 745                 750

Tyr Gly Thr Gln Leu Glu Glu Phe Leu Asn Ala Thr Val Leu Ser Gln
        755                 760                 765

Met Arg Gly Leu Ala Ile Arg Leu Ser Ser Gln Glu Leu Lys Asp Gly
    770                 775                 780

Phe Asp Val Gln Leu Glu Ser Ser Cys Gln Asp Asn Leu Gln His Leu
785                 790                 795                 800

Leu Val Tyr Arg Ala Ser Arg Asp Leu Ala Ala Cys Lys Arg Ala Thr
                805                 810                 815

Cys Pro Ala Glu Leu Asp Pro Lys Ile Leu Val Leu Pro Val Gly Ala
            820                 825                 830

Phe Ile Ala Ser Val Met Lys Met Ile Glu Arg Gly Asp Glu Pro Leu
        835                 840                 845

Ala Gly Ala Tyr Leu Arg His Arg Pro His Ser Phe Gly Trp Gln Ile
    850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
                885                 890                 895

Ser Ala Gln Tyr Gly Pro Val Leu Trp Leu Asn Ser Ser Ser Tyr Ser
            900                 905                 910

Gln Ser Gln Tyr Leu Asp Gly Phe Leu Ser Gln Pro Lys Asn Trp Ser
        915                 920                 925

Met Arg Val Leu Pro Gln Ala Gly Ser Val Arg Val Glu Gln Arg Val
    930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
                965                 970                 975

Gly Ser Gly Asp Glu Ala Val Leu Ala Pro Asn Arg Tyr Leu Gly Leu
            980                 985                 990

Phe Pro His Ser Gly Gly Ile Glu  Tyr Ala Val Val Asp  Val Leu Asp
        995                 1000                 1005

Ser Ala  Gly Phe Lys Ile Leu  Glu Arg Gly Thr Ile  Ala Val Asn
    1010                 1015                 1020

Gly Phe  Ser Gln Lys Arg Gly  Glu Arg Gln Glu Glu  Ala His Arg
    1025                 1030                 1035

Glu Lys  Gln Arg Arg Gly Ile  Ser Asp Ile Gly Arg  Lys Lys Pro
    1040                 1045                 1050

Val Gln  Ala Glu Val Asp Ala  Ala Asn Glu Leu His  Arg Lys Tyr
    1055                 1060                 1065

Thr Asp  Val Ala Thr Arg Leu  Gly Cys Arg Ile Val  Val Gln Trp
    1070                 1075                 1080

Ala Pro  Gln Pro Lys Pro Gly  Thr Ala Pro Thr Ala  Gln Thr Val
    1085                 1090                 1095

Tyr Ala  Arg Ala Val Arg Thr  Glu Ala Pro Arg Ser  Gly Asn Gln
    1100                 1105                 1110

Glu Asp  His Ala Arg Met Lys  Ser Ser Trp Gly Tyr  Thr Trp Gly
    1115                 1120                 1125

Thr Tyr  Trp Glu Lys Arg Lys  Pro Glu Asp Ile Leu  Gly Ile Ser
```

```
    1130                1135                1140

Thr Gln  Val Tyr Trp Thr Gly  Gly Ile Gly Glu Ser  Cys Pro Ala
    1145                1150                1155

Val Ala  Val Ala Leu Leu Gly  His Ile Arg Ala Thr  Ser Thr Gln
    1160                1165                1170

Thr Glu  Trp Glu Lys Glu Glu  Val Val Phe Gly Arg  Leu Lys Lys
    1175                1180                1185

Phe Phe  Pro Ser
    1190


<210> SEQ ID NO 7
<211> LENGTH: 1192
<212> TYPE: PRT
<213> ORGANISM: Unknown
<220> FEATURE:
<223> OTHER INFORMATION: Synthetic sequence

<400> SEQUENCE: 7

Met Ala Glu Ser Lys Gln Met Gln Cys Arg Lys Cys Gly Ala Ser Met
1               5                   10                  15

Lys Tyr Glu Val Ile Gly Leu Gly Lys Lys Ser Cys Arg Tyr Met Cys
            20                  25                  30

Pro Asp Cys Gly Asn His Thr Ser Ala Arg Lys Ile Gln Asn Lys Lys
        35                  40                  45

Lys Arg Asp Lys Lys Tyr Gly Ser Ala Ser Lys Ala Gln Ser Gln Arg
    50                  55                  60

Ile Ala Val Ala Gly Ala Leu Tyr Pro Asp Lys Lys Val Gln Thr Ile
65                  70                  75                  80

Lys Thr Tyr Lys Tyr Pro Ala Asp Leu Asn Gly Glu Val His Asp Arg
                85                  90                  95

Gly Val Ala Glu Lys Ile Glu Gln Ala Ile Gln Glu Asp Glu Ile Gly
            100                 105                 110

Leu Leu Gly Pro Ser Ser Glu Tyr Ala Cys Trp Ile Ala Ser Gln Lys
        115                 120                 125

Gln Ser Glu Pro Tyr Ser Val Val Asp Phe Trp Phe Asp Ala Val Cys
    130                 135                 140

Ala Gly Gly Val Phe Ala Tyr Ser Gly Ala Arg Leu Leu Ser Thr Val
145                 150                 155                 160

Leu Gln Leu Ser Gly Glu Glu Ser Val Leu Arg Ala Ala Leu Ala Ser
                165                 170                 175

Ser Pro Phe Val Asp Asp Ile Asn Leu Ala Gln Ala Glu Lys Phe Leu
            180                 185                 190

Ala Val Ser Arg Arg Thr Gly Gln Asp Lys Leu Gly Lys Arg Ile Gly
        195                 200                 205

Glu Cys Phe Ala Glu Gly Arg Leu Glu Ala Leu Gly Ile Lys Asp Arg
    210                 215                 220

Met Arg Glu Phe Val Gln Ala Ile Asp Val Ala Gln Thr Ala Gly Gln
225                 230                 235                 240

Arg Phe Ala Ala Lys Leu Lys Ile Phe Gly Ile Ser Gln Met Pro Glu
                245                 250                 255

Ala Lys Gln Trp Asn Asn Asp Ser Gly Leu Thr Val Cys Ile Leu Pro
            260                 265                 270

Asp Tyr Tyr Val Pro Glu Glu Asn Arg Ala Asp Gln Leu Val Val Leu
        275                 280                 285

Leu Arg Arg Leu Arg Glu Ile Ala Tyr Cys Met Gly Ile Glu Asp Glu
```

-continued

```
    290                 295                 300

Ala Gly Phe Glu His Leu Gly Ile Asp Pro Gly Ala Leu Ser Asn Phe
305                 310                 315                 320

Ser Asn Gly Asn Pro Lys Arg Gly Phe Leu Gly Arg Leu Leu Asn Asn
                325                 330                 335

Asp Ile Ile Ala Leu Ala Asn Asn Met Ser Ala Met Thr Pro Tyr Trp
            340                 345                 350

Glu Gly Arg Lys Gly Glu Leu Ile Glu Arg Leu Ala Trp Leu Lys His
        355                 360                 365

Arg Ala Glu Gly Leu Tyr Leu Lys Glu Pro His Phe Gly Asn Ser Trp
    370                 375                 380

Ala Asp His Arg Ser Arg Ile Phe Ser Arg Ile Ala Gly Trp Leu Ser
385                 390                 395                 400

Gly Cys Ala Gly Lys Leu Lys Ile Ala Lys Asp Gln Ile Ser Gly Val
                405                 410                 415

Arg Thr Asp Leu Phe Leu Leu Lys Arg Leu Leu Asp Ala Val Pro Gln
            420                 425                 430

Ser Ala Pro Ser Pro Asp Phe Ile Ala Ser Ile Ser Ala Leu Asp Arg
        435                 440                 445

Phe Leu Glu Ala Ala Glu Ser Ser Gln Asp Pro Ala Glu Gln Val Arg
    450                 455                 460

Ala Leu Tyr Ala Phe His Leu Asn Ala Pro Ala Val Arg Ser Ile Ala
465                 470                 475                 480

Asn Lys Ala Val Gln Arg Ser Asp Ser Gln Glu Trp Leu Ile Lys Glu
                485                 490                 495

Leu Asp Ala Val Asp His Leu Glu Phe Asn Lys Ala Phe Pro Phe Phe
            500                 505                 510

Ser Asp Thr Gly Lys Lys Lys Lys Lys Gly Ala Asn Ser Asn Gly Ala
        515                 520                 525

Pro Ser Glu Glu Glu Tyr Thr Glu Thr Glu Ser Ile Gln Gln Pro Glu
    530                 535                 540

Asp Ala Glu Gln Glu Val Asn Gly Gln Glu Gly Asn Gly Ala Ser Lys
545                 550                 555                 560

Asn Gln Lys Lys Phe Gln Arg Ile Pro Arg Phe Phe Gly Glu Gly Ser
                565                 570                 575

Arg Ser Glu Tyr Arg Ile Leu Thr Glu Ala Pro Gln Tyr Phe Asp Met
            580                 585                 590

Phe Cys Asn Asn Met Arg Ala Ile Phe Met Gln Leu Glu Ser Gln Pro
        595                 600                 605

Arg Lys Ala Pro Arg Asp Phe Lys Cys Phe Leu Gln Asn Arg Leu Gln
    610                 615                 620

Lys Leu Tyr Lys Gln Thr Phe Leu Asn Ala Arg Ser Asn Lys Cys Arg
625                 630                 635                 640

Ala Leu Leu Glu Ser Val Leu Ile Ser Trp Gly Glu Phe Tyr Thr Tyr
                645                 650                 655

Gly Ala Asn Glu Lys Lys Phe Arg Leu Arg His Glu Ala Ser Glu Arg
            660                 665                 670

Ser Ser Asp Pro Asp Tyr Val Val Gln Gln Ala Leu Glu Ile Ala Arg
        675                 680                 685

Arg Leu Phe Leu Phe Gly Phe Glu Trp Arg Asp Cys Ser Ala Gly Glu
    690                 695                 700

Arg Val Asp Leu Val Glu Ile His Lys Lys Ala Ile Ser Phe Leu Leu
705                 710                 715                 720
```

-continued

```
Ala Ile Thr Gln Ala Glu Val Ser Val Gly Ser Tyr Asn Trp Leu Gly
                725                 730                 735

Asn Ser Thr Val Ser Arg Tyr Leu Ser Val Ala Gly Thr Asp Thr Leu
            740                 745                 750

Tyr Gly Thr Gln Leu Glu Glu Phe Leu Asn Ala Thr Val Leu Ser Gln
        755                 760                 765

Met Arg Gly Leu Ala Ile Arg Leu Ser Ser Gln Glu Leu Lys Asp Gly
    770                 775                 780

Phe Asp Val Gln Leu Glu Ser Ser Cys Gln Asp Asn Leu Gln His Leu
785                 790                 795                 800

Leu Val Tyr Arg Ala Ser Arg Asp Leu Ala Ala Cys Lys Arg Ala Thr
                805                 810                 815

Cys Pro Ala Glu Leu Asp Pro Lys Ile Leu Val Leu Pro Ala Gly Ala
            820                 825                 830

Phe Ile Ala Ser Val Met Lys Met Ile Glu Arg Gly Asp Glu Pro Leu
        835                 840                 845

Ala Gly Ala Tyr Leu Arg His Arg Pro His Ser Phe Gly Trp Gln Ile
    850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
                885                 890                 895

Ser Ala Gln Tyr Gly Pro Val Leu Trp Leu Asn Ser Ser Ser Tyr Ser
            900                 905                 910

Gln Ser Gln Tyr Leu Asp Gly Phe Leu Ser Gln Pro Lys Asn Trp Ser
        915                 920                 925

Met Arg Val Leu Pro Gln Ala Gly Ser Val Arg Val Glu Gln Arg Val
    930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
                965                 970                 975

Gly Ser Gly Asp Glu Ala Val Leu Ala Pro Asn Arg Tyr Leu Gly Leu
            980                 985                 990

Phe Pro His Ser Gly Gly Ile Glu  Tyr Ala Val Val Asp  Val Leu Asp
        995                 1000                 1005

Ser Ala  Gly Phe Lys Ile Leu  Glu Arg Gly Thr Ile  Ala Val Asn
    1010                 1015                 1020

Gly Phe  Ser Gln Lys Arg Gly  Glu Arg Gln Glu Glu  Ala His Arg
    1025                 1030                 1035

Glu Lys  Gln Arg Arg Gly Ile  Ser Asp Ile Gly Arg  Lys Lys Pro
    1040                 1045                 1050

Val Gln  Ala Glu Val Asp Ala  Ala Asn Glu Leu His  Arg Lys Tyr
    1055                 1060                 1065

Thr Asp  Val Ala Thr Arg Leu  Gly Cys Arg Ile Val  Val Gln Trp
    1070                 1075                 1080

Ala Pro  Gln Pro Lys Pro Gly  Thr Ala Pro Thr Ala  Gln Thr Val
    1085                 1090                 1095

Tyr Ala  Arg Ala Val Arg Thr  Glu Ala Pro Arg Ser  Gly Asn Gln
    1100                 1105                 1110

Glu Asp  His Ala Arg Met Lys  Ser Ser Trp Gly Tyr  Thr Trp Ser
    1115                 1120                 1125
```

Thr Tyr Trp Glu Lys Arg Lys Pro Glu Asp Ile Leu Gly Ile Ser
1130 1135 1140

Thr Gln Val Tyr Trp Thr Gly Gly Ile Gly Glu Ser Cys Pro Ala
1145 1150 1155

Val Ala Val Ala Leu Leu Gly His Ile Arg Ala Thr Ser Thr Gln
1160 1165 1170

Thr Glu Trp Glu Lys Glu Glu Val Val Phe Gly Arg Leu Lys Lys
1175 1180 1185

Phe Phe Pro Ser
1190

<210> SEQ ID NO 8
<211> LENGTH: 1193
<212> TYPE: PRT
<213> ORGANISM: Unknown
<220> FEATURE:
<223> OTHER INFORMATION: Synthetic sequence

<400> SEQUENCE: 8

Met Lys Arg Ile Ala Lys Phe Arg His Asp Lys Pro Val Lys Arg Glu
1 5 10 15

Ala Trp Ser Lys Gly Tyr Arg Val His Lys Asn Arg Ile Ile Asn Lys
20 25 30

Val Thr Arg Ser Ile Lys Tyr Pro Leu Val Val Lys Asp Glu Trp Lys
35 40 45

Lys Arg Leu Ile Asp Asp Ala Ala His Asp Tyr Arg Trp Leu Val Gly
50 55 60

Pro Ile Asn Tyr Ser Asp Trp Cys Arg Asp Pro Asn Gln Tyr Ser Ile
65 70 75 80

Leu Glu Phe Trp Ile Asp Phe Leu Cys Val Gly Gly Val Phe Gln Ser
85 90 95

Ser His Ser Asn Ile Cys Arg Leu Ala Ile Gln Leu Ser Gly Gly Ser
100 105 110

Val Phe Glu Gln Glu Trp Lys Asp Leu Ser Pro Phe Val Arg Ala Asn
115 120 125

Leu Ile Gln Gly Ile Lys Pro Ala Glu Phe Ile Gly Phe Leu Thr Ala
130 135 140

Glu Phe Arg Ser Ser Ser Asn Pro Lys Asn Phe Ile Ser Lys Phe Phe
145 150 155 160

Glu Gly Ser Asn Glu Asp Leu Glu Ser Leu Thr Asn Glu Phe Ala Ser
165 170 175

Ile Val Asp Phe Ile Lys Ala Lys Asp Ile Ser Leu Leu Arg Lys Ser
180 185 190

Leu Pro Ser Cys Lys Lys Ile Ala Pro Asn Leu Trp Glu Lys Ala Val
195 200 205

Gly Ser His Ser Thr Asn Glu Leu Leu Lys Leu Leu Thr Lys Tyr Thr
210 215 220

Arg Val Met Leu Val Ala Glu Pro Ser His Ser Asp Arg Val Phe Ser
225 230 235 240

Gln Thr Val Leu Gln Ser Asn Asp Gln Asp Asp Pro Glu Leu Thr Gly
245 250 255

Pro Leu Pro Ser His Lys Val Gly Lys Ala Ser Tyr Leu Phe Ile Pro
260 265 270

Glu Phe Ile Arg Glu Val Asn Leu Asp Lys Ile Ser Lys Leu Asp Leu
275 280 285

-continued

```
Ser Ala Lys Ser Lys Leu Ala Val Glu Gln Val Lys Lys Leu Ser Glu
    290                 295                 300

Leu Thr Ser Asp Phe Lys Gln Ile Glu Asn Gln Ser Glu Ala Tyr Phe
305                 310                 315                 320

Gly Leu Ser Thr Ser Phe Asn Glu Leu Ser Asn Phe Leu Gly Ile Leu
                325                 330                 335

Ile Arg Thr Leu Arg Asn Ala Pro Glu Ala Ile Leu Lys Asp Gln Ile
            340                 345                 350

Ala Leu Cys Ala Pro Leu Asp Lys Asp Ile Leu Lys Ile Thr Leu Asp
        355                 360                 365

Trp Leu Cys Asp Arg Ala Gln Ala Leu Pro Glu Asn Pro Arg Phe Glu
    370                 375                 380

Thr Asn Trp Ala Glu Tyr Arg Ser Tyr Leu Gly Gly Lys Ile Lys Ser
385                 390                 395                 400

Trp Phe Ser Asn Tyr Glu Asn Phe Phe Glu Ile Pro Gln Ala Ala Ser
                405                 410                 415

Ser Gln Gln Asn Asn Asn Arg Glu Lys Lys Leu Gly Asn Arg Ser Ala
            420                 425                 430

Ile Arg Ala Leu Asn Leu Lys Lys Glu Ala Phe Glu Lys Ala Arg Glu
        435                 440                 445

Thr Phe Lys Gly Asp Lys Gly Thr Leu Glu Lys Ile Asp Leu Ala Tyr
    450                 455                 460

Arg Leu Leu Gly Ser Ile Ser Pro Glu Val Leu Gln Cys Asp Glu Gly
465                 470                 475                 480

Leu Lys Leu Tyr Gln Gln Phe Asn Asp Glu Leu Leu Val Leu Asn Glu
                485                 490                 495

Thr Ile Asn Gln Lys Phe Gln Asp Ala Lys Arg Asp Ile Lys Ala Lys
            500                 505                 510

Lys Glu Lys Glu Ser Phe Glu Lys Leu Gln Arg Asn Leu Ser Ser Pro
        515                 520                 525

Leu Pro Arg Ile Pro Glu Phe Phe Gly Glu Arg Ala Lys Lys Gly Tyr
    530                 535                 540

Gln Lys Ala Arg Val Ser Pro Lys Leu Ala Arg His Leu Leu Glu Cys
545                 550                 555                 560

Leu Asn Asp Trp Leu Ala Arg Phe Ala Lys Val Glu Glu Ser Ala Phe
                565                 570                 575

Ser Glu Lys Glu Phe Gln Arg Ile Leu Asp Trp Leu Arg Thr Ser Asp
            580                 585                 590

Phe Leu Pro Val Phe Ile Arg Lys Ser Lys Asp Pro Pro Ser Trp Leu
        595                 600                 605

Arg Tyr Ile Ala Arg Val Ala Thr Gly Lys Tyr Tyr Phe Trp Val Ser
    610                 615                 620

Glu Tyr Ser Arg Lys Arg Val Gln Ile Ile Asp Lys Pro Ile Ala Gln
625                 630                 635                 640

Asn Pro Leu Lys Glu Leu Ile Ser Trp Phe Leu Leu Asn Lys Asp Ala
                645                 650                 655

Phe Ser Arg Asp Asn Glu Leu Phe Lys Gly Leu Ser Ser Lys Met Val
            660                 665                 670

Thr Leu Ala Arg Ile Met Ala Gly Ile Leu Arg Asp Arg Gly Glu Gly
        675                 680                 685

Leu Lys Glu Leu Gln Ala Met Thr Ser Lys Leu Asp Asn Ile Gly Leu
    690                 695                 700

Leu His Pro Ser Phe Ser Val Pro Val Thr Asp Ser Leu Lys Asp Ala
```

-continued

```
705                 710                 715                 720

Ala Phe Tyr Arg Ala Phe Phe Ser Glu Leu Glu Gly Leu Leu Asn Ile
                725                 730                 735

Gly Arg Ser Arg Leu Ile Ile Glu Arg Ile Thr Leu Gln Ser Gln Gln
            740                 745                 750

Ser Lys Asn Lys Lys Thr Arg Arg Pro Leu Met Pro Glu Pro Phe Ile
        755                 760                 765

Asn Glu Asp Lys Glu Val Phe Leu Ala Phe Pro Lys Phe Glu Thr Lys
    770                 775                 780

Asn Lys Val Lys Gly Thr Arg Val Val Tyr Asn Ser Pro Asp Glu Val
785                 790                 795                 800

Asn Trp Leu Leu Ser Pro Ile Arg Ser Ser Lys Gly Gln Leu Ser Phe
                805                 810                 815

Met Phe Arg Cys Leu Ser Glu Asp Ala Lys Ile Met Thr Thr Ser Gly
            820                 825                 830

Gly Cys Ser Tyr Ile Val Glu Phe Lys Lys Leu Leu Glu Ala Gln Glu
        835                 840                 845

Glu Val Leu Ser Ile His Asp Cys Asp Ile Ile Pro Arg Ala Phe Val
    850                 855                 860

Ser Ile Pro Phe Thr Leu Glu Arg Glu Ser Glu Glu Thr Lys Pro Asp
865                 870                 875                 880

Trp Lys Pro Asn Arg Phe Met Gly Val Asp Ile Gly Glu Tyr Ala Val
                885                 890                 895

Ala Tyr Cys Val Ile Glu Lys Gly Thr Asp Ser Ile Glu Ile Leu Asp
            900                 905                 910

Cys Gly Ile Val Arg Asn Gly Ala His Arg Val Leu Lys Glu Lys Val
        915                 920                 925

Asp Arg Leu Lys Arg Arg Gln Arg Ser Met Thr Phe Gly Ala Met Asp
    930                 935                 940

Thr Ser Ile Ala Ala Ala Arg Glu Ser Leu Val Gly Asn Tyr Arg Asn
945                 950                 955                 960

Arg Leu His Ala Ile Ala Leu Lys His Gly Ala Lys Leu Val Tyr Glu
                965                 970                 975

Tyr Glu Val Ser Ala Phe Glu Ser Gly Gly Asn Arg Ile Lys Lys Val
            980                 985                 990

Tyr Glu Thr Leu Lys Lys Ser Asp  Cys Thr Gly Glu Thr  Glu Ala Asp
        995                 1000                1005

Lys Asn  Ala Arg Lys His Ile  Trp Gly Glu Thr Asn  Ala Val Gly
    1010                1015                1020

Asp Gln  Ile Gly Ala Gly Trp  Thr Ser Gln Thr Cys  Ala Lys Cys
    1025                1030                1035

Gly Arg  Ser Phe Gly Ala Asp  Leu Lys Ala Gly Asn  Phe Gly Val
    1040                1045                1050

Ala Val  Pro Val Pro Glu Lys  Val Glu Asp Ser Lys  Gly His Tyr
    1055                1060                1065

Ala Tyr  His Glu Phe Pro Phe  Glu Asp Gly Leu Lys  Val Arg Gly
    1070                1075                1080

Phe Leu  Lys Pro Asn Lys Ile  Ile Ser Asp Gln Lys  Glu Leu Ala
    1085                1090                1095

Lys Ala  Val His Ala Tyr Met  Arg Pro Pro Leu Val  Ala Leu Gly
    1100                1105                1110

Lys Arg  Lys Leu Pro Lys Asn  Ala Arg Tyr Arg Arg  Gly Asn Ser
    1115                1120                1125
```

```
Ser Leu Phe Arg Cys Pro Phe Ser Asp Cys Gly Phe Thr Ala Asp
    1130                1135                1140

Ala Asp Ile Gln Ala Ala Tyr Asn Ile Ala Val Lys Gln Leu Tyr
    1145                1150                1155

Lys Pro Lys Lys Gly Tyr Pro Lys Glu Arg Lys Trp Gln Asp Phe
    1160                1165                1170

Val Ile Leu Lys Pro Lys Glu Pro Ser Lys Leu Phe Asp Lys Gln
    1175                1180                1185

Phe Tyr Arg Pro Asn
    1190


<210> SEQ ID NO 9
<211> LENGTH: 4
<212> TYPE: PRT
<213> ORGANISM: Artificial Sequence
<220> FEATURE:
<223> OTHER INFORMATION: Synthetic sequence

<400> SEQUENCE: 9

Ala Ala Ala Ala
1


<210> SEQ ID NO 10
<211> LENGTH: 4
<212> TYPE: PRT
<213> ORGANISM: Artificial Sequence
<220> FEATURE:
<223> OTHER INFORMATION: Synthetic sequence

<400> SEQUENCE: 10

Ala Ala Ala Ala
1


<210> SEQ ID NO 11
<211> LENGTH: 25
<212> TYPE: RNA
<213> ORGANISM: Artificial sequence
<220> FEATURE:
<223> OTHER INFORMATION: Synthetic sequence

<400> SEQUENCE: 11

cuccgaaagu aucggggaua aaggc                                           25


<210> SEQ ID NO 12
<211> LENGTH: 25
<212> TYPE: RNA
<213> ORGANISM: Artificial sequence
<220> FEATURE:
<223> OTHER INFORMATION: Synthetic sequence

<400> SEQUENCE: 12

caccgaaauu uggagaggau aaggc                                           25


<210> SEQ ID NO 13
<211> LENGTH: 25
<212> TYPE: RNA
<213> ORGANISM: Artificial sequence
<220> FEATURE:
<223> OTHER INFORMATION: Synthetic sequence

<400> SEQUENCE: 13

cuccgaauua ucgggaggau aaggc                                           25
```

<210> SEQ ID NO 14
<211> LENGTH: 25
<212> TYPE: RNA
<213> ORGANISM: Artificial sequence
<220> FEATURE:
<223> OTHER INFORMATION: Synthetic sequence

<400> SEQUENCE: 14
ccccgaauau aggggacaaa aaggc 25

<210> SEQ ID NO 15
<211> LENGTH: 36
<212> TYPE: RNA
<213> ORGANISM: Artificial sequence
<220> FEATURE:
<223> OTHER INFORMATION: Synthetic sequence

<400> SEQUENCE: 15
gucuagacau acagguggaa aggugagagu aaagac 36

<210> SEQ ID NO 16
<211> LENGTH: 25
<212> TYPE: RNA
<213> ORGANISM: Artificial sequence
<220> FEATURE:
<223> OTHER INFORMATION: Synthetic sequence

<400> SEQUENCE: 16
cuccgugaau acguggggua aaggc 25

<210> SEQ ID NO 17
<211> LENGTH: 10
<212> TYPE: RNA
<213> ORGANISM: Artificial sequence
<220> FEATURE:
<223> OTHER INFORMATION: Synthetic sequence

<400> SEQUENCE: 17
aaaaaaaaaa 10

<210> SEQ ID NO 18
<211> LENGTH: 10
<212> TYPE: RNA
<213> ORGANISM: Artificial sequence
<220> FEATURE:
<223> OTHER INFORMATION: Synthetic sequence

<400> SEQUENCE: 18
aaaaaaaaaa 10

<210> SEQ ID NO 19
<211> LENGTH: 10
<212> TYPE: RNA
<213> ORGANISM: Artificial sequence
<220> FEATURE:
<223> OTHER INFORMATION: Synthetic sequence

<400> SEQUENCE: 19
aaaaaaaaaa 10

<210> SEQ ID NO 20
<211> LENGTH: 43
<212> TYPE: RNA
<213> ORGANISM: Artificial sequence
<220> FEATURE:
<223> OTHER INFORMATION: Synthetic sequence

<400> SEQUENCE: 20
cuccgaaagu aucggggaua aaggcaucaa uaccaaacuc ugg 43

<210> SEQ ID NO 21
<211> LENGTH: 6430
<212> TYPE: DNA
<213> ORGANISM: Artificial sequence
<220> FEATURE:
<223> OTHER INFORMATION: Synthetic sequence

<400> SEQUENCE: 21
ttaaaaggac agtttctaat agcatataat cattatagca ttacatacgg aaaactactt 60
caaatttgcg gcagatcgga ttttgctggc ccagagatat attttccttc tttgttaaaa 120
gcggatttat ggcaagggca gagccagttt ttatttttat cttcccattc aacgatgcat 180
ccaagatgtg ggcaaattgg agagagtttt aaaatttctc ctttttcatt tttgtatacg 240
gcaactttct ttccttctat ctcaacaatt tttcctgtgt tgttttttaa attgtctaaa 300
gtacccgaag ttttcataaa gcgccccttc ataaaaagat aaggaaaaag aaatatttgt 360
tttaataatg ttaacatata gcttgttgaa ttataacatt tatccgagag gtggtctaac 420
ttatgcaact tattgattct tactttagga gaatagttct actctaggcg tatagagaac 480
ttttgttgaa aggtttttgc aatatctcta ctttctggcc aaaaatcggt ttttcccgcg 540
aatctgccgt atagtttgta tcctgcttta acaggtctgc ctccgctagg ttttcccggg 600
aaaggtacta taaatctctt atttcctaag agataagagc gcaaaccgag aattaagcca 660
tgatagagtt cctgaaaagt agcagtttgg cgagttgctg caacataaat ttctgtatcc 720
atgaaatcct ttaggttttc cattgtatag ggaagtgttt tactttcatc cccaccgttt 780
tcttgtatct cttttattgt attaaaggcg actccgtcga taaaacctct atatggttcc 840
atcaaatcgt agattagaga ggggtaatct gaaggtgtgt gggtgtatcc gtgaaaagga 900
ctaaaatgat ggtaaaccac ccaacgcaag ataataccgc taacaaattt tgaagaagca 960
tctaaaacat tacagataaa attacctttt gatcgtcgcc tatctttagg atatcccaaa 1020
gacttgtaga aatgttccca atatcttttg gcatgccacg attccactcc aactatagac 1080
tccacggacg ataagccctg cagttcctgc gttggggctg ggattaacca ttccatggat 1140
ttgaatttag cgtaaatcaa tcttttcgtt atatatgcgc gtttcttttc attttgtctg 1200
aatagaatct gttttgttag taaatcttct ctattagatg ttgtagaagg aacgatccaa 1260
acaccgcggg gcatatttcg tcgatgtatt gttaaaggaa tgccccaagc actgcatttt 1320
tctagaaatt cttgttctag cggacaaacg ctaccataaa acatgataga gtgaatctct 1380
ggaaaggaca aatccagctc accacctttg taagagaatt taacactctt tcccgataag 1440
tctatggatt ttacataggg taaccagata aattgtttac gcttggcgaa atatctcctc 1500
atttcgtatt ggatatatgt ctcaaattat gctatattta aggtacattt tcaagcggtt 1560
tttagctcgt ttacatttta atatcaacaa aatcggggag aagtctccga aagtatcggg 1620
gataaaggca tcaataccaa actctggctc cgaaagtatc ggggataaag gcattcccaa 1680
tatctcatta ctccgaaagt atcggggata aaggctcctc ccgtatctgt caactccgaa 1740
agtatcgggg ataaaggctt aaaaaggaat accccactcc gaaagtatcg gggataaagg 1800
cttgtactcc acatccgcta ctccgaaagt atcggggata aaggcactga aacttgaatt 1860
gtactccgaa agtatcgggg ataaaggcat cttgcgactt tctcttctcc gaaagtatcg 1920
gggataaagg ctcttcggtt ggtacgggtt ctccgaaagt atcggggata aaggcttatg 1980

-continued

```
gcagtatcgc atactccgaa agtatcgggg ataaaggctt cataagtacg cctaaactcc   2040
gaaagtatcg gggataaagg cagatgaggc tatacttaac tccgaaagta tcggggataa   2100
aggcacaaac ataaagggaa aactccgaaa gtatcgggga taaaggcata aatctggtga   2160
acttactccg aaagtatcgg ggataaaggc tactgttatt gttgtacact ccgaaagtat   2220
cggggataaa ggcataacta gcgttcccat tctccgaaag tatcaaaata aaaagggttt   2280
ccagttttta actaaacttt agccttccac cctttcctga ttttgttgat aattaataat   2340
gcgcaaaaaa ttgtttaagg gttacatttt acataataag aggcttgtat atacaggtaa   2400
agctgcaata cgttctatta aatatccatt agtcgctcca aataaaacag ccttaaacaa   2460
tttatcagaa aagataattt atgattatga gcatttattc ggacctttaa atgtggctag   2520
ctatgcaaga aattcaaaca ggtacagcct tgtggatttt tggatagata gcttgcgagc   2580
aggtgtaatt tggcaaagca aaagtacttc gctaattgat ttgataagta agctagaagg   2640
atctaaatcc ccatcagaaa agatatttga acaaatagat tttgagctaa aaaataagtt   2700
ggataaagag caattcaaag atattattct tcttaataca ggaattcgtt ctagcagtaa   2760
tgttcgcagt ttgagggggc gctttctaaa gtgttttaaa gaggaattta gagataccga   2820
agaggttatc gcctgtgtag ataaatggag caaggacctt atcgtagagg gtaaaagtat   2880
actagtgagt aaacagtttc tttattggga agaagagttt ggtattaaaa tttttcctca   2940
ttttaaagat aatcacgatt taccaaaact aacttttttt gtggagcctt ccttggaatt   3000
tagtccgcac ctccctttag ccaactgtct tgagcgtttg aaaaaattcg atatttcgcg   3060
tgaaagtttg ctcgggttag acaataattt ttcggccttt tctaattatt tcaatgagct   3120
ttttaactta ttgtccaggg gggagattaa aaagattgta acagctgtcc ttgctgtttc   3180
taaatcgtgg gagaatgagc cagaattgga aaagcgctta catttttttga gtgagaaggc  3240
aaagttatta gggtacccta agcttacttc ttcgtgggcg gattatagaa tgattattgg   3300
cggaaaaatt aaatcttggc attctaacta taccgaacaa ttaataaaag ttagagagga   3360
cttaaagaaa catcaaatcg cccttgataa attacaggaa gatttaaaaa aagtagtaga   3420
tagctcttta agagaacaaa tagaagctca acgagaagct ttgcttcctt tgcttgatac   3480
catgttaaaa gaaaaagatt tttccgatga tttagagctt tacagattta tcttgtcaga   3540
ttttaagagt ttgttaaatg ggtcttatca aagatatatt caaacagaag aggagagaaa   3600
ggaggacaga gatgttacca aaaaatataa agatttatat agtaatttgc gcaacatacc   3660
tagatttttt ggggaaagta aaaaggaaca attcaataaa tttataaata aatctctccc   3720
gaccatagat gttggtttaa aaatacttga ggatattcgt aatgctctag aaactgtaag   3780
tgttcgcaaa ccccccttcaa taacagaaga gtatgtaaca aagcaacttg agaagttaag 3840
tagaaagtac aaaattaacg cctttaattc aaacagattt aaacaaataa ctgaacaggt   3900
gctcagaaaa tataataacg gagaactacc aaagatctcg gaggtttttt atagataccc   3960
gagagaatct catgtggcta taagaatatt acctgttaaa ataagcaatc caagaaagga   4020
tatatcttat cttctcgaca aatatcaaat tagccccgac tggaaaaaca gtaacccagg   4080
agaagttgta gatttgatag agatatataa attgacattg ggttggctct tgagttgtaa   4140
caaggatttt tcgatggatt tttcatcgta tgacttgaaa ctcttcccag aagccgcttc   4200
cctcataaaa aattttggct cttgcttgag tggttactat ttaagcaaaa tgatatttaa   4260
ttgcataacc agtgaaataa aggggatgat tactttatat actagagaca agtttgttgt   4320
```

```
tagatatgtt acacaaatga taggtagcaa tcagaaattt cctttgttat gtttggtggg   4380
agagaaacag actaaaaact tttctcgcaa ctggggtgta ttgatagaag agaagggaga   4440
tttgggggag gaaaaaaacc aggaaaaatg tttgatattt aaggataaaa cagattttgc   4500
taaagctaaa gaagtagaaa tttttaaaaa taatatttgg cgtatcagaa cctctaagta   4560
ccaaatccaa tttttgaata ggctttttaa gaaaaccaaa gaatgggatt taatgaatct   4620
tgtattgagc gagcctagct tagtattgga ggaggaatgg ggtgtttcgt gggataaaga   4680
taaactttta cctttactga agaaagaaaa atcttgcgaa gaaagattat attactcact   4740
tcccccttaac ttggtgcctg ccacagatta taaggagcaa tctgcagaaa tagagcaaag   4800
gaatacatat ttgggtttgg atgttggaga atttggtgtt gcctatgcag tggtaagaat   4860
agtaagggac agaatagagc ttctgtcctg gggattcctt aaggacccag ctcttcgaaa   4920
aataagagag cgtgtacagg atatgaagaa aaagcaggta atggcagtat tttctagctc   4980
ttccacagct gtcgcgcgag tacgagaaat ggctatacac tctttaagaa atcaaattca   5040
tagcattgct ttggcgtata aagcaaagat aatttatgag atatctataa gcaattttga   5100
gacaggtggt aatagaatgg ctaaaatata ccgatctata aaggtttcag atgtttatag   5160
ggagagtggt gcggataccc tagtttcaga gatgatctgg ggcaaaaaga ataagcaaat   5220
gggaaaccat atatcttcct atgcgacaag ttacacttgt tgcaattgtg caagaacccc   5280
ttttgaactt gttatagata atgacaagga atatgaaaag ggaggcgacg aatttatttt   5340
taatgttggc gatgaaaaga aggtaagggg gtttttacaa aagagtctgt taggaaaaac   5400
aattaaaggg aaggaagtgt tgaagtctat aaaagagtac gcaaggccgc ctataaggga   5460
agtcttgctt gaaggagaag atgtagagca gttgttgaag aggagaggaa atagctatat   5520
ttatagatgc cctttttgtg gatataaaac tgatgcggat attcaagcgg cgttgaatat   5580
agcttgtagg ggatatattt cggataacgc aaaggatgct gtgaaggaag gagaaagaaa   5640
attagattac attttggaag ttagaaaatt gtgggagaag aatggagctg ttttgagaag   5700
cgccaaattt ttatagttat attggatata tcttttcaaa aaatctgaat tggtctagga   5760
ccgcggaatc ctatggtaat ttctacgtcc agaatgtagc gccatgccat tagaccagtc   5820
cccgaattaa acatcgccga acttcttggt gatgttatgg caaagagaat gcgacagcgc   5880
ctattcattg agcaagatat ggaaagtatt cctccagggc aaacaatggt tttgaatatg   5940
ggggagcctg ttgtgggaac ggaatttaca catcggcgga atattaatgg gaaagagtgc   6000
gttttatttt ttgcagttga actttttaaa gacgacagcg cgtagtcagt acatcttcgg   6060
cccatcttaa tcttccattg gggttattaa gactgcccac tttagcagca agatttttaa   6120
ggtgactcct taattctttc tcgtgcggag ttagatctat ttttccaaaa tctttatccg   6180
catggtttag gaatatttgt atagagtcta ggggaatttc cttaccgatg tcccccgctg   6240
cggtaacaac tctgtaaaga tccatcttta ttgaatttaa tataaactgt ctgtcttttt   6300
tcatatttct aaatgctttt ttgttaattc aaataaccta cccctcacat tcttatcgta   6360
tatctcatat gtatacttac ctagtgcagg tttgtaattt ctcatagcca tatattcaac   6420
ttcttttgaa                                                          6430
```

<210> SEQ ID NO 22
<211> LENGTH: 13819
<212> TYPE: DNA
<213> ORGANISM: Artificial sequence
<220> FEATURE:
<223> OTHER INFORMATION: Synthetic sequence

<400> SEQUENCE: 22

```
ctctttttct tgactatggt catcgcttag cttggcgggg acgtttgatc tttgcttcta     60
gtttaatcct ttttctgtcc ttgttgtttt taatgaatta ccctctaatt tggggtttat    120
tagctttgag tttattggct ttagtgattc taacttggtg gaaaaaggct tggactaaat    180
ggttgttagt cccactgata atttttctgc tggctggcac tctagcgatt tttgcttcaa    240
aacctatttt agctaaacca atttttgatc taaatcaaag tttgaaaatt aatagttttg    300
attcgcgacc taatttagat agcactgctc aagtgactaa agccagtttg aaagctcatc    360
cctttttagg ttttggtcca aatcgttttt ggcgagcttg gactctttat aagccaaaat    420
tatttaatca atcagtaatc tggtcagttg attatcgtct ggcttatggt tttattccaa    480
caatgttagt aactcaaggt ggcctcggtt ttctggcttg gttaattctg ataatttcta    540
gttttattta tctttatcat ttattcaaac aaagttcagt agaagatttt tccacgataa    600
ttttattgag tctaagtttt atttatctct ggttaaattt actcattctt aatcctaatt    660
ttgttatcct ctctctggct tttgggtgct tggggtggtt gttagttttt aatcataaaa    720
tttctaatca gctttcttgg cacattaaat tagatacgtt tctaaaaagt ttagtggcaa    780
aactaggtct tagtattatt ttgggttttt tatttttaat cattattttg tcactgctta    840
attatagttc tttgatctta tttcatcggg gtctttcatc tttggatcgg ggggattttt    900
ccgccaccga aaaaaattgg cgtttagcta gtcgtttgag tcctcagaca gtttataatc    960
gttctttggc tgatcttaaa ctgcgtcaga ttaatcaact tctgacgact cctaattctg   1020
attctcaaaa aactttagcc gagttttccc gtttttatgg tgagtcaatt ggatttggct   1080
tgactgctcg tgaccaagat ccttttgatt atttaaattg gttaatttta ggtcaagttt   1140
atgaagctgg gattccgctt aaaattaaag gggccgatat tcaagctcgg aaaatttatc   1200
aagaagtgct tagattaaac ccggtttggc cagtcatttg gctaaatttg gctcgagtgg   1260
aattaggctc tgatcaccct gatttagcgc gagaagattt acttaaagct ttggaattaa   1320
aagccgatta ttccgatgct ctgttagctt tagccgaatt agattatagt caaggtcgat   1380
tatcaaaagc tttagcggga gctaaggtgg cagttctgaa agaaccaaat aatttgggag   1440
cttggttttc ccttggtttt ttccagtatc aaattggaca ttatgatgaa gctgtcattt   1500
ctttagaaaa agtcttaacc tttaatcaaa attcagctga tactaaatat tttcttggtt   1560
taagtttagc tgaacttgat cgaacgactg aggcgattga cctatttcaa tctttagttc   1620
gggctaatcc cgacaatcaa gagcttaaaa atattttaac taatctcaaa gctggtcgaa   1680
cagctttagc gccaccagag accaaaacca aaacaaaata ataattcatg gtgtctaaaa   1740
ttactcgctt acttcaaaaa gaatttacca atcttcacca agcagctttt ttgttggcta   1800
cttcggcctt gctgtctcaa tttttgggtt tgtggcggga tcgtttatta gcctctggtt   1860
ttggagctag tcatcaatta gatatttatt atacggcttt tcgcttaccg gatttaattt   1920
acgtttcggt ggcttctttt gtttcgatca cggtccatat tcctttgatt attaataaga   1980
tggaaactgg tggtaaaccg gcggtggaaa aatttctcaa ttcagtgctg acagtttttt   2040
taattgggat ggtttcagtt tccgcgttat tatttatttt tatgccctgg ttatcgaaaa   2100
ttaccgctcc cgggttttct tcagttgatc aacaaacctt agtcacctta tctcgaattt   2160
tattgttgtc tcccttattg ttgggtttgt ctaatctctt gggaggagcc actcaagctt   2220
ttcgtaaatt tgccgcctat gcctttagtc ctattttta taatttggga attatttttg   2280
```

ggattttctt tttctatcct ttgcttggtt tgccgggctt agtctgggga gtaattctcg 2340
gtgcagtctt acatttatca attcaattgc cagttttaag tcaattaggt ttacgtcttc 2400
gtttatcgag attaattaat tggccggaaa tgagaaaagt gatgctcata tccctaccgc 2460
gaactattac cttatcggct aatcaactat ctttattagt tttagtggct ttagcttcgt 2520
ttttgcccaa agggtcaatt tcggttttta atttttcgct caatcttcaa tcagtccccc 2580
tgtcgattat cggagtttct tattcggtgg cggcttttcc cgtcttggcc aaattttttg 2640
tcgctggtca acacaaagaa tttgctggtg aaattatcgc cgccattcga catattattt 2700
tttggtctgc tccagtggtc gttttgttta ttgttttacg agctcaaatc gtccgggtga 2760
ttttaggttc aggacgtttt gattggtcgg ccactcgatt gacggcagct tgtttggcga 2820
ttttttctgt gtcagtgatt gctcaaagtt tgattttagt tttagtccga gcttactatg 2880
ccgctgggga aaccaaaact cccttgatca ttaattcctt atcatctttg ggaacaatta 2940
ttttggcttt aattttatgg caactgttca aagtttggcc ggcctttcat ctgattttgg 3000
aacaaattct aagattgaaa gatttaccag ggacaattat tttagtctta cctctcgctt 3060
tttcgattgg agcgattatc aatgtttttg ttttatggtg ggctttcgaa cgacgctttg 3120
ctatcggaat ttggcgcaat ttagaggtag ttagtcttca gtctttagtc gcttctttat 3180
ttggtggctt tgtggcctat aacttactaa atgtctttag tctgtattat aaattagata 3240
ctttttggtc aatctttgag cagggatttt tagccggtat tttgggctta attgcctgga 3300
tttcggtctt aattcttttg aaaagtgaag aattggctga attgggacgt tctctgtcag 3360
cccgagtctg gaaagttgtc cctattgtcc cagaacgaga agaactgtag gatgggaaag 3420
tctttatatg gatttaaaac actatcgtaa tttttctatt attgctcacc ccagtagaac 3480
agccaagctg tctacggggc aagtattgat cataaattag tcttatggat ttaaaacact 3540
atcgtaattt ttctattatt gcccatatag atcatgggaa gagtactttg tctgatcggc 3600
ttttagattt gacagggaca attgaaaagc gaaaaatgcg agaacaagtc cttgattcga 3660
tggagttaga acgtgaacga ggaataacca tcaaaatgca accagtccga atgaattata 3720
aattggctgg tgaagattat attctgaatc taattgatac tccgggtcat attgattttt 3780
cttatgaagt gtctcgttcg cttcaagcag tggaaggggt cttgcttttg gttgacgcca 3840
ctcaaggggt ccaagctcaa acttttactg ttttagcgat ggctcaagaa ttgggtttaa 3900
cgattattcc cgttttaaac aaaattgatt taccaattgc tcgaacagct gaagtcaaac 3960
aagagattgt taatctatta aaatgtcagc ccgaagatat tatggcggtt tctggcaaaa 4020
ccggtgaagg agtagataaa ttattaattg agattattaa aaaaattcct agtccaattt 4080
cagaaataaa agttgttaaa ccttgccgag cgctggtatt tgattttgaa tattctattc 4140
ataaaggagt ggtggtctat gttcgagttt tagatggcga aattactccc gctgatcaac 4200
taaactttgt cgcttctggt gaaaaatttt cggttttaga attaggttat tttcgacctc 4260
aagctgaacc acaaaaaaaa ttacaggcgg gtgacattgg ttatttagtc actggaatta 4320
aaaaaccagg caatgctaaa gtgggggata cgattaccac tttagtgagt cctcttccag 4380
ctgtaccggg ctatatgact cctcgaccgg tggtctgggc ttctctttat ccagctagcc 4440
aagatgattt tgctctactc aagcaatccc tcgaacgatt aaatcttcaa gatgccgctc 4500
tgtcttttga agaggaaagc tcgggtgctt tgggacgagg ttttagagct ggtttctgg 4560 gaatgcttca tttggaaatc attagcgaac gattgaagcg agaattttct ttaaatttaa 4620
ttgtgacgac accgagtatt agttatcgtc taattaatac tcggaccaaa gaagaagtca 4680

```
ggattttctc tcctcacctt tttccacttg aaatcaagga ttatgaaatt tacgaatctt   4740
gggtagcggt tagaattatt agtcccgccg attatcttag tccgattatt caattacttc   4800
atgaacacga agcggaagta atgactatgg aaacttttag ttctagtcgc accgctttgt   4860
ctatcctcat gcctttacga gaattgatgc gtaatttttt tgatagttta aaaagtgtct   4920
cttctggctt tgcttctttt tcttatgaat tagccgaaga acgtctcgct gatgtctctc   4980
gcttggatat tttaattaat ggtgaaataa ttccggcttt ttcgcgaatt gtttcgcgtc   5040
gacgaatcga aaaggatgct tcggaaatgg ctgaacgttt agagggtttg attcccaaac   5100
aattgattac gattaaaatc caagttcaag gtttagggcg aattttggcg gcgcgttcaa   5160
tttccgctct acgaaaagat gtcactgact atctctatgg cggcgatatt actcgaaaaa   5220
tgaaattacg agaaaagcag aaaaaaggca agaaaaaaat gcaacagctg ggtaaggtaa   5280
atatccccca agaagttttt ctaaagatga tgcgaaatgc ggactagcgc ggactggacg   5340
cagactaatg cgaatttacc ctatggagta gcttgctata ctccataggg taaacgcaga   5400
tagtcacaaa caagacactg atcagatcag cgttttttta gcattgatcg gcgttttatc   5460
taaacaagaa ggggagagag taaagggcga ccatacttaa aataacaaga ataccaactg   5520
tcgctgagat gatttgaaag attttttgt gtttgctctg aaataacatt agttgtagta   5580
taaggctgtg accagatttt atcaagtcga aaaacatttt aagtggctaa atgttctctt   5640
tcttattgtc actttaatct tggtgatttt tttggctcga ggggtttggc gagtttataa   5700
tcagagtcgt tttgctaatt ctaattatct tttgactaaa gatcgtctta ctaaattaga   5760
agacagacaa aaacaaatta ctgatcgtct agaaaaatta tcaaccgatc gtggtttaga   5820
agaagaattt agaaataatt tttcagtcgt gcgaccaggg gaaaaaatga ttttaattgt   5880
cgatagtatt gaaacagcta ctgatacagc cactactagt gaggctagtc tttgggggac   5940
tttaaaagcc ttattattaa gtcgttaatt aaaaaagcga gattggttca gcttgccctc   6000
ttaaatttct tgtgcaaata tgcgggtatg gtttagtttg ccctttaaaa ttttttgtcc   6060
gaacatgcga gtatggttta gtggtagaat gcgaccttcc caaggttgag acgcgagttc   6120
gattctcgct actcgcacaa aaaacttttt agggtgaata gaatgcgacc cccgaagaac   6180
agcaaagctg tctacggggc aggcttccca agcataagac gctggttcga ttcccgcatt   6240
tcgcacaatt ggccgattaa aatagtattt tattttttta tgtcctccac ctttaaacga   6300
actatcgaaa attttacttg tgctcattgt ggagcggagg tgattggtaa tggttatact   6360
gatcactgtc ctaaatgcct ctggggcctc catgtagatg atttcccggg agatcgagct   6420
aatccttgtt tgggcttaat gaagccgatt ggagtggatt tagcgaaggg agattatact   6480
ttaagctatc aatgtgaaaa atgtcacatc attaaaacta ataaaactgc tccggacgat   6540
gaacttaaca agtacttgac cggtatgtta taattgttaa ataagttaaa tttaaaatat   6600
aaaatgaaga aagttaccat ttattccact cccacttgtg gttattgtaa aattgctaaa   6660
caattcttta aagataaggg aattgatttt acagagattg atgtcactac tgatttagct   6720
gggcgacagg ccttagaaca aaaaattggc cgaattacgg gtgtgccagt aattacgatt   6780
gacgaagaag ccgtcgtggg ttttgatcaa gctcatattg cgaagatgtt agggatttaa   6840
actagtgaca atttaccccg ccttctgcca gccggtagag gatgggtttt tttggtaatt   6900
tgctaacaac aaacaaggag tctattatga agattaagtt tttgcctctg tagttcccgc   6960
cataatcctt aaataaattt aggattatgg cgggcgggaa acaagccggt taacgctctc   7020
```

-continued

```
atagttcaaa ggatagaact gtctcgtcct aagagaccaa tctccgttcg agtcggagtg   7080
agagcacaga ttaaaaaaca ttgactagag tcctacttgc cagcctaaga tttgctttag   7140
taaagttttg gcgggaggga aagatgtagg ttcgattcct accagaggca caattcgtaa   7200
cttggtcaaa tcattttcaa aacaaatgat accacacaca gaggagagga tatggggcac   7260
agccttcgtc agtttgataa ctcaaggaaa caaatctaaa aataaaactt caccgatgtt   7320
atcatttgga agccatctgc ttttcgtgcg tatttgaaac atttttggca acactccaga   7380
aatcggtagg gccggccgtc cttccatata gtttgtaacc aacttttact ggtcggccac   7440
cgtttggttt tcctggaatt ggtacgatga attgtcgcga tattccctgt aagtatgatc   7500
gtaacgataa tacagacccg tgtaataatt cttgaaaagt tactatctga cgagtagtgt   7560
tggtataaag atttgagtcg agataatctt caacggcgat tatacacctt gccagaaaat   7620
ccttttcttc aaccttttcc gatttagctt gctgtattgt attgaataca attttttcaa   7680
tatttcctct ataaggttcc attagatcgt aaactaaaga aggataatct gtcggaatgt   7740
ggagaaatcc atgatagggg ctcattcggt ggtaaattat ataacgcagt gtaataccgc   7800
ttattaattt tgaaaccgcg tccaaaatag attttatcgt atttgcccct cctctgcgtg   7860
aatatccact gtatccgagt attttataat atttttttcca atataccttt gcatgctgtg   7920
cctcaatgtt taccatttgt ttaatagaat atcttttacc gtcaaataac attggatatg   7980
aaaccagcca actcatactt ttgaatttgg cttgtaaaat cttcttggca atgtggacac   8040
gtttcttctc attatttcta aatgagattt gcttacttaa gatatcatct ttggccgagg   8100
tttttacgct tggagtaatc catacggcat tactcattgt tcttcggtgt agacatatag   8160
gaacgccata ttttgcgcaa agttgtaaaa aattttcact taaatcacaa gttccaccat   8220
aaagcataat cgaaagaatg tttttaatgt ttgcggtata tttgccacct ttatattgaa   8280
aagttacaat atttttcttt acttctattt ggaaggtgta gggtagccat aagggtatct   8340
ttttattctt gctaatagac atgtttttttg atattattac cctagaaaga gttaggtttt   8400
gaatacaaaa tctaacttat attttgtatt ttgtcaagta aaataaagag aaaagagaga   8460
acctcaccga aatttggaga ggataaggca agacaacaca catcttgcac cgaaatttgg   8520
agaggataag gcataccgct ctggctttga acaccgaaat ttggagagga taaggcaata   8580
ttcaaaatat ctagcaccga aatttggaga ggataaggct caatcttttt atagcctaca   8640
ccgaaatttg gagaggataa ggcaactcaa cataaagggt gcaccgaaat ttggagagga   8700
taaggcggat cgagataagt cgaacaccga aatttggaga ggataaggcg ctaacaaaat   8760
taccacccac cgaaatttgg agaggataag gcaaaccagc agggacttca caccgaaatt   8820
tggagaggat aaggcacaat tgtcatgttt attcaccgaa atttggagag gataaggctc   8880
gtttatgtta gcgaccacac cgaaatttgg agaggataag gcaagaaaca ataaccgcag   8940
aacaccgaaa tttggagagg ataaggccaa ttataatata gcctgcaccg aaatttggag   9000
aggataaggc aagatactgt tccaataaca ccgaaatttg gagaggataa ggcaaattat   9060
cataatccat tcaccgaaat ttggagagga taaggcatgg cttgtttttg taatcaccga   9120
aatttggaga ggataaggca cagggagaaa ttgcgaacac cgaaatttgg agaggataag   9180
gcgtttggca ataagtctcg caccgaaatt tggagaggat aaggcatggg tcaatccaac   9240
ccgtcaccga aatttggaga ggatgatggg tttggttcaa aaattctaag aatctgcttt   9300
attttcttca cttcacctac acggtctttc gtctcgttcc ttctagtaac acgagacctc   9360
gcctttccga ccgttctctt tgtctcttta ttttatctga cagaatatgc aaaaagtaag   9420
```

aaaaacttta tcagaggtac ataaaaatcc ttatggtaca aaagtccgta atgcaaagac 9480
tggctactca ctacagatag agaggctttc gtatactgga aaagagggga tgagaagttt 9540
taagattcca ctcgaaaata aaaataaaga agtttttgat gaattcgtaa aaaagatcag 9600
gaatgattat atcagtcagg ttgggttgct caatctttct gattggtatg aacattatca 9660
ggagaaacaa gaacattatt ctttggcgga tttttggtta gatagtttga gggccggagt 9720
gatttttgcg cacaaagaaa ctgagataaa gaatcttatc tctaagatac gtggtgataa 9780
atcgattgtt gataaattta atgcaagtat aaagaaaaaa cacgccgatc tttatgccct 9840
tgtcgatata aaagctctct acgattttct tacctccgac gcaagaaggg gattaaagac 9900
cgaagaagaa ttttttaact caaaaaggaa taccttgttt ccgaaattta gaaaaaaaga 9960
taacaaagcc gtcgaccttt gggtcaaaaa atttattggg ctggataata aagacaaatt 10020
aaattttacc aaaaagttta tcggtttcga tccaaatcct cagattaaat atgaccatac 10080
tttcttcttt catcaagaca ttaattttga tctagagaga atcacgactc cgaaggaact 10140
tatttcgact tataagaaat tcttaggaaa aaataaggat ctatacggtt ctgatgaaac 10200
aacggaagat caacttaaaa tggtattagg ttttcataat aatcacggcg ctttttctaa 10260
gtatttcaac gcgagcttgg aagcttttag ggggagagac aactccttgg ttgaacaaat 10320
aattaataat tctccttact ggaatagcca tcggaaagaa ttggaaaaga gaatcatttt 10380
tttgcaagtt cagtctaaaa aaataaaaga gaccgaactg ggaaagcctc acgagtatct 10440
tgcgagtttt ggcgggaagt ttgaatcttg ggtttcaaac tatttacgtc aggaagaaga 10500
ggtcaaacgt caacttttg gttatgagga gaataaaaaa ggccagaaaa aatttatcgt 10560
gggcaacaaa caagagctag ataaaatcat cagagggaca gatgagtatg agattaaagc 10620
gatttctaag gaaaccattg gacttactca gaaatgttta aaattacttg aacaactaaa 10680
agatagtgtc gatgattata cacttagcct atatcggcaa ctcatagtcg aattgagaat 10740
cagactgaat gttgaattcc aagaaactta tccggaatta atcggtaaga gtgagaaaga 10800
taaagaaaaa gatgcgaaaa ataaacgggc agacaagcgt tacccgcaaa tttttaagga 10860
tataaaatta atccccaatt ttctcggtga aacgaaacaa atggtatata agaaatttat 10920
tcgttccgct gacatccttt atgaaggaat aaattttatc gaccagatcg ataaacagat 10980
tactcaaaat ttgttgcctt gttttaagaa cgacaaggaa cggattgaat ttaccgaaaa 11040
acaatttgaa actttacggc gaaaatacta tctgatgaat agttcccgtt ttcaccatgt 11100
tattgaagga ataatcaata ataggaaact tattgaaatg aaaaagagag aaaatagcga 11160
gttgaaaact ttctccgata gtaagtttgt tttatctaag ctttttctta aaaaaggcaa 11220
aaaatatgaa aatgaggtct attatacttt ttatataaat ccgaaagctc gtgaccagcg 11280
acggataaaa attgttcttg atataaatgg gaacaattca gtcggaattt tacaagatct 11340
tgtccaaaag ttgaaaccaa aatgggacga catcataaag aaaaatgata tgggagaatt 11400
aatcgatgca atcgagattg agaaagtccg gctcggcatc ttgatagcgt tatactgtga 11460
gcataaattc aaaattaaaa aagaactctt gtcattagat ttgtttgcca gtgcctatca 11520
atatctagaa ttggaagatg accctgaaga actttctggg acaaacctag gtcggttttt 11580
acaatccttg gtctgctccg aaattaaagg tgcgattaat aaaataagca ggacagaata 11640
tatagagcgg tatactgtcc agccgatgaa tacggagaaa aactatcctt tactcatcaa 11700
taaggaggga aaagccactt ggcatattgc tgctaaggat gacttgtcca agaagaaggg 11760
tgggggcact gtcgctatga atcaaaaaat cggcaagaat ttttttggga aacaagatta 11820
taaaactgtg tttatgcttc aggataagcg gtttgatcta ctaacctcaa agtatcactt 11880
gcagttttta tctaaaactc ttgatactgg tggagggtct tggtggaaaa acaaaaatat 11940
tgatttaaat ttaagctctt attctttcat tttcgaacaa aaagtaaaag tcgaatggga 12000
tttaaccaat cttgaccatc ctataaagat taagcctagc gagaacagtg atgatagaag 12060
gcttttcgta tccattcctt ttgttattaa accgaaacag acaaaaagaa aggatttgca 12120
aactcgagtc aattatatgg ggattgatat cggagaatat ggtttggctt ggacaattat 12180
taatattgat ttaaagaata aaaaaataaa taagatttca aaacaaggtt tcatctatga 12240
gccgttgaca cataaagtgc gcgattatgt tgctaccatt aaagataatc aggttagagg 12300
aacttttggc atgcctgata cgaaactagc cagattgcga gaaaatgcca ttaccagctt 12360
gcgcaatcaa gtgcatgata ttgctatgcg ctatgacgcc aaaccggtat atgaatttga 12420
aatttccaat tttgaaacgg ggtctaataa agtgaaagta atttatgatt cggttaagcg 12480
agctgatatc ggccgaggcc agaataatac cgaagcagac aatactgagg ttaatcttgt 12540
ctgggggaag acaagcaaac aatttggcag tcaaatcggc gcttatgcga caagttacat 12600
ctgttcattt tgtggttatt ctccatatta tgaatttgaa aattctaagt cgggagatga 12660
agaaggggct agagataatc tatatcagat gaagaaattg agtcgcccct ctcttgaaga 12720
tttcctccaa ggaaatccgg tttataagac atttagggat tttgataagt ataaaaacga 12780
tcaacggttg caaaagacgg gtgataaaga tggtgaatgg aaaacacaca gagggaatac 12840
tgcaatatac gcctgtcaaa agtgtagaca tatctctgat gcggatatcc aagcatcata 12900
ttggattgct ttgaagcaag ttgtaagaga tttttataaa gacaaagaga tggatggtga 12960
tttgattcaa ggagataata aagacaagag aaaagtaaac gagcttaata gacttattgg 13020
agtacataaa gatgtgccta taataaataa aaatttaata acatcactcg acataaactt 13080
actatagagt tctcttcatt ggattgaaaa tagatccgat tcctaccaga gacaccaaat 13140
aaatttaaaa ttaaaaatta cctgccaaaa tttcgttcaa cgaaacttaa gcaggcaaga 13200
aaatttaaaa ttaaatccgc tggtgggcgg ataaagtcaa aaattgaaaa tatattaaat 13260
tgacaatatg ttctttatta gagtgcgatg tttgaatacc tcggggcttc gaatcagtag 13320
attcgtggct tggccataaa tccacaggta ttcaaacacg cgatgtgttt tgtatggccg 13380
ggtgggccat acctattcta acaaaacaac catggtgttt ggcgtgccta atacctcatc 13440
ggctctgccg tgaggatagg acacgcaact tgttttatta tgatataatg aaaggtagaa 13500
attgtcattt tgtaatggaa cagtaaaaaa gaggtgccgg tgatgaacaa aagagtgact 13560
aaaggagaca tcaggattta cctgatgatg tggaagggtg ctattatgac cgtctgtgtc 13620
gcgagtctgg ttggcatcat ccttggtcca gtctatcttt tgatcatttt tccgttgaag 13680
aaaatgatca gaaggtattc gatcgatttt tcggatttgc tcaaaggtct ttgatgactt 13740
ttaggcaaga agattgtttg ttagctctct accgcaagga ggagggcttt ttcttttttt 13800
taaattaatt tacctttca 13819

<210> SEQ ID NO 23
<211> LENGTH: 34045
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (29562)..(29573)
<223> OTHER INFORMATION: n is a, c, g, or t

<400> SEQUENCE: 23
atgttccctc ttcttttcgt tgcctctgaa taagatttgc ttactcaaga tatcttcctt 60
agaagacgtc tttatgcttg ggtaatccag atcgcggta ctcatcgttc tgcgatggat 120
gcaaacagga acactatatt tagtgcatag ttgcaagaaa tcctccttta aatcacaggt 180
gccgccataa agcattatcg ataagatgtt tttgacgtca gcagaataga cacctccttt 240
gtaatggaaa gttatcttat cttttttcac ctctattgcg gaagtataag ggaaccatag 300
ggggattctt ctgttgttat ttttcatgtt ttgatatata attacactag atatgggcac 360
atttcaggag taaaatctaa cccatttttt gtattttgtc aaataaaata aaggtaaagg 420
agagaacctc tccgaattat cgggaggata aggcagcgtc tgataattct tcctccgaat 480
tatcgggagg ataaggcaag actggtaaac tctagctccg aattatcggg aggataaggc 540
acagtaacaa catacgggct ccgaattatc gggaggataa ggcaaactaa ccgttgctct 600
actccgaatt atcgggagga taaggcaaag cgtttaaagc cgacactccg aattatcggg 660
aggataaggc aaacgcccta taacgcaatc tccgaattat cgggaggata aggcgtagtt 720
agtggataat ttactccgaa ttatcgggag gataaggcga cgctgacgat aaactgctcc 780
gaattatcgg gaggataagg cacaaacatt tcctcgacat ctccgaatta tcgggaggat 840
aaggcataat tactcgctcg acactccgaa ttatcgggag gataaggcaa aatcatatcg 900
ttcttgctcc gaattatcgg gaggataagg caccccgaca aaattaagcc tccgaattat 960
cgggaggata agtatggata tttccacaat cttgaaagaa agatttgtta gcctttaatc 1020
cattctcctt tccctttatt ttatctgaca acatatgaaa gctaaaaaaa gtttttataa 1080
tcaaaagcgg aagttcggta aaagaggtta tcgtcttcac gatgaacgta tcgcgtattc 1140
aggagggatt ggatcgatgc gatctattaa atatgaattg aaggattcgt atggaattgc 1200
tgggcttcgt aatcgaatcg ctgacgcaac tatttctgat aataagtggc tgtacgggaa 1260
tataaatcta aatgattatt tagagtggcg atcttcaaag actgacaaac agattgaaga 1320
cggagaccga gaatcatcac tcctgggttt ttggctggaa gcgttacgac tgggattcgt 1380
gttttcaaaa caatctcatg ctccgaatga ttttaacgag accgctctac aagatttgtt 1440
tgaaactctt gatgatgatt tgaaacatgt tcttgatagg aaaaaatggt gtgactttat 1500
caagatagga acacctaaga caaatgacca aggtcgttta aaaaaacaaa tcaagaattt 1560
gttaaaagga aacaagagag aggaaattga aaaaactctc aatgaatcag acgatgaatt 1620
gaaagagaaa ataaacagaa ttgccgatgt ttttgcaaaa aataagtctg ataaatacac 1680
aattttcaaa ttagataaac ccaatacgga aaaatacccc agaatcaacg atgttcaggt 1740
ggcgtttttt tgtcatcccg attttgagga aattacagaa cgagatagaa caaagactct 1800
agatctgatc attaatcggt ttaataagag atatgaaatt accgaaaata aaaaagatga 1860
caaaacttca aacaggatgg ccttgtattc cttgaaccag ggctatattc ctcgcgtcct 1920
gaatgattta ttcttgtttg tcaaagacaa tgaggatgat tttagtcagt ttttatctga 1980
tttggagaat ttcttctctt tttccaacga acaaattaaa ataataaagg aaaggttaaa 2040
aaaacttaaa aaatatgctg aaccaattcc cggaaagccg caacttgctg ataaatggga 2100
cgattatgct tctgattttg gcggtaaatt ggaaagctgg tactccaatc gaatagagaa 2160
attaaagaag attccggaaa gcgtttccga tctgcggaat aatttggaaa agatacgcaa 2220

-continued

```
tgttttaaaa aaacaaaata atgcatctaa aatcctggag ttatctcaaa agatcattga   2280
atacatcaga gattatggag tttcttttga aaagccggag ataattaagt tcagctggat   2340
aaataagacg aaggatggtc agaaaaaagt tttctatgtt gcgaaaatgg cggatagaga   2400
attcatagaa aagcttgatt tatggatggc tgatttacgc agtcaattaa atgaatacaa   2460
tcaagataat aaagtttctt tcaaaaagaa aggtaaaaaa atagaagagc tcggtgtctt   2520
ggattttgct cttaataaag cgaaaaaaaa taaaagtaca aaaaatgaaa atggctggca   2580
acaaaaattg tcagaatcta ttcaatctgc cccgttattt tttggcgaag ggaatcgtgt   2640
acgaaatgaa gaagtttata atttgaagga ccttctgttt tcagaaatca agaatgttga   2700
aaatatttta atgagctcgg aagcggaaga cttaaaaaat ataaaaattg aatataaaga   2760
agatggcgcg aaaaaaggga actatgtctt gaatgtcttg gctagatttt acgcgagatt   2820
caatgaggat ggctatggtg gttggaacaa agtaaaaacc gttttggaaa atattgcccg   2880
agaggcgggg actgattttt caaaatatgg aaataataac aatagaaatg ccggcagatt   2940
ttatctaaac ggccgcgaac gacaagtttt tactctaatc aagtttgaaa aaagtatcac   3000
ggtggaaaaa atacttgaat tggtaaaatt acctagccta cttgatgaag cgtatagaga   3060
tttagtcaac gaaaataaaa atcataaatt acgcgacgta attcaattga gcaagacaat   3120
tatggctctg gttttatctc attctgataa agaaaaacaa attggaggaa attatatcca   3180
tagtaaattg agcggataca atgcgcttat ttcaaagcga gattttatct cgcggtatag   3240
cgtgcaaacg accaacggaa ctcaatgtaa attagccata ggaaaaggca aaagcaaaaa   3300
aggtaatgaa attgacaggt atttctacgc ttttcaattt tttaagaatg acgacagcaa   3360
aattaattta aaggtaatca aaaataattc gcataaaaac atcgatttca acgacaatga   3420
aaataaaatt aacgcattgc aagtgtattc atcaaactat cagattcaat tcttagactg   3480
gttttttgaa aaacatcaag ggaagaaaac atcgctcgag gtcggcggat cttttaccat   3540
cgccgaaaag agtttgacaa tagactggtc ggggagtaat ccgagagtcg gttttaaaag   3600
aagcgacacg gaagaaaaga gggtttttgt ctcgcaacca tttacattaa taccagacga   3660
tgaagacaaa gagcgtcgta aagaaagaat gataaagacg aaaaaccgtt ttatcggtat   3720
cgatatcggt gaatatggtc tggcttggag tctaatcgaa gtggacaatg gagataaaaa   3780
taatagagga attagacaac ttgagagcgg ttttattaca gacaatcagc agcaagtctt   3840
aaagaaaaac gtaaaatcct ggaggcaaaa ccaaattcgt caaacgttta cttcaccaga   3900
cacaaaaatt gctcgtcttc gtgaaagttt gatcggaagt tacaaaaatc aactggaaag   3960
tctgatggtt gctaaaaaag caaatcttag ttttgaatac gaagtttccg ggtttgaagt   4020
tgggggaaag agggttgcaa aaatatacga tagtataaag cgtgggtcgg tgcgtaaaaa   4080
ggataataac tcacaaaatg atcaaagttg ggtaaaaag ggaattaatg agtggtcatt    4140
cgagacgacg gctgccggaa catcgcaatt ttgtactcat tgcaagcggt ggagcagttt   4200
agcgatagta gatattgaag aatatgaatt aaaagattac aacgataatt tatttaaggt   4260
aaaaattaat gatggtgaag ttcgtctcct tggtaagaaa ggttggagat ccggcgaaaa   4320
gatcaaaggg aaagaattat ttggtcccgt caaagacgca atgcgcccaa atgttgacgg   4380
actagggatg aaaattgtaa aaagaaaata tctaaaactt gatctccgcg attgggtttc   4440
aagatatggg aatatggcta ttttcatctg tccttatgtc gattgccacc atatctctca   4500
tgcggataaa caagctgctt ttaatattgc cgtgcgaggg tatttgaaaa gcgttaatcc   4560
tgacagagca ataaaacacg gagataaagg tttgtctagg gactttttgt gccaagaaga   4620
```

```
gggtaagctt aattttgaac aaatagggtt attatgaatc taaaaatagt cgtgatcaac   4680
aaactcaatc atttgaaaaa tttttatcgt cgccatccaa agaaaatcct ttggttgggg   4740
gtgccattgc tattgcttat cgggttgggg gcttgggctt atactcggag gactcaaccc   4800
gagttcgaaa cagaggtggt gaagttgggc gaggtggccg atgtggtgag cgatactggt   4860
ttggtgacgg ccgagaatga tctcactctc tcgttcgaga cgggcggggt cgttcgcacg   4920
gttaaggtta ccgaaggtga cgcggtttat cgaggacaga cgttagtctc gctggatgcc   4980
agtttgaagg cggcggaagt ggcgagcgcg cgcgccacgt tggccgctca agaagccaaa   5040
ttggctgaac tggtggcggg cccgaccaag ctagatttag cttcggccaa gacgaaactc   5100
gagaacgccc gcaagacctt gctgaccgcc gacctgcaag cgtacttcgc cggtccttca   5160
gccgattatg cggcttcttc attcacttat acggcgccga cggttttggg gacttacaat   5220
tccgatcaag agggcgaata cgtgcttgag ttatatcaat caggcgcgcc gtcgggctac   5280
tcggtggagt actccggttt ggagacgggg attatggagg gcgccgaagg acgagccgag   5340
cccttgggcc ggcgcggtct ctatctccaa ttcccggaga acttcattcg ggcgccagag   5400
gtaatttggc gcgtgcctat ccccaacacc aagtccgctt cttatgctac taaccggcgc   5460
gcctacgaac aggctcaagc cgattacgac ctgaaagtgg ctggcactcg cgccgaacaa   5520
attgtcgccg ccgaagccca agcgcgccaa gcccgcgcca ccctccaatc ggcgcaggcc   5580
tcgctgtcca agctctccct tacggcgccg gtggccggtt tggtgaagtc cgttccggtt   5640
accgtagggg agacggttac cgttggttca ccagctgtgg cgttggtctc ggatcataat   5700
tattacgtga ccctctatgt gccggaggct gagatggcca acttgacggt cggcgacttg   5760
gccgagatcc ggctcaaggc cttccccgat cgcgtcttcc gcgccaccgt ggggagtgtg   5820
gccccggcgg ccgaagatcg tgatggcgtg gcttcgttta aagttaaatt atatttccaa   5880
gaatccgatc cccaaattag agtggggatg tcggctgacg tcgaccttga ggcgcttaag   5940
aagaccgacg tcatggtggt gcccgggcgg gcggtggtgc gctctaatgg gcgaatcttt   6000
gtccgggttt ggagcaataa gaccgtcgag gaacgctcgg tggagattgg tctgcgtggc   6060
tctgatggct cggtggagat tgtctcggga ctctcggtgg gcgaagaggt gattactttt   6120
atccgtgacg aggagttgga tcgcttggcg gactaattcc ctttcggcgt ttatggcttt   6180
acttgaactc gaccaagtta ctaaatctta ttatagcgac gatctcacca ctcagatctt   6240
gcgcgggatt tcgtttacca ttaatgaagg cgaattcgtc tcgattatgg gcccgtccgg   6300
ttcgggcaaa tcaaccctct tgcacgttct cggattcttg gctgatcgca ccgccggtac   6360
ttaccgcttc aacggcaagc aatttgccga acataccgat gaggagatcg cgcgggtacg   6420
caatgaagaa atggggttcg tcttccagac tttcaactta cttggtcgta ataccgtctt   6480
cgaaaatgtg cgcttgccgc tcatctactc gcgcgtgccc gaaggagagt ggccggcctt   6540
ggttgatcag gctatcgccc aagttaagct tgatcatcgg cgcgactatg cctgctccaa   6600
gctctccggc ggcgagcaac aacgcgtcgc catcgctcgc gccttggtca accgacccaa   6660
cgtcctcttc gccgacgaac cgaccggcaa cttagactcc gcttcggggg gagcggtgat   6720
ggatacttta caacacttgc atgaagattc tggtcagacg gtgatcttaa tcactcacga   6780
gacctatacc gccgagcatg ctcagcggat catcaagatt ttggatggcc gggtcgaagc   6840
cgatttcaga cttgagacca gacgacgcgc cagcgagggt tatcataagt agttcgattt   6900
aatttatcct gagggtaatc gaaggactca ccacaagtaa aatgcaacgt tacaaattta   6960
```

-continued

```
gcttcctttc ggccttggag gcgatcaaaa ccaatcgtac gcgctctatc ctcaccactt   7020
tggggatcgt tattggggtg gcggcgatca ttgtgattat gtcgttgggc gccggcgccc   7080
agagtttaat tttaaatgag atcaatcaga tgggggccga gacggtcatc gtgttgccgg   7140
gtgagatcac tgatgccgcg gcggttttct cggactcact gacgcaacgt gacctggccg   7200
cggtgaaggt taagtccaat gtgcccaatt tggcgcgcgc cgcgccggcg gtcatcgtcc   7260
caggcaagac cacttataga ggtacgactt ataccccgc catgattatc ggcactgaag   7320
cggaattctt cggtgaggtt tttaatattt accctaaggt gggcacaatc tatgatcaag   7380
atgatatcga gacagcggcg cgggtggcga ttattggcga caaggttaag accgagcttt   7440
ttggcgcttc tgacgcggtg ggcgagcgga tcgatatcaa gggcaagcaa ttccgcgtgg   7500
tgggggtgta tccaacgacg gggcaaaaag gacctttcga tatcgacggc ttggtgatga   7560
ttccgcacac caccgcccag acttatctct taggcactaa ctattatcat cgccttatga   7620
ctcaagccga cagttcggac aatgtcgaga aattggcaca cgacatcacc gcgaccctgc   7680
gggagactca tggtctttat cctggtgatg acgacgactt ctcggtggta actcaacaag   7740
cgctggtgga tcaaatttcg atcattatca acattctcac ggccttcttg gcggccgtgg   7800
tggcgatctc cttggtggtg ggcggtatcg gcgtgatgaa tattatgctc gtgtcggtga   7860
ccgaacgcac taaagagatt ggtttgcgca aggcgctcgg ggcgacccgc tcggccatta   7920
tgacgcaatt tctctttgag gcgattgcgc tgaccttgtt tgggggcgtg ctggggatca   7980
tgatcggcgc ctcgctctcg ctcgtgctct cggggattct cacttacgcc gtggggctca   8040
attggtcctt ccacttcccc attagcgccg cgatgctcgg ggtcacggtc tcggcggcgg   8100
tcggactggt gtttggcctc tatccggcgc gtcgcgccgc cgccaaagac ccaatcgaag   8160
cgttgcggta tgaatagaac cggggaggtt tgacgtgact attgattagt gttagactat   8220
tgaaggaagt taatttgatt ttttgttcga aacaaagaaa aaaagaagga ggttaccatg   8280
tcggataaaa tcgtgagatt gcctcacctt aaagtttggc aacgagatcg gtgttggtgg   8340
ggacaattac tcttcactga tcgctcgatg agcgaagagt tcaacggcaa gttcttggcc   8400
ttggtcgctc tgcttgaagc ccaagagcga aaaagtgttg ttaatgaaga catcctcgat   8460
ctacttgatc agattgggaa atccccattg tcggagacag attgtcttcg gctacgacgt   8520
gacggtcatg ataaggtaga tgtggttctg gttaaaatta tgagaaattg ggtccgcgac   8580
tcggctcaaa atgagcgacg tgaatttgag ctcgtaagtt ttaaaaccac cattatgtcc   8640
aaacaggcgg cgaaagccac cttcaactga aatttttctc gcctgcgaat ctccaagcag   8700
accggtccga gcacgtgttg ctcgggccct ttatttttaa taaatatttg cccgaggatt   8760
gttttctcaa attctctttt ttctttaagt cggggtttt ggactgaaac ggaagagttg   8820
taatctagaa actcactttt tttggatggt ttttcaacaa atagctgtta caatagaaga   8880
gtggaaaaat aaaatgagtt gttttaaacc aggtacgggt aatcgaaagc tcagcacaat   8940
tccgggtttt accttgattg aaatcttggt ggtggttgcc attatcggta ttttgtcggg   9000
aataatttcg aataatttaa ggggtgctaa aattaaagcc cgagaagcct cggcccttca   9060
aaatgcgcgg caattagatt tggcggtatc gctttttgaa atagataaag gttattatcc   9120
gggaaccctg ggggttgaga caaatcaaga tgaccaaacg actggttgga aagaaggacc   9180
aggaaccctg cacgacgatc tggttcccaa atatatttct aaattaccca cgagtgatga   9240
gataaagttt atttatcttg ccgatgaacc atgtcccaac gaccagacga aaccttgtcg   9300
agctaagata gttatcgata ctgaccaaat tgtcgatggt gacggaggga cacccccacc   9360
```

-continued acccccacca cccccaccac cagctaaggt gattgttccg gacttggtta ataaaaccga 9420
agccgaagcc ctcggggcca tctcggcggc taatttagca gtaggcttca atgatgatgg 9480
gtgtagtgat atggtttctt ctggttatgt tttttctcaa tcgttgacgg ccggtgctag 9540
tgttgatgaa ggtacggcga ttaatattgt tgtttctgcc ggagggtgta tttctccgcc 9600
accggtcggg tcgatcccta tctcaagttg tggcacaata ataactcaac ctggagatta 9660
ccatctggcc ctggtggagg agaccgagtt gaatcaaact aattccggga tctgtattta 9720
tgttaacaat gttgataatg ttaatttaga ctgtcagaat ataaagataa agggtaccga 9780
taccacagag tcatcgaaac aatatggcgt aattgtcggt aattcgtctg ggtggccgt 9840
taaaaattgt ctgattgaaa acgtcggcac cggaattagg gtatattcgt ctgataacat 9900
ctcgattgaa aacaatcgac tgtcaaactt aggcagggaa gggatgtatc ttaaagataa 9960
ttcagatgtg attattcgaa ataatcagct gaccaacgcc ggtgcaagag cgattgctat 10020
ttatcgagaa tgggcgagtc ttatttccgg ttacgctgtt gataataaca ccatcaaggg 10080
ggggtcctat ggtattacgt tcgggcatct gtttaccgac agtcgtcctc ccggtgagat 10140
taaagagatc gttataaacg gcaataattt atatgatatt gtcactacgg ctctatcctt 10200
aaatttagtc gagaacctct caatcattaa taattacatt tatgacccga aaatattcct 10260
ccaaatagac gattctaaaa atttactcat agacaacaac ttcggccaaa atatcacctg 10320
ggacatgttt atcggctatt cagataatgt aaccttttct aacaataagc ttaagagcgc 10380
ttcggcgact aaatcggtgg ttttagtttg gatgtttagg gttaataact tagatttctc 10440
tcgcaacgaa attgaaggct acaatcgtaa tttgttaaaa cttgacgata gttatgattt 10500
ctcgatcaaa aataatattt tcaatagccg ggttggtgtt tatgaagggg tgattttggg 10560
taaaggtttt ctcggtgtat ctggtgaagt ttctgaaaat gatttttacg gcggtggcga 10620
gggcgtctct ttagctttag atatttatca taattcggcc aaccgtctgg cgatctttaa 10680
taataatttt attgattatt tgggggcgtc gttaagatat gattctagtt ttttggattt 10740
aggagctaat tattatggta caaccgactg tgccttattg cgggcgacaa cttggcccga 10800
ctgggtgata ataccacctt cttctggttt acccagtcct ttgctttact tggattcgtt 10860
ttggcctaaa gggaacgttc aaacttgcaa ttaatttagg ctaaactgcg agtgaggtgt 10920
ttttcttgat atttagatta aaaagtgata taagtataaa agagaaagga ggttctgatg 10980
tctcaaatgg gtattgccca cgcgctcttt tacaagcgag gggattgtct ccaagctcgg 11040
atcgttttcg gcgacggtcg cttgagcgaa gagttcagct cccgtctcga agggatggag 11100
attctgacaa aatctcgtca ggataagctc atttctcatc aagagatgac ctctctggcg 11160
ttggaatttg cggaatcgac tttgccggcg agaactccgt cggcggaaat tgttgacggc 11220
cttctgatgg cgatgaagct tgacctttga aagctttatc aaaaccgctc tccggctgat 11280
ctcggggcgg tttttttgtt taaatttaaa gggatggagt tatttcgagc gggggatgcg 11340
atgcttctga tgagtgaagt tggcgttgaa gtttgacttg aagttttgat tgttcggccc 11400
gcccgatttc tgaaacttga agactgacgg ggtgcggaaa ccggcgttgc ccggttgttg 11460
ctgtttgttt tgtttgctcc gattggtgtt tttcatatcc tttaattata aatcgaagtt 11520
ggattatggc aagcagtaag ataaacgtcc taattgtgac gtgattgaca gaaaagataa 11580
aacaatgtag gatagatttc ggatcctgaa ccttcaactc tcctcaacag aatcaacaga 11640
aaggaagaca gaatgaagaa gatgcttgtc ttgttgtccg cgtttgtctt gaccatcgcc 11700

```
gagctggctt cggccggatc gttctctgac ccgttcgatg cccttgattc ggcttgggtg  11760
accgatcggt tcgagccggc cggattctcc agcgtcgtct tcgacggcga caatcggttg  11820
gagattgcga ttagcgcgac cgactcggag gctaatcgtc cggccgggtt cactagtggg  11880
ttttataaca cgcaaggccg tcaacgagat gccttgatgg cggaaccttg ggtcatctcc  11940
ggcgatcttt acttgtcgct ggatatgctc ttgggcgaca atttgcgccg gactgatctc  12000
tgggcgcgaa cttcggacgg tccggaggct aatgcgcaat acccgattat cgggatgcgt  12060
cggtttgacc cgcttgatcc cttcaacccg ctggcgggtg atattgcctc aacttggcga  12120
gtctgggatt cggacacggt cgacggttgg gtcaatttgg ccacgccgat ggtggctggt  12180
tggaacacgc tttcgattga gagtgacggt ctatcatatc tctatcggat caacggggtt  12240
gaggtctatg aggacctcac catcagcgct ttcgcgaccg atctgaccac ggtctttctc  12300
caaggttata acttcggcgg tgactacgaa gtctattggg acaatgtctc tgccgccacc  12360
ttggctccgg tgcccgagcc ggccacgatc ttgcttttaa tgctgggggc cggcgtggtg  12420
gcgattcgtc gtcatttcgc gaaacaacaa taactaactt gagaggttag ggtccgccaa  12480
cccgttcgct gtcgcgagcg ggttttttta ttggcgagaa gttaaggggt gatgtttagt  12540
tgaccaaggt aatagcgaag ggtgtagagc caatcctcgt cttcttcgcc ggcttccagt  12600
ttttgtttca gaagccattc gagataaccg cgatcggtct tggccacttc ggcgagcgtt  12660
cggtctttat gcttgccaaa accgaatttt ttgaagagtg acggacgaga cgagatctca  12720
atcattttgg cgagcgtttc ttcgtcggag agttcgcgcg aacccaagag cgagccgtcg  12780
ccggctttca atttttgcca taaccgatta aacagcgctt cggtcaccaa aacatcgccc  12840
acggcgtcat gagcggtgcc atcaagatcc aagtcgagat aataacgcaa gaattgcaga  12900
ttgtattccg gaatcacccc ttcggtatcc agttcgcgag ccaagcgcag ggtgcagata  12960
tattgcggca ctttgactcc ttcggcggcc aagatagcga tgtcgaattt ggcattgtgc  13020
gccaccaaca cgtgatcagc gagaagggtt tccagctcgc gacggaaggc gctctcggcg  13080
aagggttctt tgtcggccac cagcttattg gtgatgtgag tgatactcat cgacttaacc  13140
gagatgggga ctggcggctt gaagtaggcg gtgcgagtgg tggttttggt tttgtagcag  13200
acctgacaaa ggcgatcttt ggtcacgtcg ttgccggtgg tttcggtatc taagaataag  13260
atttccatgg tcggttaagc ggccggttgg tcggtcgaat caaccttaac gttttggata  13320
attacgggcg tgacggggcg atcgttttgg tcagtggcga cttggccgat ctggtttaca  13380
atttcttgtc caacagttac ccgaccgaag atggtgtagt tattgggtag cggataatct  13440
tcgagcatga taaagaattg actgccgttg gtattgggac cggcgttggc catcgccaac  13500
acgccttgcc ggtagccggc ctggtatgac ggagtggccg gatcgagctc gtcggcgaat  13560
tggtaaccgg ggccgccggt accgcagggg ccggtggcgg ggactttggc ggattcaggt  13620
gaacagttcg ggtcgccgcc ttggatcata aaacccttga tcactcgatg gaaggtgaga  13680
ccgttgtaat aaccggctcg ggccagcttg ataaagttgg caaccgtgtt gggggcgtct  13740
ttttcgtaga gaacgagggt aatctcgcca agattggttt gcaaggtgat ttggttaggc  13800
atagttgagg tggtcagtcc cgagcttgct cgcggtgagt tcgtcgaatc cgtcgaggtg  13860
gcttgagatt gataaatgtt acttgttaaa tcggcaggat tgggcgctct ctgatttaac  13920
ttttgccaac caaaaagtcc agccaggccg agtaaaataa taagaactaa aatcacctgt  13980
ttgttcatgg gaattgagaa acgggttaaa gatgggctga taattgtgaa ttataacaat  14040
aaccgttaga gtaaggcaat gaagagtgaa gaaccggaag attatcggct aggttggcgg  14100
```

-continued cccttcttgg gttgccaagt ggatctctct cagcgaccgt tgattccgcg cgaggagacg 14160
gaattctggg ttgatcaagc aatcaaggaa cttaaaccag aatcaaccgc cggcaaacaa 14220
gtcttggact tgtttgccgg ttccggttgc atcggcttgg cggtgcttga gcactgtccg 14280
ggcgtggcgg tgactttcgg cgaaagggag gaaaaatttt gtgggcagat tcggaagaac 14340
ctcaagttaa acccgccagc cagatttgat ttcccgccag accttcgggc ggcctctcaa 14400
ggtctggcgg gtggaaggac catggcctct caaggtctgg cgggtgaaag gaccatggcc 14460
tctcaaggtc tggcggggcg aattagagtc gagtcgtcgg gaaaggttgt ccaaaccgac 14520
atttttttcca aaatcaaagg gcagtttgat tttattttcg ccaacccgcc ttatgtcgcg 14580
accagaagaa gtcgggttca agcctcggtg cgcgactggg agccggccgg agcgctcttt 14640
gccggccccg acggtttggc ggtgattcga ccgtttttgg ttgaagcgaa aaaacgtttg 14700
cacccgggtg gccggattta tttggaattc ggttacggcc aaaaaggcgc tctggaagag 14760
ttattgcggc aaaacggata taaaggttgg tcgtttcggc gcgaccagtt tggccgctgg 14820
cgttgggtcg tgatacaata gcggtatcaa aagttaattt tttaattcta aaattttatg 14880
acagacaaaa acaaagcttt cattctctgg ttcaatgatt tgacaattgg cgacgtcggt 14940
ttggttggcg gcaagaacgc cgctttgggc gaaatggtca acaacctggt tccgcttgga 15000
gttaatgtgc cgaatggttt cgcgattacg gcgcacgctt acgcctactt cttagacaag 15060
acaggcttaa aacagaggat taaggaaatt ttgaccgatc tcaatactca caatatcaac 15120
gatttgcaaa aacgcggcgc ccaagtccgc gccgcgatta ttaaagaaga attgccggaa 15180
gaactgcaag tggagattat caacgcttat cgcaagctta gcgccaacta tcacagccag 15240
gccgtggatg tggcggtgcg gtcttccgcc acggccgagg atttgcccgg ggcctcgttt 15300
gccggtcaac aagaaactta tcttaatgtc gccagcgaaa aggagttgat gttgtcggtg 15360
cgcaagtgct tcgcctcgct ctttaccaat cgcgccatct cttatcgggt tgataagggt 15420
ttctcaatgt ttgatgtttt gctttcggtc ggggtacaga agatggtgcg cagcgatttg 15480
gccgcggccg gcgtgatgtt ttcggtcgac accgaaaccg gtttcgataa ggtggtggtg 15540
atcaacggtg cctacggttt gggcgagatg gtggtcttgg gcaaagtcac tcccgatgaa 15600
ttcgtggtct tcaagccgtc gctggagcgc ggttatcagg cgattctctc caagacgctt 15660
ggtcgcaagg acgtgaagtt ggtttacggc gccaagggca ccaaacaggt gtcggtgccg 15720
gccaaagagg tgaaccgttt ttgtctcaaa gacgaggagg tttccaaact ggccgcttgg 15780
ggcctgacca ttgagaaata tttttccggc aaacacaatc gctatcaacc gatggatatg 15840
gagtgggcca aggacggcaa gaccggcgaa ctctttattg ttcaagctcg ccccgagacg 15900
gtccacgccg aagccgacaa gaatgtttac gaagagcata ttttgaaaga gaaaggcaag 15960
gagttggttc gtggcaacgc catcggcgcc aagatcactg ccggcaaagt gcgcctgatc 16020
aagagcgcca accagatgaa caccttcaag ccgggcgaga tcttggttac cgagatcacc 16080
gatccggatt gggaaccgat tatgaagatc gcggcggcga ttatcaccga gaagggcggg 16140
cggaccagtc atgcggccat tgtctcgcgt gagcttggag tgccctccat cgtgggcacg 16200
ggcaacgcca ccaaggtgct aaaaaacggc cagctggtga ccgtggattg ttcctccggc 16260
aaagaaggag tggtttacga aggcaagctt gcctttgaga aaaaagaaca tcgtctaacc 16320
gctaccgcca agacgcgcac caaggtaatg gtcaatatcg gttcacccga cgatgccttc 16380
cgcaatttct atttgcccgt ttccggggtc ggtttaggtc ggttggaatt tatcattaat 16440

-continued

```
tcttacatca aggttcaccc caacgcgctc ttggattaca aagagcttaa ggccagtcgc  16500
gatccgcgcg ccaagaaggc ggttaaggcg attgatgagt tgacggttga atacaaaaac  16560
aagaccgatt attacgtcgg cgaattggcc gaaggggttg ccaaaatcgc ggccaccttc  16620
tacccgcacg acgtgattat ccgtttctcc gatttcaaga ccaacgagta ccgcactctg  16680
atcggcggcg atctctacga gccggaagag gagaacccga tgatcggttg gcgcggcgct  16740
tcgcgttatt atgatcccaa tttccgtcgc gctttcgcct tggaatgtcg cgctctctac  16800
caagtgcgta gcgagatggg cctttccaac gtgatcccga tgattccctt ctgtcgcacg  16860
gcggaagaag gccggcaagt ggtggagatt atgaccgaag ccggtctgga ccgtcaggct  16920
gacccttcgc tcaagattta tgtgatgtgc gagattcctt ccaacgtggt ggaggccgat  16980
gcctttttgg aagtcttcga cgggatgtcg atcggttcca acgacctgac ccagctgatg  17040
cttggtttgg atcgcgattc caacttgatc agccatatcg ccaacgagaa tcatccggcc  17100
gtcaagaaga tgattgaggt ggcgattaaa gcttgtcggg ccaagggcaa gtatatcggc  17160
atttgcggtc aggcgccgtc cgattatccg gagtttgccg attttttggt gcagaacggg  17220
atcgggagca tctcgctcaa tcccgattcg gtgattaaga ccttacccgt gattgaggcg  17280
gccgaagaga agtatcccca aagataataa aaatatgaaa atcgcttttt ttgaattgga  17340
gacttgggaa aaaaaatact tgcaagagcg aactctgccc ggcgaggtcg tttttatcga  17400
cggaccgttg gatgagacca agttgccgga gcaaaacgat ttcgacgcca tttcggtttt  17460
tgttaattcc attgtcggcg acaaagtgtt gggacatttt cccaatctcc agttgattgc  17520
cacccgctcg accggttatg atcattttga cctgccaact tgcgccgctc ggggggtcaa  17580
ggtggccaac gtgccgagtt acggcgaaga taccgtggcc gagtacgcct tcgccttaat  17640
gctcactctc tcgcgcaaga tttgcgagag ttatgagcgt attcgcgaga ccggcagttt  17700
cgatctcacc ggcctgcgcg gctttgatct gaagggcaag accttggggg tgatcggcac  17760
tggtcggatc ggcaaaaacg cgatcgagat cgcgcggggc ttcaatatga atatcgtcgc  17820
ttacgacaaa tttcccgacc cggtttatgc cgaaaagatg ggctatcgtt atctgtctct  17880
ggacgaggtg ctggccacgg ccgatatctt gaccttgcac gtgccctacc tgccggagaa  17940
tcatcatttg atcaatgccg aaacgctggc caaaatgaag tcgggggctt acctgatcaa  18000
caccgctcgc ggtggcttga ttgacaccgc ggctctgctc gtggcgctta agtcggggca  18060
aattgccgga gccggtttgg acgtgctcga agaggagggc gtaatcaaag atgaggtcaa  18120
tttcttaacc aacggtcgct tggatcaagg cgatctgaag acggtgctcg gcaatcatat  18180
tttgattgat ttgcccaacg tgatcattac tccgcataat gccttcaaca cttgggaggc  18240
gctgaagcgc attttagaca ccaccgtggc gaatctggtg gcttttgaag ctggaatgcc  18300
gcaaaatttg atcagtggcg attaaggcgg tttattgacg ttttaccttg ataacggtac  18360
aataaggtca gattccgttc ggggtgagtg gaaaaacgtc ggttctagac aacggaagga  18420
gattttatgg cccagaagtc tgccactgaa attgtttgag ctcgtctgtc tgcgtgaccg  18480
acgagcttgt gttttgttta aataaaaaga tggctgaatt caatttcaaa atcgaaaaga  18540
aaattgccgg ccgtctcggc cgagcgggaa caataatgac gcctcacgga gacatctcca  18600
ctccggcgtt tatcaccgtg gggaccaagg ccaccgtcaa ggcgctctcg ccggagcaag  18660
taatggcctc cggttcaccg gcggcgttgg ccaatactta ccacctcctc ttggagccgg  18720
gcgcggaagc ggtggcgcgg gctggcggtt tgcatcgcta tatgaattgg ccggggccgc  18780
tgattaccga ttcgggcggc ttccaggtct tctcgctcgg cgcggcttat gacgagggcg  18840
```

ggatcaataa attcctcaag ccgggcctac cctcgcggac cgcaccgaag cgaccttcgg 18900
aagaaggtcc gcgggagccg aagccggcca agattgacga agacggagtg acgtttcgtt 18960
cgcctttgga tggcgccgaa caccgcctga cgccggagag ctcgattcaa attcaacatc 19020
aacttggcgc cgatattatt tttgctttcg acgaatgcac ggcgcccacg gccgattacg 19080
tttatcagaa ggaagccatg aatcgcactc accgctgggc cgagcggagt ttggctgaac 19140
acgagcggct aacccaggct aagactcggg aaaatgcttc taaaaaagtc ctcggtcctc 19200
ttcaggcttc gcttgaggcc agactttttg ataagcattt tcccgagtct tattcggcct 19260
tgttcggcat cgtccaaggc ggccgcttcc aagacttgag ggaggcgagc gccaaattta 19320
ttgccagctt gcctttcgcc ggttttggga ttggcggttc cttcgataag accgatatgg 19380
gcacggcggt cgggtgggtc aatgcgatct tgccgaccga caaaccgcgc cacctgctgg 19440
ggattggcga accggaggat atgtttgagg cggtggcgca aggggccgac actttcgatt 19500
gtgtcactcc aacgcgcttg gcgcgccatg ccactttatt gacggcgacc ggccggctca 19560
atattttgaa tgccgctcac cgtgacgatc cgacatcgat cgaagccgat tgtgactgtt 19620
acgcctgcca aaattattcg cgcgcttact tggctcacct tttccgcgcc ggtgagattt 19680
ttggcgccac tttggccacg attcacaatt tgcgctttat gaatcgtctg tcggagcaaa 19740
tgcgcgccgc gattttggcc gagcgatttt tggagttcaa ggccgagtgg ctagccaaat 19800
atcaaagatg aagaaacccc cctcaacccc aaaacttttt cgtttggaaa gcgccttcgc 19860
gccggccggc gatcaaccgg cagcgattaa ggcgctgacc gaaggtctgg cacgcaatct 19920
tcgtcatcaa accttgttgg gggtgaccgg ttcgggcaaa acttttacca tggcgggagt 19980
gattgccgct tacaacaagc cgaccttggt gattgcccat aataaaactt tggcggccca 20040
attggcgcag gagtatcgaa gtttttttccc cgaccacgcg gtgcattact ttgtttctta 20100
ttacgattat tatcaaccgg aggcttacgt ggcggccagc gacacttata tcgagaaaga 20160
cgccagcatc aacgaagaga tcgaacggct tcgtcacgcc tctaccgaag cgcttctgac 20220
gcggcgcgac gtgatcattg tcgcttcggt gtcgtgcatc tacggtttgg gcagtccgga 20280
ggaatacgcc aaaagtttta tcaattttaa tcttggcggg aaaattgaac gccaagcctt 20340
gattgagaaa ctggtcagtc tttattatga gcgaatcaac gccgatctct cgcccggcac 20400
ctttcgcgcc atcggcaatt ctgtggagat tatgccgccc ggtcaacgag agatcatcaa 20460
tctcaagttg accggggacc accttgccga aattttgatc gttgacgctg tttcgcgccg 20520
agtggtgaac cagccgggcg agatttcaat ttatccggct aagcacttta tcaccagcgc 20580
cgacgaacgc cagcgcgcca tcgctttgat taagaccgag ttggctgaga ggttgaaaga 20640
gttggttgcc gccggcaaga atctggaggc cgaacgcctg aagcgccgca ccaattacga 20700
tttggcgatg atcaaagaaa tcggctactg caatggcatt gagaattatt cacgccacct 20760
ctcggggcgg gcggcgggcg aggcgccggc caccttgctt gattattttc ctaagacttc 20820
tttcggtcgg cccgattttt tgaccatcat tgatgagtct cacgtaacgg tgccgcagct 20880
tggcgggatg tttgccggcg acgagaaccg gaagaaaaat ttggtggcct atggttttcg 20940
tctgcccagc gctctggaca atcgcccgct caagtttccc gagtttgaag cccgaattgg 21000
tcccactatc tataccagcg ccaccccggg caaatacgag cttgaagcca gtaatcccca 21060
aaaaggcggg cagatcatcg aacagattat ccggcccacc ggcctggtgg atccggcaat 21120
tgaaattaaa ccgatcgttt cgaccgcgcg ctatctcggg caaatccagg attttatcgc 21180
cgaggtgaaa aaagaaattg ctcaaggtcg gcgggctatc gccacgacct taaccaaacg 21240
gatggccgaa gatttgagcg agtatttgaa aggtgagggg attaaggccg aatatttgca 21300
cagcgagatc aaaacgttgg agcggatcaa aatcctcacc gacttccgcc gcggcgagtt 21360
cgactgcttg gtcggcgtta atctcttgcg cgaaggtttg gatctgcccg aagtgtcgct 21420
gatcggcatt ttggatgctg ataaggaggg cttcttgcgg tcggaagtgg cgttgatcca 21480
gaccattggc cgggcggcgc gcaatttggc cggccgggtg attctctacg cggagacgat 21540
aaccgactcg atgaagcggg cgatggatga gacggcgcgc cggcggacca aacaactggc 21600
ttacaatcag caacatggca ttacgccggt ttcaatcgtg aagaagatta aagacatcac 21660
cgacagtttg gctaaagatc ggcaacaatc ggttaccgct ctcttggcaa tagatgaaga 21720
gctttatggt aaaaacaaga aaaaattaat cagggagaag gtcaagcaaa tgagcgaagc 21780
ggtcaagaac ctcgatttcg aaaccgccgc tctcctccgc gacgaaatca agatcttgga 21840
aaacgtcaag actaaggcca aatgatatcg gaggatgatg ttggcgtgac atcccgccga 21900
caatttttat cccaattcat acacgaccgt gcacggatag ggatgattag gaagtctgag 21960
gcaggttgaa aaattttctc aaccaacgat cattttcgat ttgggtgact tccagatata 22020
aaatttcatt tccgattcgg taattggctt taatcatcgc gacaatttcg cggcaatcat 22080
aaggcgaaac ccagacgctg ttttgcaatc tgactaagcc aaggtggtgt aaccaacgac 22140
gaagtttgtc tcgggtgctt cgcttccatt ccttaatatc aaagatgatg attcgatatt 22200
tgcggtccca tttggacggt ttttttatgg tcaacttctt taactggtat tctcttaatc 22260
tcgcttgacc ttttttagtt aaacgaacaa ttttttgatt ttgatgattg gtttgaatct 22320
caagcaaccc ttggttcttc atttttctcta ttaccgtatt ggtgtaatat tttttctttg 22380
attgttgtcc gggcaaatat tttagcagtt gaacgcagtt gggggccaac aaggtaaaag 22440
caatcacccc ggtgataccg atgatactta aaataagctc ttgataatcc gctttgtcta 22500
ttcgtgacat ataccttatt ataaacggtc gtataagata agggaagata gaaaagatag 22560
gaaaagaggg aatccctcaa agcttttttg tttgggtcgg atgtgttata atcgctaggt 22620
tccctatggg ccggcccacg gggggtttcg gcgtcatccg gaataagatt aagaaatttt 22680
tatggatcag aaacatcagg ataaaatcaa aatcaaaggg gcgcggacgc acaacctgaa 22740
gaatatcagt ttggagattc cgcgcgatca actcacggtg attaccggtt tatcgggctc 22800
gggcaagtct agcttggctt tcgacactat ttttgccgaa ggccagcgac gctatattga 22860
gtcactttca gcttacgcgc gccaattttt gaaacaatta cccaaaccgg aggtggacga 22920
gatctctggt ctctcgccgg cgattgccat tgaccagaaa tcgcgttcgc acaatccgcg 22980
ctcaaccgtg gcgaccgtga ccgagatcta cgattatctg cgcgtgctct acgcgcggat 23040
cggccggccg cactgtccgg tgtgtggagt ggcgattgag aaactctcgc tggaggaaat 23100
cgtgaatttc gccaaagaga aaattgccgt cagtcatcgg ggtaaaaaaa atctcaagat 23160
ttcaattacc gcgcccttgg tgcgcggacg gaaaggggag tattatcagc tcctctacga 23220
tttactggac aagggttacc tcgaagtgtt ggtggacggt caaacttatc aactgcgcga 23280
acgcatcgta atgaccaaga ccaagaagca tgatattgac gccgtggtcg acatgattga 23340
ttggagcgat cagggcgagg ttgtcgcggc cggccagcgt ttggccgagg cggtggaacg 23400
ggcgctcaaa gagtcggacg gtctagtgaa gattgtgatt gataacgaga acttcctgct 23460
ttcctccaaa ttttcttgcc ccaacgatgg cttctctttt cccgagattg aaccgcgact 23520
cttctccttc aattcgcctt acggcgcttg tcccacttgt cacggtattg gcaccaagca 23580
cctcttcggt ggcgaacctt gcgatacttg ccaaggggct cgcctgcgtc gggaggcctt 23640
ggaggtgaga attggcggca aaaacattat ggaagcggtg tcgctctcaa ttgccgacgc 23700
ggccagcttt ttcgacaagc tgaagttgac cccgaaagag aaaacaattt ccgaggtgct 23760
gtggcgcgag atcaaggcgc gattgaagtt tttgctcgat gtgggtttgg attacgtgga 23820
gttgaatcgc cgcgccgaca cgctctcggg cggtgaggcc caacgcatcc gcctggcttc 23880
gcagttgggg tcgcgtttgg tcggcacgct ctacgtgctt gatgaaccca cgattggttt 23940
gcatgctcgc gataacgcca aactgattaa gactttgctt gagttgcgcg atttgggcaa 24000
caccattgtg gtggtggagc acgacgaaga cacaattttt gcctctgatt atttggtgga 24060
tatcggccct ggggccgggg tgcacggggg caaggtggtg gccgccggtc caaccgagaa 24120
atttttaacc agcaagaaga acgattataa ttctttgacg attgattacc ttcggggcga 24180
caagactatc gctttgccgg aaaaacggcg aggaaaccag aagggcgcgc tgaaaattcg 24240
cggggggcaaa atttttaaca tcaagaatct caatgtggac ctgccgctct cgcgcttggt 24300
ggcgattacc ggcgtgtcgg gttcgggcaa atcctctttc gtctacgaaa ttctttataa 24360
aaatttgcag gccaaactgg agcgtcgtta tcgcaccaac accttgttta attgtcggga 24420
atttggcgga acggaatact tgagccgagt ggtcttagtg gatcagtcac cgatcggtcg 24480
gaccccgcgc tccaatccgg ccacttatac cggcgccttc accttcatcc gggaactttt 24540
tgcggcttcg gctctggccc gggcgcgcgg ctggaagccg tctcgcttct ccttcaacgt 24600
ggctggcggc cggtgcgagg cctgccaagg taacggcgaa gtggcggtgg agatgcattt 24660
cttacctacc atctttgttc cttgcgatgt ttgcggcggc aaacgctacg agaaggaaac 24720
tctggaagcg ctctataaag gaaaaaatat ttacgaagtg ttgcagatga cggtggaaga 24780
agcctttagt tttttcgaag atattccggc catcttcgac cggctcaaaa cgttgaacga 24840
agtcggtttg ggttatttgg aattgggtca atcggccacc accctctcgg gaggcgaggc 24900
ccaacgggtc aaaatctcca ctgaacttta tcggccgttt accgaacgca cgatttatat 24960
cttggacgaa ccaacggtcg gattgcatta cgaagatgtt aaaaacctaa acgaaatttt 25020
gcaaaaattg gtgaccaaag gcaataccgt ggtggtgatt gagcataatt tggaagtggt 25080
caagagcgcc gattacgtga ttgatctcgg gcccgccggc ggcaaagacg gcggcgagtt 25140
ggtggcggtc ggaacgccgg aagaattggc ctacgctcct ggctcccata ccgggaaata 25200
tctcaagcgt ctgttgaaac aacaataatt aaagttgaaa gatggaaagc cgggagctta 25260
aaaaatatca attgcccgat gggcccgggg tctacttctt caagcagggc cggcgaatcc 25320
tttatgtggg caaagccacg tcgctcaagg atcgggtgcg cagttatttt gccggtgatt 25380
tgggcgaaac gcgcggacca aaaattgagc ggatgcttga gttggccaac cgcgtggact 25440
ggcaaaccac ggactcggtg ttggaagcgc tcttgctgga gtcggccttg atcaagaaac 25500
atcaaccgcc ctataacacc agagaaaaag atgacaagag ctactggttc gtggtgatta 25560
ctcacgaacc ttttccccga gtattgttgt gtcggggccg gcaattgtcg aacggttcat 25620
tctctcttgc gcttaaaatc aaaaaaattt tcggcccttt tccccgttca agcgaaatca 25680
aggccgcctt gctcgtgatc cgaaaaattt ttccttatcg cgaccgttgt caactggcgg 25740
tggccggccg accctgtttt aatcgtcagc tcggactctg ccccggggtg tgcaccggcg 25800
aaattaacca aaccgattat cggcggctga ttgccaacat tgaacgcttg tttgccgggc 25860
gtaaaaggga attgctcgtt cgtctggaac gcgccatgaa acgagcggcc agaactcaac 25920
gtttcgaagc ggcgggtcaa attcgcaatc aaattttcgc cctcaaacat attcaagatt 25980
tggcgttgtt gaaatcaagc cccaaccgcc tcaagggaaa atccgttcgg atcgaggctt 26040
acgatgtggc tcattggcaa ggcgaggccg cggtgggagc catggcggtt tggcaagacg 26100
gagagttgga tcgaagtcag ttccgccaat tcaaacttcg ggcgacaacg ccgggggacg 26160
atttggccgg gttgcgcgaa atcttgactc gacgtctggg tcatcgggag tggcccgagc 26220
cctctctggt ggtggtggat ggagaccagc gacaggtcgc cacggcccaa gtcgcattgg 26280
ctcgtcaagg tcttgactgg ccggtagtcg gagtgaccaa agaccgtcat caccgcgccg 26340
tcgctttggc gggcaatctt gaggcagaga gttttgaccg tcaagccgtg attgaagtca 26400
acgacgcggc tcatcgcgtg gccattgctc atcatcgccg acgtttgcgt ttgggtcggt 26460
aaggtcaggg cttatccctt ggagcgctct tccgaaatat ggtaaaataa aggtcggata 26520
atcaacttta tgttttggtc tgacttagtc gcaaagttgc ccaccgagcc ctcggtttgg 26580
attgccgcgt tgggtttgtt tggggtcgcc tttttccttg gttatttttg gcaggatcaa 26640
tcgaccagga cgagatggca ggtcaagcag gagatgttga agaaccagca gattattgaa 26700
ctggaaaaag tcaaccagaa cttggcggcc aaaaatcgtg aactctatgc caaagaattg 26760
gagctgacca tcgccaacaa acatctccaa gcgctggaag cagccaaatc caaatttatc 26820
gccgtgacca ctcaccaatt gcgcacgccg ctctcggctg tgaagtggac gctggatttg 26880
gcggccaaag gtcaattggg caaggtcgac gaagagcaaa aaagtttctt aaacaaaggc 26940
ttgattagtg tcaaccgggt tattgccatc gtgaacgaac tcttgcgcgt ggactcggtg 27000
gagaccgatc aagtcgtcta ttgtttccaa cccgtcaatt ttatcaagct gttcgacgaa 27060
gtgttgtttg aattcgaagt gcaggccaag agcaaagggg tgaaactctc ggtgcgtcgg 27120
ccggagactg acctgcctcc aattgatttg gatgaaacca agattaaaat ggtgatggaa 27180
aatcttttcg acaacgccat taaatacacg ccggtgggcg gtctggtgga agtggttgtc 27240
tccgacaagc gtctcaaccg cgccgaaggg gcgattgagg tgacggtgcg cgattccggc 27300
atcggcatcc cgagcgagga aaagaacaac attttccaaa aatttttccg cgcgaccaac 27360
gcgatcaagg ccgagcccga cggttccggt ctcggtctct ttatcgctca cgatattgtg 27420
actcggcata atggctcaat gtggtttgag ccggccgcgg gcggaggcac gatttttacc 27480
ttcactttac cgattcatca gaagacgcta taattttaaa gactcttatc aatttaatct 27540
taaaagacaa tggacaagaa aaaaatccta atcgtggagg acgacgagtt cctccgttcc 27600
ctcaacgcca agaagctgga gagcgagggt tatgccgtta gtgtgtcgcc cgacgggacc 27660
agcgcgatcg aattgattcc tgaagaattg cccgacttgg tgtttctgga tcttctgttg 27720
ccgggcggca aagacggttt cgatgtttta acggcgatca aggccgacga aaaaaccaag 27780
aatattccgg tcgtggtttt ctccaatctc ggccaagccg aggatatcaa gaaggctaag 27840
gacttgggcg cgattgactt tttgatcaaa gccaacttta cccttgacga cgtggtgacg 27900
aaaattaaag aaattttgaa ataaaacaaa tcaatggcgc ccattcgagt cggtatcttg 27960
cgcggtggca tcggatccga gtatgaagtt tcgcttcgaa ccggcgccgg tgttttgcgc 28020
cacttgccgg gcgacaagta tcagccggtg gatattttgc tgtctcgaga cggggcgtgg 28080
tatgccggcg gtttgcgcgc caccccccgag cgggcggtac ggggagtcga tgtgatcttc 28140
aacgccttgc acggcgagtt cggcgaagac ggtcaagcgc aacaactgct tgattatctg 28200
ttcaagccct atactggttc cggcgcggtc gccagcgctc tggggatgga taagcctcga 28260
gccaaagagc tcttccggca ggctggtctg cgggtgccca acggcgcggt gcttcggcga 28320
gcggatcgtc ccgaggaaac cgatgccgag gcggtggctt acgatgtctt caaaaaaatt 28380
ccgccgcctt ggatcgtgaa gccggccagc ggtggctcct cggtggatct ccggctggcg 28440
cgccattacc ccgagttagt ggcggcggtg gccgccggcc ttaagcagaa cgatcgaatc 28500
ttggttgagg aatacgtgcg cggtcaagaa gccacggtgg gggtcgtcga tcgtctgcgc 28560
ggccgcgatc attatccgtt gttgccggtt gagattgtca cgctgccaga caaggtcttg 28620
tttgattacg aagcgaagta cggcggccaa accaaagaaa tttgccccgg ccgctttcgg 28680
ccggaagaca agcttgagtt ggaacgtcaa gccgttttga ttcatcaaca attaggcctg 28740
cgtcactatt ctcgttccga ttttatcatc tcgcctcgcg gtatctacgt gctggaagtc 28800
aacactttgc ccggcctgac cgaagagtct ctggtgccca aggcgctggc cgctgccggc 28860
atcgcttacc cgcagttttt ggatcacttg gtgaccttgg cgttagaacg acgctgaatt 28920
tgaaggacaa aaaagccccg cgagagaaga tgcagtgatc tcaaggggc aagaggaggg 28980 gatgaaaggt atgaaggaac taccaatgaa ggggatggaa ctgggacaaa agaacaaatt 29040
aggtggcaga gccttcagtg ccactcgaaa gctctgccgg ttagggtgta aaggtcgagc 29100
gagcgaccta tcttcaggtt atcataaggt gtgatttttt gcaagggcgg agggattatc 29160
ttggtggtgt tattataata gcatttgctc gaacttattt tcaagacaaa atgaaggact 29220
gaacgccccg ccacccgcct cgcggacttg gcggacacca gaaacaaaaa atttcttaa 29280 cattttccga tttggcgcga ggaagaattt ctcttaaatg gaaaagaaaa ttttgtttct 29340
ggtgttctgt cctcaaggtc tcgggcagtt ggcggggctt cagaaattcg gacagaaaat 29400
taaaaagtgt catccccccc aaaccccaac cactttttaa ttttctgatt cctacaatgt 29460
ttcgtttggt ggtgttattt tagcatttgc tcgaacttat ttccaagaaa aaatgaaaga 29520
ctagcgttcc ccgcgcgctg aagcgcctct gtgcaaagca cnnnnnnnnn nnnggggatt 29580
ttgaattttg tccgcgcgga ggcagggtct gggagggaat ccgcgcgggc tttattttt 29640 tgaattttt tggcgtagag cttgtataaa atacaattat atggtataaa aatagtaaga 29700
gaaagtcatc gtggctttct caaaaccgct cattgacaac taaaaaagga ggatccaatg 29760
attatttcat tcagtgggcc ctccggtatc ggtaagggct tcatcaaaga acgactatta 29820
cagctttatc cagacatcca agaattggtg tggtatacaa ctcgcacctt gcgaccaaac 29880
gaacaagggt caaacagaat tcaagtttca ctttccgagt ttaaccagtc ggttgaactt 29940
ggcaagctta ctttagtgca agatcttttt ggtcatcgtt atggtctaaa aaaagaagat 30000
ctcgtaacga gttcgggtat caagttgact gagttgcatc cagcaaatct agtggaagca 30060
ctcaaaatca acccgaagat ttttgcaatt ggtcttgtaa cttctgattt atcactactt 30120
cgtaaaagac ttactgttgt gagaaagacg gaaagcgaag cagagataga gaaaagagtt 30180
acgaaagcta aaagcgagat cgagataatt ctacaacaca ggtcttttta tgcttccgtg 30240
attgaaatta cagaagctga agaagatcaa gtgttcaaca aggttcatgc aatattgcaa 30300
tcacaaatca aaccgaaagg aggaaaaaat gaaactagaa acacaagttg gtagtctgaa 30360
gttgcacaca ccgttgttgc tggcttcagg ttacattacc gaaacaccag agttctttct 30420
gagagctcaa ccctacggct gttcgggtat cgttacccga tcacttaaac aaaatgttcc 30480
agcggaacga tcacggatta catctccacg ctatgcagtc tttggtaatg acagcatgct 30540
taactgcgag tggggaaatg aaagaccgtg gacggattgg cgagatcatg gagtgcaaca 30600
ggtcaaagca attggttgtc taatcatcat ttcgctttcg gggcgagatt tggatagctg 30660

-continued

```
ttgtaatttg attcgtgcat tcgataagat cggtgttgat gcctacgaaa tcaacatctc  30720
atgttcgcat tctggagcac tgcatgggaa tctgaatgtt gatgtgcttc acctagaaca  30780
actgatgaaa agagtgcgta acattacgac gactccaatc tggatcaagt tgtcgtattc  30840
aaacctgctg ttctcaatgg caaaacaagc cgaagagttt agagcagatg cgatagtgtg  30900
cacaaatagc atcggtccag gaatgttgat cgacaccaaa accgctaaac cgaaactcgg  30960
aatcaagggc ggaggcggtg gaatgacggg aaaagcaatt ttcccgatcg ctctatggtg  31020
tgtgcatcag ctttcaaaaa ccgtgagtat ccctgttgtc ggttgtggtg gaattttcac  31080
cgcagacgat gtaattcaaa tgctcatggc aggtgctagt gcagttcaac tctacacagc  31140
tcctgcgctg aaaggtccta cggtctttag acgagtaaag gctggactac aaaggtttct  31200
cgatgagaat ccgaagtatg cttcagtcaa agacctcgtt ggacttacgc tcgacaaaac  31260
aggtgagcat aagttttctt cacctcgtcc agtcgtgatt gaagaaaagt gcacaggatg  31320
tggaatctgt attcaatcct gtgcatttga cgccctgtca atggttcgta gtgctgatag  31380
caaagcactg gcggtcattg ccgataactg catctcatgc aacgcttgcg ttggagtatg  31440
tcctccgaaa ttcgacgcta tcaaagcatc attctaggag gtaatacaga aatgaaaaaa  31500
aacacataca tcatcgcggt tcactgcaat gcgtgtcgaa ccctactgta tcgttacaaa  31560
aaagaaggtg gtggacatct cctcaagtgt tatgccgaca tgataatgtc ggattacact  31620
aaaggcgatc taaggtgtcc ttcttgcggt caagagtttg ctcgacatgc aatcatccac  31680
aatcgctcag cacataagat aatccgaggg agagtctttg tgaagggtca tcatggataa  31740
catcatcaca acgggtggtt tgattcaatc agaccacccg ttattttttt attttagttc  31800
aaatctgttt ttgaaataat tagatgtata gtttttataa tcaaaaatct cattagattc  31860
tttatttagt ttttctacat attcaaaaaa ttgtttttta tcaaaaatat caagactaag  31920
ttctttacaa acatttgcaa ttcctttaac caattcatcg ccattttcat taccagaggc  31980
catttttttct gcttcgtaat aataactatg tcccggtact tctaccaatg caaattcaat  32040
atccttatat tcatatactt tactttttct aacacaaagc atacctttac caaatccaag  32100
ttcgccgaaa atttcaacca acgtgtcaaa atcgccttgt ttagtgaaaa ccgagagctc  32160
tttacgttgc tcatttcctc cccattcgcc aattttaaga ataatttcag gaattccatt  32220
ggtcactcgc aatcgtatat cttttttttct atgttctacc cctccctcta gaaaagttga  32280
ataatcaatc aatactctat ttttctctga tttctttttt ccactactgt caaaaaattt  32340
taccagattc tcaaattctc cttttgataa aggtcctcgt atttcaattt ctatattttc  32400
atccatattt attgattttt taggtttata aatagttgct ttattatcat ggtcgcataa  32460
ctaccagtag gtaagtaaaa ggaaagtgta attttcattt tatttttatg aagatcgtca  32520
gactctaaat catgagcata catattagtg gcgaccaaga gatttctctt gttcagtttt  32580
ggttttgcta aaaaatttttc tggaattagt tcaaaccctc cagcttcaca aatatgtgga  32640
cattgaaata cagcatttgt tggcaaatat aatttgccaa catttttgaa tataaatttt  32700
ttacttttag tatttttctc tatcaacaaa gatgcctgtg tattccacag aaaactatta  32760
tatgcggaca caaaaaaaga aacttttttt ggattcatga catcaaaaac ctttttgtag  32820
tctgagatat cttttgcttt tagttcagct ccttgcgtaa tattatttgt aatttttagt  32880
tgttcataag cctgtttcca attatcttct actattgcct taccaatcag atgagtatta  32940
taggggccac caggcattcc aaatctttga ttgtcatagt aatttataaa ataaagttgt  33000
ttgtgattgt ggacataatt tgaaagatta tctgcaatcg tagaatttaa atttcttacc  33060
```

```
actattttaa aagcatttcc gtgtaaagcc ctttctttta ttggtttttc cccatgaccc  33120
attacaaact taatttttga aaattgattt ttaaatttgt gtttcttgtt aaatactatg  33180
atatcttttt ctttcaagat ttttttgatg gaaataagtt gttcggtaat agcatcctca  33240
tcttttaatc cttggctaca tacatcctca aatgaaagtt taaaaaatag ctttatttgt  33300
tctaaggctt caaatgttgt aaatccagat ttttgtagcc aaatataagt aaacttacgt  33360
ttaccttttg atataaatga tggcataaga gagacctccg tcatctgaaa gtcttcgttt  33420
atgtgtttta ttttataatc ctcatattta tccataatat aaataattta acataaataa  33480
ccttatttgt aaataattcg ccaaaaaatc ccaaaaaaca aaagcccgcg cggattccct  33540
cccagaccct gcctccgcgc ggacaaaatt caaaatcccc gccgaatttc aaaaacatta  33600
gtctcggttt tgcgaaccct tctcccagaa aatagttttt gcaaaaccga gtccatattt  33660
gcatttctgc acctcgcctc attctcccag attattagtg gcgaggggca gggcgtttcc  33720
ccgcacttct gcttcagcag aagctctgtg ctttgcacag aggcgcttca gcgcgcgggg  33780
aacgctagtc tttcattttt tcttggaaat aagttcgagc aaatgctaaa ataacaccac  33840
caaacgaaac ttgttcggaa ttaagaaagc ggagcgattt tgcgggagcc aaaatcgcgc  33900
tatcattttt ttcaaaaccc tttccgccta cggcggaagc ggtgaattcc caaagttccc  33960
cccaattgaa atcatgaaag acctcaaacc aaaatatttt ctctacgcga ggaaatcaac  34020
agaggatgat gaccaccaaa taatg                                        34045
```

<210> SEQ ID NO 24
<211> LENGTH: 11142
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (6655)..(6659)
<223> OTHER INFORMATION: n is a, c, g, or t

<400> SEQUENCE: 24

```
catcttcatt tgtatgcgta tcagagagat caaaaactat gttatcaatg atggcgcggt     60
atggttcaat gagatcgaag gcgagagcgg ggtaatcagt cgtctcgtgc aggaacccat    120
ggaagggaga gaggtgatgg tagtgaatcc atcggagaaa aattcctatt aaaaattttg    180
acatcgcatt cagcgcgttg ctggccgggt ttttaccgcg cctcatgaag gctgaatgtc    240
cgagcttctt gaaatatgcg ctccaatagc gctggctgtg gagcgcttcg tgattgcgca    300
gttcctgaat ggtcatggtg cgggagagtt tttttgcagg aggaacgata agccacgcca    360
tgctgttgaa ttttgcgttt agaatttgcc gcgcgatata ctttttgatg cgcaaatcag    420
agcgctttac aagttgttga gaaagcaggt catttccatc tgcacggtta ctggcggtaa    480
tccagactgt attggttaaa tttctcctat gaataatgat aggaatttta tgacgcgctg    540
tgaattcaag tgtgctcggg gctaagggag ggctatctcc gtaaatcatg atggagagga    600
gcttggcagg attgcaggtt acttcgcctc ctttatactt aatgtgaata tttttccctt    660
tgacttcaaa tgtttcaaca taaggcgccc aaagaggtat tttttgcgag tatgttttca    720
tgttatagaa taaagtgagt attgaaatat aaaactttat atggtaatgt aagacacata    780
attttgcaag atgtgttgca aaaaagcgat tttttgaggg gtcgccccga atatagggga    840
caaaaaggct agcatacttt tttggaaccc cgaatatagg ggacaaaaag gcttatgagc    900
```

```
tgaaaaagat ccccgaatat aggggacaaa aaggcacgcc gctttcgcgt tcaaccccga    960
atatagggga caaaaaggca attaccgcat aaatcatccc cgaatatagg ggacaaaaag   1020
gcaacatgac ccaccctcct ccccgaatat aggggacaaa aaggctatga gacttctgaa   1080
atccccccga atatagggga caaaaaggct taagccccat gctttctccc cgaatatagg   1140
ggacaaaaag gctgaagtac gcaatctgca accccgaata taggggacaa aaaggcatgc   1200
tgtttgtatc ttcaccccga atatagggga caaaaaggca aggatattca agcgcacccc   1260
ccgaatatag gggacaaaaa ggcttaccac acaacttatt gaccccgaat ataggggaca   1320
aaaaggctgt gagcgatgta aaccaccccg aatataggag acaaaaaggc gcgtggtcaa   1380
tgctcgtgcc ccgaatatag gggacaaaaa ggcctttagc ttcatttaag attttaggta   1440
tttccggaca gcggcttgac cgcatcgtcc tcgccttttc ctaaaatcgc ccctcttaaa   1500
tcgcttgcct tacagacgca tgtataaaga tattttgaag attaagttat cgcatacttt   1560
atgagtaagc gacatcctag aattagcggc gtaaaagggt accgtttgca tgcgcaacgg   1620
ctggaatata ccggcaaaag tggggcaatg cgaacgatta aatatcctct ttattcatct   1680
ccgagcggtg gaagaacggt tccgcgcgag atagtttcag caatcaatga tgattatgta   1740
gggctgtacg gtttgagtaa ttttgacgat ctgtataatg cggaaaagcg caacgaagaa   1800
aaggtctact cggttttaga tttttggtac gactgcgtcc aatacggcgc ggtttttttcg   1860
tatacagcgc cgggtctttt gaaaaatgtt gccgaagttc gcgggggaag ctacgaactt   1920
acaaaaacgc ttaaagggag ccatttatat gatgaattgc aaattgataa agtaattaaa   1980
tttttgaata aaaaagaaat ttcgcgagca aacggatcgc ttgataaact gaagaaagac   2040
atcattgatt gcttcaaagc agaatatcgg gaacgacata aagatcaatg caataaactg   2100
gctgatgata ttaaaaatgc aaaaaaagac gcgggagctt ctttagggga gcgtcaaaaa   2160
aaattatttc gcgatttttt tggaatttca gagcagtctg aaaatgataa accgtctttt   2220
actaatccgc taaacttaac ctgctgttta ttgccttttg acacagtgaa taacaacaga   2280
aaccgcggcg aagttttgtt taacaagctc aaggaatatg ctcaaaaatt ggataaaaac   2340
gaagggtcgc ttgaaatgtg ggaatatatt ggcatcggga acagcggcac tgccttttct   2400
aattttttag gagaagggtt tttgggcaga ttgcgcgaga ataaaattac agagctgaaa   2460
aaagccatga tggatattac agatgcatgg cgtgggcagg aacaggaaga agagttagaa   2520
aaacgtctgc ggatacttgc cgcgcttacc ataaaattgc gcgagccgaa atttgacaac   2580
cactggggag ggtatcgcag tgatataaac ggcaaattat ctagctggct tcagaattac   2640
ataaatcaaa cagtcaaaat caaagaggac ttaaagggac acaaaaagga cctgaaaaaa   2700
gcgaaagaga tgataaatag gtttggggaa agcgacacaa aggaagaggc ggttgtttca   2760
tctttgcttg aaagcattga aaaaattgtt cctgatgata gcgctgatga cgagaaaccc   2820
gatattccag ctattgctat ctatcgccgc tttctttcgg atggacgatt aacattgaat   2880
cgctttgtcc aaagagaaga tgtgcaagag gcgctgataa aagaaagatt ggaagcggag   2940
aaaaagaaaa aaccgaaaaa gcgaaaaaag aaaagtgacg ctgaagatga aaaagaaaca   3000
attgacttca aggagttatt tcctcatctt gccaaaccat taaaattggt gccaaacttt   3060
tacggcgaca gtaagcgtga gctgtacaag aaatataaga acgccgctat ttatacagat   3120
gctctgtgga aagcagtgga aaaaatatac aaaagcgcgt tctcgtcgtc tctaaaaaat   3180
tcatttttg atacagattt tgataaagat ttttttatta agcggcttca gaaaattttt   3240
tcggtttatc gtcggtttaa tacagacaaa tggaaaccga ttgtgaaaaa ctctttcgcg   3300
```

```
ccctattgcg acatcgtctc acttgcggag aatgaagttt tgtataaacc gaaacagtcg   3360
cgcagtagaa aatctgccgc gattgataaa aacagagtgc gtctcccttc cactgaaaat   3420
atcgcaaaag ctggcattgc cctcgcgcgg gagctttcag tcgcaggatt tgactggaaa   3480
gatttgttaa aaaaagagga gcatgaagaa tacattgatc tcatagaatt gcacaaaacc   3540
gcgcttgcgc ttcttcttgc cgtaacagaa acacagcttg acataagcgc gttggatttt   3600
gtagaaaatg ggacggtcaa ggattttatg aaaacgcggg acggcaatct ggttttggaa   3660
gggcgtttcc ttgaaatgtt ctcgcagtca attgtgtttt cagaattgcg cgggcttgcg   3720
ggtttaatga gccgcaagga atttatcact cgctccgcga ttcaaactat gaacggcaaa   3780
caggcggagc ttctctacat tccgcatgaa ttccaatcgg caaaaattac aacgccaaag   3840
gaaatgagca gggcgtttct tgaccttgcg cccgcggaat ttgctacatc gcttgagcca   3900
gaatcgcttt cggagaagtc attattgaaa ttgaagcaga tgcggtacta tccgcattat   3960
tttggatatg agcttacgcg aacaggacag ggattgatg gtggagtcgc ggaaaatgcg   4020
ttacgacttg agaagtcgcc agtaaaaaaa cgagagataa aatgcaaaca gtataaaact   4080
ttgggacgcg gacaaaataa aatagtgtta tatgtccgca gttcttatta tcagacgcaa   4140
tttttggaat ggtttttgca tcggccgaaa aacgttcaaa ccgatgttgc ggttagcggt   4200
tcgtttctta tcgacgaaaa gaaagtaaaa actcgctgga attatgacgc gcttacagtc   4260
gcgcttgaac cagtttccgg aagcgagcgg gtctttgtct cacagccgtt tactattttt   4320
ccggaaaaaa gcgcagagga agaaggacag aggtatcttg gcatagacat cggcgaatac   4380
ggcattgcgt atactgcgct tgagataact ggcgacagtg caaagattct tgatcaaaat   4440
tttatttcag acccccagct taaaactctg cgcgaggagg tcaaaggatt aaaacttgac   4500
caaaggcgcg ggacatttgc catgccaagc acgaaaatcg cccgcatccg cgaaagcctt   4560
gtgcatagtt tgcggaaccg catacatcat cttgcgttaa agcacaaagc aaagattgtg   4620
tatgaattgg aagtgtcgcg ttttgaagag ggaaagcaaa aaattaagaa agtctacgct   4680
acgttaaaaa aagcggatgt gtattcagaa attgacgcgg ataaaaattt acaaacgaca   4740
gtatggggaa aattggccgt tgcaagcgaa atcagcgcaa gctatacaag ccagttttgt   4800
ggtgcgtgta aaaaattgtg gcgggcggaa atgcaggttg acgaaacaat tacaacccaa   4860
gaactaatcg gcacagttag agtcataaaa gggggcactc ttattgacgc gataaaggat   4920
tttatgcgcc cgccgatttt tgacgaaaat gacactccat ttccaaaata tagagacttt   4980
tgcgacaagc atcacatttc caaaaaaatg cgtggaaaca gctgtttgtt catttgtcca   5040
ttctgccgcg caaacgcgga tgctgatatt caagcaagcc aaacaattgc gcttttaagg   5100
tatgttaagg aagagaaaaa ggtagaggac tactttgaac gatttagaaa gctaaaaaac   5160
attaaagtgc tcggacagat gaagaaaata tgatagacgt tgtttttaca ccatcgctat   5220
tgactaggtg atctttacgt cagaacccca tcagaaattc cttaaactcc tcaaacttgt   5280
ttgaaagcgg gagaacctgt ttttgtttgt gtagaagctt tttgagatca gcggggagag   5340
gtattttttt gccgatgagt ggttccacta ttgcgttgaa tttcactgga tgcgcggtct   5400
caagaaaaat gccgagagta tttttctttt tattttgagc acaatatttt ttgaggccta   5460
aataggcaac cgcgccgtgc ggatctgcac tatagccaca gcggttatac agttcagaaa   5520
ttgccccgcg cgtttcagcg tcagtaaacg atgcgccgaa aatatctttt tgcatttcag   5580
cgcgttcatc atgatacaga gtgcgcatac gcgcgaagtt actcggattt ccgatatcca   5640
```

-continued

```
tggcatttga aattgttcgt attgacggtt ttggaatgaa cggctcaccg cataaatatc   5700
gcgggacgac atcattgctg tttgtggcgg cgatgaattg tctcacagga agccccattt   5760
tttttgcaat gagccctgcg gtgaggttgc caaaatttcc gcacggcact gaaaatacaa   5820
gcggcgggca tacagcgaac gagcgagctt gcgcttgggc atacgcgtaa aaataataga   5880
atgtctgcga aataagccgc gcgatattga ttgaatttgc agaggcaagg cgcaatgttc   5940
gggcaagctc ccgatcggca aatgcttgtt ttacgagggt ttggcagtcg tcaaacgtgc   6000
cgtttatctc aagcgccgtg atgtttttgc ctaagccagt aatctgtttt tcctgaatag   6060
cacttactcc gtcttttggg tatagaatta taatgtgcac gcgctcactt tgaaaaaagc   6120
tgtgcgccac tgccgcgccg gtgtctccgc ttgttgcggc aagaatggtt aaacatctgt   6180
cgtcattttc caaaaaataa cacatcaatt ccgccatgaa tcgcgcgcca aaatctttaa   6240
acgagagtgt ttggccgtga aaaagttcaa gtacagcgag cgtttcattt aaaaacacaa   6300
gaggcgcgtc aaatgtgaga gatttttcaa taatgcggtt gatgtcttgt tttggaattt   6360
tagggaacca caactcgctt gtttcccgcg caatatcttt gagggatttt ttggcaatgc   6420
ttttgaaaaa tgatgaagag agccggggaa tttcaagcgg catgaacagg ccgccatccg   6480
gcgcgagcgg ggaaaagaga ccatgtttaa aggaaaaaat tttattgttt ctatttgtgc   6540
ttttaagctt catggcaggt ttgtataaaa ttctctgctg aaaattcggg cgaccgtagt   6600
ctgtgatagg ggatggttgc gtgcgcgtat tgtttatagc gattggtgcg atagnnnnnc   6660
agttttgggt aacatcgcgc gagcgcagag cgattgtttt cgttattccg cttttcaaac   6720
atattccccc acagcacggg ctttggatcg cgaaggtact gttcaaacat ttctttgcgt   6780
acttttgccg gcgtgtataa atataccaca cgcgtatatt ttttgagcag attgcataat   6840
gcggggtcaa cataaataac actccctgtc gtgtcaataa ctgtgcgaca atcaagtttt   6900
ctttttgtta ttaaaccgat aatttttcgt ataacgctac gctcgcaacg caaataatgg   6960
ctttgattcg cgttgtattg ggactcgtat ggctggccaa gccatcgcga tacatcttga   7020
atgcccttat agccgtgctt tttaagcaag gaagcaagct ttttttcaat taaatcgtca   7080
cagcagatat gcgcgtaccc aaagcgcgca agctgttgcg cccagtatga ttttcccgcg   7140
cctgacatgc cgataagcgc gattggtttt tcttgcacac tatatatgtt cataaacgca   7200
ctgccttaaa aatatctgaa aaaactcctg cggatgtcac ctctgcgcct gctcctttgc   7260
ctcgtacgat aagcggtgtt tcatggtaat gatcggtggt aaatgaaaat atattgtcgc   7320
tcccgcggag cccggcaaac ggatgattag aggcaacttc tttaagaaac atttttgcct   7380
tgccattttc tatttcagca acaaagcgaa gcactgcgcc gcgtgcgatc gcgcgttgtt   7440
tttttgcttc aaattgggcg tcgtaccgtt caagtgtttt taaaaattct ttaacggttt   7500
cctttttttct gccttgcgga atgagctgtt ctatttcaac atccgcgcat tccatgggga   7560
gagcgcactc tcttgcaaca atcaccaatt ttcgcgccgc gtccatgccg tttaagtcgt   7620
ttcgcggatc tggttccgtg taaccgagct tctgcgcctc gcgcaccgct ttgctcaatg   7680
ttgtatttcc ctcaaatgag ttaaagatat agcttagcgt tccagaaacg attgctgaaa   7740
ttttttctac gcggtcgccg cagagcatga aatctcgtat ggtggaaagc acaggaagcc   7800
ctgccccgac ggttgtttca tataaaaacc gcgtatggtt ttgagaggcg agtagtttta   7860
aatttttata gaatttaaaa ttggatgaaa ggcctttttt attcggcgtt acaatggcaa   7920
tgcgctctgc aagtatggtg ttatagaggg cgggaatttc ttcgctcgcg gtgcagtcca   7980
caaacacggc gtttggaagg cgcattgcct tcatgccggc gacaaattga gcaagatcag   8040
```

ctttttgtcc gcgcgtgtta agctcttctt tccagccaga aagcgtgccg aggtgttccc 8100
caagaaccat tttcttggtg ttgacgatgc ctgcaacttt gagcgcaata ccctcctctg 8160
ccaaaagccg ctctctttga gcattgattt tcgtaagaag cgcagatccg ataagcccgc 8220
ttcccgcgag aaacacgtga atgttttgtg gtgccatagg tataaaaaaa ccgctccaga 8280
catgtgggta atgtccggag cggaagaagt tataatgcgc cttgttttta tttttaactc 8340
ttcacaacca aacatcaccc gccttttgcg gtaatagtgg tgatgatggt agtgatgcta 8400
ttttgacgca taagaatttt tttgactctc atagtatagc acaagtaaaa ttttttgcgc 8460
aaggttttgg tgagttgata gagttttgag gttgatatct aattgtcaag aaacggggat 8520
aatgtgcaca cattatcaca acagattgaa tatatgcggg ttttgtgaaa taatggcatt 8580
atatatcttg atgaacctca ccaaactcgc caatttttc tttgaacttg gcatgatgaa 8640
acgggaaaag catcagggtt ttgctattgc gggcgtgcat cacgacatgg ggtctttagc 8700
ggatcatacg tgtcgcgcgg ctttaattgg cgcaatttta gcggaaatgg aaggcgcgga 8760
cgtgaataaa gttgccatga tggtgctttt gcacgatata ccggaaacgc gcattgggga 8820
tcatcataaa gttgcggcgc ggtatttgga tacgaaaaaa gtggaacgcg ctattttttt 8880
agaacaaatt cagtttctgc ctgatccttt gcaaaaaaaa tggctcgcgc tctacgacga 8940
aaaagcaaag agaagcacta aagagggtat tgtcgcaaaa gacgcggact ggcttgaact 9000
ggcgatttcc gcgcgtgaat acatacacat cggctataaa gatttgcagt tgtgggttga 9060
taatgttcgg agcgcgcttg aaactgaatc cgccaaaaaa cttcttgcag aaatagaaaa 9120
acaaggcacc tacgactggg cccgcggttt agaaaagatg acatatcaga aattatcgtg 9180
atctgcaatt ttttgctata attataaaaa agtttcattc caacatctaa cgcaacattg 9240
aggaaaaact tcaatgcaat gatgagtatt gtgaaaaagt tgggaccagc tctctttccc 9300
attttgcagg atatgcgtct ctcgtatcag gtgcatggaa aggagtaaaa aaatacacgc 9360
cgcttgcaaa tttagaagac gtacggaata gagccgttgc gattagaaaa gaagcagaca 9420
aagaaaagcc agatagttta gagattgatc gtattttaac ggattttatg aatgcggagc 9480
taaaggaatt atggaatacc atagataaac gtattgttga tgcggcgaaa aagtttatac 9540
aaaacttcaa agatcatccc gaagacgcga ggagagcgaa ggtggagagt tggggactag 9600
aagaatggaa aagagattta gaacggatag tcaaaacccc aattaatcaa atgatggggg 9660
acgcatcatt tgtgattaac agaggagtgg atcagtatcg tgcgcgcgat atggcgaaaa 9720
ttatgggtaa gataagtgtt ttttatcaac cccttgtgtg ggagaaggcg tcataaccca 9780
tgagaattat cacaaaattc tctgcttcat atacaccatc gctccgtaaa gccccgagga 9840
atcgcagagc tttgattttt gaatcggcgg aaaggacggg aacaggggtt gatttgattt 9900
cttgacacgc tgtgagttgg gcagtagagt agtaagaaag taatattttt ttatattcat 9960
gaacactaag ataatacaaa aagctacatc tcgggggaaa attacgcttc caggacagtg 10020
gcgtaaaaag tttcctacga accaatatct tgttgaagtg gaagaagatt tgcttaagat 10080
taagcctttt gaagtggaca cggcggggca attagaagaa caagtaaaag tgttgaattg 10140
tgtcaataga tttgagggac ttgcgataaa aggaagaaaa tttgctaaaa agagaggaat 10200
taaaatggac gatgttttaa aagatgatta aagcagtact tgatacgaat attttaattt 10260
ccgcactttt ttggaaaggc accccatata ttattgtgca ggatggatta gagggtgtgt 10320
ttgaaatggt tacttcaaaa gcaataatga gtgaaacgaa agagaagttg attcaaaaat 10380
ttgaattttc tgttgaagat actctaagat acttggaact cttggtttgt aagtcgttcg 10440
ttgtatcacc gatggtacag cataatgtgg tgaaaaatga tagtactgat aataaaattc 10500
ttgagtgtgc ggtaagcgcc aacgcagatt atattgtgac aggagataaa catctactaa 10560
atatcaagca ttatcaaggg atcactattc tcactgcacg cagatttgat gagatacttg 10620
aaaatgaacg gagtagaatg agaagaaata agcgataggg acagaataac ttggatccaa 10680
ccttctaacg caacagcgtt aagaatgaat taattgattg aaaacctcgt atggtgtttg 10740
aaagtcgagt gtttttctcg gtcggccatt caggagatgt tgcgctcgtt tcacttcgta 10800
ccgcgatacc ttggtaaagt tggttccttt cggaaaaaat tgtctgatga gtccattggt 10860
gttttcgttc gtgcctcgtt cccatggact ccggggatgg gcgaagtaga ctttgactcc 10920
ggtcagattc gtgaataatt tgtggctggc catttcccgc ccttggtcgt atgtcatcgt 10980
cagtctcatt tgtttcggca attttttcac ttccttggca aacgctttgg ccacatcttc 11040
ggcagatttg cttttcacgg ggataaggat agtcgtgcgg gtcgtgcgct caaccagagt 11100
gccaagagcc gaacgattgt tctttccaac aatgagatcg cc 11142

<210> SEQ ID NO 25
<211> LENGTH: 13879
<212> TYPE: DNA
<213> ORGANISM: Artificial sequence
<220> FEATURE:
<223> OTHER INFORMATION: Synthetic sequence

<400> SEQUENCE: 25
tttccaccgc cgctcaatca gtctagacat acaggtggaa aggtgagagt aaagacgtga 60
caaccttctc atcctcttca aagtctagac atacaggtgg aaaggtgaga gtaaagacaa 120
accgtgccac actaaaccga tgagtctaga catacaggtg gaaaggtgag agtaaagact 180
caagtaacta cctgttcttt cacaagtcta gacctgcagg tggtaaggtg agagtaaaga 240
cttttatcct cctctctatg cttctgagtc tagacattta ggtggaaagg tgagagtaaa 300
gacttgtgga gatccatgaa cttcggcagt ctagacctgc aggtggaaag gtgagagtaa 360
agacgtcctt cacacgatct tcctctgtta gtctaggcct gcaggtggaa aggtgagagt 420
aaagacgcat aagcgtaatt gaagctctct ccggtccaga ccttgtcgcg cttgtgttgc 480
gacaaaggcg gagtccgcaa taagttcttt ttacaatgtt ttttccataa aaccgataca 540
atcaagtatc ggttttgctt tttttatgaa aatatgttat gctatgtgct caaataaaaa 600
tatcaataaa atagcgtttt tttgataatt tatcgctaaa attatacata atcacgcaac 660
attgccattc tcacacagga gaaaagtcat ggcagaaagc aagcagatgc aatgccgcaa 720
gtgcggcgca agcatgaagt atgaagtaat tggattgggc aagaagtcat gcagatatat 780
gtgcccagat tgcggcaatc acaccagcgc gcgcaagatt cagaacaaga aaaagcgcga 840
caaaaagtat ggatccgcaa gcaaagcgca gagccagagg atagctgtgg ctggcgcgct 900
ttatccagac aaaaaagtgc agaccataaa gacctacaaa tacccagcgg atcttaatgg 960
cgaagttcat gacagcggcg tcgcagagaa gattgcgcag gcgattcagg aagatgagat 1020
cggcctgctt ggcccgtcca gcgaatacgc ttgctggatt gcttcacaaa aacagagcga 1080
gccgtattca gttgtagatt tttggtttga cgcggtgtgc gcaggcggag tattcgcgta 1140
ttctggcgcg cgcctgcttt ccacagtcct ccagttgagt ggcgaggaaa gcgttttgcg 1200
cgctgcttta gcatctagcc cgtttgtaga tgacattaat ttggcgcaag cggaaaagtt 1260
cctagccgtt agccggcgca caggccaaga taagctaggc aagcgcattg gagaatgttt 1320

-continued

```
tgcggaaggc cggcttgaag cgcttggcat caaagatcgc atgcgcgaat tcgtgcaagc   1380
gattgatgtg gcccaaaccg cgggccagcg gttcgcggcc aagctaaaga tattcggcat   1440
cagtcagatg cctgaagcca agcaatggaa caatgattcc gggctcactg tatgtatttt   1500
gccggattat tatgtcccgg aagaaaaccg cgcggaccag ctggttgttt tgcttcggcg   1560
cttacgcgag atcgcgtatt gcatgggaat tgaggatgaa gcaggatttg agcatctagg   1620
cattgaccct ggtgctcttt ccaatttttc caatggcaat ccaaagcgag gatttctcgg   1680
ccgcctgctc aataatgaca ttatagcgct ggcaaacaac atgtcagcca tgacgccgta   1740
ttgggaaggc agaaaaggcg agttgattga gcgccttgca tggcttaaac atcgcgctga   1800
aggattgtat ttgaaagagc cacatttcgg caactcctgg gcagaccacc gcagcaggat   1860
tttcagtcgc attgcgggct ggctttccgg atgcgcgggc aagctcaaga ttgccaagga   1920
tcagatttca ggcgtgcgta cggatttgtt tctgctcaag cgccttctgg atgcggtacc   1980
gcaaagcgcg ccgtcgccgg actttattgc ttccatcagc gcgctggatc ggtttttgga   2040
agcggcagaa agcagccagg atccggcaga acaggtacgc gctttgtacg cgtttcatct   2100
gaacgcgcct gcggtccgat ccatcgccaa caaggcggta cagaggtctg attcccagga   2160
gtggcttatc aaggaactgg atgctgtaga tcaccttgaa ttcaacaaag catttccgtt   2220
tttttcggat acaggaaaga aaaagaagaa aggagcgaat agcaacggag cgccttctga   2280
agaagaatac acggaaacag aatccattca acaaccagaa gatgcagagc aggaagtgaa   2340
tggtcaagaa ggaaatggcg cttcaaagaa ccagaaaaag tttcagcgca ttcctcgatt   2400
tttcggggaa gggtcaagga gtgagtatcg aattttaaca gaagcgccgc aatattttga   2460
catgttctgc aataatatgc gcgcgatctt tatgcagcta gagagtcagc cgcgcaaggc   2520
gcctcgtgat ttcaaatgct ttctgcagaa tcgtttgcag aagctttaca agcaaacctt   2580
tctcaatgct cgcagtaata aatgccgcgc gcttctggaa tccgtcctta tttcatgggg   2640
agaattttat acttatggcg cgaatgaaaa gaagtttcgt ctgcgccatg aagcgagcga   2700
gcgcagctcg gatccggact atgtggttca gcaggcattg gaaatcgcgc gccggctttt   2760
cttgttcgga tttgagtggc gcgattgctc tgctggagag cgcgtggatt tggttgaaat   2820
ccacaaaaaa gcaatctcat ttttgcttgc aatcactcag gccgaggttt cagttggttc   2880
ctataactgg cttgggaata gcaccgtgag ccggtatctt tcggttgctg gcacagacac   2940
attgtacggc actcaactgg aggagttttt gaacgccaca gtgctttcac agatgcgtgg   3000
gctggcgatt cggctttcat ctcaggagtt aaaagacgga tttgatgttc agttggagag   3060
ttcgtgccag gacaatctcc agcatctgct ggtgtatcgc gcttcgcgcg acttggctgc   3120
gtgcaaacgc gctacatgcc cggctgaatt ggatccgaaa attcttgttc tgccggttgg   3180
tgcgtttatc gcgagcgtaa tgaaaatgat tgagcgtggc gatgaaccat tagcaggcgc   3240
gtatttgcgt catcggccgc attcattcgg ctggcagata cgggttcgtg gagtggcgga   3300
agtaggcatg gatcagggca cagcgctagc attccagaag ccgactgaat cagagccgtt   3360
taaaataaag ccgttttccg ctcaatacgg cccagtactt tggcttaatt cttcatccta   3420
tagccagagc cagtatctgg atggattttt aagccagcca aagaattggt ctatgcgggt   3480
gctacctcaa gccggatcag tgcgcgtgga acagcgcgtt gctctgatat ggaatttgca   3540
ggcaggcaag atgcggctgg agcgctctgg agcgcgcgcg tttttcatgc cagtgccatt   3600
cagcttcagg ccgtctggtt caggagatga agcagtattg gcgccgaatc ggtacttggg   3660
```

-continued

```
acttttttccg cattccggag gaatagaata cgcggtggtg gatgtattag attccgcggg   3720
tttcaaaatt cttgagcgcg gtacgattgc ggtaaatggc ttttcccaga agcgcggcga   3780
acgccaagag gaggcacaca gagaaaaaca gagacgcgga atttctgata taggccgcaa   3840
gaagccggtg caagctgaag ttgacgcagc caatgaattg caccgcaaat acaccgatgt   3900
tgccactcgt ttagggtgca gaattgtggt tcagtgggcg ccccagccaa agccgggcac   3960
agcgccgacc gcgcaaacag tatacgcgcg cgcagtgcgg accgaagcgc cgcgatctgg   4020
aaatcaagag gatcatgctc gtatgaaatc ctcttgggga tatacctggg gcacctattg   4080
ggagaagcgc aaaccagagg atattttggg catctcaacc caagtatact ggaccggcgg   4140
tataggcgag tcatgtcccg cagtcgcggt tgcgcttttg gggcacatta gggcaacatc   4200
cactcaaact gaatgggaaa aagaggaggt tgtattcggt cgactgaaga agttctttcc   4260
aagctagacg atctttttaa aaactgggct gctggctatc gtatggtcag tagctcttat   4320
tttttactt gatatatggt attatctcaa taatatgcat ctcttcatag atacaacaga   4380
aaaagaatca tttgatattg ctttgattga tgatgagcgc gttatcaaaa agaagcgaat   4440
caaatcaatc cgccaacatt cggaaaagct tttgaaatca attgacgcgc ttttgttgtc   4500
cgcaaaatca tctctgaaag atatacaagg catcatcgcg gtaaaaggcc ctgggtcatt   4560
tacctcattg cgcattggaa tcgcgacagc caacgcgttg gcattcgctt tgggagtggg   4620
gattgctgga gttgacaaaa cagatgagtg gagtaagatt gtttcttcag cagatttgat   4680
ctttaaaaag caaaaaaaga acttaaatat cgtcataccc gaatacggca gagagccgga   4740
cattacctaa ataggagggt ttagaaatgt tattgctcat tttgattctc acaatagttt   4800
tgagcatcat tcttttgtgc ttttgcgcgt ttattctctg cataatcaca gaagatggca   4860
gggaaatgct tttgatgttt ggaataggca aatgccactt gaattattaa agtggctttt   4920
ttatttgtac aaaaacagtg tcagagcgcc gattcggcgc tctgacactg ttttacaaac   4980
cctcacccca accctctccc gaatacagga gagggaattt ttatactgtg cataacttgt   5040
gcgcaaatag tgcctagata agggttgcgt aaaattacaa gagtggtgta taatatcatc   5100
atagtggtga ggagtgggga taagtggtgg agaacctcat caataataga taccaatgtt   5160
cataggagaa tacaaacata ctattgatac caaaggaaga atggcaatac ctgccaaatt   5220
tcggcaggat ttgaaaaagg gcgcaatcgt aacaaaagga ttggataatt gcctttttgt   5280
atacactcaa gatgaatgga aaaaactcgt ggacaagcta tctaatcttc caatctcaca   5340
gcagaaaagc cgggcatttg ccagattaat gctagcagga gcaatggacg tgcaaattga   5400
ctcccaaggc agaattctta taccagaata tcttcgcaaa ttcgcgtcaa tcaagaaaga   5460
caccataata gcagggcttt acagtcggct tgaaatatgg gattcaaaag aatgggaaaa   5520
atacaaatca gccactgaaa agataagcac aaaaatagct gaagagctca cgctctaggc   5580
caaaaacaaa aataaaattc aaaacaatca cgagatcctt cgactccgcg agtacgcttc   5640
gctcagagcc tgccccgagt attccgaggg gatgacggtt gaaattcgga tggcataata   5700
attttatttt tggagctggt cttttagtag ctccattttt tatcccatga gcaaatcaga   5760
acacatacca gtattattaa acgaagtaat tgaaggtctt gacttgtcct ctaatgatac   5820
agtaatagac gccacagtag gcggagcagg acacgcgcaa gctattttag aaaaaaccgc   5880
gccatcaggc aagcttcttg gaattgattg ggacgcgaaa gcaatcgagc gcgcgcgaga   5940
acatctaaaa agatttagca accgaattat attaaaaaca ggaaattaca cagatataaa   6000
acaacttctc tatgaatcag gaattaataa ggttaatgct atattattgg acttgggctt   6060
```

-continued

```
atctcttgat caactcaaag attcctctag aggatttagc ttccaatctg aaggaccatt   6120
ggacatgagg ttttctgacc agatggacac aacagctttt gatattgtga acacctggcc   6180
agagaatgat ctggtacaaa tctttcaaga atacggtgaa gagaggcgcg ctgcacgtgc   6240
agcacgcaat atcgccactg cgcgcagtca cgcgccaatc aacaccgcaa aagatctggc   6300
agaattagtt atgcgcgggg ccggaaggcg aggcaaggtt catcccgcta cccgcatatt   6360
ccaggccctg cgcattgcta caaatcatga attagacaat gtcaaacaag cattgcctaa   6420
tatgattgat atgctttctt cagaaggaag attagcagtt atcacattcc attccttaga   6480
agaccgcatt gtgaagcagt atttcaagcc attggctaaa gaggaaaatc cgcgcattaa   6540
gctcatcaat aagaaagtaa taaagccaag ccgagaggag caagtgaaaa atccagcatc   6600
cagaagcgcg aaattgagaa tcgtggaaaa gatttaatca ttccaaaaac aaaaatagca   6660
tcacatgaca acatattcgc acaaaaaaac gccgtatctg tggcacgcat tttcaatatt   6720
gctgatttta gtattagtgg ttacttattt agtacagata aacagccaag cagaaacatc   6780
ttactctatt aaaggattag aagaaaaaaa gcaagaattg aatagtatta tagaagataa   6840
agaacttgaa gcagtttcag cgcgatcttt aaatggaatc gcgcttaagg caaaagaaat   6900
gaatttgcag gatccaaagg atgttacatt cataaaaata ggattaagca cagttgccgt   6960
gagcgaagag ctttctccat aacatgactt catattcatc atcaaaaaag agcaattcag   7020
ctacgcgcgc gaaattcata attggcgcgg tttttatttt tggcgttatt ttgatttacc   7080
gcttagctga tttacagctt atcaatactc aagaaattca ggcatctgcc gcgcgccagc   7140
agtcaacagt gcgcatcctt ccagctgaac gaggcaagat tttttacaag gagagaatag   7200
gtgatgaaga atttccagtc gcgactaata gatcatataa ccaggtattc attattccaa   7260
aagacataca ggatccaatc aaagccgcgg aaaagctatt gcctttggtt gagccatatg   7320
ggcttgatga agaaacatta ttattccgat taagcaagca aaatgacatt tacgagccat   7380
tagcgcataa attaacagat gaagagcttg agccatttat tgggcttgat ttaattgggc   7440
ttgaatcaga agatgaaaaa gctaggtttt acccggacgc tgatttgctc gcgcatataa   7500
ctgggtttgt cggggtttca gaacaaggca aggttggtca atatgggctt gagggatttt   7560
ttgaaaatga gctcaaagga aaggacgggc ttattgaggg caaaacagat atatttggca   7620
ggcttataca aacaggaact ttaaaacgca cccaaggcga gccaggagat gatttattat   7680
taaccataca gcgcactttg caggcatatg tgtgcagaaa attagatgaa aaaattgagc   7740
aaataagagc tgctggcgga tcagtaataa ttgtgaaccc agatactggc gctattctcg   7800
cgatgtgctc ttcaccatca tttgatccga ataattataa tcaagttgaa gatattagcg   7860
tatacatgaa tccagcagtg agctcaagct atgagccagg atcaattttc aagccattta   7920
caatggccgc ggcaattaat gagaaagcag ttactagcga tacaacatat attgatgagg   7980
gagtggaaga gatcggcaaa tacaaaatcc gcaattctga caacaaagcg cacggggaag   8040
ttaatatggt aactgtttta gatgaatcat tgaatactgg cgcgattttt gtccagcgtc   8100
agattggaaa tgagaagttc aaagattatg ttgaaaaatt cggatttggc agaacaacag   8160
atattgaatt aggaaatgag gtttctggaa atatttcttc attgtataag gatggagata   8220
tttacgcggc aactggctcg tttggccaag gaattactgt tacgcctatt cagatggtaa   8280
tggcatatgc ggcgattgct aatggaggaa aattaatgca gccatatctt attgctcagc   8340
gacaaagaca ggataaaact attgtaactg agccagttca aattgatgag ccgatttcag   8400
```

-continued

```
tgcaggcctc aactattata tctggaatgt tggtgagcgt ggtgcgtgct gggcacgcta   8460
tatctgctgg agtggaagga tattatattg ccggcaaaac tggaaccgcg caggtcgcgg   8520
aaggcggagg gtatggaagc aagaccattc attcatttgc cgggtttggg cctgttgatg   8580
agccagtgtt tgcaatgctt gtgaaattag attatcctca atacggcgca tgggcagcta   8640
atactgcggc tcctttgttt ggcgaattag ccaaatttat actacaatac tatgaaatac   8700
ctcctgatga ggcgatataa ataaaatatg aaaaaaataa taattacaat tttacaaact   8760
ctggccaaaa gagttattta caaatataag cccaaagtgg tggctattac tggctcagtc   8820
ggaaaaaccg cgactaagga ggcagtgttt gctgtattga ataagaaatt gcaagtgcgc   8880
aagaatgaag gcaattttaa cacggaaatc gggttgcctt tgacaatcat tggcttgcaa   8940
aaatcaccag gcaaaaatcc attcaaatgg cttgcagtgt acgcgcgcgc tattggcctt   9000
ttaatcttta ggattgatta tccaaaagtt ttggttcttg aaatgggcgc tgataagcca   9060
ggagatattg ctgaattaat aagtattgct aagccagaca ttggcataat taccgcgatt   9120
agcgctgttc atacagagca gtttaatagt attgctggcg ttgtgcgtga aaaaggaaag   9180
ctctttcgcg ttgttgaaaa ggatggttgg attatcgtga ataacgaccg atctgaagtt   9240
tatgatatcg cgcaaaagtg cgacgcgaaa aaagtatata ttgggcagtg cgctgaatta   9300
tctgataaca cccctttttc agtatgcgcg tccgagattt cagtgagcat gtcagaagct   9360
caagaaaccg gcattgctgg cacttcattt aagcttcata ctgatggaaa ggttattccg   9420
gttttgatga aaggaattat tggggagcat tggacatatc ctgccatgta cgcggcagct   9480
gttgcgcgca ttcttggggt tcatatggtt gatgttactg agggtttgcg cgagattaat   9540
cctcaatcag gaaggatgcg agttttagct ggcattaaaa aaacaatttt aattgatgat   9600
acttataatt cttcgccaaa cgcggctaag agcgcggttg atactttagc gttattgcgt   9660
attggaaggg agaaatattg cgtgtttggg gatatgttgg agcttggttc tatatctgaa   9720
gaagagcatc aaaaattagg catgcttgtc gcgcgcgagg ggattgatta tctgatttgc   9780
gttggcgagc gcgcgcgcga cattgcgcgg ggcgctataa aagcaaagat gccgaaggat   9840
catgtgtttg aatttgataa tactaaagat gctgggctct ttatccaaaa gcgtttggag   9900
caaggggata tggttctgat taaaggttcg caaggcgtgc gcatggagcg cgtgaccaaa   9960
gagattatgg cgcatccgga aaaatcaaaa gaacttcttg tgcggcaaag taaagaatgg  10020
ttgagtaagg cctagtgcgt atttttgata atttcctcca cttcttccgc attttctgca  10080
tccatcaatt tcacgcgcaa ttgctttgcc ccatcccagc cagaaacata ggccttgaaa  10140
tgttttttca ttacagcgaa tgatttgtgt ttgataagtt tttcgtagag tttggcgtgc  10200
tctattaaaa cgcgcaattt gttatctttg ctgggataga aaacggagaa aacggtgtca  10260
agagtcgttt tctgtaaaaa acgactcctg acaccgtttt ctttgaagaa ccacggattg  10320
ccgaaaattg cgcggccgat cataacgcca tcaacaccgg tctcccgggc tttttgatgc  10380
gcatcgtcta aatacgaaac atctccattc ccgataataa gcgtcttggg cgcgattttg  10440
tctcgcatct gaataacgct tttagccaaa tgccatttag caggaacgcg ggacatttct  10500
tttctagtgc gccagtgaat cgtcaaagcc gcaatgtctg tcttcagaag aataggaatc  10560
caggtatcaa tttcattttt cgtatatcca atgcgcgttt taacagaaat tggcaatttt  10620
ggcgcgcctt ttttggctgc agcaatcaaa gcgcgcgcta aatcagggtt tttcatcaaa  10680
ccagccccag cgccttgctt ttcaactttc cggtccgggc atcccatgtt aatatctaat  10740
ccatcaaaac ccaaatcctg aattatgcga gctgtttttt tcatattatc tggatttgct  10800
```

-continued

```
gtaaatactt gcgcgacaat aggccgctct ttcgcggaaa atttaagatt tttaagaatt  10860
tcatctttgt cgccaagagc aatgccatcc gcggacacga attcagtcca cattacatct  10920
ggcttgccat actttgcgat aatccgccta aaagccgcgt ctgtcacgtc agacatagga  10980
gccaaacaga agaatggttt tttgagttgt tgccaaaaat tattcatgtc atcttgcgct  11040
tatttgtcat cccgaggctt aattatatat ttttagaaaa taggatgtgg taaacggatt  11100
atataagtgt aatagtaatg ccacacaagc cgagaggatc tcgtctttaa gagctcgaga  11160
tgacaataca aggcgagaga atctcgcgac taataactat gcttattatc aaataaatcc  11220
ttccaatcag aattgaattt gtttataagc aacaccttat ttctgtggct tagttttttt  11280
agcttctttt cgcgctcaat agcatacgag atattgtcaa agtgttcata atacaccagt  11340
ttatcagtat tgtattttga agtaaaccct ggtatttttt tatttttatg ttcccaaatt  11400
cttctggata atgaattgca tactccggta taaaataccg tatgtcgtat gtttgttgtt  11460
atatatacat aaaagttata ttgattttgt cttggcatgt ttttgtttca taagatcctc  11520
tcggcctgca aggattttg ttttggactc catgattcgt ttaccacata ttcgatatta  11580
tgtagtattg taaggtctcg ggatgacagg taaaaggcat gggaatggca tctaaatctc  11640
ctcctttttc tcatgcacat aattcatcca ttcctcaatc acttttataa acgccttgaa  11700
cggagcctct ataataaaat ccaacgcaaa aatgaaaatg ttaatttgcg cgaaccgcgt  11760
ggacatccat ttgccagcat gcagaatcgg aattgtaaaa aacgcccata agccccggat  11820
aaatccttgc tttgggggca ggacaatcat ttcctgattt gactggcgga tgcggtacgc  11880
gaataaggaa acaaacgaga ggaacaagag aaagataaaa atgccgataa acgtgaaatt  11940
cagcgcgatc aaaatataaa tcatcaaacc gaacgaaatg ccaaatagca ttccgtacaa  12000
caaagtaaac accgcgcgca ggaaaaagct acgcttgcta gatttgcgca tctgaataat  12060
ttcgccttga ttttggataa tatgatttat gccacttatc atttgattgg tgtttcttc  12120
atcaggcagt ttagttgaga gtgcgataag cgcgagcaag gcaggcggaa aaattaaatt  12180
aatagccaaa ggcatataat caattttgtg aatcaataaa taatcaacag gaatttccag  12240
aaccacggct aataaaaatt tagtaattac caaataaata atacttcgct taatgcctcg  12300
gtgtaaagaa gcgcgggatt tttcgtactg cttttggcag atggcgcgca ccctttgctc  12360
aaattcatgc ccggtgttca tatcagacca ggcttttcct ggatcctgcg caatcgcgtc  12420
ttgcaaaata gtgaaatatc caacgtattt cctgaacaaa ggagcgagtt tttcttttat  12480
aggcgagttt aaatcttgcg ttattgtaga gtgtatttca ttcaaatgct ctcctatttc  12540
ccgtataaga tcgtgatttg cgcgcgtcca ttctggataa taggtcaata gcaaatgata  12600
tccaatagtg tcattgtcgt ttttatatag aattcggcta gtggctatat aaatctgctt  12660
caaacgttct cgatcattaa tttcatcctc aattctaacg cgctcctgaa gatattcata  12720
catggcattg attgacgcgt gcattacata tggtggcata aggaattcgt caatttccgt  12780
tgctgctatg ccagagagcc aaaatgaaag agaagaagaa tcattgatat cttttatagg  12840
agcgtgacca agcaaggtga aatatttttc aaatataata tcaagttctt ttatttttcg  12900
ttcagggata gtattgttcg gaaggtaccg cgcgtggata agttctgaaa ttagattttc  12960
tgagatatta tttttatggc ctgatgaaat cattctacgc aaaatgcgct caatcgcgtt  13020
tctgcggatt aaatgttctt ctttatattc aaccgcgttg cgcatgcgct cgtatataaa  13080
agttgcctgt ccagcgcggg tggttatgga gatttttggt tcggtcgggt ctgtatcttt  13140
```

tgagcgcgct tcttccctgg ccgcgcgcac gattcgctgg attgtttctg gtatttgcat 13200
ttctttatac tagctgattt tgcttgtttt ttcaattgtt ttataaaaaa agtgcccgga 13260
atgcaaattg cgcattccgg gcttggggag acagggcagg ggatgccctg tttggggctt 13320
actgccggtc ggtcagatca cgggctacta ccgccgcaat cctcgccacc gcccaggcag 13380
taacgagacg actctttttt tacctgattg acgaccgtac cgtcgagcag gacgttatcg 13440
ccgagcagat tcgctgtatt gatgtccgta gccgcggtag ccgcgatagt cgtggtcgtc 13500
gtcgtggttt ccgtagtggc tgtgccgacc gcgctgtttt cgccgccctc ttttgtcatc 13560
cgaatgacat catcgccatt cagagtcgtt tcctcgctga ccgggttgtt ggtcccgcag 13620
ccgatcattc cgatcagggc gaccagcgcg atacagaaga aaatcatgaa atacttcatc 13680
gggtgctcct ttttatgagg tttttggaaa acgatatcac gctttgtatt attcacctcc 13740
cttccaaagc aagcgcaata tcggtctttt ttactatttt aagaacggac gagcatctta 13800
tactatttta aaaataatgt caagagtgtt aacaaataca aaaaattgac tcatataaaa 13860
acggtgtcag gagtcgttt 13879

<210> SEQ ID NO 26
<211> LENGTH: 7532
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2669)..(2692)
<223> OTHER INFORMATION: n is a, c, g, or t

<400> SEQUENCE: 26
tacctaatcc tgggcgtctt tggtgtatta tgcacttgcg gttagaatac acccgaacat 60
aattgacaaa gaccataaaa tgtcttatta tccttttaga aaaatcgtgt tcatttataa 120
tatatacata ccccaattcc aaggatttct tgactggcag cgggcttggt atcctgcgaa 180
acacagccag tttgggaaac ctgggtcttt atttttaaag acacaggaat tcccgcgtct 240
tttgccttgg aacaccaacc acctattgcg cctttttttct cattttagca aaagtggctg 300
tctagacctt caggtggaaa ggtgagagta aagacattgg gcctgcacga ttcatgggcc 360
ggtctagacc ttcaggtgga aaggtgagag taaagactct accgcgtcca gcactatctt 420
ggtccgtcta gacatttaga tggaaaggcg agagtaaaga tgcgcgaaag acggctacat 480
tgttccacaa ggcagaaagg attagccgcc tactgcttga acatccgcag tatttaaccc 540
attttcccaa aggaggaaaa tcatgggtac gcagattatc aagcggatag accttgactg 600
gcagtcaagt tttccgcacg ccaagatgct ggtgaatcag gaagcatcat ttaaccacat 660
tgcagagtcc ggactcacgg cgctcataga agcgccgacc ggatccggaa aaaccgcgac 720
tggctatacc tttctttcgg ccatagccct tcgcgcgcgc aagagtccgc aatttaaggg 780
ccggctcgtg tatgttgctc cgaataaagc attagtcggg caggtgcaga acatgcatcc 840
agatgtgaaa gtcgcgcttg gtcgcaacga gcatacatgc tcgtattacg atggaattca 900
tcaagcagac gaagtgccgt gttcgttttt ggttcgctcc ggccggtgtg gccactatgt 960
gaatcaagaa accggcgcaa cacttgaatt tggagctgaa ccatgttcgt attatcagca 1020
aatctatgag gcaaagcgcg gcatcggaat tctggcatgc actgacgcgt tttggctgtt 1080
cacgcatttg tttaatccaa agcagtggcc tcagcccatg ggtttggtat tggacgaggt 1140
tgaccgcttg gctgatattg ttcgcaggtg cttgtcatac gaaatttctg attggcgcat 1200

```
tgagcgcgcc attaatttgc ttgaaaaagt cggttcagtt caggtgcagt atctctcgtc   1260
tttttgcgc accttgaatc gggtggtatc aaaaaagccg gccctggagc ccattttgct   1320
ggatgatgag gagattcgcc aactgtttga aaaagtgggg cgcatcagcg cggatgtcat   1380
caaatccgat ttggacgccg cgattgcgag caacaaggtt gaccctatgg ctgagcgcga   1440
aatccttaag cagatagaaa cactttgctt tgacatcagc cggtatgtgc ggagtttggg   1500
atacgcgctt ccgaatcgca gaggcaaggg tgatgaacgc aagcgcgatg ctcctctttc   1560
gtacgcgtac gcgtatcata aatccgagcg cgacgctggg gcgcatgtgc agaacaaagt   1620
tgtggtgtgt tcctattggg tgcggcctct tatccgcaag ctctttggaa agaacacgct   1680
cgcgtattca gcgtttgtcg gggataaaac gattttggat tatgaggctg gagttgattt   1740
tccattaatc tctctgcggt cccaatttcc ggcgagcaat gcgcgattgt atgtgccgag   1800
cgattctcca aatttggcat ataatgagca ggatgtcggt gacatggcta agactttgcg   1860
ccatattgcc atatcaactc ggcggtttgc cgagcgcggc tttcgttctc tcttgctgac   1920
tgtttcaaat agagagcgtg aattgctgta cgtcgcgtgc gcggaactga aagggctgga   1980
tgctataagt tatggcagtg gcgttactgc gcgcgcggcc gcggatagat tcaaagaagg   2040
agaaggggac gctcttattg gcgttttgtc gcattatggc actgggctgg atttgccagg   2100
caagattgct aacattgttt ttctcctgcg gccgaatttt cctccaccaa aagatcctat   2160
ggcacagttt gagattcgcc gggccgagcg catcaaaaag tcgcattggc ccgtgtggta   2220
ctggcgcgcg taccgagagg ctctgaatgc ccagggacgc ccgatacgaa gcgccgatga   2280
caaaggggtc gcgttcttta tctcccagca attcaagaag cgtttattca acattttgcc   2340
ggagcatctt gagagcgcat atcggagccg cctcacatgg gaccagtgcg agaaagacgc   2400
gctgaaactg tttgaggaat aggggtatta tttcgttgtt tttatggccc ggatggtgtt   2460
ttttatacat catccgggtt tttatgttga tttgatgcga taatcatgat ttttgcgtgg   2520
tattgacaaa cattataaaa aacgctatta tccgcgtaca aaacctataa atcgttcatt   2580
tataatatat acatacccca attccaagga tttcttgact ggcagcgggc ttggtatcct   2640
gcgaaacaca gccagtttgg gaaacctgnn nnnnnnnnnn nnnnnnnnnn nngccagttt   2700
gggaaacctg ggtctttatt tttaaagaca caggaattcc cgcgtctttt gccttggaac   2760
accaaccacc tattgcgtct ttttcgctca ttttagcaaa agtggctgtc tagacataca   2820
ggtggaaagg tgagagtaaa gacatggcct gaatagcgtc ctcgtcctcg tctagacata   2880
caggtggaaa ggtgagagta aagaccggag cactcatcct ctcactctat tttgtctaga   2940
catacaggtg gaaaggtgag agtaaagaca aaccgtgcca cactaaaccg atgagtctag   3000
acatacaggt ggaaaggtga gagtaaagac tcaagtaact acctgttctt tcacaagtct   3060
agacatacag gtggaaaggt gagagtaaag actcaagtaa ctacctgttc tttcacaagt   3120
ctagacctgc aggtggtaag gtgagagtaa agactcaagt aactacctgt tctttcacaa   3180
gtctagacct gcaggtggta aggtgagagt aaagactttt atcctcctct ctatgcttct   3240
gagtctagac atttaggtgg aaaggtgaga gtaaagactt gtggagatcc atgaacttcg   3300
gcagtctaga cctgcaggtg gaaaggtgag agtaaagacg tccttcacac gatcttcctc   3360
tgttagtcta ggcctgcagg tggaaaggtg agagtaaaga cgcataagcg taattgaagc   3420
tctctccggt ccagaccttg tcgcgcttgt gttgcgacaa aggcggagtc cgcaataagt   3480
tctttttaca atgtttttc cataaaaccg atacaatcaa gtatcggttt tgcttttttt   3540
```

-continued

```
atgaaaatat gttatgctat gtgctcaaat aaaaatatca ataaaatagc gtttttttga   3600
taatttatcg ctaaaattat acataatcac gcaacattgc cattctcaca caggagaaaa   3660
gtcatggcag aaagcaagca gatgcaatgc cgcaagtgcg gcgcaagcat gaagtatgaa   3720
gtaattggat tgggcaagaa gtcatgcaga tatatgtgcc cagattgcgg caatcacacc   3780
agcgcgcgca agattcagaa caagaaaaag cgcgacaaaa agtatggatc cgcaagcaaa   3840
gcgcagagcc agaggatagc tgtggctggc gcgctttatc cagacaaaaa agtgcagacc   3900
ataaagacct acaaataccc agcggatctg aatggcgaag ttcatgacag aggcgtcgca   3960
gagaagattg agcaggcgat tcaggaagat gagatcggcc tgcttggccc gtccagcgaa   4020
tacgcttgct ggattgcttc acaaaaacaa agcgagccgt attcagttgt agatttttgg   4080
tttgacgcgg tgtgcgcagg cggagtattc gcgtattctg gcgcgcgcct gctttccaca   4140
gtcctccagt tgagtggcga ggaaagcgtt ttgcgcgctg ctttagcatc tagcccgttt   4200
gtagatgaca ttaatttggc gcaagcggaa aagttcctag ccgttagccg gcgcacaggc   4260
caagataagc taggcaagcg cattggagaa tgtttcgcgg aaggccggct tgaagcgctt   4320
ggcatcaaag atcgcatgcg cgaattcgtg caagcgattg atgtggccca aaccgcgggc   4380
cagcggttcg cggccaagct aaagatattc ggcatcagtc agatgcctga agccaagcaa   4440
tggaacaatg attccgggct cactgtatgt attttgccgg attattatgt cccggaagaa   4500
aaccgcgcgg accagctggt tgttttgctt cggcgcttac gcgagatcgc gtattgcatg   4560
ggaattgagg atgaagcagg atttgagcat ctaggcattg accctggcgc tctttccaat   4620
ttttccaatg gcaatccaaa gcgaggattt ctcggccgcc tgctcaataa tgacattata   4680
gcgctggcaa acaacatgtc agccatgacg ccgtattggg aaggcagaaa aggcgagttg   4740
attgagcgcc ttgcatggct taaacatcgc gctgaaggat tgtatttgaa agagccacat   4800
ttcggcaact cctgggcaga ccaccgcagc aggattttca gtcgcattgc gggctggctt   4860
tccggatgcg cgggcaagct caagattgcc aaggatcaga tttcaggcgt gcgtacggat   4920
ttgtttctgc tcaagcgcct tctggatgcg gtaccgcaaa gcgcgccgtc gccggacttt   4980
attgcttcca tcagcgcgct ggatcggttt ttggaagcgg cagaaagcag ccaggatccg   5040
gcagaacagg tacgcgcttt gtacgcgttt catctgaacg cgcctgcggt ccgatccatc   5100
gccaacaagg cggtacagag gtctgattcc caggagtggc ttatcaagga actggatgct   5160
gtagatcacc ttgaattcaa caaagcattt ccgttttttt cggatacagg aaagaaaaag   5220
aagaaaggag cgaatagcaa cggagcgcct tctgaagaag aatacacgga aacagaatcc   5280
attcaacaac cagaagatgc agagcaggaa gtgaatggtc aagaaggaaa tggcgcttca   5340
aagaaccaga aaaagtttca gcgcattcct cgatttttcg gggaagggtc aaggagtgag   5400
tatcgaattt taacagaagc gccgcaatat tttgacatgt tctgcaataa tatgcgcgcg   5460
atctttatgc agctagagag tcagccgcgc aaggcgcctc gtgatttcaa atgctttctg   5520
cagaatcgtt tgcagaagct ttacaagcaa acctttctca atgctcgcag taataaatgc   5580
cgcgcgcttc tggaatccgt ccttatttca tggggagaat tttatactta tggcgcgaat   5640
gaaaagaagt ttcgtctgcg ccatgaagcg agcgagcgca gctcggatcc ggactatgtg   5700
gttcagcagg cattggaaat cgcgcgccgg cttttcttgt tcggatttga gtggcgcgat   5760
tgctctgctg gagagcgcgt ggatttggtt gaaatccaca aaaaagcaat ctcatttttg   5820
cttgcaatca ctcaggccga ggtttcagtt ggttcctata actggcttgg gaatagcacc   5880
gtgagccggt atctttcggt tgctggcaca gacacattgt acggcactca actggaggag   5940
```

```
tttttgaacg ccacagtgct ttcacagatg cgtgggctgg cgattcggct ttcatctcag   6000

gagttaaaag acggatttga tgttcagttg gagagttcgt gccaggacaa tctccagcat   6060

ctgctggtgt atcgcgcttc gcgcgacttg gctgcgtgca aacgcgctac atgcccggct   6120

gaattggatc cgaaaattct tgttctgccg gctggtgcgt ttatcgcgag cgtaatgaaa   6180

atgattgagc gtggcgatga accattagca ggcgcgtatt tgcgtcatcg gccgcattca   6240

ttcggctggc agatacgggt tcgtggagtg gcggaagtag gcatggatca gggcacagcg   6300

ctagcattcc agaagccgac tgaatcagag ccgtttaaaa taaagccgtt ttccgctcaa   6360

tacggcccag tactttggct taattcttca tcctatagcc agagccagta tctggatgga   6420

tttttaagcc agccaaagaa ttggtctatg cgggtgctac ctcaagccgg atcagtgcgc   6480

gtggaacagc gcgttgctct gatatggaat ttgcaggcag gcaagatgcg gctggagcgc   6540

tctggagcgc gcgcgttttt catgccagtg ccattcagct tcaggccgtc tggttcagga   6600

gatgaagcag tattggcgcc gaatcggtac ttgggacttt ttccgcattc cggaggaata   6660

gaatacgcgg tggtggatgt attagattcc gcgggtttca aaattcttga gcgcggtacg   6720

attgcggtaa atggcttttc ccagaagcgc ggcgaacgcc aagaggaggc acacagagaa   6780

aaacagagac gcggaatttc tgatataggc cgcaagaagc cggtgcaagc tgaagttgac   6840

gcagccaatg aattgcaccg caaatacacc gatgttgcca ctcgtttagg gtgcagaatt   6900

gtggttcagt gggcgcccca gccaaagccg ggcacagcgc cgaccgcgca aacagtatac   6960

gcgcgcgcag tgcggaccga agcgccgcga tctggaaatc aagaggatca tgctcgtatg   7020

aaatcctctt ggggatatac ctggagcacc tattgggaga agcgcaaacc agaggatatt   7080

ttgggcatct caacccaagt atactggacc ggcggtatag gcgagtcatg tcccgcagtc   7140

gcggttgcgc ttttggggca cattagggca acatccactc aaactgaatg ggaaaaagag   7200

gaggttgtat tcggtcgact gaagaagttc tttccaagct agacgatctt tttaaaaact   7260

gggctgctgg ctatcgtatg gtcagtagct cttatttttt tacttgatat atggtattat   7320

ctcaataata tgcatctctt catagataca acagaaaaag aatcatttga tattgctttg   7380

attgatgatg agcgcgttat caaaaagaag cgaatcaaat caatccgcca acattcggaa   7440

aagcttttga aatcaattga cgcgcttttg ttgtccgcaa aatcatctct gaaagatata   7500

caaggcatca tcgcggtaaa aggccctggg tc                                  7532
```

<210> SEQ ID NO 27
<211> LENGTH: 16262
<212> TYPE: DNA
<213> ORGANISM: Artificial sequence
<220> FEATURE:
<223> OTHER INFORMATION: Synthetic sequence

<400> SEQUENCE: 27

```
cggaaaggcg gcccagaaac gggttgacca aattttgtgt tcagtggtga tgatggcgat     60

gycgatgtcg ctgcttacgc gggcgttgtg caggccgatg gagtcggaaa tcagaatggc    120

ctggacgtgg gggagggtgg ccagccagcg caggtaatga tgccgtttgc gcagtttggt    180

ttcggtgagg ccgtagcggg ccaggcgcag ggggacgagg tgggagcggt ttttgaggtg    240

ataaaagcca tcggtgtgag tgatgtgtgg gtgagtggcg agggcggcag tgagttcggc    300

gggcgtggtg gtgtgttgcc acagccagcg ctggagttca ccggcggtca gcggaaattc    360

catgaggtca aagtagctca tggtggcggt gatggcgtgc tcgagttggg ggcgacaagc    420
```

-continued

```
gggtttcatg ctcctattat agcagatttt cagagttgga tttttgctgt tttttcttgg    480
ccggagtacc cgttttttta ttgtttgaaa aatcagggct taaaaatttt aggtgagagt    540
ctttttgcta tatccaagaa gaaattttgc catatttttt ggtcaatttt tattttcatt    600
cttggtaggt cttttaattc ggtcactttt aatagttggc ttcccatttg tactgggtcg    660
atgtgccagt caaattttat cttggccttt tttatcagat catcgaatgt ccattctttt    720
ttttggagaa tacaatacag gtctataaaa tcccgtgaac gtggtttttg atacatggta    780
aatactttgt tgacggcaat gtctaacagg ctgtcaattt tcagaccgtt tgttttcaag    840
ccctttttgta taatcggaaa ggggtagtag gtaaattccg ttttgataac atccttgtcg    900
atatggataa aaaacagatt ccggttgaag ctctgctgaa aatctatctt tttaaatttt    960
accttttttct gtattttttt gagtatagta aaaatatccg tagaatcgaa ttctttttcc   1020
gaaaagaaat ccaaatcttc ggataaccga tgatgcagat aaaattctgc gagagcggtg   1080
ccaccggaaa gataaaattt ttcccggatg agtttttctt gtgatagctg ctgaaggaga   1140
gcgctttggt tggttgtcag gattgttggc cccataggag aaaagataaa aatttttttct   1200
tacctgggtc gaggtccagc ctatcccagt actttttcag ttgacttcgc ttgatttttt   1260
ttccacccaa gccaaaattt accatctgtt cgagtttcca gatagtgtat ttttctttat   1320
tttttttttag ctctgtgagg tcaatattcc aattgtacat ggctgtattt tagcatatag   1380
cagcttaaat ttcaatttta ttttagccaa aatagtagaa tggtggcggt gttagatgaa   1440
tatttcgtag ttgtcttttg atatcacctg gaattttgcg tcttggtagg catcgctgaa   1500
tgcctttggc gctcgggctg atttttttccc ccatttgaat tcaaatgccc tgagttttcc   1560
atttttttctt tccaagtaat caatttctgc cttttggtgc gtgcgccaga aatatctgtt   1620
taccgaattt tcagtatttt ccaatttttt cattctttct acgaggagaa aatttttccca   1680
gagcccccccg acatcttcgc gtaaggagag aggattgaga ttattaatga gtgcgttgcg   1740
aatgccgaga tcatagaagt aaattttccg cagttttttg agttcgttgc gaatgtttcg   1800
actgtatggt ttcaaagtaa aaacaatgaa agccttctca agaatgccta tataattagc   1860
cacggttttt tgatcgatat tgagcaggtt ggacagttcc cggtaggaaa cttctttacc   1920
tatctggagt gccagcgcct gcaggagttt gtcgagtact tcaggattgc ggatgttctg   1980
aaatgccaga atgtctttat ataaataact tctggtgata ttgcgcagca attcctcagc   2040
ttccgatgat ttgaggacaa tttccggata cataccgaaa atcattcttt gttccagtgt   2100
tctttttttct tcctgtatat tctgtatctg cctgagttct tccagtgaaa agggatagag   2160
gataaattca tattttcttc ctgtgagcgg ctcaacgatc tgattagcga gatcaaaaga   2220
agatgatccg gtggcgataa tctgcatttc cggaaagttg tcaacaagta gtttcagtgt   2280
cagtccgata ttttttactc tttgcgcctc gtcaaggaag ataatgtttg catctcccag   2340
ataggccttg agttcggtcg aagttttgtc ggtaagagcg gtgcgaacgt ccggttcatc   2400
acagttgagg tagcgagagg tgtggctcgc aagcttttcc tcaagggctt tgaggatagt   2460
tgtcttacct acctgtctgg cgccatagat aataataacc ttttttttga aaaggtgttt   2520
ttcaataata ggctgaaggt ctctgctaat ccgcatagta tatatgattt agatgattat   2580
actcctctca ttatatatta aaatgcggat ttagtcaatg cattctacta taaatgcttt   2640
atattagcca aaatgtcaga aaattgatat ttttgaccat ttttactata tttcggacac   2700
cttattttgg ttctcgattc atgtatcact gcccgctgta ggttgcgggc caatttttaa   2760
aggagaattt tatgatgcct gttgtgctct ttataaaatc gttttttttg attttccata   2820
```

```
gttctctctt gtagggactt gaaataaaat gtttttttata ctactatagg cctagttcct   2880
taacaatatt ttgcttactt taaagcgaaa ataggtaagg cacacctata ccataaggat   2940
ttaaagactc tttggcgaca gctttccacc gaccctgagt agttaaagac tgacgtatca   3000
tgtcataaca ccaacatttc tagatataaa gacgcgacag ctttcaggcg ataccgacgt   3060
ttctagacat aaagactttg gataaaccat aatgcaccga cgttcctcga tataaagacc   3120
cgttgtggtc ccaaaattca ccgacatttt aagaggtaaa gacaagtgca cctgagtcgc   3180
tgcaccgaca ttcccgatat aaagactgtc gctcaacccc aaaacaccga cattcccgat   3240
ataaagactc gccctagatc ttcttgcacc gactgtataa ggaataaaga cgtccgacca   3300
cgtgcaccac accgactcgt gtgaacctaa agactcaccg ccgcactacc ctcaccgact   3360
atatcaaacc taaagattgg taacttgttt gtctgacacc gactgtatca gagataaaga   3420
ctgttttcca tgcgttgcgc accgacgttc ctagatataa agactatcat tatcggggaa   3480
accgccgact gtactagata taaagacccg tcgctttgtt tgaacgccga cattcttaag   3540
aaataaagac gtggtaagag tagtgtttca ccgacattcc tttatgtaaa gacaatgaat   3600
agtctttttc acaccgactg tgaatgtatg aaatctaaag acctgaaagt gcaatgcaaa   3660
tgctgacagt gttagtctaa agacaaagta ggaatcagga tccgccgact aaataaaact   3720
taaagacaag ccagatatcc aggccacacc gacgtcccta gatgtaaaga ctagtgactc   3780
catgctatgc accgacattc cgaggcctaa agacagagag gctaacattt gtgcaccgac   3840
ccttcaagag gtaaagacat agggaacacg ctgaatcacc gacgttccta ggtatacaga   3900
cgaaatgcaa tgaaaaacgt caccgacatt tcaagacgta aagacccaag aatctttgcc   3960
cgtccccgac attccaagac gtaaagacta gccaaaacct ccagaccccc gacattccaa   4020
gacataaaga caagcgctcc aacatgtgtc accgacatta ttccgcccca gcatcgatca   4080
ttttgacttg gaaagagaca ttcttctttc caagttttta ttttgagcaa aatttgactt   4140
tttattggtt atcctttatt actatgggtg cttagtgcat cgaaaggtgg gctaagcaca   4200
acaaaagtgt tctttttatc ttaaacttga ggttttagac ctcatcaacc caaaaagggt   4260
gtaacatcat gaaacatcag aaacatcaag aaaatgcagt ctctgacgaa acatctaacc   4320
cttccgccga gccatggatt tttgattttg agaaatggtg gccctacgat acgtatccca   4380
ccatgcatca taatcaatcc gaggctttca aattaattcg aagtgtccta cggaaagaag   4440
gtgtgggtaa aaccatcctt gaacttccta ccggatctgg gaagacggtc attgggatcg   4500
tgtatctcct tactttgcat cacaagatgc aggaaggcga gattcctaca gctccgctgt   4560
tttacatcgt gcctaataag gcgctggtaa agcaggtgtg tgaaatgttc ccagatatca   4620
cctttggtgt gtatggccgg aatgaatatg attgtctgta ttaccagccg aaagaaacgt   4680
ttacagccga tcagattccc tgtttggttc taccatgcaa gcatcgggtg aaccaggatg   4740
atggaactac gcaagaatct ggtgctgagc catgtccgta ttatttggtg aagtataagg   4800
cgaagcagct gactcagaag gctcgaatca ttgtctgtac cgcttctttt tatcttttca   4860
ctcaactcat tcatgagtgg ccgctgcctg gaggactggt tattgacgaa acggatgagc   4920
tggctgaaat ttttcggcgg gcgctctcca cgaaagtcag tgattggcac ctgagtcagt   4980
gcgtcacgat gatgcggcaa agtgggatgg atggtgaagc ggatctcatg cagaaatttt   5040
atgacgccgt ggttagaatt gtcggagtca agtctcctca aaagcctacg cttttgaaga   5100
aacacgaaat cagtgagctc ctcgaggtag ttcctcagtt cgacaccaga aaactgaaaa   5160
```

```
ggcgtataaa tgccctcatc aaagacggaa agattgatgc agagaattcg cgtgaagtgc   5220
tgaatcagct gactgtggtt gccaatgatc tgaaacgata cgccgtttcg cttgcctatg   5280
ccttgcctga gggtgaccgt agggccctta attacctcta tgcatattat gaaggaccgg   5340
atgatcttcc agggaagaag aaagttcggt gtgtcattaa tatctgcaat tggtacatgc   5400
cgcctctcat taggcggatt ctctcgcctc ggaccctggc atatacagcc actatcggtg   5460
agtatagtga ctttgcctac gataccggaa ttgaaggttc gttttatacc atgaactctg   5520
attttccggt ggagaactcc cgtatcttca tgcccgatga cgttgccaac ttggctgtga   5580
aatcggtcaa accaggcgac aaagatcgga tgatgcgtct gattgctaag tcagctcgtg   5640
aatttgcgga tcaaggtcat cggagtctgg tggtggtcat ttccaatgag gagcgttcaa   5700
ggtttctgga aattgttgaa gaatacagtc tcaaaatgct cacctatgga aatggtgttt   5760
cggcgcgcga ggctattgca aggtttcagg ctggtgaagg ggaggtgttt gtgggaacgg   5820
cagccaactg ttctcatggc ctgaacttcg ataagcagac tgctccggtg attttttttc   5880
tgcggcctgg ttatccggtg cagggagatc cactcgcaga tttcgaagaa gagcggatgg   5940
gaaataagag gtggggtgtt tggacctggc gggttatgcg gcagttactt caggtgcgtg   6000
gccggaatat ccgcagtccg gaggatttgg gagttatttt cctgatgtca ggccagttta   6060
aacgtttcgc agggaaggcg attccggggt ggcttatcaa agcctatatc tccggcaaga   6120
aattcagggc ctgtgtgtca gaggccaaaa agctcctgaa aaagtcttaa ttaagccaaa   6180
aaaattgttt ttttgtctct gtccttgaca atataattga actttgctaa gttagggtcc   6240
cctgttagag gaaacagcag caaagggaag tctgagcgcg agaggcctta gtctttagag   6300
ttcttaataa gaacttttct gggcccaaag tgcgctttag tctttattcc ctgagctctg   6360
tctactttga tggggccttt ttttattcaa attttttat tttcgctacg tcttgacaaa   6420
aatatagatg tatactatat ttcgcccgag gtaataaaga aaatagcggt aaagctataa   6480
gattttatta tttcatttat aagaactttg aaaaccgaca ttatcaaaaa ccatgcaaag   6540
ccctttagat gagggcagga ggttgaaaaa atgaagagaa ttctgaacag tctgaaagtt   6600
gctgccttga gacttctgtt tcgaggcaaa ggttctgaat tagtgaagac agtcaaatat   6660
ccattggttt ccccggttca aggcgcggtt gaagaacttg ctgaagcaat tcggcacgac   6720
aacctgcacc tttttgggca gaaggaaata gtggatctta tggagaaaga cgaaggaacc   6780
caggtgtatt cggttgtgga tttttggttg gataccctgc gtttagggat gtttttctca   6840
ccatcagcga atgcgttgaa aatcacgctg ggaaaattca attctgatca ggtttcacct   6900
tttcgtaagg ttttggagca gtcacctttt tttcttgcgg gtcgcttgaa ggttgaacct   6960
gcggaaagga tactttctgt tgaaatcaga aagattggta aaagagaaaa cagagttgag   7020
aactatgccg ccgatgtgga gacatgcttc attggtcagc tttcttcaga tgagaaacag   7080
agtatccaga agctggcaaa tgatatctgg gatagcaagg atcatgagga acagagaatg   7140
ttgaaggcgg atttttttgc tatacctctt ataaaagacc ccaaagctgt cacagaagaa   7200
gatcctgaaa atgaaacggc gggaaaacag aaaccgcttg aattatgtgt ttgtcttgtt   7260
cctgagttgt atacccgagg tttcggctcc attgctgatt ttctggttca gcgacttacc   7320
ttgctgcgtg acaaaatgag taccgacacg gcggaagatt gcctcgagta tgttggcatt   7380
gaggaagaaa aaggcaatgg aatgaattcc ttgctcggca ctttttttgaa gaacctgcag   7440
ggtgatggtt ttgaacagat ttttcagttt atgcttgggt cttatgttgg ctggcagggg   7500
aaggaagatg tactgcgcga acgattggat ttgctggccg aaaaagtcaa aagattacca   7560
```

```
aagccaaaat ttgccggaga atggagtggt catcgtatgt ttctccatgg tcagctgaaa   7620
agctggtcgt cgaatttctt ccgtcttttt aatgagacgc gggaacttct ggaaagtatc   7680
aagagtgata ttcaacatgc caccatgctc attagctatg tggaagagaa aggaggctat   7740
catccacagc tgttgagtca gtatcggaag ttaatggaac aattaccggc gttgcggact   7800
aaggttttgg atcctgagat tgagatgacg catatgtccg aggctgttcg aagttacatt   7860
atgatacaca agtctgtagc gggatttctg ccggatttac tcgagtcttt ggatcgagat   7920
aaggataggg aatttttgct ttccatcttt cctcgtattc caaagataga taagaagacg   7980
aaagagatcg ttgcatggga gctaccgggc gagccagagg aaggctattt gttcacagca   8040
aacaaccttt tccggaattt tcttgagaat ccgaaacatg tgccacgatt tatggcagag   8100
aggattcccg aggattggac gcgtttgcgc tcggcccctg tgtggtttga tgggatggtg   8160
aagcaatggc agaaggtggt gaatcagttg gttgaatctc caggcgccct ttatcagttc   8220
aatgaaagtt ttttgcgtca aagactgcaa gcaatgctta cggtctataa gcgggatctc   8280
cagactgaga agtttctgaa gctgctggct gatgtctgtc gtccactcgt tgattttttc   8340
ggacttggag gaaatgatat tatcttcaag tcatgtcagg atccaagaaa gcaatggcag   8400
actgttattc cactcagtgt cccagcggat gtttatacag catgtgaagg cttggctatt   8460
cgtctccgcg aaactcttgg attcgaatgg aaaaatctga aaggacacga gcgggaagat   8520
tttttacggc tgcatcagtt gctgggaaat ctgctgttct ggatcaggga tgcgaaactt   8580
gtcgtgaagc tggaagactg gatgaacaat ccttgtgttc aggagtatgt ggaagcacga   8640
aaagccattg atcttccctt ggagatttc ggatttgagg tgccgatttt tctcaatggc   8700
tatctctttt cggaactgcg ccagctggaa ttgttgctga ggcgtaagtc ggtgatgacg   8760
tcttacagcg tcaaaacgac aggctcgcca aataggctct tccagttggt ttacctacct   8820
ctaaaccctt cagatccgga aaagaaaaat tccaacaact ttcaggagcg cctcgataca   8880
cctaccggtt tgtcgcgtcg ttttctggat cttacgctgg atgcatttgc tggcaaactc   8940
ttgacggatc cggtaactca ggaactgaag acgatggccg gtttttacga tcatctcttt   9000
ggcttcaagt tgccgtgtaa actggcggcg atgagtaacc atccaggatc ctcttccaaa   9060
atggtggttc tggcaaaacc aaagaagggt gttgctagta acatcggctt tgaacctatt   9120
cccgatcctg ctcatcctgt gttccgggtg agaagttcct ggccggagtt gaagtacctg   9180
gaggggttgt tgtatcttcc cgaagataca ccactgacca ttgaactggc ggaaacgtcg   9240
gtcagttgtc agtctgtgag ttcagtcgct ttcgatttga agaatctgac gactatcttg   9300
ggtcgtgttg gtgaattcag ggtgacggca gatcaacctt tcaagctgac gcccattatt   9360
cctgagaaag aggaatcctt catcgggaag acctacctcg gtcttgatgc tggagagcga   9420
tctggcgttg gtttcgcgat tgtgacggtt gacggcgatg ggtatgaggt gcagaggttg   9480
ggtgtgcatg aagatactca gcttatggcg cttcagcaag tcgccagcaa gtctcttaag   9540
gagccggttt tccagccact ccgtaagggc acatttcgtc agcaggagcg cattcgcaaa   9600
agcctccgcg gttgctactg gaatttctat catgcattga tgatcaagta ccgagctaaa   9660
gttgtgcatg aggaatcggt gggttcatcc ggtctggtgg ggcagtggct gcgtgcattt   9720
cagaaggatc tcaaaaaggc tgatgttctg cccaagaagg gtggaaaaaa tggtgtagac   9780
aaaaaaaaga gagaaagcag cgctcaggat accttatggg gaggagcttt ctcgaagaag   9840
gaagagcagc agatagcctt tgaggttcag gcagctggat caagccagtt ttgtctgaag   9900
```

-continued

```
tgtggttggt ggtttcagtt ggggatgcgg gaagtaaatc gtgtgcagga gagtggcgtg   9960
gtgctggact ggaaccggtc cattgtaacc ttcctcatcg aatcctcagg agaaaaggta  10020
tatggtttca gtcctcagca actggaaaaa ggctttcgtc ctgacatcga aacgttcaaa  10080
aaaatggtaa gggattttat gagacccccc atgtttgatc gcaaaggtcg gccggccgcg  10140
gcgtatgaaa gattcgtact gggacgtcgt caccgtcgtt atcgctttga taaagttttt  10200
gaagagagat ttggtcgcag tgctcttttc atctgcccgc gggtcgggtg tgggaatttc  10260
gatcactcca gtgagcagtc agccgttgtc cttgccctta ttggttacat tgctgataag  10320
gaagggatga gtggtaagaa gcttgtttat gtgaggctgg ctgaacttat ggctgagtgg  10380
aagctgaaga aactggagag atcaagggtg gaagaacaga gctcggcaca ataatttgag  10440
aagtaaaata gtttttttaga ttcagtttcg caaaggaggt gatttggttc tttgaagaga  10500
ggtgtcatta tatgtggcat ctcttttcat tttgagagat tttttctaaa aataaaactt  10560
ggaaagaaat agttctttcc aagtcaaaat gatcgatttt aaggaatgtc ggtgaagtga  10620
tttatgaaca aatgtcttta tatttcatat ggtcggtgta agtacgaatg cgagttgcct  10680
ttaggttttt accgtcggta atccacatta ttcacttggt ctttaggctt catagcgtcg  10740
gtattctttt tatatatgca agtctttaca ttgaggaacg tcgatgttca aaccagatgt  10800
gtttgtcttt atacctcgga atgtcggtga agtgatttat gaacaaagtc tttaattttt  10860
acacagtcgg tggctttccg agcaagagta gtctttatat ttagaacagt cggcgtcggc  10920
agtgcttttt ataagtcttt gtatctcatg tagtcggtgc attgtctttg caactgggtc  10980
tttatctctt aatatggtcg gtggaaactc ttgtgggaat ctttatctca agaaaagtcg  11040
gtgtcgcctg aaagctgtcg cgtctttagg tctcatgcag tcggtgtcgg tcaaaagctc  11100
gcttgtcttt atattttata cagtcggtgt aaaggtgagc tggctgagtc tttatccctc  11160
ttaaagtcgg tgcaagaagt atggcggtat gtctttactt gtcgttaggt cggtgttcat  11220
ccgtctctag ggtgtcttta tctttatgaa tgtcggtgta ggtccaaacg atgtatgtct  11280
tacatcagga attcaggaat gtcggggtta ctaatatgca atggagtctt tatgtctggg  11340
aacgtcgtta ttttactctt gcgagattgt ctttactcag gaagtcggag ctcgattgat  11400
tgacattgcg tcttttagat accatactgt cggtgtggac ggctcgcctg atggtcttta  11460
ccttttatac ggtcggtggg ttgctgggcg cttcagtctt tacgtttcat gcggtcggtg  11520
tcattctcat gccctacgtc tttatctcta agaatgtcgg tggagcgact taggtgcact  11580
ggtctttatg tttagaaatg tcggtgtgat tacaggtatc aaatgtcttt agctctggga  11640
aggtcggtat cgatccaaag atccggggtt ttaaattgtt gtcaatgaac taggcacata  11700
gtaatataaa aaacatttta ttacaagccc ccctcctttt tgtttggcgc ccaacaaaaa  11760
aaatcgccca aaagagcagc ttttcgggcg cggcgcctcc atatatagcg caccaaacta  11820
tttcaacgcc ctggccaaat acctccccgt gtgactcttt tttaccttgg ccacatcacg  11880
cggcgtacct tcggccacca gcaaaccacc gtgattgcca ccttccggac ccagatcaat  11940
cacccagtcc gaagatttaa taacttccaa attgtgttca ataatcaata gactgttgcc  12000
cttatccacc agcttgctca gcacgtgcag caaccgtttc acatcatcaa aatgcaaacc  12060
cgtcgtcggc tcatccaaaa tatacaacgt ctttcccgtc gagcgccgtg acaattccgt  12120
cgccagcttc acacgctgcg cttcaccacc actcagcgtc gtcgcattct gtcccagctg  12180
aatatagccc aaacccactt caaacagcgt cttcaacttt tcatgaataa tcggaatatt  12240
gctgaaaaat ttcgtcgcat cttcgaccgt catgttcagt acctcggaaa tatttttccc  12300
```

cttgtaatga atttccaaag cctgctcgtt gtagcggcgg cctttgcatt cgtcgcaatc 12360
cacatacacg tccggcagga agtgcatctc aattttggtc acaccatcgc cctgacaggc 12420
ttcgcagcgg ccacccttca cattgaaact gaaacgcccg gccttgtagc cgcgcatctt 12480
cgcttccggc acctgcgtga acagatcgcg aatgtaggta aacacgccgg tgtaggtggc 12540
ggcgttggag cggggagtac ggccgatcgg cgactgatca atatcaatca ccttatcgag 12600
atattccagt ccgcgcagct ctttgtgttt gccgggaata tccttggcat tatgaaaatg 12660
ttgtgacaac gcgcgggcga gaatatcggt catcaacgtc gatttgccgc tgccggaaac 12720
gccggtgatg cacactaatt ttcccagcgg aatgcgcacg ttgatatttt gtaggttgtg 12780
ggcggtggca ccgcggattt caatatattt gccgttgccg cggcggtact tgtgcggcgc 12840
ttcaatgaat tttttgccgc tcagatattg accggtcaat gacgctttat ttttaataat 12900
ttcctgaggt gtgccaaggg caacaatttc gccaccgtgt ttgccggcac caggccccac 12960
gtcaataaca taatcagcgg agcgaatcgt ttcttcatcg tgctcgacga cgatcacggt 13020
attgcctaat tcgcgcagcg ctttgagtgt gtctatgagt ttggagttgt cgcgttggtg 13080
caagccaatg ctgggttcat cgaggatata gataacgccg accaaagatg aaccgatttg 13140
cgtggccaga cgaatgcgtt gcgcttcacc gccgcttaaa gtcgaagcag cgcgatctaa 13200
agtcaaataa tccagaccta cattatgtaa aaaagtcagg cgttcgcgga tttctttcat 13260
gatctgatgc gaaattttgg cttcgcgtac ggacatgacg tagacattat tttttgccat 13320
gctgttgccg ccggagttgg caccaccttt gccggccgcg tttttggcgc cagcaccctt 13380
cgcgccagca cccgcaccac caaccacaaa cccctcaaaa aatgcctgcg cttcttcaat 13440
gctcaacccc gtcgtgtcag aaatggattt gccgcgaatc gttacggcca gtgcaatttt 13500
gttcaaccgt ttcccgtgac acgtcggaca atcaaagacg cgcatgtagc gttcgatttc 13560
cgagcggata tattccgact cggtttcttt gtagcgccgt tccaaattcg gtatcacgcc 13620
ttcatacgtc gtcacaaatt cacggatttt ggatgtcgag ttcatgccgc tgttgacgtc 13680
gaaagattct tcgccggtgc cgtaaaacac cagcttcagt tgcgcggcgg tcattttttt 13740
caccggttcg tccaaagaaa aaccgtattt ggccgccact gtcgccagaa tccgcagcat 13800
ccagccctga ttcgaagacg tgcgtgacca gggtctgatg gcaccctgat tgatgctcaa 13860
atttttattg ggaatgatca gttcagcgtc gacttcgagc ttggtgccca atccagtgca 13920
ttccacgcag gcgccgtgcg ggctgttaaa cgaaaacagg cgcggttcaa tttccggcag 13980
gttgatgccg cagcgcggac aggcgaagtg ctgactgaac agctgatctt tttcgctggt 14040
actgtcgtgc acaatcacca taccatcacc caaatccaag gcggtttcca gagattcgtg 14100
caagcggctg cggtttttgc gcagctcttt gtcaacaacc aagcgatcta caacaacatc 14160
aatggtatgt ttctttttct tatcgaggac gagatcgagt gcttcttcga tgctcatcat 14220
attcccgttg acgcgcacgc gcacaaaacc ggctttgcgc gtttcttcaa agacgtgttt 14280
gtgttcacct tttttgtcgc ggataatttg cgcgatgagc ataaatttcg tatccgcttt 14340
caggcgcaga atttgttcga ggatttgttc ggtggtttgt ttgctgactt tatcaccgca 14400
gttggggcag tgtggttggc cgatgcgggc gtagagcaaa cgcaggtaat cgtaaatttc 14460
ggtgacggtg ccgacggtgg atcggggatt gtgggatgtg gttttttgat cgatggagat 14520
ggcgggcgag aggccttcaa tgctgtcgac gtcaggcttg tccatcaggc cgaggaattg 14580
gcgggcgtag gaagacaggc tttcgacgta gcggcgctga ccttcggcat agatcgtatc 14640
aaaagccagg gaagattttc ccgagccgga caggccggtg atgacgacga gctggtcacg 14700
ggggatgtcc aggctgatat ttttcaggtt gtggacgcgg gcgcctttga tgatgatcga 14760
attttcacct gccataattg atcgttatga gacaacaaaa atttttagag caaagcccgt 14820
aacctgcttt cgaggcagaa ttttcaaaat actgccgagg cgaaggaaaa aattttgagg 14880
aatactgtta gtatttcgag aaattttttta caagccgcag gcggattttg aaaattatga 14940
tccggaatga ggttgcgggt tttactctag acgaacttcc gccagtctac tactttttttt 15000 tgcgtaagtc aaccgtttgt gggcggggct gattcggttt tgtggtggtt tcgggagcag 15060
catagatgta gcggaaaatt caaaaaactg gtataatatt gctacaacct atacaaacaa 15120
aagcgtaaaa atcatgcatt tttcacgttt cggattttat ttccgtaacc gacgcatggt 15180
agaacgtttc ttcgttctat tttgtgctat tttttctgct gtcctggttt tgtcgcttgt 15240
tgccctggtg ctggtggctg acaaaattaa tatcaatccc attgtgcaca tcttgtttcg 15300 ttttttttcag cgaccctttg tcagtgcgct gattctgtct tttttcgtca caacccttct 15360
ttacgccgtt tttgttctgg tgcatccagt gcagcatcat accgtgtatt ggcagcgtca 15420
ttcgcagcga tatcatattc gcaagaaatc ccatattcac cgcagattgc gtcacattcc 15480
cgcgcagaca tcacataagc tgttggcgct cagttcactt tttgttgtgg ttaaaattgt 15540
ttttgtcagt tttgcctccg gttttttacc gcatgatgtt ttggcacaga ccgttgatcc 15600
gagcggacag aaaagtcagt cggtgttggt ggcggcgttt tatgtccagg tgcttgattc 15660
cgatgatttg tatatttgga tttttatgtt gggccttttg ccgctggcgg ttctgatttt 15720
tttcatcgtt tttcgttcgc atatttttcc gcataagaat tttcattatg agagcgcaca 15780
tctggatacg aatattgtca cttttgcggc ccggaagaag gcggagcagc ggcgcaaaaa 15840
gccatcacct ccggccggta ttgtaccttt gcatgatgca taacctatga attctgtttt 15900
gcagaaaaaa ttagctggtc tgccgcatca acccggcgtc tatgtgtata aagacgcacg 15960
gggtgatgtt ttgtacgtgg ggaaggccaa agatttggcg aagcgcgtgc gatcgtattg 16020
gcagtcgggt cgctcgctgg tgccggacaa agctttgatg gtgagtcagg cggctgatat 16080
cgatatcacg gtggtgagtt cggaaacgga agctttttttg ctcgaagcga gtttcattaa 16140
aaaataccgg ccgcggttta atattatttt gaaagatgat aaaagttttt cgtatattaa 16200
ggtgacgttg cgggaagaat ttccgagggt gctggtggtg cggcgcgtga cgcgcgatgg 16260
ca 16262

<210> SEQ ID NO 28
<211> LENGTH: 10
<212> TYPE: DNA
<213> ORGANISM: Artificial sequence
<220> FEATURE:
<223> OTHER INFORMATION: Synthetic sequence

<400> SEQUENCE: 28
aaaaaaaaaa 10

<210> SEQ ID NO 29
<211> LENGTH: 10
<212> TYPE: DNA
<213> ORGANISM: Artificial sequence
<220> FEATURE:
<223> OTHER INFORMATION: Synthetic sequence

<400> SEQUENCE: 29
aaaaaaaaaa 10

<210> SEQ ID NO 30
<211> LENGTH: 10
<212> TYPE: DNA
<213> ORGANISM: Artificial sequence
<220> FEATURE:
<223> OTHER INFORMATION: Synthetic sequence

<400> SEQUENCE: 30
aaaaaaaaaa 10

<210> SEQ ID NO 31
<211> LENGTH: 25
<212> TYPE: DNA
<213> ORGANISM: Artificial sequence
<220> FEATURE:
<223> OTHER INFORMATION: Synthetic sequence

<400> SEQUENCE: 31
ctccgaaagt atcggggata aaggc 25

<210> SEQ ID NO 32
<211> LENGTH: 25
<212> TYPE: DNA
<213> ORGANISM: Artificial sequence
<220> FEATURE:
<223> OTHER INFORMATION: Synthetic sequence

<400> SEQUENCE: 32
caccgaaatt tggagaggat aaggc 25

<210> SEQ ID NO 33
<211> LENGTH: 25
<212> TYPE: DNA
<213> ORGANISM: Artificial sequence
<220> FEATURE:
<223> OTHER INFORMATION: Synthetic sequence

<400> SEQUENCE: 33
ctccgaatta tcgggaggat aaggc 25

<210> SEQ ID NO 34
<211> LENGTH: 25
<212> TYPE: DNA
<213> ORGANISM: Artificial sequence
<220> FEATURE:
<223> OTHER INFORMATION: Synthetic sequence

<400> SEQUENCE: 34
ccccgaatat aggggacaaa aaggc 25

<210> SEQ ID NO 35
<211> LENGTH: 36
<212> TYPE: DNA
<213> ORGANISM: Artificial sequence
<220> FEATURE:
<223> OTHER INFORMATION: Synthetic sequence

<400> SEQUENCE: 35
gtctagacat acaggtggaa aggtgagagt aaagac 36

<210> SEQ ID NO 36
<211> LENGTH: 25
<212> TYPE: DNA
<213> ORGANISM: Artificial sequence
<220> FEATURE:

<223> OTHER INFORMATION: Synthetic sequence

<400> SEQUENCE: 36
ctccgtgaat acgtggggta aaggc 25

<210> SEQ ID NO 37
<211> LENGTH: 10
<212> TYPE: RNA
<213> ORGANISM: Artificial sequence
<220> FEATURE:
<223> OTHER INFORMATION: Synthetic sequence

<400> SEQUENCE: 37
aaaaaaaaaa 10

<210> SEQ ID NO 38
<211> LENGTH: 10
<212> TYPE: RNA
<213> ORGANISM: Artificial sequence
<220> FEATURE:
<223> OTHER INFORMATION: Synthetic sequence

<400> SEQUENCE: 38
aaaaaaaaaa 10

<210> SEQ ID NO 39
<211> LENGTH: 10
<212> TYPE: RNA
<213> ORGANISM: Artificial sequence
<220> FEATURE:
<223> OTHER INFORMATION: Synthetic sequence

<400> SEQUENCE: 39
aaaaaaaaaa 10

<210> SEQ ID NO 40
<211> LENGTH: 10
<212> TYPE: RNA
<213> ORGANISM: Artificial sequence
<220> FEATURE:
<223> OTHER INFORMATION: Synthetic sequence

<400> SEQUENCE: 40
aaaaaaaaaa 10

<210> SEQ ID NO 41
<211> LENGTH: 10
<212> TYPE: RNA
<213> ORGANISM: Artificial sequence
<220> FEATURE:
<223> OTHER INFORMATION: Synthetic sequence

<400> SEQUENCE: 41
aaaaaaaaaa 10

<210> SEQ ID NO 42
<211> LENGTH: 10
<212> TYPE: RNA
<213> ORGANISM: Artificial sequence
<220> FEATURE:
<223> OTHER INFORMATION: Synthetic sequence

<400> SEQUENCE: 42
aaaaaaaaaa 10

<210> SEQ ID NO 43
<211> LENGTH: 10
<212> TYPE: RNA
<213> ORGANISM: Artificial sequence
<220> FEATURE:
<223> OTHER INFORMATION: Synthetic sequence

<400> SEQUENCE: 43
aaaaaaaaaa 10

<210> SEQ ID NO 44
<211> LENGTH: 10
<212> TYPE: RNA
<213> ORGANISM: Artificial sequence
<220> FEATURE:
<223> OTHER INFORMATION: Synthetic sequence

<400> SEQUENCE: 44
aaaaaaaaaa 10

<210> SEQ ID NO 45
<211> LENGTH: 10
<212> TYPE: RNA
<213> ORGANISM: Artificial sequence
<220> FEATURE:
<223> OTHER INFORMATION: Synthetic sequence

<400> SEQUENCE: 45
aaaaaaaaaa 10

<210> SEQ ID NO 46
<211> LENGTH: 10
<212> TYPE: RNA
<213> ORGANISM: Artificial sequence
<220> FEATURE:
<223> OTHER INFORMATION: Synthetic sequence

<400> SEQUENCE: 46
aaaaaaaaaa 10

<210> SEQ ID NO 47
<211> LENGTH: 10
<212> TYPE: RNA
<213> ORGANISM: Artificial sequence
<220> FEATURE:
<223> OTHER INFORMATION: Synthetic sequence

<400> SEQUENCE: 47
aaaaaaaaaa 10

<210> SEQ ID NO 48
<211> LENGTH: 10
<212> TYPE: RNA
<213> ORGANISM: Artificial sequence
<220> FEATURE:
<223> OTHER INFORMATION: Synthetic sequence

<400> SEQUENCE: 48
aaaaaaaaaa 10

<210> SEQ ID NO 49
<211> LENGTH: 10
<212> TYPE: RNA
<213> ORGANISM: Artificial sequence
<220> FEATURE:
<223> OTHER INFORMATION: Synthetic sequence

<400> SEQUENCE: 49
aaaaaaaaaa 10

<210> SEQ ID NO 50
<211> LENGTH: 10
<212> TYPE: RNA
<213> ORGANISM: Artificial sequence
<220> FEATURE:
<223> OTHER INFORMATION: Synthetic sequence

<400> SEQUENCE: 50
aaaaaaaaaa 10

<210> SEQ ID NO 51
<211> LENGTH: 10
<212> TYPE: RNA
<213> ORGANISM: Artificial sequence
<220> FEATURE:
<223> OTHER INFORMATION: Synthetic sequence

<400> SEQUENCE: 51
aaaaaaaaaa 10

<210> SEQ ID NO 52
<211> LENGTH: 10
<212> TYPE: RNA
<213> ORGANISM: Artificial sequence
<220> FEATURE:
<223> OTHER INFORMATION: Synthetic sequence

<400> SEQUENCE: 52
aaaaaaaaaa 10

<210> SEQ ID NO 53
<211> LENGTH: 10
<212> TYPE: RNA
<213> ORGANISM: Artificial sequence
<220> FEATURE:
<223> OTHER INFORMATION: Synthetic sequence

<400> SEQUENCE: 53
aaaaaaaaaa 10

<210> SEQ ID NO 54
<211> LENGTH: 10
<212> TYPE: RNA
<213> ORGANISM: Artificial sequence
<220> FEATURE:
<223> OTHER INFORMATION: Synthetic sequence

<400> SEQUENCE: 54
aaaaaaaaaa 10

<210> SEQ ID NO 55
<211> LENGTH: 10
<212> TYPE: RNA
<213> ORGANISM: Artificial sequence
<220> FEATURE:
<223> OTHER INFORMATION: Synthetic sequence

<400> SEQUENCE: 55
aaaaaaaaaa 10

<210> SEQ ID NO 56
<211> LENGTH: 10

<212> TYPE: RNA
<213> ORGANISM: Artificial sequence
<220> FEATURE:
<223> OTHER INFORMATION: Synthetic sequence

<400> SEQUENCE: 56
aaaaaaaaaa 10

<210> SEQ ID NO 57
<211> LENGTH: 10
<212> TYPE: RNA
<213> ORGANISM: Artificial sequence
<220> FEATURE:
<223> OTHER INFORMATION: Synthetic sequence

<400> SEQUENCE: 57
aaaaaaaaaa 10

<210> SEQ ID NO 58
<211> LENGTH: 10
<212> TYPE: RNA
<213> ORGANISM: Artificial sequence
<220> FEATURE:
<223> OTHER INFORMATION: Synthetic sequence

<400> SEQUENCE: 58
aaaaaaaaaa 10

<210> SEQ ID NO 59
<211> LENGTH: 10
<212> TYPE: RNA
<213> ORGANISM: Artificial sequence
<220> FEATURE:
<223> OTHER INFORMATION: Synthetic sequence

<400> SEQUENCE: 59
aaaaaaaaaa 10

<210> SEQ ID NO 60
<211> LENGTH: 10
<212> TYPE: RNA
<213> ORGANISM: Artificial sequence
<220> FEATURE:
<223> OTHER INFORMATION: Synthetic sequence

<400> SEQUENCE: 60
aaaaaaaaaa 10

<210> SEQ ID NO 61
<211> LENGTH: 10
<212> TYPE: RNA
<213> ORGANISM: Artificial sequence
<220> FEATURE:
<223> OTHER INFORMATION: Synthetic sequence

<400> SEQUENCE: 61
aaaaaaaaaa 10

<210> SEQ ID NO 62
<211> LENGTH: 10
<212> TYPE: RNA
<213> ORGANISM: Artificial sequence
<220> FEATURE:
<223> OTHER INFORMATION: Synthetic sequence

<400> SEQUENCE: 62
aaaaaaaaaa 10

<210> SEQ ID NO 63
<211> LENGTH: 10
<212> TYPE: RNA
<213> ORGANISM: Artificial sequence
<220> FEATURE:
<223> OTHER INFORMATION: Synthetic sequence

<400> SEQUENCE: 63
aaaaaaaaaa 10

<210> SEQ ID NO 64
<211> LENGTH: 10
<212> TYPE: RNA
<213> ORGANISM: Artificial sequence
<220> FEATURE:
<223> OTHER INFORMATION: Synthetic sequence

<400> SEQUENCE: 64
aaaaaaaaaa 10

<210> SEQ ID NO 65
<211> LENGTH: 10
<212> TYPE: RNA
<213> ORGANISM: Artificial sequence
<220> FEATURE:
<223> OTHER INFORMATION: Synthetic sequence

<400> SEQUENCE: 65
aaaaaaaaaa 10

<210> SEQ ID NO 66
<211> LENGTH: 10
<212> TYPE: RNA
<213> ORGANISM: Artificial sequence
<220> FEATURE:
<223> OTHER INFORMATION: Synthetic sequence

<400> SEQUENCE: 66
aaaaaaaaaa 10

<210> SEQ ID NO 67
<211> LENGTH: 10
<212> TYPE: RNA
<213> ORGANISM: Artificial sequence
<220> FEATURE:
<223> OTHER INFORMATION: Synthetic sequence

<400> SEQUENCE: 67
aaaaaaaaaa 10

<210> SEQ ID NO 68
<211> LENGTH: 10
<212> TYPE: RNA
<213> ORGANISM: Artificial sequence
<220> FEATURE:
<223> OTHER INFORMATION: Synthetic sequence

<400> SEQUENCE: 68
aaaaaaaaaa 10

<210> SEQ ID NO 69
<211> LENGTH: 10
<212> TYPE: RNA
<213> ORGANISM: Artificial sequence
<220> FEATURE:
<223> OTHER INFORMATION: Synthetic sequence

<400> SEQUENCE: 69
aaaaaaaaaa 10

<210> SEQ ID NO 70
<211> LENGTH: 10
<212> TYPE: RNA
<213> ORGANISM: Artificial sequence
<220> FEATURE:
<223> OTHER INFORMATION: Synthetic sequence

<400> SEQUENCE: 70
aaaaaaaaaa 10

<210> SEQ ID NO 71
<211> LENGTH: 10
<212> TYPE: RNA
<213> ORGANISM: Unknown
<220> FEATURE:
<223> OTHER INFORMATION: Synthetic sequence

<400> SEQUENCE: 71
aaaaaaaaaa 10

<210> SEQ ID NO 72
<211> LENGTH: 10
<212> TYPE: RNA
<213> ORGANISM: Unknown
<220> FEATURE:
<223> OTHER INFORMATION: Synthetic sequence

<400> SEQUENCE: 72
aaaaaaaaaa 10

<210> SEQ ID NO 73
<211> LENGTH: 10
<212> TYPE: RNA
<213> ORGANISM: Artificial sequence
<220> FEATURE:
<223> OTHER INFORMATION: Synthetic sequence

<400> SEQUENCE: 73
aaaaaaaaaa 10

<210> SEQ ID NO 74
<211> LENGTH: 10
<212> TYPE: RNA
<213> ORGANISM: Artificial sequence
<220> FEATURE:
<223> OTHER INFORMATION: Synthetic sequence

<400> SEQUENCE: 74
aaaaaaaaaa 10

<210> SEQ ID NO 75
<211> LENGTH: 10
<212> TYPE: RNA
<213> ORGANISM: Artificial sequence
<220> FEATURE:
<223> OTHER INFORMATION: Synthetic sequence

<400> SEQUENCE: 75
aaaaaaaaaa 10

<210> SEQ ID NO 76
<211> LENGTH: 10
<212> TYPE: RNA
<213> ORGANISM: Artificial sequence
<220> FEATURE:
<223> OTHER INFORMATION: Synthetic sequence

<400> SEQUENCE: 76
aaaaaaaaaa 10

<210> SEQ ID NO 77
<211> LENGTH: 10
<212> TYPE: RNA
<213> ORGANISM: Artificial sequence
<220> FEATURE:
<223> OTHER INFORMATION: Synthetic sequence

<400> SEQUENCE: 77
aaaaaaaaaa 10

<210> SEQ ID NO 78
<211> LENGTH: 10
<212> TYPE: RNA
<213> ORGANISM: Artificial sequence
<220> FEATURE:
<223> OTHER INFORMATION: Synthetic sequence

<400> SEQUENCE: 78
aaaaaaaaaa 10

<210> SEQ ID NO 79
<211> LENGTH: 10
<212> TYPE: RNA
<213> ORGANISM: Artificial sequence
<220> FEATURE:
<223> OTHER INFORMATION: Synthetic sequence

<400> SEQUENCE: 79
aaaaaaaaaa 10

<210> SEQ ID NO 80
<211> LENGTH: 10
<212> TYPE: RNA
<213> ORGANISM: Artificial sequence
<220> FEATURE:
<223> OTHER INFORMATION: Synthetic sequence

<400> SEQUENCE: 80
aaaaaaaaaa 10

<210> SEQ ID NO 81
<211> LENGTH: 10
<212> TYPE: RNA
<213> ORGANISM: Artificial sequence
<220> FEATURE:
<223> OTHER INFORMATION: Synthetic sequence

<400> SEQUENCE: 81
aaaaaaaaaa 10

<210> SEQ ID NO 82
<211> LENGTH: 10
<212> TYPE: RNA
<213> ORGANISM: Artificial sequence
<220> FEATURE:
<223> OTHER INFORMATION: Synthetic sequence

<400> SEQUENCE: 82
aaaaaaaaaa 10

<210> SEQ ID NO 83
<211> LENGTH: 84
<212> TYPE: PRT
<213> ORGANISM: Artificial Sequence
<220> FEATURE:
<223> OTHER INFORMATION: Synthetic sequence

<400> SEQUENCE: 83

Met Ala Ser Met Ile Ser Ser Ser Ala Val Thr Thr Val Ser Arg Ala
1 5 10 15

Ser Arg Gly Gln Ser Ala Ala Met Ala Pro Phe Gly Gly Leu Lys Ser
20 25 30

Met Thr Gly Phe Pro Val Arg Lys Val Asn Thr Asp Ile Thr Ser Ile
35 40 45

Thr Ser Asn Gly Gly Arg Val Lys Cys Met Gln Val Trp Pro Pro Ile
50 55 60

Gly Lys Lys Lys Phe Glu Thr Leu Ser Tyr Leu Pro Pro Leu Thr Arg
65 70 75 80

Asp Ser Arg Ala

<210> SEQ ID NO 84
<211> LENGTH: 57
<212> TYPE: PRT
<213> ORGANISM: Artificial Sequence
<220> FEATURE:
<223> OTHER INFORMATION: Synthetic sequence

<400> SEQUENCE: 84

Met Ala Ser Met Ile Ser Ser Ser Ala Val Thr Thr Val Ser Arg Ala
1 5 10 15

Ser Arg Gly Gln Ser Ala Ala Met Ala Pro Phe Gly Gly Leu Lys Ser
20 25 30

Met Thr Gly Phe Pro Val Arg Lys Val Asn Thr Asp Ile Thr Ser Ile
35 40 45

Thr Ser Asn Gly Gly Arg Val Lys Ser
50 55

<210> SEQ ID NO 85
<211> LENGTH: 85
<212> TYPE: PRT
<213> ORGANISM: Artificial Sequence
<220> FEATURE:
<223> OTHER INFORMATION: Synthetic sequence

<400> SEQUENCE: 85

Met Ala Ser Ser Met Leu Ser Ser Ala Thr Met Val Ala Ser Pro Ala
1 5 10 15

Gln Ala Thr Met Val Ala Pro Phe Asn Gly Leu Lys Ser Ser Ala Ala
20 25 30

Phe Pro Ala Thr Arg Lys Ala Asn Asn Asp Ile Thr Ser Ile Thr Ser
35 40 45

Asn Gly Gly Arg Val Asn Cys Met Gln Val Trp Pro Pro Ile Glu Lys
50 55 60

Lys Lys Phe Glu Thr Leu Ser Tyr Leu Pro Asp Leu Thr Asp Ser Gly
65 70 75 80

```
Gly Arg Val Asn Cys
                85


<210> SEQ ID NO 86
<211> LENGTH: 76
<212> TYPE: PRT
<213> ORGANISM: Artificial Sequence
<220> FEATURE:
<223> OTHER INFORMATION: Synthetic sequence

<400> SEQUENCE: 86

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 87
<211> LENGTH: 76
<212> TYPE: PRT
<213> ORGANISM: Artificial Sequence
<220> FEATURE:
<223> OTHER INFORMATION: Synthetic sequence

<400> SEQUENCE: 87

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75


<210> SEQ ID NO 88
<211> LENGTH: 72
<212> TYPE: PRT
<213> ORGANISM: Artificial Sequence
<220> FEATURE:
<223> OTHER INFORMATION: Synthetic sequence

<400> SEQUENCE: 88

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70
```

<210> SEQ ID NO 89
<211> LENGTH: 69
<212> TYPE: PRT
<213> ORGANISM: Artificial Sequence
<220> FEATURE:
<223> OTHER INFORMATION: Synthetic sequence

<400> SEQUENCE: 89

Met Ala Ala Leu Val Thr Ser Gln Leu Ala Thr Ser Gly Thr Val Leu
1 5 10 15

Ser Val Thr Asp Arg Phe Arg Arg Pro Gly Phe Gln Gly Leu Arg Pro
20 25 30

Arg Asn Pro Ala Asp Ala Ala Leu Gly Met Arg Thr Val Gly Ala Ser
35 40 45

Ala Ala Pro Lys Gln Ser Arg Lys Pro His Arg Phe Asp Arg Arg Cys
50 55 60

Leu Ser Met Val Val
65

<210> SEQ ID NO 90
<211> LENGTH: 77
<212> TYPE: PRT
<213> ORGANISM: Artificial Sequence
<220> FEATURE:
<223> OTHER INFORMATION: Synthetic sequence

<400> SEQUENCE: 90

Met Ala Ala Leu Thr Thr Ser Gln Leu Ala Thr Ser Ala Thr Gly Phe
1 5 10 15

Gly Ile Ala Asp Arg Ser Ala Pro Ser Ser Leu Leu Arg His Gly Phe
20 25 30

Gln Gly Leu Lys Pro Arg Ser Pro Ala Gly Gly Asp Ala Thr Ser Leu
35 40 45

Ser Val Thr Thr Ser Ala Arg Ala Thr Pro Lys Gln Gln Arg Ser Val
50 55 60

Gln Arg Gly Ser Arg Arg Phe Pro Ser Val Val Val Cys
65 70 75

<210> SEQ ID NO 91
<211> LENGTH: 57
<212> TYPE: PRT
<213> ORGANISM: Artificial Sequence
<220> FEATURE:
<223> OTHER INFORMATION: Synthetic sequence

<400> SEQUENCE: 91

Met Ala Ser Ser Val Leu Ser Ser Ala Ala Val Ala Thr Arg Ser Asn
1 5 10 15

Val Ala Gln Ala Asn Met Val Ala Pro Phe Thr Gly Leu Lys Ser Ala
20 25 30

Ala Ser Phe Pro Val Ser Arg Lys Gln Asn Leu Asp Ile Thr Ser Ile
35 40 45

Ala Ser Asn Gly Gly Arg Val Gln Cys
50 55

<210> SEQ ID NO 92
<211> LENGTH: 65
<212> TYPE: PRT
<213> ORGANISM: Artificial Sequence
<220> FEATURE:
<223> OTHER INFORMATION: Synthetic sequence -continued

<400> SEQUENCE: 92

```
Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65
```

<210> SEQ ID NO 93
<211> LENGTH: 72
<212> TYPE: PRT
<213> ORGANISM: Artificial Sequence
<220> FEATURE:
<223> OTHER INFORMATION: Synthetic sequence

<400> SEQUENCE: 93

```
Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30

Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70
```

<210> SEQ ID NO 94
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 94

```
Gly Leu Phe Xaa Ala Leu Leu Xaa Leu Leu Xaa Ser Leu Trp Xaa Leu
1               5                   10                  15

Leu Leu Xaa Ala
            20
```

<210> SEQ ID NO 95
<211> LENGTH: 20
<212> TYPE: PRT
<213> ORGANISM: Artificial Sequence
<220> FEATURE:
<223> OTHER INFORMATION: Synthetic sequence

<400> SEQUENCE: 95

Gly Leu Phe His Ala Leu Leu His Leu Leu His Ser Leu Trp His Leu
1 5 10 15

Leu Leu His Ala
20

<210> SEQ ID NO 96
<211> LENGTH: 7
<212> TYPE: PRT
<213> ORGANISM: Artificial Sequence
<220> FEATURE:
<223> OTHER INFORMATION: Synthetic sequence

<400> SEQUENCE: 96

Pro Lys Lys Lys Arg Lys Val
1 5

<210> SEQ ID NO 97
<211> LENGTH: 16
<212> TYPE: PRT
<213> ORGANISM: Artificial Sequence
<220> FEATURE:
<223> OTHER INFORMATION: Synthetic sequence

<400> SEQUENCE: 97

Lys Arg Pro Ala Ala Thr Lys Lys Ala Gly Gln Ala Lys Lys Lys Lys
1 5 10 15

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence

<400> SEQUENCE: 98

Pro Ala Ala Lys Arg Val Lys Leu Asp
1 5

<210> SEQ ID NO 99
<211> LENGTH: 11
<212> TYPE: PRT
<213> ORGANISM: Artificial Sequence
<220> FEATURE:
<223> OTHER INFORMATION: Synthetic sequence

<400> SEQUENCE: 99

Arg Gln Arg Arg Asn Glu Leu Lys Arg Ser Pro
1 5 10

<210> SEQ ID NO 100
<211> LENGTH: 38
<212> TYPE: PRT
<213> ORGANISM: Artificial Sequence
<220> FEATURE:
<223> OTHER INFORMATION: Synthetic sequence

<400> SEQUENCE: 100

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 101
<211> LENGTH: 42
<212> TYPE: PRT
<213> ORGANISM: Artificial Sequence
<220> FEATURE:
<223> OTHER INFORMATION: Synthetic sequence

<400> SEQUENCE: 101

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 102
<211> LENGTH: 8
<212> TYPE: PRT
<213> ORGANISM: Artificial Sequence
<220> FEATURE:
<223> OTHER INFORMATION: Synthetic sequence

<400> SEQUENCE: 102

Val Ser Arg Lys Arg Pro Arg Pro
1 5

<210> SEQ ID NO 103
<211> LENGTH: 8
<212> TYPE: PRT
<213> ORGANISM: Artificial Sequence
<220> FEATURE:
<223> OTHER INFORMATION: Synthetic sequence

<400> SEQUENCE: 103

Pro Pro Lys Lys Ala Arg Glu Asp
1 5

<210> SEQ ID NO 104
<211> LENGTH: 8
<212> TYPE: PRT
<213> ORGANISM: Artificial Sequence
<220> FEATURE:
<223> OTHER INFORMATION: Synthetic sequence

<400> SEQUENCE: 104

Pro Gln Pro Lys Lys Lys Pro Leu
1 5

<210> SEQ ID NO 105
<211> LENGTH: 12
<212> TYPE: PRT
<213> ORGANISM: Artificial Sequence
<220> FEATURE:
<223> OTHER INFORMATION: Synthetic sequence

<400> SEQUENCE: 105

Ser Ala Leu Ile Lys Lys Lys Lys Lys Met Ala Pro
1 5 10

<210> SEQ ID NO 106
<211> LENGTH: 5
<212> TYPE: PRT
<213> ORGANISM: Artificial Sequence
<220> FEATURE:
<223> OTHER INFORMATION: Synthetic sequence

<400> SEQUENCE: 106

Asp Arg Leu Arg Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic sequence

<400> SEQUENCE: 107

Pro Lys Gln Lys Lys Arg Lys
1               5

<210> SEQ ID NO 108
<211> LENGTH: 10
<212> TYPE: PRT
<213> ORGANISM: Artificial Sequence
<220> FEATURE:
<223> OTHER INFORMATION: Synthetic sequence

<400> SEQUENCE: 108

Arg Lys Leu Lys Lys Lys Ile Lys Lys Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic sequence

<400> SEQUENCE: 109

Arg Glu Lys Lys Lys Phe Leu Lys Arg Arg
1               5                   10

<210> SEQ ID NO 110
<211> LENGTH: 20
<212> TYPE: PRT
<213> ORGANISM: Artificial Sequence
<220> FEATURE:
<223> OTHER INFORMATION: Synthetic sequence

<400> SEQUENCE: 110

Lys Arg Lys Gly Asp Glu Val Asp Gly Val Asp Glu Val Ala Lys Lys
1               5                   10                  15

Lys Ser Lys Lys
            20

<210> SEQ ID NO 111
<211> LENGTH: 17
<212> TYPE: PRT
<213> ORGANISM: Artificial Sequence
<220> FEATURE:
<223> OTHER INFORMATION: Synthetic sequence

<400> SEQUENCE: 111

Arg Lys Cys Leu Gln Ala Gly Met Asn Leu Glu Ala Arg Lys Thr Lys
1               5                   10                  15

Lys

<210> SEQ ID NO 112
<211> LENGTH: 11
<212> TYPE: PRT
<213> ORGANISM: Artificial Sequence
<220> FEATURE:
<223> OTHER INFORMATION: Synthetic sequence

<400> SEQUENCE: 112

Tyr Gly Arg Lys Lys Arg Arg Gln Arg Arg Arg
1 5 10

<210> SEQ ID NO 113
<211> LENGTH: 12
<212> TYPE: PRT
<213> ORGANISM: Artificial Sequence
<220> FEATURE:
<223> OTHER INFORMATION: Synthetic sequence

<400> SEQUENCE: 113

Arg Arg Gln Arg Arg Thr Ser Lys Leu Met Lys Arg
1 5 10

<210> SEQ ID NO 114
<211> LENGTH: 27
<212> TYPE: PRT
<213> ORGANISM: Artificial Sequence
<220> FEATURE:
<223> OTHER INFORMATION: Synthetic sequence

<400> SEQUENCE: 114

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 115
<211> LENGTH: 33
<212> TYPE: PRT
<213> ORGANISM: Artificial Sequence
<220> FEATURE:
<223> OTHER INFORMATION: Synthetic sequence

<400> SEQUENCE: 115

Lys Ala Leu Ala Trp Glu Ala Lys Leu Ala Lys Ala Leu Ala Lys Ala
1 5 10 15

Leu Ala Lys His Leu Ala Lys Ala Leu Ala Lys Ala Leu Lys Cys Glu
20 25 30

Ala

<210> SEQ ID NO 116
<211> LENGTH: 16
<212> TYPE: PRT
<213> ORGANISM: Artificial Sequence
<220> FEATURE:
<223> OTHER INFORMATION: Synthetic sequence

<400> SEQUENCE: 116

Arg Gln Ile Lys Ile Trp Phe Gln Asn Arg Arg Met Lys Trp Lys Lys
1 5 10 15

<210> SEQ ID NO 117
<211> LENGTH: 11

<212> TYPE: PRT
<213> ORGANISM: Artificial Sequence
<220> FEATURE:
<223> OTHER INFORMATION: Synthetic sequence

<400> SEQUENCE: 117

Tyr Gly Arg Lys Lys Arg Arg Gln Arg Arg Arg
1 5 10

<210> SEQ ID NO 118
<211> LENGTH: 9
<212> TYPE: PRT
<213> ORGANISM: Artificial Sequence
<220> FEATURE:
<223> OTHER INFORMATION: Synthetic sequence

<400> SEQUENCE: 118

Arg Lys Lys Arg Arg Gln Arg Arg Arg
1 5

<210> SEQ ID NO 119
<211> LENGTH: 11
<212> TYPE: PRT
<213> ORGANISM: Artificial Sequence
<220> FEATURE:
<223> OTHER INFORMATION: Synthetic sequence

<400> SEQUENCE: 119

Tyr Gly Arg Lys Lys Arg Arg Gln Arg Arg Arg
1 5 10

<210> SEQ ID NO 120
<211> LENGTH: 8
<212> TYPE: PRT
<213> ORGANISM: Artificial Sequence
<220> FEATURE:
<223> OTHER INFORMATION: Synthetic sequence

<400> SEQUENCE: 120

Arg Lys Lys Arg Arg Gln Arg Arg
1 5

<210> SEQ ID NO 121
<211> LENGTH: 11
<212> TYPE: PRT
<213> ORGANISM: Artificial Sequence
<220> FEATURE:
<223> OTHER INFORMATION: Synthetic sequence

<400> SEQUENCE: 121

Tyr Ala Arg Ala Ala Ala Arg Gln Ala Arg Ala
1 5 10

<210> SEQ ID NO 122
<211> LENGTH: 11
<212> TYPE: PRT
<213> ORGANISM: Artificial Sequence
<220> FEATURE:
<223> OTHER INFORMATION: Synthetic sequence

<400> SEQUENCE: 122

Thr His Arg Leu Pro Arg Arg Arg Arg Arg Arg
1 5 10

<210> SEQ ID NO 123
<211> LENGTH: 11
<212> TYPE: PRT

<213> ORGANISM: Artificial Sequence
<220> FEATURE:
<223> OTHER INFORMATION: Synthetic sequence

<400> SEQUENCE: 123

Gly Gly Arg Arg Ala Arg Arg Arg Arg Arg Arg
1 5 10

<210> SEQ ID NO 124
<211> LENGTH: 5
<212> TYPE: PRT
<213> ORGANISM: Artificial Sequence
<220> FEATURE:
<223> OTHER INFORMATION: Synthetic sequence

<400> SEQUENCE: 124

Gly Ser Gly Gly Ser
1 5

<210> SEQ ID NO 125
<211> LENGTH: 6
<212> TYPE: PRT
<213> ORGANISM: Artificial Sequence
<220> FEATURE:
<223> OTHER INFORMATION: Synthetic sequence

<400> SEQUENCE: 125

Gly Gly Ser Gly Gly Ser
1 5

<210> SEQ ID NO 126
<211> LENGTH: 4
<212> TYPE: PRT
<213> ORGANISM: Artificial Sequence
<220> FEATURE:
<223> OTHER INFORMATION: Synthetic sequence

<400> SEQUENCE: 126

Gly Gly Gly Ser
1

<210> SEQ ID NO 127
<211> LENGTH: 4
<212> TYPE: PRT
<213> ORGANISM: Artificial Sequence
<220> FEATURE:
<223> OTHER INFORMATION: Synthetic sequence

<400> SEQUENCE: 127

Gly Gly Ser Gly
1

<210> SEQ ID NO 128
<211> LENGTH: 5
<212> TYPE: PRT
<213> ORGANISM: Artificial Sequence
<220> FEATURE:
<223> OTHER INFORMATION: Synthetic sequence

<400> SEQUENCE: 128

Gly Gly Ser Gly Gly
1 5

<210> SEQ ID NO 129
<211> LENGTH: 5
<212> TYPE: PRT
<213> ORGANISM: Artificial Sequence
<220> FEATURE:
<223> OTHER INFORMATION: Synthetic sequence

<400> SEQUENCE: 129

Gly Ser Gly Ser Gly
1 5

<210> SEQ ID NO 130
<211> LENGTH: 5
<212> TYPE: PRT
<213> ORGANISM: Artificial Sequence
<220> FEATURE:
<223> OTHER INFORMATION: Synthetic sequence

<400> SEQUENCE: 130

Gly Ser Gly Gly Gly
1 5

<210> SEQ ID NO 131
<211> LENGTH: 5
<212> TYPE: PRT
<213> ORGANISM: Artificial Sequence
<220> FEATURE:
<223> OTHER INFORMATION: Synthetic sequence

<400> SEQUENCE: 131

Gly Gly Gly Ser Gly
1 5

<210> SEQ ID NO 132
<211> LENGTH: 5
<212> TYPE: PRT
<213> ORGANISM: Artificial Sequence
<220> FEATURE:
<223> OTHER INFORMATION: Synthetic sequence

<400> SEQUENCE: 132

Gly Ser Ser Ser Gly
1 5

<210> SEQ ID NO 133
<211> LENGTH: 16
<212> TYPE: PRT
<213> ORGANISM: Artificial Sequence
<220> FEATURE:
<223> OTHER INFORMATION: Synthetic sequence

<400> SEQUENCE: 133

Arg Gln Ile Lys Ile Trp Phe Gln Asn Arg Arg Met Lys Trp Lys Lys
1 5 10 15

<210> SEQ ID NO 134
<211> LENGTH: 11
<212> TYPE: PRT
<213> ORGANISM: Artificial Sequence
<220> FEATURE:
<223> OTHER INFORMATION: Synthetic sequence

<400> SEQUENCE: 134

Tyr Gly Arg Lys Lys Arg Arg Gln Arg Arg Arg
1 5 10

<210> SEQ ID NO 135
<211> LENGTH: 40
<212> TYPE: DNA
<213> ORGANISM: Artificial Sequence
<220> FEATURE:

<223> OTHER INFORMATION: Synthetic sequence

<400> SEQUENCE: 135
gacatgatcg ctaatcaata ccaaactctg gaccgaattc 40

<210> SEQ ID NO 136
<211> LENGTH: 40
<212> TYPE: DNA
<213> ORGANISM: Artificial Sequence
<220> FEATURE:
<223> OTHER INFORMATION: Synthetic sequence

<400> SEQUENCE: 136
gaattcggtc cagagtttgg tattgattag cgatcatgtc 40

<210> SEQ ID NO 137
<211> LENGTH: 43
<212> TYPE: DNA
<213> ORGANISM: Artificial Sequence
<220> FEATURE:
<223> OTHER INFORMATION: Synthetic sequence

<400> SEQUENCE: 137
ctccgaaagt atcggggata aaggcatcaa taccaaactc tgg 43

<210> SEQ ID NO 138
<211> LENGTH: 410
<212> TYPE: PRT
<213> ORGANISM: Unknown
<220> FEATURE:
<223> OTHER INFORMATION: Synthetic sequence

<400> SEQUENCE: 138

```
Glu His Pro Glu Thr Pro Ile Ile Gly Ile Asp Arg Gly Glu Arg Asn
1               5                   10                  15

Leu Ile Tyr Ile Thr Val Ile Asp Ser Thr Gly Lys Ile Leu Glu Gln
            20                  25                  30

Arg Ser Leu Asn Thr Ile Gln Gln Phe Asp Tyr Gln Lys Lys Leu Asp
        35                  40                  45

Asn Arg Glu Lys Glu Arg Val Ala Ala Arg Gln Ala Trp Ser Val Val
    50                  55                  60

Gly Thr Ile Lys Asp Leu Lys Gln Gly Tyr Leu Ser Gln Val Ile His
65                  70                  75                  80

Glu Ile Val Asp Leu Met Ile His Tyr Gln Ala Val Val Val Leu Glu
                85                  90                  95

Asn Leu Asn Phe Gly Phe Lys Ser Lys Arg Thr Gly Ile Ala Glu Lys
            100                 105                 110

Ala Val Tyr Gln Gln Phe Glu Lys Met Leu Ile Asp Lys Leu Asn Cys
        115                 120                 125

Leu Val Leu Lys Asp Tyr Pro Ala Glu Lys Val Gly Gly Val Leu Asn
    130                 135                 140

Pro Tyr Gln Leu Thr Asp Gln Phe Thr Ser Phe Ala Lys Met Gly Thr
145                 150                 155                 160

Gln Ser Gly Phe Leu Phe Tyr Val Pro Ala Pro Tyr Thr Ser Lys Ile
                165                 170                 175

Asp Pro Leu Thr Gly Phe Val Asp Pro Phe Val Trp Lys Thr Ile Lys
            180                 185                 190

Asn His Glu Ser Arg Lys His Phe Leu Glu Gly Phe Asp Phe Leu His
        195                 200                 205
```

Tyr Asp Val Lys Thr Gly Asp Phe Ile Leu His Phe Lys Met Asn Arg
    210                 215                 220

Asn Leu Ser Phe Gln Arg Gly Leu Pro Gly Phe Met Pro Ala Trp Asp
225                 230                 235                 240

Ile Val Phe Glu Lys Asn Glu Thr Gln Phe Asp Ala Lys Gly Thr Pro
                245                 250                 255

Phe Ile Ala Gly Lys Arg Ile Val Pro Val Ile Glu Asn His Arg Phe
            260                 265                 270

Thr Gly Arg Tyr Arg Asp Leu Tyr Pro Ala Asn Glu Leu Ile Ala Leu
        275                 280                 285

Leu Glu Glu Lys Gly Ile Val Phe Arg Asp Gly Ser Asn Ile Leu Pro
    290                 295                 300

Lys Leu Leu Glu Asn Asp Asp Ser His Ala Ile Asp Thr Met Val Ala
305                 310                 315                 320

Leu Ile Arg Ser Val Leu Gln Met Arg Asn Ser Asn Ala Ala Thr Gly
                325                 330                 335

Glu Asp Tyr Ile Asn Ser Pro Val Arg Asp Leu Asn Gly Val Cys Phe
            340                 345                 350

Asp Ser Arg Phe Gln Asn Pro Glu Trp Pro Met Asp Ala Asp Ala Asn
        355                 360                 365

Gly Ala Tyr His Ile Ala Leu Lys Gly Gln Leu Leu Leu Asn His Leu
    370                 375                 380

Lys Glu Ser Lys Asp Leu Lys Leu Gln Asn Gly Ile Ser Asn Gln Asp
385                 390                 395                 400

Trp Leu Ala Tyr Ile Gln Glu Leu Arg Asn
                405                 410

<210> SEQ ID NO 139
<211> LENGTH: 406
<212> TYPE: PRT
<213> ORGANISM: Unknown
<220> FEATURE:
<223> OTHER INFORMATION: Synthetic sequence

<400> SEQUENCE: 139

His Asp Asp Asn Pro Tyr Val Ile Gly Ile Asp Arg Gly Glu Arg Asn
1               5                   10                  15

Leu Leu Tyr Ile Val Val Val Asp Gly Lys Gly Asn Ile Val Glu Gln
            20                  25                  30

Tyr Ser Leu Asn Glu Ile Ile Asn Asn Phe Asn Gly Ile Arg Ile Lys
        35                  40                  45

Thr Asp Tyr His Ser Leu Leu Asp Lys Lys Glu Lys Glu Arg Phe Glu
    50                  55                  60

Ala Arg Gln Asn Trp Thr Ser Ile Glu Asn Ile Lys Glu Leu Lys Ala
65                  70                  75                  80

Gly Tyr Ile Ser Gln Val Val His Lys Ile Cys Glu Leu Val Glu Lys
                85                  90                  95

Tyr Asp Ala Val Ile Ala Leu Glu Asp Leu Asn Ser Gly Phe Lys Asn
            100                 105                 110

Ser Arg Val Lys Val Glu Lys Gln Val Tyr Gln Lys Phe Glu Lys Met
        115                 120                 125

Leu Ile Asp Lys Leu Asn Tyr Met Val Asp Lys Lys Ser Asn Pro Cys
    130                 135                 140

Ala Thr Gly Gly Ala Leu Lys Gly Tyr Gln Ile Thr Asn Lys Phe Glu
145                 150                 155                 160

-continued

```
Ser Phe Lys Ser Met Ser Thr Gln Asn Gly Phe Ile Phe Tyr Ile Pro
                165                 170                 175

Ala Trp Leu Thr Ser Lys Ile Asp Pro Ser Thr Gly Phe Val Asn Leu
            180                 185                 190

Leu Lys Thr Lys Tyr Thr Ser Ile Ala Asp Ser Lys Lys Phe Ile Ser
        195                 200                 205

Ser Phe Asp Arg Ile Met Tyr Val Pro Glu Glu Asp Leu Phe Glu Phe
    210                 215                 220

Ala Leu Asp Tyr Lys Asn Phe Ser Arg Thr Asp Ala Asp Tyr Ile Lys
225                 230                 235                 240

Lys Trp Lys Leu Tyr Ser Tyr Gly Asn Arg Ile Arg Ile Phe Ala Ala
                245                 250                 255

Ala Lys Lys Asn Asn Val Phe Ala Trp Glu Glu Val Cys Leu Thr Ser
            260                 265                 270

Ala Tyr Lys Glu Leu Phe Asn Lys Tyr Gly Ile Asn Tyr Gln Gln Gly
        275                 280                 285

Asp Ile Arg Ala Leu Leu Cys Glu Gln Ser Asp Lys Ala Phe Tyr Ser
    290                 295                 300

Ser Phe Met Ala Leu Met Ser Leu Met Leu Gln Met Arg Asn Ser Ile
305                 310                 315                 320

Thr Gly Arg Thr Asp Val Asp Phe Leu Ile Ser Pro Val Lys Asn Ser
                325                 330                 335

Asp Gly Ile Phe Tyr Asp Ser Arg Asn Tyr Glu Ala Gln Glu Asn Ala
            340                 345                 350

Ile Leu Pro Lys Asn Ala Asp Ala Asn Gly Ala Tyr Asn Ile Ala Arg
        355                 360                 365

Lys Val Leu Trp Ala Ile Gly Gln Phe Lys Lys Ala Glu Asp Glu Lys
    370                 375                 380

Leu Asp Lys Val Lys Ile Ala Ile Ser Asn Lys Glu Trp Leu Glu Tyr
385                 390                 395                 400

Ala Gln Thr Ser Val Lys
                405
```

<210> SEQ ID NO 140
<211> LENGTH: 56
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 140
nnnnnnnnnn nnnnnnnnnn cuuucaauaa acaaauaaau cuuaguaaua uguaac 56

<210> SEQ ID NO 141
<211> LENGTH: 86
<212> TYPE: RNA
<213> ORGANISM: Artificial Sequence
<220> FEATURE:
<223> OTHER INFORMATION: Synthetic sequence

<400> SEQUENCE: 141
cuccauggac gaccucggau uguacgugcg cuugggauug cagauccgaa gaaaguuauu 60
uguuuauuau aaucguuauc ggucaa 86

<210> SEQ ID NO 142
<211> LENGTH: 110
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 142
nnnnnnnnnn nnnnnnnnnn cuuucaauaa acaaauaaaa acuuauuugu uuauugaaag 60
aagccuagac guuaggguuc gcgugcaugu uaggcuccag cagguaccuc 110

<210> SEQ ID NO 143
<211> LENGTH: 56
<212> TYPE: RNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(20)
<223> OTHER INFORMATION: n is a, c, g, or u

<400> SEQUENCE: 143
nnnnnnnnnn nnnnnnnnnn cuuacaaucg acacuuaaau aauuugcaug uguaag 56

<210> SEQ ID NO 144
<211> LENGTH: 181
<212> TYPE: RNA
<213> ORGANISM: Artificial Sequence
<220> FEATURE:
<223> OTHER INFORMATION: Synthetic sequence

<400> SEQUENCE: 144
auuuucguga ggggcuuucg uaggaauggg gguugguaug aguuuaaccc ucacuuuugu 60
uaucacuuca cuucgaaugg uuugguuuug gucucuauug aaaccuauca cuucuauaau 120
guuuguauau auuaaagugg gcgauccaca aauguuaguu guggaccuau accagguacg 180
g 181

<210> SEQ ID NO 145
<211> LENGTH: 205
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(20)
<223> OTHER INFORMATION: n is a, c, g, or u

<400> SEQUENCE: 145
nnnnnnnnnn nnnnnnnnnn cuuacaaucg acauuaaaca gguguugauu guaaacaccu 60
agcgggugaa auuauauaug uuuguaauau cuucacuauc caaaguuauc ucugguuuug 120
guuugguaag cuucacuuca cuauuguuuu cacucccaau uugaguaugg uuggggguaa 180
gguagcuuuc gggggagugc uuuua 205

<210> SEQ ID NO 146
<211> LENGTH: 308
<212> TYPE: PRT
<213> ORGANISM: Unknown
<220> FEATURE:

<223> OTHER INFORMATION: Synthetic sequence

<400> SEQUENCE: 146

Ile Glu Gln Arg Asn Thr Tyr Leu Gly Leu Asp Val Gly Glu Phe Gly
1 5 10 15

Val Ala Tyr Ala Val Val Arg Ile Val Arg Asp Arg Ile Glu Leu Leu
20 25 30

Ser Trp Gly Phe Leu Lys Asp Pro Ala Leu Arg Lys Ile Arg Glu Arg
35 40 45

Val Gln Asp Met Lys Lys Lys Gln Val Met Ala Val Phe Ser Ser Ser
50 55 60

Ser Thr Ala Val Ala Arg Val Arg Glu Met Ala Ile His Ser Leu Arg
65 70 75 80

Asn Gln Ile His Ser Ile Ala Leu Ala Tyr Lys Ala Lys Ile Ile Tyr
85 90 95

Glu Ile Ser Ile Ser Asn Phe Glu Thr Gly Gly Asn Arg Met Ala Lys
100 105 110

Ile Tyr Arg Ser Ile Lys Val Ser Asp Val Tyr Arg Glu Ser Gly Ala
115 120 125

Asp Thr Leu Val Ser Glu Met Ile Trp Gly Lys Lys Asn Lys Gln Met
130 135 140

Gly Asn His Ile Ser Ser Tyr Ala Thr Ser Tyr Thr Cys Cys Asn Cys
145 150 155 160

Ala Arg Thr Pro Phe Glu Leu Val Ile Asp Asn Asp Lys Glu Tyr Glu
165 170 175

Lys Gly Gly Asp Glu Phe Ile Phe Asn Val Gly Asp Glu Lys Lys Val
180 185 190

Arg Gly Phe Leu Gln Lys Ser Leu Leu Gly Lys Thr Ile Lys Gly Lys
195 200 205

Glu Val Leu Lys Ser Ile Lys Glu Tyr Ala Arg Pro Pro Ile Arg Glu
210 215 220

Val Leu Leu Glu Gly Glu Asp Val Glu Gln Leu Leu Lys Arg Arg Gly
225 230 235 240

Asn Ser Tyr Ile Tyr Arg Cys Pro Phe Cys Gly Tyr Lys Thr Asp Ala
245 250 255

Asp Ile Gln Ala Ala Leu Asn Ile Ala Cys Arg Gly Tyr Ile Ser Asp
260 265 270

Asn Ala Lys Asp Ala Val Lys Glu Gly Glu Arg Lys Leu Asp Tyr Ile
275 280 285

Leu Glu Val Arg Lys Leu Trp Glu Lys Asn Gly Ala Val Leu Arg Ser
290 295 300

Ala Lys Phe Leu
305

<210> SEQ ID NO 147
<211> LENGTH: 323
<212> TYPE: PRT
<213> ORGANISM: Unknown
<220> FEATURE:
<223> OTHER INFORMATION: Synthetic sequence

<400> SEQUENCE: 147

Leu Gln Thr Arg Val Asn Tyr Met Gly Ile Asp Ile Gly Glu Tyr Gly
1 5 10 15

Leu Ala Trp Thr Ile Ile Asn Ile Asp Leu Lys Asn Lys Lys Ile Asn
20 25 30

Lys Ile Ser Lys Gln Gly Phe Ile Tyr Glu Pro Leu Thr His Lys Val
35 40 45

Arg Asp Tyr Val Ala Thr Ile Lys Asp Asn Gln Val Arg Gly Thr Phe
50 55 60

Gly Met Pro Asp Thr Lys Leu Ala Arg Leu Arg Glu Asn Ala Ile Thr
65 70 75 80

Ser Leu Arg Asn Gln Val His Asp Ile Ala Met Arg Tyr Asp Ala Lys
85 90 95

Pro Val Tyr Glu Phe Glu Ile Ser Asn Phe Glu Thr Gly Ser Asn Lys
100 105 110

Val Lys Val Ile Tyr Asp Ser Val Lys Arg Ala Asp Ile Gly Arg Gly
115 120 125

Gln Asn Asn Thr Glu Ala Asp Asn Thr Glu Val Asn Leu Val Trp Gly
130 135 140

Lys Thr Ser Lys Gln Phe Gly Ser Gln Ile Gly Ala Tyr Ala Thr Ser
145 150 155 160

Tyr Ile Cys Ser Phe Cys Gly Tyr Ser Pro Tyr Tyr Glu Phe Glu Asn
165 170 175

Ser Lys Ser Gly Asp Glu Glu Gly Ala Arg Asp Asn Leu Tyr Gln Met
180 185 190

Lys Lys Leu Ser Arg Pro Ser Leu Glu Asp Phe Leu Gln Gly Asn Pro
195 200 205

Val Tyr Lys Thr Phe Arg Asp Phe Asp Lys Tyr Lys Asn Asp Gln Arg
210 215 220

Leu Gln Lys Thr Gly Asp Lys Asp Gly Glu Trp Lys Thr His Arg Gly
225 230 235 240

Asn Thr Ala Ile Tyr Ala Cys Gln Lys Cys Arg His Ile Ser Asp Ala
245 250 255

Asp Ile Gln Ala Ser Tyr Trp Ile Ala Leu Lys Gln Val Val Arg Asp
260 265 270

Phe Tyr Lys Asp Lys Glu Met Asp Gly Asp Leu Ile Gln Gly Asp Asn
275 280 285

Lys Asp Lys Arg Lys Val Asn Glu Leu Asn Arg Leu Ile Gly Val His
290 295 300

Lys Asp Val Pro Ile Ile Asn Lys Asn Leu Ile Thr Ser Leu Asp Ile
305 310 315 320

Asn Leu Leu

<210> SEQ ID NO 148
<211> LENGTH: 281
<212> TYPE: PRT
<213> ORGANISM: Unknown
<220> FEATURE:
<223> OTHER INFORMATION: Synthetic sequence

<400> SEQUENCE: 148

Ile Lys Thr Lys Asn Arg Phe Ile Gly Ile Asp Ile Gly Glu Tyr Gly
1 5 10 15

Leu Ala Trp Ser Leu Ile Glu Val Asp Asn Gly Asp Lys Asn Asn Arg
20 25 30

Gly Ile Arg Gln Leu Glu Ser Gly Phe Ile Thr Asp Asn Gln Gln Gln
35 40 45

Val Leu Lys Lys Asn Val Lys Ser Trp Arg Gln Asn Gln Ile Arg Gln
50 55 60

Thr Phe Thr Ser Pro Asp Thr Lys Ile Ala Arg Leu Arg Glu Ser Leu
65 70 75 80

Ile Gly Ser Tyr Lys Asn Gln Leu Glu Ser Leu Met Val Ala Lys Lys
85 90 95

Ala Asn Leu Ser Phe Glu Tyr Glu Val Ser Gly Phe Glu Val Gly Gly
100 105 110

Lys Arg Val Ala Lys Ile Tyr Asp Ser Ile Lys Arg Gly Ser Val Arg
115 120 125

Lys Lys Asp Asn Asn Ser Gln Asn Asp Gln Ser Trp Gly Lys Lys Gly
130 135 140

Ile Asn Glu Trp Ser Phe Glu Thr Thr Ala Ala Gly Thr Ser Gln Phe
145 150 155 160

Cys Thr His Cys Lys Arg Trp Ser Ser Leu Ala Ile Val Asp Ile Glu
165 170 175

Glu Tyr Glu Leu Lys Asp Tyr Asn Asp Asn Leu Phe Lys Val Lys Ile
180 185 190

Asn Asp Gly Glu Val Arg Leu Leu Gly Lys Lys Gly Trp Arg Ser Gly
195 200 205

Glu Lys Ile Lys Gly Lys Glu Leu Phe Gly Pro Val Lys Asp Ala Met
210 215 220

Arg Pro Asn Val Asp Gly Leu Gly Met Lys Ile Val Lys Arg Lys Tyr
225 230 235 240

Leu Lys Leu Asp Leu Arg Asp Trp Val Ser Arg Tyr Gly Asn Met Ala
245 250 255

Ile Phe Ile Cys Pro Tyr Val Asp Cys His His Ile Ser His Ala Asp
260 265 270

Lys Gln Ala Ala Phe Asn Ile Ala Val
275 280

<210> SEQ ID NO 149
<211> LENGTH: 282
<212> TYPE: PRT
<213> ORGANISM: Unknown
<220> FEATURE:
<223> OTHER INFORMATION: Synthetic sequence

<400> SEQUENCE: 149

Gly Gln Arg Tyr Leu Gly Ile Asp Ile Gly Glu Tyr Gly Ile Ala Tyr
1 5 10 15

Thr Ala Leu Glu Ile Thr Gly Asp Ser Ala Lys Ile Leu Asp Gln Asn
20 25 30

Phe Ile Ser Asp Pro Gln Leu Lys Thr Leu Arg Glu Glu Val Lys Gly
35 40 45

Leu Lys Leu Asp Gln Arg Arg Gly Thr Phe Ala Met Pro Ser Thr Lys
50 55 60

Ile Ala Arg Ile Arg Glu Ser Leu Val His Ser Leu Arg Asn Arg Ile
65 70 75 80

His His Leu Ala Leu Lys His Lys Ala Lys Ile Val Tyr Glu Leu Glu
85 90 95

Val Ser Arg Phe Glu Glu Gly Lys Gln Lys Ile Lys Lys Val Tyr Ala
100 105 110

Thr Leu Lys Lys Ala Asp Val Tyr Ser Glu Ile Asp Ala Asp Lys Asn
115 120 125

Leu Gln Thr Thr Val Trp Gly Lys Leu Ala Val Ala Ser Glu Ile Ser
130 135 140

```
Ala Ser Tyr Thr Ser Gln Phe Cys Gly Ala Cys Lys Lys Leu Trp Arg
145                 150                 155                 160

Ala Glu Met Gln Val Asp Glu Thr Ile Thr Thr Gln Glu Leu Ile Gly
                165                 170                 175

Thr Val Arg Val Ile Lys Gly Gly Thr Leu Ile Asp Ala Ile Lys Asp
            180                 185                 190

Phe Met Arg Pro Pro Ile Phe Asp Glu Asn Asp Thr Pro Phe Pro Lys
        195                 200                 205

Tyr Arg Asp Phe Cys Asp Lys His His Ile Ser Lys Lys Met Arg Gly
    210                 215                 220

Asn Ser Cys Leu Phe Ile Cys Pro Phe Cys Arg Ala Asn Ala Asp Ala
225                 230                 235                 240

Asp Ile Gln Ala Ser Gln Thr Ile Ala Leu Leu Arg Tyr Val Lys Glu
                245                 250                 255

Glu Lys Lys Val Glu Asp Tyr Phe Glu Arg Phe Arg Lys Leu Lys Asn
            260                 265                 270

Ile Lys Val Leu Gly Gln Met Lys Lys Ile
        275                 280


<210> SEQ ID NO 150
<211> LENGTH: 210
<212> TYPE: PRT
<213> ORGANISM: Unknown
<220> FEATURE:
<223> OTHER INFORMATION: Synthetic sequence

<400> SEQUENCE: 150

Val Leu Ala Pro Asn Arg Tyr Leu Gly Leu Phe Pro His Ser Gly Gly
1               5                   10                  15

Ile Glu Tyr Ala Val Val Asp Val Leu Asp Ser Ala Gly Phe Lys Ile
            20                  25                  30

Leu Glu Arg Gly Thr Ile Ala Val Asn Gly Phe Ser Gln Lys Arg Gly
        35                  40                  45

Glu Arg Gln Glu Glu Ala His Arg Glu Lys Gln Arg Arg Gly Ile Ser
    50                  55                  60

Asp Ile Gly Arg Lys Lys Pro Val Gln Ala Glu Val Asp Ala Ala Asn
65                  70                  75                  80

Glu Leu His Arg Lys Tyr Thr Asp Val Ala Thr Arg Leu Gly Cys Arg
                85                  90                  95

Ile Val Val Gln Trp Ala Pro Gln Pro Lys Pro Gly Thr Ala Pro Thr
            100                 105                 110

Ala Gln Thr Val Tyr Ala Arg Ala Val Arg Thr Glu Ala Pro Arg Ser
        115                 120                 125

Gly Asn Gln Glu Asp His Ala Arg Met Lys Ser Ser Trp Gly Tyr Thr
    130                 135                 140

Trp Gly Thr Tyr Trp Glu Lys Arg Lys Pro Glu Asp Ile Leu Gly Ile
145                 150                 155                 160

Ser Thr Gln Val Tyr Trp Thr Gly Gly Ile Gly Glu Ser Cys Pro Ala
                165                 170                 175

Val Ala Val Ala Leu Leu Gly His Ile Arg Ala Thr Ser Thr Gln Thr
            180                 185                 190

Glu Trp Glu Lys Glu Glu Val Val Phe Gly Arg Leu Lys Lys Phe Phe
        195                 200                 205

Pro Ser
    210
```

<210> SEQ ID NO 151
<211> LENGTH: 210
<212> TYPE: PRT
<213> ORGANISM: Unknown
<220> FEATURE:
<223> OTHER INFORMATION: Synthetic sequence

<400> SEQUENCE: 151

```
Val Leu Ala Pro Asn Arg Tyr Leu Gly Leu Phe Pro His Ser Gly Gly
1               5                   10                  15

Ile Glu Tyr Ala Val Val Asp Val Leu Asp Ser Ala Gly Phe Lys Ile
            20                  25                  30

Leu Glu Arg Gly Thr Ile Ala Val Asn Gly Phe Ser Gln Lys Arg Gly
        35                  40                  45

Glu Arg Gln Glu Glu Ala His Arg Glu Lys Gln Arg Arg Gly Ile Ser
    50                  55                  60

Asp Ile Gly Arg Lys Lys Pro Val Gln Ala Glu Val Asp Ala Ala Asn
65                  70                  75                  80

Glu Leu His Arg Lys Tyr Thr Asp Val Ala Thr Arg Leu Gly Cys Arg
                85                  90                  95

Ile Val Val Gln Trp Ala Pro Gln Pro Lys Pro Gly Thr Ala Pro Thr
            100                 105                 110

Ala Gln Thr Val Tyr Ala Arg Ala Val Arg Thr Glu Ala Pro Arg Ser
        115                 120                 125

Gly Asn Gln Glu Asp His Ala Arg Met Lys Ser Ser Trp Gly Tyr Thr
    130                 135                 140

Trp Ser Thr Tyr Trp Glu Lys Arg Lys Pro Glu Asp Ile Leu Gly Ile
145                 150                 155                 160

Ser Thr Gln Val Tyr Trp Thr Gly Gly Ile Gly Glu Ser Cys Pro Ala
                165                 170                 175

Val Ala Val Ala Leu Leu Gly His Ile Arg Ala Thr Ser Thr Gln Thr
            180                 185                 190

Glu Trp Glu Lys Glu Glu Val Val Phe Gly Arg Leu Lys Lys Phe Phe
        195                 200                 205

Pro Ser
    210
```

<210> SEQ ID NO 152
<211> LENGTH: 349
<212> TYPE: PRT
<213> ORGANISM: Unknown
<220> FEATURE:
<223> OTHER INFORMATION: Synthetic sequence

<400> SEQUENCE: 152

```
Gly Lys Thr Tyr Leu Gly Leu Asp Ala Gly Glu Arg Ser Gly Val Gly
1               5                   10                  15

Phe Ala Ile Val Thr Val Asp Gly Asp Gly Tyr Glu Val Gln Arg Leu
            20                  25                  30

Gly Val His Glu Asp Thr Gln Leu Met Ala Leu Gln Gln Val Ala Ser
        35                  40                  45

Lys Ser Leu Lys Glu Pro Val Phe Gln Pro Leu Arg Lys Gly Thr Phe
    50                  55                  60

Arg Gln Gln Glu Arg Ile Arg Lys Ser Leu Arg Gly Cys Tyr Trp Asn
65                  70                  75                  80

Phe Tyr His Ala Leu Met Ile Lys Tyr Arg Ala Lys Val Val His Glu
                85                  90                  95
```

```
Glu Ser Val Gly Ser Ser Gly Leu Val Gly Gln Trp Leu Arg Ala Phe
            100                 105                 110

Gln Lys Asp Leu Lys Lys Ala Asp Val Leu Pro Lys Lys Gly Gly Lys
        115                 120                 125

Asn Gly Val Asp Lys Lys Lys Arg Glu Ser Ser Ala Gln Asp Thr Leu
    130                 135                 140

Trp Gly Gly Ala Phe Ser Lys Lys Glu Glu Gln Gln Ile Ala Phe Glu
145                 150                 155                 160

Val Gln Ala Ala Gly Ser Ser Gln Phe Cys Leu Lys Cys Gly Trp Trp
                165                 170                 175

Phe Gln Leu Gly Met Arg Glu Val Asn Arg Val Gln Glu Ser Gly Val
            180                 185                 190

Val Leu Asp Trp Asn Arg Ser Ile Val Thr Phe Leu Ile Glu Ser Ser
        195                 200                 205

Gly Glu Lys Val Tyr Gly Phe Ser Pro Gln Gln Leu Glu Lys Gly Phe
    210                 215                 220

Arg Pro Asp Ile Glu Thr Phe Lys Lys Met Val Arg Asp Phe Met Arg
225                 230                 235                 240

Pro Pro Met Phe Asp Arg Lys Gly Arg Pro Ala Ala Ala Tyr Glu Arg
                245                 250                 255

Phe Val Leu Gly Arg Arg His Arg Arg Tyr Arg Phe Asp Lys Val Phe
            260                 265                 270

Glu Glu Arg Phe Gly Arg Ser Ala Leu Phe Ile Cys Pro Arg Val Gly
        275                 280                 285

Cys Gly Asn Phe Asp His Ser Ser Glu Gln Ser Ala Val Val Leu Ala
    290                 295                 300

Leu Ile Gly Tyr Ile Ala Asp Lys Glu Gly Met Ser Gly Lys Lys Leu
305                 310                 315                 320

Val Tyr Val Arg Leu Ala Glu Leu Met Ala Glu Trp Lys Leu Lys Lys
                325                 330                 335

Leu Glu Arg Ser Arg Val Glu Glu Gln Ser Ser Ala Gln
            340                 345


<210> SEQ ID NO 153
<211> LENGTH: 1128
<212> TYPE: PRT
<213> ORGANISM: Unknown
<220> FEATURE:
<223> OTHER INFORMATION: Synthetic sequence

<400> SEQUENCE: 153

Met Arg Lys Lys Leu Phe Lys Gly Tyr Ile Leu His Asn Lys Arg Leu
1               5                   10                  15

Val Tyr Thr Gly Lys Ala Ala Ile Arg Ser Ile Lys Tyr Pro Leu Val
            20                  25                  30

Ala Pro Asn Lys Thr Ala Leu Asn Asn Leu Ser Glu Lys Ile Ile Tyr
        35                  40                  45

Asp Tyr Glu His Leu Phe Gly Pro Leu Asn Val Ala Ser Tyr Ala Arg
    50                  55                  60

Asn Ser Asn Arg Tyr Ser Leu Val Asp Phe Trp Ile Asp Ser Leu Arg
65                  70                  75                  80

Ala Gly Val Ile Trp Gln Ser Lys Ser Thr Ser Leu Ile Asp Leu Ile
                85                  90                  95

Ser Lys Leu Glu Gly Ser Lys Ser Pro Ser Glu Lys Ile Phe Glu Gln
            100                 105                 110
```

```
Ile Asp Phe Glu Leu Lys Asn Lys Leu Asp Lys Glu Gln Phe Lys Asp
        115                 120                 125

Ile Ile Leu Leu Asn Thr Gly Ile Arg Ser Ser Ser Asn Val Arg Ser
    130                 135                 140

Leu Arg Gly Arg Phe Leu Lys Cys Phe Lys Glu Glu Phe Arg Asp Thr
145                 150                 155                 160

Glu Glu Val Ile Ala Cys Val Asp Lys Trp Ser Lys Asp Leu Ile Val
                165                 170                 175

Glu Gly Lys Ser Ile Leu Val Ser Lys Gln Phe Leu Tyr Trp Glu Glu
            180                 185                 190

Glu Phe Gly Ile Lys Ile Phe Pro His Phe Lys Asp Asn His Asp Leu
        195                 200                 205

Pro Lys Leu Thr Phe Phe Val Glu Pro Ser Leu Glu Phe Ser Pro His
    210                 215                 220

Leu Pro Leu Ala Asn Cys Leu Glu Arg Leu Lys Lys Phe Asp Ile Ser
225                 230                 235                 240

Arg Glu Ser Leu Leu Gly Leu Asp Asn Asn Phe Ser Ala Phe Ser Asn
                245                 250                 255

Tyr Phe Asn Glu Leu Phe Asn Leu Leu Ser Arg Gly Glu Ile Lys Lys
            260                 265                 270

Ile Val Thr Ala Val Leu Ala Val Ser Lys Ser Trp Glu Asn Glu Pro
        275                 280                 285

Glu Leu Glu Lys Arg Leu His Phe Leu Ser Glu Lys Ala Lys Leu Leu
    290                 295                 300

Gly Tyr Pro Lys Leu Thr Ser Ser Trp Ala Asp Tyr Arg Val Ile Ile
305                 310                 315                 320

Gly Gly Lys Ile Lys Ser Trp His Ser Asn Tyr Thr Glu Gln Leu Ile
                325                 330                 335

Lys Val Arg Glu Asp Leu Lys Lys His Gln Ile Ala Leu Asp Lys Leu
            340                 345                 350

Gln Glu Asp Leu Lys Lys Val Val Asp Ser Ser Leu Arg Glu Gln Ile
        355                 360                 365

Glu Ala Gln Arg Glu Ala Leu Leu Pro Leu Leu Asp Thr Met Leu Lys
    370                 375                 380

Glu Lys Asp Phe Ser Asp Asp Leu Glu Leu Tyr Arg Phe Ile Leu Ser
385                 390                 395                 400

Asp Phe Lys Ser Leu Leu Asn Gly Ser Tyr Gln Arg Tyr Ile Gln Thr
                405                 410                 415

Glu Glu Glu Arg Lys Glu Asp Arg Asp Val Thr Lys Lys Tyr Lys Asp
            420                 425                 430

Leu Tyr Ser Asn Leu Arg Asn Ile Pro Arg Phe Phe Gly Glu Ser Lys
        435                 440                 445

Lys Glu Gln Phe Asn Lys Phe Ile Asn Lys Ser Leu Pro Thr Ile Asp
    450                 455                 460

Val Gly Leu Lys Ile Leu Glu Asp Ile Arg Asn Ala Leu Glu Thr Val
465                 470                 475                 480

Ser Val Arg Lys Pro Pro Ser Ile Thr Glu Glu Tyr Val Thr Lys Gln
                485                 490                 495

Leu Glu Lys Leu Ser Arg Lys Tyr Lys Ile Asn Ala Phe Asn Ser Asn
            500                 505                 510

Arg Phe Lys Gln Ile Thr Glu Gln Val Leu Arg Lys Tyr Asn Asn Gly
        515                 520                 525
```

```
Glu Leu Pro Lys Ile Ser Glu Val Phe Tyr Arg Tyr Pro Arg Glu Ser
    530                 535                 540

His Val Ala Ile Arg Ile Leu Pro Val Lys Ile Ser Asn Pro Arg Lys
545                 550                 555                 560

Asp Ile Ser Tyr Leu Leu Asp Lys Tyr Gln Ile Ser Pro Asp Trp Lys
                565                 570                 575

Asn Ser Asn Pro Gly Glu Val Val Asp Leu Ile Glu Ile Tyr Lys Leu
            580                 585                 590

Thr Leu Gly Trp Leu Leu Ser Cys Asn Lys Asp Phe Ser Met Asp Phe
        595                 600                 605

Ser Ser Tyr Asp Leu Lys Leu Phe Pro Glu Ala Ala Ser Leu Ile Lys
    610                 615                 620

Asn Phe Gly Ser Cys Leu Ser Gly Tyr Tyr Leu Ser Lys Met Ile Phe
625                 630                 635                 640

Asn Cys Ile Thr Ser Glu Ile Lys Gly Met Ile Thr Leu Tyr Thr Arg
                645                 650                 655

Asp Lys Phe Val Val Arg Tyr Val Thr Gln Met Ile Gly Ser Asn Gln
            660                 665                 670

Lys Phe Pro Leu Leu Cys Leu Val Gly Glu Lys Gln Thr Lys Asn Phe
        675                 680                 685

Ser Arg Asn Trp Gly Val Leu Ile Glu Glu Lys Gly Asp Leu Gly Glu
    690                 695                 700

Glu Lys Asn Gln Glu Lys Cys Leu Ile Phe Lys Asp Lys Thr Asp Phe
705                 710                 715                 720

Ala Lys Ala Lys Glu Val Glu Ile Phe Lys Asn Asn Ile Trp Arg Ile
                725                 730                 735

Arg Thr Ser Lys Tyr Gln Ile Gln Phe Leu Asn Arg Leu Phe Lys Lys
            740                 745                 750

Thr Lys Glu Trp Asp Leu Met Asn Leu Val Leu Ser Glu Pro Ser Leu
        755                 760                 765

Val Leu Glu Glu Glu Trp Gly Val Ser Trp Asp Lys Asp Lys Leu Leu
    770                 775                 780

Pro Leu Leu Lys Lys Glu Lys Ser Cys Glu Glu Arg Leu Tyr Tyr Ser
785                 790                 795                 800

Leu Pro Leu Asn Leu Val Pro Ala Thr Asp Tyr Lys Glu Gln Ser Ala
                805                 810                 815

Glu Ile Glu Gln Arg Asn Thr Tyr Leu Gly Leu Asp Val Gly Glu Phe
            820                 825                 830

Gly Val Ala Tyr Ala Val Val Arg Ile Val Arg Asp Arg Ile Glu Leu
        835                 840                 845

Leu Ser Trp Gly Phe Leu Lys Asp Pro Ala Leu Arg Lys Ile Arg Glu
    850                 855                 860

Arg Val Gln Asp Met Lys Lys Lys Gln Val Met Ala Val Phe Ser Ser
865                 870                 875                 880

Ser Ser Thr Ala Val Ala Arg Val Arg Glu Met Ala Ile His Ser Leu
                885                 890                 895

Arg Asn Gln Ile His Ser Ile Ala Leu Ala Tyr Lys Ala Lys Ile Ile
            900                 905                 910

Tyr Glu Ile Ser Ile Ser Asn Phe Glu Thr Gly Gly Asn Arg Met Ala
        915                 920                 925

Lys Ile Tyr Arg Ser Ile Lys Val Ser Asp Val Tyr Arg Glu Ser Gly
    930                 935                 940

Ala Asp Thr Leu Val Ser Glu Met Ile Trp Gly Lys Lys Asn Lys Gln
```

```
945                 950                 955                 960

Met Gly Asn His Ile Ser Ser Tyr Ala Thr Ser Tyr Thr Cys Cys Asn
                965                 970                 975

Cys Ala Arg Thr Pro Phe Glu Leu Val Ile Asp Asn Asp Lys Glu Tyr
            980                 985                 990

Glu Lys Gly Gly Asp Glu Phe Ile  Phe Asn Val Gly Asp  Ile Ile Ile
        995                 1000                1005

Glu Lys  Lys Val Arg Gly Phe  Leu Gln Lys Ser Leu  Leu Gly Lys
    1010                1015                1020

Thr Ile  Lys Gly Lys Glu Val  Leu Lys Ser Ile Lys  Glu Tyr Ala
    1025                1030                1035

Arg Pro  Pro Ile Arg Glu Val  Leu Leu Glu Gly Glu  Asp Val Glu
    1040                1045                1050

Gln Leu  Leu Lys Arg Arg Gly  Asn Ser Tyr Ile Tyr  Arg Cys Pro
    1055                1060                1065

Phe Cys  Gly Tyr Lys Thr Asp  Ala Asp Ile Gln Ala  Ala Leu Asn
    1070                1075                1080

Ile Ala  Cys Arg Gly Tyr Ile  Ser Asp Asn Ala Lys  Asp Ala Val
    1085                1090                1095

Lys Glu  Gly Glu Arg Lys Leu  Asp Tyr Ile Leu Glu  Val Arg Lys
    1100                1105                1110

Leu Trp  Glu Lys Asn Gly Ala  Val Leu Arg Ser Ala  Lys Phe Leu
    1115                1120                1125


<210> SEQ ID NO 154
<211> LENGTH: 1226
<212> TYPE: PRT
<213> ORGANISM: Unknown
<220> FEATURE:
<223> OTHER INFORMATION: Synthetic sequence

<400> SEQUENCE: 154

Met Gln Lys Val Arg Lys Thr Leu Ser Glu Val His Lys Asn Pro Tyr
1               5                   10                  15

Gly Thr Lys Val Arg Asn Ala Lys Thr Gly Tyr Ser Leu Gln Ile Glu
            20                  25                  30

Arg Leu Ser Tyr Thr Gly Lys Glu Gly Met Arg Ser Phe Lys Ile Pro
        35                  40                  45

Leu Glu Asn Lys Asn Lys Glu Val Phe Asp Glu Phe Val Lys Lys Ile
    50                  55                  60

Arg Asn Asp Tyr Ile Ser Gln Val Gly Leu Leu Asn Leu Ser Asp Trp
65                  70                  75                  80

Tyr Glu His Tyr Gln Glu Lys Gln Glu His Tyr Ser Leu Ala Asp Phe
                85                  90                  95

Trp Leu Asp Ser Leu Arg Ala Gly Met Ile Phe Ala His Lys Glu Thr
            100                 105                 110

Glu Ile Lys Asn Leu Ile Ser Lys Ile Arg Gly Asp Lys Ser Ile Val
        115                 120                 125

Asp Lys Phe Asn Ala Ser Ile Lys Lys Lys His Ala Asp Leu Tyr Ala
    130                 135                 140

Leu Val Asp Ile Lys Ala Leu Tyr Asp Phe Leu Thr Ser Asp Ala Arg
145                 150                 155                 160

Arg Gly Leu Lys Thr Glu Glu Glu Phe Phe Asn Ser Lys Arg Asn Thr
                165                 170                 175

Leu Phe Pro Lys Phe Arg Lys Lys Asp Asn Lys Ala Val Asp Leu Trp
```

```
            180                 185                 190

Val Lys Lys Phe Ile Gly Leu Asp Asn Lys Asp Lys Leu Asn Phe Thr
        195                 200                 205

Lys Lys Phe Ile Gly Phe Asp Pro Asn Pro Gln Ile Lys Tyr Asp His
    210                 215                 220

Thr Phe Phe Phe His Gln Asp Ile Asn Phe Asp Leu Glu Arg Ile Thr
225                 230                 235                 240

Thr Pro Lys Glu Leu Ile Ser Thr Tyr Lys Lys Phe Leu Gly Lys Asn
                245                 250                 255

Lys Asp Leu Tyr Gly Ser Asp Glu Thr Thr Glu Asp Gln Leu Lys Met
            260                 265                 270

Val Leu Gly Phe His Asn Asn His Gly Ala Phe Ser Lys Tyr Phe Asn
        275                 280                 285

Ala Ser Leu Glu Ala Phe Arg Gly Arg Asp Asn Ser Leu Val Glu Gln
    290                 295                 300

Ile Ile Asn Asn Ser Pro Tyr Trp Asn Ser His Arg Lys Glu Leu Glu
305                 310                 315                 320

Lys Arg Ile Ile Phe Leu Gln Val Gln Ser Lys Lys Ile Lys Glu Thr
                325                 330                 335

Glu Leu Gly Lys Pro His Glu Tyr Leu Ala Ser Phe Gly Gly Lys Phe
            340                 345                 350

Glu Ser Trp Val Ser Asn Tyr Leu Arg Gln Glu Glu Glu Met Lys Arg
        355                 360                 365

Gln Leu Phe Gly Tyr Glu Glu Asn Lys Lys Gly Gln Lys Lys Phe Ile
    370                 375                 380

Val Gly Asn Lys Gln Glu Leu Asp Lys Ile Ile Arg Gly Thr Asp Glu
385                 390                 395                 400

Tyr Glu Ile Lys Ala Ile Ser Lys Glu Thr Ile Gly Leu Thr Gln Lys
                405                 410                 415

Cys Leu Lys Leu Leu Glu Gln Leu Lys Asp Ser Val Asp Asp Tyr Thr
            420                 425                 430

Leu Ser Leu Tyr Arg Gln Leu Ile Val Glu Leu Arg Ile Arg Leu Asn
        435                 440                 445

Val Glu Phe Gln Glu Thr Tyr Pro Glu Leu Ile Gly Lys Ser Glu Lys
    450                 455                 460

Asp Lys Glu Lys Asp Ala Lys Asn Lys Arg Ala Asp Lys Arg Tyr Pro
465                 470                 475                 480

Gln Ile Phe Lys Asp Ile Lys Leu Ile Pro Asn Phe Leu Gly Glu Ile
                485                 490                 495

Lys Gln Met Val Tyr Lys Lys Phe Ile Arg Ser Ala Asp Ile Leu Tyr
            500                 505                 510

Glu Gly Ile Asn Phe Ile Asp Gln Ile Asp Lys Gln Ile Thr Gln Asn
        515                 520                 525

Leu Leu Pro Cys Phe Lys Asn Asp Lys Glu Arg Ile Glu Phe Thr Glu
    530                 535                 540

Lys Gln Phe Glu Thr Leu Arg Arg Lys Tyr Tyr Leu Met Asn Ser Ser
545                 550                 555                 560

Arg Phe His His Val Ile Glu Gly Ile Ile Asn Asn Arg Lys Leu Ile
                565                 570                 575

Glu Met Lys Lys Arg Glu Asn Ser Glu Leu Lys Thr Phe Ser Asp Ser
            580                 585                 590

Lys Phe Val Leu Ser Lys Leu Phe Leu Lys Lys Gly Lys Lys Tyr Glu
        595                 600                 605
```

-continued

```
Asn Glu Val Tyr Tyr Thr Phe Tyr Ile Asn Pro Lys Ala Arg Asp Gln
    610                 615                 620

Arg Arg Ile Lys Ile Val Leu Asp Ile Asn Gly Asn Asn Ser Val Gly
625                 630                 635                 640

Ile Leu Gln Asp Leu Val Gln Lys Leu Lys Pro Lys Trp Asp Asp Ile
                645                 650                 655

Ile Lys Lys Asn Asp Met Gly Glu Leu Ile Asp Ala Ile Glu Ile Glu
            660                 665                 670

Lys Val Arg Leu Gly Ile Leu Ile Ala Leu Tyr Cys Glu His Lys Phe
        675                 680                 685

Lys Ile Lys Lys Glu Leu Leu Ser Leu Asp Leu Phe Ala Ser Ala Tyr
    690                 695                 700

Gln Tyr Leu Glu Leu Glu Asp Asp Pro Glu Glu Leu Ser Gly Thr Asn
705                 710                 715                 720

Leu Gly Arg Phe Leu Gln Ser Leu Val Cys Ser Glu Ile Lys Gly Ala
                725                 730                 735

Ile Asn Lys Ile Ser Arg Thr Glu Tyr Ile Glu Arg Tyr Thr Val Gln
            740                 745                 750

Pro Met Asn Thr Glu Lys Asn Tyr Pro Leu Leu Ile Asn Lys Glu Gly
        755                 760                 765

Lys Ala Thr Trp His Ile Ala Ala Lys Asp Asp Leu Ser Lys Lys Lys
    770                 775                 780

Gly Gly Gly Thr Val Ala Met Asn Gln Lys Ile Gly Lys Asn Phe Phe
785                 790                 795                 800

Gly Lys Gln Asp Tyr Lys Thr Val Phe Met Leu Gln Asp Lys Arg Phe
                805                 810                 815

Asp Leu Leu Thr Ser Lys Tyr His Leu Gln Phe Leu Ser Lys Thr Leu
            820                 825                 830

Asp Thr Gly Gly Gly Ser Trp Trp Lys Asn Lys Asn Ile Asp Leu Asn
        835                 840                 845

Leu Ser Ser Tyr Ser Phe Ile Phe Glu Gln Lys Val Lys Val Glu Trp
    850                 855                 860

Asp Leu Thr Asn Leu Asp His Pro Ile Lys Ile Lys Pro Ser Glu Asn
865                 870                 875                 880

Ser Asp Asp Arg Arg Leu Phe Val Ser Ile Pro Phe Val Ile Lys Pro
                885                 890                 895

Lys Gln Thr Lys Arg Lys Asp Leu Gln Thr Arg Val Asn Tyr Met Gly
            900                 905                 910

Ile Asp Ile Gly Glu Tyr Gly Leu Ala Trp Thr Ile Ile Asn Ile Asp
        915                 920                 925

Leu Lys Asn Lys Lys Ile Asn Lys Ile Ser Lys Gln Gly Phe Ile Tyr
    930                 935                 940

Glu Pro Leu Thr His Lys Val Arg Asp Tyr Val Ala Thr Ile Lys Asp
945                 950                 955                 960

Asn Gln Val Arg Gly Thr Phe Gly Met Pro Asp Thr Lys Leu Ala Arg
                965                 970                 975

Leu Arg Glu Asn Ala Ile Thr Ser Leu Arg Asn Gln Val His Asp Ile
            980                 985                 990

Ala Met Arg Tyr Asp Ala Lys Pro  Val Tyr Glu Phe Glu  Ile Ser Asn
        995                 1000                1005

Phe Glu  Thr Gly Ser Asn Lys  Val Lys Val Ile Tyr  Asp Ser Val
    1010                1015                1020
```

```
Lys Arg  Ala Asp Ile Gly Arg  Gly Gln Asn Asn Thr  Glu Ala Asp
    1025                 1030                 1035

Asn Thr  Glu Val Asn Leu Val  Trp Gly Lys Thr Ser  Lys Gln Phe
    1040                 1045                 1050

Gly Ser  Gln Ile Gly Ala Tyr  Ala Thr Ser Tyr Ile  Cys Ser Phe
    1055                 1060                 1065

Cys Gly  Tyr Ser Pro Tyr Tyr  Glu Phe Glu Asn Ser  Lys Ser Gly
    1070                 1075                 1080

Asp Glu  Glu Gly Ala Arg Asp  Asn Leu Tyr Gln Met  Lys Lys Leu
    1085                 1090                 1095

Ser Arg  Pro Ser Leu Glu Asp  Phe Leu Gln Gly Asn  Pro Val Tyr
    1100                 1105                 1110

Lys Thr  Phe Arg Asp Phe Asp  Lys Tyr Lys Asn Asp  Gln Arg Leu
    1115                 1120                 1125

Gln Lys  Thr Gly Asp Lys Asp  Gly Glu Trp Lys Thr  His Arg Gly
    1130                 1135                 1140

Asn Thr  Ala Ile Tyr Ala Cys  Gln Lys Cys Arg His  Ile Ser Asp
    1145                 1150                 1155

Ala Asp  Ile Gln Ala Ser Tyr  Trp Ile Ala Leu Lys  Gln Val Val
    1160                 1165                 1170

Arg Asp  Phe Tyr Lys Asp Lys  Glu Met Asp Gly Asp  Leu Ile Gln
    1175                 1180                 1185

Gly Asp  Asn Lys Asp Lys Arg  Lys Val Asn Glu Leu  Asn Arg Leu
    1190                 1195                 1200

Ile Gly  Val His Lys Asp Val  Pro Ile Ile Asn Lys  Asn Leu Ile
    1205                 1210                 1215

Thr Ser  Leu Asp Ile Asn Leu  Leu
    1220                 1225
```

<210> SEQ ID NO 155
<211> LENGTH: 1160
<212> TYPE: PRT
<213> ORGANISM: Unknown
<220> FEATURE:
<223> OTHER INFORMATION: Synthetic sequence

<400> SEQUENCE: 155

```
Met Lys Ala Lys Lys Ser Phe Tyr Asn Gln Lys Arg Lys Phe Gly Lys
1               5                   10                  15

Arg Gly Tyr Arg Leu His Asp Glu Arg Leu Ala Tyr Ser Gly Gly Ile
            20                  25                  30

Gly Ser Met Arg Ser Ile Lys Tyr Glu Leu Lys Asp Ser Tyr Gly Ile
        35                  40                  45

Ala Gly Leu Arg Asn Arg Ile Ala Asp Ala Thr Ile Ser Lys Asn Lys
    50                  55                  60

Trp Leu Tyr Gly Asn Ile Asn Leu Asn Asp Tyr Leu Glu Trp Arg Ser
65                  70                  75                  80

Ser Lys Thr Asp Lys Gln Ile Glu Asp Gly Asp Arg Glu Ser Ser Leu
                85                  90                  95

Leu Gly Phe Trp Leu Glu Ala Leu Arg Leu Gly Phe Val Phe Ser Lys
            100                 105                 110

Gln Ser His Ala Pro Asn Asp Phe Asn Glu Thr Ala Leu Gln Asp Leu
        115                 120                 125

Phe Glu Thr Leu Asp Asp Asp Leu Lys His Val Leu Asp Arg Lys Lys
    130                 135                 140
```

```
Trp Cys Asp Phe Ile Lys Ile Gly Thr Pro Lys Thr Asn Asp Gln Gly
145                 150                 155                 160

Arg Leu Lys Lys Gln Ile Lys Asn Leu Leu Lys Gly Asn Lys Arg Glu
                165                 170                 175

Glu Ile Glu Lys Thr Leu Asn Glu Ser Asp Asp Glu Leu Lys Glu Lys
            180                 185                 190

Ile Asn Arg Ile Ala Asp Val Phe Ala Lys Asn Lys Ser Asp Lys Tyr
        195                 200                 205

Thr Ile Phe Lys Leu Asp Lys Pro Asn Thr Glu Lys Tyr Pro Arg Ile
    210                 215                 220

Asn Asp Val Gln Val Ala Phe Phe Cys His Pro Asp Phe Glu Glu Ile
225                 230                 235                 240

Thr Glu Arg Asp Arg Thr Lys Thr Leu Asp Leu Ile Ile Asn Arg Phe
                245                 250                 255

Asn Lys Arg Tyr Glu Ile Thr Glu Asn Lys Lys Asp Asp Lys Thr Ser
            260                 265                 270

Asn Arg Met Ala Leu Tyr Ser Leu Asn Gln Gly Tyr Ile Pro Arg Val
        275                 280                 285

Leu Asn Asp Leu Phe Leu Phe Val Lys Asp Asn Glu Asp Asp Phe Ser
    290                 295                 300

Gln Phe Leu Ser Asp Leu Glu Asn Phe Phe Ser Phe Ser Asn Glu Gln
305                 310                 315                 320

Ile Lys Ile Ile Lys Glu Arg Leu Lys Lys Leu Lys Lys Tyr Ala Glu
                325                 330                 335

Pro Ile Pro Gly Lys Pro Gln Leu Ala Asp Lys Trp Asp Asp Tyr Ala
            340                 345                 350

Ser Asp Phe Gly Gly Lys Leu Glu Ser Trp Tyr Ser Asn Arg Ile Glu
        355                 360                 365

Lys Leu Lys Lys Ile Pro Glu Ser Val Ser Asp Leu Arg Asn Asn Leu
    370                 375                 380

Glu Lys Ile Arg Asn Val Leu Lys Lys Gln Asn Asn Ala Ser Lys Ile
385                 390                 395                 400

Leu Glu Leu Ser Gln Lys Ile Ile Glu Tyr Ile Arg Asp Tyr Gly Val
                405                 410                 415

Ser Phe Glu Lys Pro Glu Ile Ile Lys Phe Ser Trp Ile Asn Lys Thr
            420                 425                 430

Lys Asp Gly Gln Lys Lys Val Phe Tyr Val Ala Lys Met Ala Asp Arg
        435                 440                 445

Glu Phe Ile Glu Lys Leu Asp Leu Trp Met Ala Asp Leu Arg Ser Gln
    450                 455                 460

Leu Asn Glu Tyr Asn Gln Asp Asn Lys Val Ser Phe Lys Lys Lys Gly
465                 470                 475                 480

Lys Lys Ile Glu Glu Leu Gly Val Leu Asp Phe Ala Leu Asn Lys Ala
                485                 490                 495

Lys Lys Asn Lys Ser Thr Lys Asn Glu Asn Gly Trp Gln Gln Lys Leu
            500                 505                 510

Ser Glu Ser Ile Gln Ser Ala Pro Leu Phe Phe Gly Glu Gly Asn Arg
        515                 520                 525

Val Arg Asn Glu Glu Val Tyr Asn Leu Lys Asp Leu Leu Phe Ser Phe
    530                 535                 540

Ile Lys Asn Val Glu Asn Ile Leu Met Ser Ser Glu Ala Glu Asp Leu
545                 550                 555                 560

Lys Asn Ile Lys Ile Glu Tyr Lys Glu Asp Gly Ala Lys Lys Gly Asn
```

-continued

```
                565                 570                 575

Tyr Val Leu Asn Val Leu Ala Arg Phe Tyr Ala Arg Phe Asn Glu Asp
            580                 585                 590

Gly Tyr Gly Gly Trp Asn Lys Val Lys Thr Val Leu Glu Asn Ile Ala
        595                 600                 605

Arg Glu Ala Gly Thr Asp Phe Ser Lys Tyr Gly Asn Asn Asn Asn Arg
    610                 615                 620

Asn Ala Gly Arg Phe Tyr Leu Asn Gly Arg Glu Arg Gln Val Phe Thr
625                 630                 635                 640

Leu Ile Lys Phe Glu Lys Ser Ile Thr Val Glu Lys Ile Leu Glu Leu
                645                 650                 655

Val Lys Leu Pro Ser Leu Leu Asp Glu Ala Tyr Arg Asp Leu Val Asn
            660                 665                 670

Glu Asn Lys Asn His Lys Leu Arg Asp Val Ile Gln Leu Ser Lys Thr
        675                 680                 685

Ile Met Ala Leu Val Leu Ser His Ser Asp Lys Glu Lys Gln Ile Gly
    690                 695                 700

Gly Asn Tyr Ile His Ser Lys Leu Ser Gly Tyr Asn Ala Leu Ile Ser
705                 710                 715                 720

Lys Arg Asp Phe Ile Ser Arg Tyr Ser Val Gln Thr Thr Asn Gly Thr
                725                 730                 735

Gln Cys Lys Leu Ala Ile Gly Lys Gly Lys Ser Lys Lys Gly Asn Glu
            740                 745                 750

Ile Asp Arg Tyr Phe Tyr Ala Phe Gln Phe Phe Lys Asn Asp Asp Ser
        755                 760                 765

Lys Ile Asn Leu Lys Val Ile Lys Asn Asn Ser His Lys Asn Ile Asp
    770                 775                 780

Phe Asn Asp Asn Glu Asn Lys Ile Asn Ala Leu Gln Val Tyr Ser Ser
785                 790                 795                 800

Asn Tyr Gln Ile Gln Phe Leu Asp Trp Phe Phe Glu Lys His Gln Gly
                805                 810                 815

Lys Lys Thr Ser Leu Glu Val Gly Gly Ser Phe Thr Ile Ala Glu Lys
            820                 825                 830

Ser Leu Thr Ile Asp Trp Ser Gly Ser Asn Pro Arg Val Gly Phe Lys
        835                 840                 845

Arg Ser Asp Thr Glu Glu Lys Arg Val Phe Val Ser Gln Pro Phe Thr
    850                 855                 860

Leu Ile Pro Asp Asp Glu Asp Lys Glu Arg Arg Lys Glu Arg Met Ile
865                 870                 875                 880

Lys Thr Lys Asn Arg Phe Ile Gly Ile Asp Ile Gly Glu Tyr Gly Leu
                885                 890                 895

Ala Trp Ser Leu Ile Glu Val Asp Asn Gly Asp Lys Asn Asn Arg Gly
            900                 905                 910

Ile Arg Gln Leu Glu Ser Gly Phe Ile Thr Asp Asn Gln Gln Gln Val
        915                 920                 925

Leu Lys Lys Asn Val Lys Ser Trp Arg Gln Asn Gln Ile Arg Gln Thr
    930                 935                 940

Phe Thr Ser Pro Asp Thr Lys Ile Ala Arg Leu Arg Glu Ser Leu Ile
945                 950                 955                 960

Gly Ser Tyr Lys Asn Gln Leu Glu Ser Leu Val Val Ala Lys Lys Ala
                965                 970                 975

Asn Leu Ser Phe Glu Tyr Glu Val Ser Gly Phe Glu Val Gly Gly Lys
            980                 985                 990
```

```
Arg Val Ala Lys Ile Tyr Asp Ser  Ile Lys Arg Gly Ser  Val Arg Lys
        995                 1000                 1005

Lys Asp  Asn Asn Ser Gln Asn  Asp Gln Ser Trp Gly  Lys Lys Gly
    1010                 1015                 1020

Ile Asn  Glu Trp Ser Phe Glu  Thr Thr Ala Ala Gly  Thr Ser Gln
    1025                 1030                 1035

Phe Cys  Thr His Cys Lys Arg  Trp Ser Ser Leu Ala  Ile Val Asp
    1040                 1045                 1050

Ile Glu  Glu Tyr Glu Leu Lys  Asp Tyr Asn Asp Asn  Leu Phe Lys
    1055                 1060                 1065

Val Lys  Ile Asn Asp Gly Glu  Val Arg Leu Leu Gly  Lys Lys Gly
    1070                 1075                 1080

Trp Arg  Ser Gly Glu Lys Ile  Lys Gly Lys Glu Leu  Phe Gly Pro
    1085                 1090                 1095

Val Lys  Asp Ala Met Arg Pro  Asn Val Asp Gly Leu  Gly Met Lys
    1100                 1105                 1110

Ile Val  Lys Arg Lys Tyr Leu  Lys Leu Asp Leu Arg  Asp Trp Val
    1115                 1120                 1125

Ser Arg  Tyr Gly Asn Met Ala  Ile Phe Ile Cys Pro  Tyr Val Asp
    1130                 1135                 1140

Cys His  His Ile Ser His Ala  Asp Lys Gln Ala Ala  Phe Asn Ile
    1145                 1150                 1155

Ala Val
    1160
```

<210> SEQ ID NO 156
<211> LENGTH: 1210
<212> TYPE: PRT
<213> ORGANISM: Unknown
<220> FEATURE:
<223> OTHER INFORMATION: Synthetic sequence

<400> SEQUENCE: 156

```
Met Ser Lys Arg His Pro Arg Ile Ser Gly Val Lys Gly Tyr Arg Leu
1               5                   10                  15

His Ala Gln Arg Leu Glu Tyr Thr Gly Lys Ser Gly Ala Met Arg Thr
            20                  25                  30

Ile Lys Tyr Pro Leu Tyr Ser Ser Pro Ser Gly Gly Arg Thr Val Pro
        35                  40                  45

Arg Glu Ile Val Ser Ala Ile Asn Asp Asp Tyr Val Gly Leu Tyr Gly
    50                  55                  60

Leu Ser Asn Phe Asp Asp Leu Tyr Asn Ala Glu Lys Arg Asn Glu Glu
65                  70                  75                  80

Lys Val Tyr Ser Val Leu Asp Phe Trp Tyr Asp Cys Val Gln Tyr Gly
                85                  90                  95

Ala Val Phe Ser Tyr Thr Ala Pro Gly Leu Leu Lys Asn Val Ala Glu
            100                 105                 110

Val Arg Gly Gly Ser Tyr Glu Leu Thr Lys Thr Leu Lys Gly Ser His
        115                 120                 125

Leu Tyr Asp Glu Leu Gln Ile Asp Lys Val Ile Lys Phe Leu Asn Lys
    130                 135                 140

Lys Glu Ile Ser Arg Ala Asn Gly Ser Leu Asp Lys Leu Lys Lys Asp
145                 150                 155                 160

Ile Ile Asp Cys Phe Lys Ala Glu Tyr Arg Glu Arg His Lys Asp Gln
                165                 170                 175
```

```
Cys Asn Lys Leu Ala Asp Asp Ile Lys Asn Ala Lys Lys Asp Ala Gly
            180                 185                 190

Ala Ser Leu Gly Glu Arg Gln Lys Lys Leu Phe Arg Asp Phe Phe Gly
        195                 200                 205

Ile Ser Glu Gln Ser Glu Asn Asp Lys Pro Ser Phe Thr Asn Pro Leu
    210                 215                 220

Asn Leu Thr Cys Cys Leu Leu Pro Phe Asp Thr Val Asn Asn Asn Arg
225                 230                 235                 240

Asn Arg Gly Glu Val Leu Phe Asn Lys Leu Lys Glu Tyr Ala Gln Lys
                245                 250                 255

Leu Asp Lys Asn Glu Gly Ser Leu Glu Met Trp Glu Tyr Ile Gly Ile
            260                 265                 270

Gly Asn Ser Gly Thr Ala Phe Ser Asn Phe Leu Gly Glu Gly Phe Leu
        275                 280                 285

Gly Arg Leu Arg Glu Asn Lys Ile Thr Glu Leu Lys Lys Ala Met Met
    290                 295                 300

Asp Ile Thr Asp Ala Trp Arg Gly Gln Glu Gln Glu Glu Glu Leu Glu
305                 310                 315                 320

Lys Arg Leu Arg Ile Leu Ala Ala Leu Thr Ile Lys Leu Arg Glu Pro
                325                 330                 335

Lys Phe Asp Asn His Trp Gly Gly Tyr Arg Ser Asp Ile Asn Gly Lys
            340                 345                 350

Leu Ser Ser Trp Leu Gln Asn Tyr Ile Asn Gln Thr Val Lys Ile Lys
        355                 360                 365

Glu Asp Leu Lys Gly His Lys Lys Asp Leu Lys Lys Ala Lys Glu Met
    370                 375                 380

Ile Asn Arg Phe Gly Glu Ser Asp Thr Lys Glu Glu Ala Val Val Ser
385                 390                 395                 400

Ser Leu Leu Glu Ser Ile Glu Lys Ile Val Pro Asp Asp Ser Ala Asp
                405                 410                 415

Asp Glu Lys Pro Asp Ile Pro Ala Ile Ala Ile Tyr Arg Arg Phe Leu
            420                 425                 430

Ser Asp Gly Arg Leu Thr Leu Asn Arg Phe Val Gln Arg Glu Asp Val
        435                 440                 445

Gln Glu Ala Leu Ile Lys Glu Arg Leu Glu Ala Glu Lys Lys Lys Lys
    450                 455                 460

Pro Lys Lys Arg Lys Lys Lys Ser Asp Ala Glu Asp Glu Lys Glu Thr
465                 470                 475                 480

Ile Asp Phe Lys Glu Leu Phe Pro His Leu Ala Lys Pro Leu Lys Leu
                485                 490                 495

Val Pro Val Phe Tyr Gly Asp Ser Lys Arg Glu Leu Tyr Lys Lys Tyr
            500                 505                 510

Lys Asn Ala Ala Ile Tyr Thr Asp Ala Leu Trp Lys Ala Val Glu Lys
        515                 520                 525

Ile Tyr Lys Ser Ala Phe Ser Ser Ser Leu Lys Asn Ser Phe Phe Asp
    530                 535                 540

Thr Asp Phe Asp Lys Asp Phe Phe Ile Lys Arg Leu Gln Lys Ile Phe
545                 550                 555                 560

Ser Val Tyr Arg Arg Phe Asn Thr Asp Lys Trp Lys Pro Ile Val Lys
                565                 570                 575

Asn Ser Phe Ala Pro Tyr Cys Asp Ile Val Ser Leu Ala Glu Asn Glu
            580                 585                 590
```

```
Val Leu Tyr Lys Pro Lys Gln Ser Arg Ser Arg Lys Ser Ala Ala Ile
        595                 600                 605

Asp Lys Asn Arg Val Arg Leu Pro Ser Thr Glu Asn Ile Ala Lys Ala
    610                 615                 620

Gly Ile Ala Leu Ala Arg Glu Leu Ser Val Ala Gly Arg Asp Trp Lys
625                 630                 635                 640

Asp Leu Leu Lys Lys Glu Glu His Glu Glu Tyr Ile Asp Leu Ile Glu
                645                 650                 655

Leu His Lys Thr Ala Leu Ala Leu Leu Leu Ala Val Thr Glu Thr Gln
            660                 665                 670

Leu Asp Ile Ser Ala Leu Asp Phe Val Glu Asn Gly Thr Val Lys Asp
        675                 680                 685

Phe Met Lys Thr Arg Asp Gly Asn Leu Val Leu Glu Gly Arg Phe Leu
    690                 695                 700

Glu Met Phe Ser Gln Ser Ile Val Phe Ser Glu Leu Arg Gly Leu Ala
705                 710                 715                 720

Gly Leu Met Ser Arg Lys Glu Phe Ile Thr Arg Ser Ala Ile Gln Thr
                725                 730                 735

Met Asn Gly Lys Gln Ala Glu Leu Leu Tyr Ile Pro His Glu Phe Gln
            740                 745                 750

Ser Ala Lys Ile Thr Thr Pro Lys Glu Met Ser Arg Ala Phe Leu Asp
        755                 760                 765

Leu Ala Pro Ala Glu Phe Ala Thr Ser Leu Glu Pro Glu Ser Leu Ser
    770                 775                 780

Glu Lys Ser Leu Leu Lys Leu Lys Gln Met Arg Tyr Tyr Pro His Tyr
785                 790                 795                 800

Phe Gly Tyr Glu Leu Thr Arg Thr Gly Gln Gly Ile Asp Gly Gly Val
                805                 810                 815

Ala Glu Asn Ala Leu Arg Leu Glu Lys Ser Pro Val Lys Lys Arg Glu
            820                 825                 830

Ile Lys Cys Lys Gln Tyr Lys Thr Leu Gly Arg Gly Gln Asn Lys Ile
        835                 840                 845

Val Leu Tyr Val Arg Ser Ser Tyr Tyr Gln Thr Gln Phe Leu Glu Trp
    850                 855                 860

Phe Leu His Arg Pro Lys Asn Val Gln Thr Asp Val Ala Val Ser Gly
865                 870                 875                 880

Ser Phe Leu Ile Asp Glu Lys Lys Val Lys Thr Arg Trp Asn Tyr Asp
                885                 890                 895

Ala Leu Thr Val Ala Leu Glu Pro Val Ser Gly Ser Glu Arg Val Phe
            900                 905                 910

Val Ser Gln Pro Phe Thr Ile Phe Pro Glu Lys Ser Ala Glu Glu Glu
        915                 920                 925

Gly Gln Arg Tyr Leu Gly Ile Asp Ile Gly Glu Tyr Gly Ile Ala Tyr
    930                 935                 940

Thr Ala Leu Glu Ile Thr Gly Asp Ser Ala Lys Ile Leu Asp Gln Asn
945                 950                 955                 960

Phe Ile Ser Asp Pro Gln Leu Lys Thr Leu Arg Glu Glu Val Lys Gly
                965                 970                 975

Leu Lys Leu Asp Gln Arg Arg Gly Thr Phe Ala Met Pro Ser Thr Lys
            980                 985                 990

Ile Ala Arg Ile Arg Glu Ser Leu  Val His Ser Leu Arg  Asn Arg Ile
        995                 1000                 1005

His His  Leu Ala Leu Lys His  Lys Ala Lys Ile Val  Tyr Glu Leu
```

```
    1010                1015                1020

Glu Val  Ser Arg Phe Glu Glu  Gly Lys Gln Lys Ile  Lys Lys Val
    1025                1030                1035

Tyr Ala  Thr Leu Lys Lys Ala  Asp Val Tyr Ser Glu  Ile Asp Ala
    1040                1045                1050

Asp Lys  Asn Leu Gln Thr Thr  Val Trp Gly Lys Leu  Ala Val Ala
    1055                1060                1065

Ser Glu  Ile Ser Ala Ser Tyr  Thr Ser Gln Phe Cys  Gly Ala Cys
    1070                1075                1080

Lys Lys  Leu Trp Arg Ala Glu  Met Gln Val Asp Glu  Thr Ile Thr
    1085                1090                1095

Thr Met  Glu Leu Ile Gly Thr  Val Arg Val Ile Lys  Gly Gly Thr
    1100                1105                1110

Leu Ile  Asp Ala Ile Lys Asp  Phe Met Arg Pro Pro  Ile Phe Asp
    1115                1120                1125

Glu Asn  Asp Thr Pro Phe Pro  Lys Tyr Arg Asp Phe  Cys Asp Lys
    1130                1135                1140

His His  Ile Ser Lys Lys Met  Arg Gly Asn Ser Cys  Leu Phe Ile
    1145                1150                1155

Cys Pro  Phe Cys Arg Ala Asn  Ala Asp Ala Asp Ile  Gln Ala Ser
    1160                1165                1170

Gln Thr  Ile Ala Leu Leu Arg  Tyr Val Lys Glu Glu  Lys Lys Val
    1175                1180                1185

Glu Asp  Tyr Phe Glu Arg Phe  Arg Lys Leu Lys Asn  Ile Lys Val
    1190                1195                1200

Leu Gly  Gln Met Lys Lys Ile
    1205                1210


<210> SEQ ID NO 157
<211> LENGTH: 1192
<212> TYPE: PRT
<213> ORGANISM: Unknown
<220> FEATURE:
<223> OTHER INFORMATION: Synthetic sequence

<400> SEQUENCE: 157

Met Ala Glu Ser Lys Gln Met Gln Cys Arg Lys Cys Gly Ala Ser Met
1               5                   10                  15

Lys Tyr Glu Val Ile Gly Leu Gly Lys Lys Ser Cys Arg Tyr Met Cys
            20                  25                  30

Pro Asp Cys Gly Asn His Thr Ser Ala Arg Lys Ile Gln Asn Lys Lys
        35                  40                  45

Lys Arg Asp Lys Lys Tyr Gly Ser Ala Ser Lys Ala Gln Ser Gln Arg
    50                  55                  60

Ile Ala Val Ala Gly Ala Leu Tyr Pro Asp Lys Lys Val Gln Thr Ile
65                  70                  75                  80

Lys Thr Tyr Lys Tyr Pro Ala Asp Leu Asn Gly Glu Val His Asp Ser
                85                  90                  95

Gly Val Ala Glu Lys Ile Ala Gln Ala Ile Gln Glu Asp Glu Ile Gly
            100                 105                 110

Leu Leu Gly Pro Ser Ser Glu Tyr Ala Cys Trp Ile Ala Ser Gln Lys
        115                 120                 125

Gln Ser Glu Pro Tyr Ser Val Val Asp Phe Trp Phe Asp Ala Val Cys
    130                 135                 140

Ala Gly Gly Val Phe Ala Tyr Ser Gly Ala Arg Leu Leu Ser Thr Val
```

-continued

```
145                 150                 155                 160

Leu Gln Leu Ser Gly Glu Glu Ser Val Leu Arg Ala Ala Leu Ala Ser
                165                 170                 175

Ser Pro Phe Val Asp Asp Ile Asn Leu Ala Gln Ala Glu Lys Phe Leu
            180                 185                 190

Ala Val Ser Arg Arg Thr Gly Gln Asp Lys Leu Gly Lys Arg Ile Gly
        195                 200                 205

Glu Cys Phe Ala Glu Gly Arg Leu Glu Ala Leu Gly Ile Lys Asp Arg
    210                 215                 220

Met Arg Glu Phe Val Gln Ala Ile Asp Val Ala Gln Thr Ala Gly Gln
225                 230                 235                 240

Arg Phe Ala Ala Lys Leu Lys Ile Phe Gly Ile Ser Gln Met Pro Glu
                245                 250                 255

Ala Lys Gln Trp Asn Asn Asp Ser Gly Leu Thr Val Cys Ile Leu Pro
            260                 265                 270

Asp Tyr Tyr Val Pro Glu Glu Asn Arg Ala Asp Gln Leu Val Val Leu
        275                 280                 285

Leu Arg Arg Leu Arg Glu Ile Ala Tyr Cys Met Gly Ile Glu Asp Glu
    290                 295                 300

Ala Gly Phe Glu His Leu Gly Ile Asp Pro Gly Ala Leu Ser Asn Phe
305                 310                 315                 320

Ser Asn Gly Asn Pro Lys Arg Gly Phe Leu Gly Arg Leu Leu Asn Asn
                325                 330                 335

Asp Ile Ile Ala Leu Ala Asn Asn Met Ser Ala Met Thr Pro Tyr Trp
            340                 345                 350

Glu Gly Arg Lys Gly Glu Leu Ile Glu Arg Leu Ala Trp Leu Lys His
        355                 360                 365

Arg Ala Glu Gly Leu Tyr Leu Lys Glu Pro His Phe Gly Asn Ser Trp
    370                 375                 380

Ala Asp His Arg Ser Arg Ile Phe Ser Arg Ile Ala Gly Trp Leu Ser
385                 390                 395                 400

Gly Cys Ala Gly Lys Leu Lys Ile Ala Lys Asp Gln Thr Ser Gly Val
                405                 410                 415

Arg Thr Asp Leu Phe Leu Leu Lys Arg Leu Leu Asp Ala Val Pro Gln
            420                 425                 430

Ser Ala Pro Ser Pro Asp Phe Ile Ala Ser Ile Ser Ala Leu Asp Arg
        435                 440                 445

Phe Leu Glu Ala Ala Glu Ser Ser Gln Asp Pro Ala Glu Gln Val Arg
    450                 455                 460

Ala Leu Tyr Ala Phe His Leu Asn Ala Pro Ala Val Arg Ser Ile Ala
465                 470                 475                 480

Asn Lys Ala Val Gln Arg Ser Asp Ser Gln Glu Trp Leu Ile Lys Glu
                485                 490                 495

Leu Asp Ala Val Asp His Leu Glu Phe Asn Lys Ala Phe Pro Phe Phe
            500                 505                 510

Ser Asp Thr Gly Lys Lys Lys Lys Lys Gly Ala Asn Ser Asn Gly Ala
        515                 520                 525

Pro Ser Glu Glu Glu Tyr Thr Glu Thr Glu Ser Ile Gln Gln Pro Glu
    530                 535                 540

Asp Ala Glu Gln Glu Val Asn Gly Gln Glu Gly Asn Gly Ala Ser Lys
545                 550                 555                 560

Asn Gln Lys Lys Phe Gln Arg Ile Pro Arg Phe Phe Gly Glu Gly Ser
                565                 570                 575
```

-continued

```
Arg Ser Glu Tyr Arg Ile Leu Thr Glu Ala Pro Gln Tyr Phe Asp Met
            580                 585                 590

Phe Cys Asn Asn Met Arg Ala Ile Phe Met Gln Leu Glu Ser Gln Pro
        595                 600                 605

Arg Lys Ala Pro Arg Asp Phe Lys Cys Phe Leu Gln Asn Arg Leu Gln
    610                 615                 620

Lys Leu Tyr Lys Gln Thr Phe Leu Asn Ala Arg Ser Asn Lys Cys Arg
625                 630                 635                 640

Ala Leu Leu Glu Ser Val Leu Ile Ser Trp Gly Glu Phe Tyr Thr Tyr
                645                 650                 655

Gly Ala Asn Glu Lys Lys Phe Arg Leu Arg His Glu Ala Ser Glu Arg
            660                 665                 670

Ser Ser Asp Pro Asp Tyr Val Val Gln Gln Ala Leu Glu Ile Ala Arg
        675                 680                 685

Arg Leu Phe Leu Phe Gly Phe Glu Trp Arg Asp Cys Ser Ala Gly Glu
    690                 695                 700

Arg Val Asp Leu Val Glu Ile His Lys Lys Ala Ile Ser Phe Leu Leu
705                 710                 715                 720

Ala Ile Thr Gln Ala Glu Val Ser Val Gly Ser Tyr Asn Trp Leu Gly
                725                 730                 735

Asn Ser Thr Val Ser Arg Tyr Leu Ser Val Ala Gly Thr Asp Thr Leu
            740                 745                 750

Tyr Gly Thr Gln Leu Glu Glu Phe Leu Asn Ala Thr Val Leu Ser Gln
        755                 760                 765

Met Arg Gly Leu Ala Ile Arg Leu Ser Ser Gln Glu Leu Lys Asp Gly
    770                 775                 780

Phe Asp Val Gln Leu Glu Ser Ser Cys Gln Asp Asn Leu Gln His Leu
785                 790                 795                 800

Leu Val Tyr Arg Ala Ser Arg Asp Leu Ala Ala Cys Lys Arg Ala Thr
                805                 810                 815

Cys Pro Ala Glu Leu Asp Pro Lys Ile Leu Val Leu Pro Val Gly Ala
            820                 825                 830

Phe Ile Ala Ser Val Met Lys Met Ile Glu Arg Gly Asp Glu Pro Leu
        835                 840                 845

Ala Gly Ala Tyr Leu Arg His Arg Pro His Ser Phe Gly Trp Gln Ile
    850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
                885                 890                 895

Ser Ala Gln Tyr Gly Pro Val Leu Trp Leu Asn Ser Ser Ser Tyr Ser
            900                 905                 910

Gln Ser Gln Tyr Leu Asp Gly Phe Leu Ser Gln Pro Lys Asn Trp Ser
        915                 920                 925

Met Arg Val Leu Pro Gln Ala Gly Ser Val Arg Val Glu Gln Arg Val
    930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
                965                 970                 975

Gly Ser Gly Asp Glu Ala Val Leu Ala Pro Asn Arg Tyr Leu Gly Leu
            980                 985                 990
```

Phe Pro His Ser Gly Gly Ile Glu Tyr Ala Val Val Asp Val Leu Asp
995 1000 1005

Ser Ala Gly Phe Lys Ile Leu Glu Arg Gly Thr Ile Ala Val Asn
1010 1015 1020

Gly Phe Ser Gln Lys Arg Gly Glu Arg Gln Glu Glu Ala His Arg
1025 1030 1035

Glu Lys Gln Arg Arg Gly Ile Ser Asp Ile Gly Arg Lys Lys Pro
1040 1045 1050

Val Gln Ala Glu Val Asp Ala Ala Asn Glu Leu His Arg Lys Tyr
1055 1060 1065

Thr Asp Val Ala Thr Arg Leu Gly Cys Arg Ile Val Val Gln Trp
1070 1075 1080

Ala Pro Gln Pro Lys Pro Gly Thr Ala Pro Thr Ala Gln Thr Val
1085 1090 1095

Tyr Ala Arg Ala Val Arg Thr Glu Ala Pro Arg Ser Gly Asn Gln
1100 1105 1110

Glu Asp His Ala Arg Met Lys Ser Ser Trp Gly Tyr Thr Trp Gly
1115 1120 1125

Thr Tyr Trp Glu Lys Arg Lys Pro Glu Asp Ile Leu Gly Ile Ser
1130 1135 1140

Thr Gln Val Tyr Trp Thr Gly Gly Ile Gly Glu Ser Cys Pro Ala
1145 1150 1155

Val Ala Val Ala Leu Leu Gly His Ile Arg Ala Thr Ser Thr Gln
1160 1165 1170

Thr Glu Trp Glu Lys Glu Glu Val Val Phe Gly Arg Leu Lys Lys
1175 1180 1185

Phe Phe Pro Ser
1190

<210> SEQ ID NO 158
<211> LENGTH: 1192
<212> TYPE: PRT
<213> ORGANISM: Unknown
<220> FEATURE:
<223> OTHER INFORMATION: Synthetic sequence

<400> SEQUENCE: 158

Met Ala Glu Ser Lys Gln Met Gln Cys Arg Lys Cys Gly Ala Ser Met
1 5 10 15

Lys Tyr Glu Val Ile Gly Leu Gly Lys Lys Ser Cys Arg Tyr Met Cys
20 25 30

Pro Asp Cys Gly Asn His Thr Ser Ala Arg Lys Ile Gln Asn Lys Lys
35 40 45

Lys Arg Asp Lys Lys Tyr Gly Ser Ala Ser Lys Ala Gln Ser Gln Arg
50 55 60

Ile Ala Val Ala Gly Ala Leu Tyr Pro Asp Lys Lys Val Gln Thr Ile
65 70 75 80

Lys Thr Tyr Lys Tyr Pro Ala Asp Leu Asn Gly Glu Val His Asp Arg
85 90 95

Gly Val Ala Glu Lys Ile Glu Gln Ala Ile Gln Glu Asp Glu Ile Gly
100 105 110

Leu Leu Gly Pro Ser Ser Phe Tyr Ala Cys Trp Ile Ala Ser Gln Lys
115 120 125

Gln Ser Glu Pro Tyr Ser Val Val Asp Phe Trp Phe Asp Ala Val Cys
130 135 140

Ala Gly Gly Val Phe Ala Tyr Ser Gly Ala Arg Leu Leu Ser Thr Val
145 150 155 160

Leu Gln Leu Ser Gly Glu Glu Ser Val Leu Arg Ala Ala Leu Ala Ser
165 170 175

Ser Pro Phe Val Asp Asp Ile Asn Leu Ala Gln Ala Glu Lys Phe Leu
180 185 190

Ala Val Ser Arg Arg Thr Gly Gln Asp Lys Leu Gly Lys Arg Ile Gly
195 200 205

Glu Cys Phe Ala Glu Gly Arg Leu Glu Ala Leu Gly Ile Lys Asp Arg
210 215 220

Met Arg Glu Phe Val Gln Ala Ile Asp Val Ala Gln Thr Ala Gly Gln
225 230 235 240

Arg Phe Ala Ala Lys Leu Lys Ile Phe Gly Ile Ser Gln Met Pro Glu
245 250 255

Ala Lys Gln Trp Asn Asn Asp Ser Gly Leu Thr Val Cys Ile Leu Pro
260 265 270

Asp Tyr Tyr Val Pro Glu Glu Asn Arg Ala Asp Gln Leu Val Val Leu
275 280 285

Leu Arg Arg Leu Arg Glu Ile Ala Tyr Cys Met Gly Ile Glu Asp Glu
290 295 300

Ala Gly Phe Glu His Leu Gly Ile Asp Pro Gly Ala Leu Ser Asn Phe
305 310 315 320

Ser Asn Gly Asn Pro Lys Arg Gly Phe Leu Gly Arg Leu Leu Asn Asn
325 330 335

Asp Ile Ile Ala Leu Ala Asn Asn Met Ser Ala Met Thr Pro Tyr Trp
340 345 350

Glu Gly Arg Lys Gly Glu Leu Ile Glu Arg Leu Ala Trp Leu Lys His
355 360 365

Arg Ala Glu Gly Leu Tyr Leu Lys Glu Pro His Phe Gly Asn Ser Trp
370 375 380

Ala Asp His Arg Ser Arg Ile Phe Ser Arg Ile Ala Gly Trp Leu Ser
385 390 395 400

Gly Cys Ala Gly Lys Leu Lys Ile Ala Lys Asp Gln Ile Ser Gly Val
405 410 415

Arg Thr Asp Leu Phe Leu Leu Lys Arg Leu Leu Asp Ala Val Pro Gln
420 425 430

Ser Ala Pro Ser Pro Asp Phe Ile Ala Ser Ile Ser Ala Leu Asp Arg
435 440 445

Phe Leu Glu Ala Ala Glu Ser Ser Gln Asp Pro Ala Glu Gln Val Arg
450 455 460

Ala Leu Tyr Ala Phe His Leu Asn Ala Pro Ala Val Arg Ser Ile Ala
465 470 475 480

Asn Lys Ala Val Gln Arg Ser Asp Ser Gln Glu Trp Leu Ile Lys Glu
485 490 495

Leu Asp Ala Val Asp His Leu Glu Phe Asn Lys Ala Phe Pro Phe Phe
500 505 510

Ser Asp Thr Gly Lys Lys Lys Lys Lys Gly Ala Asn Ser Asn Gly Ala
515 520 525

Pro Ser Glu Glu Glu Tyr Thr Glu Thr Glu Ser Ile Gln Gln Pro Glu
530 535 540

Asp Ala Glu Gln Glu Val Asn Gly Gln Glu Gly Asn Gly Ala Ser Lys
545 550 555 560

Asn Gln Lys Lys Phe Gln Arg Ile Pro Arg Phe Phe Gly Glu Gly Ser

```
                565                 570                 575

Arg Ser Glu Tyr Arg Ile Leu Thr Glu Ala Pro Gln Tyr Phe Asp Met
            580                 585                 590

Phe Cys Asn Asn Met Arg Ala Ile Phe Met Gln Leu Glu Ser Gln Pro
        595                 600                 605

Arg Lys Ala Pro Arg Asp Phe Lys Cys Phe Leu Gln Asn Arg Leu Gln
    610                 615                 620

Lys Leu Tyr Lys Gln Thr Phe Leu Asn Ala Arg Ser Asn Lys Cys Arg
625                 630                 635                 640

Ala Leu Leu Glu Ser Val Leu Ile Ser Trp Gly Glu Phe Tyr Thr Tyr
                645                 650                 655

Gly Ala Asn Glu Lys Lys Phe Arg Leu Arg His Glu Ala Ser Glu Arg
            660                 665                 670

Ser Ser Asp Pro Asp Tyr Val Val Gln Gln Ala Leu Glu Ile Ala Arg
        675                 680                 685

Arg Leu Phe Leu Phe Gly Phe Glu Trp Arg Asp Cys Ser Ala Gly Glu
    690                 695                 700

Arg Val Asp Leu Val Glu Ile His Lys Lys Ala Ile Ser Phe Leu Leu
705                 710                 715                 720

Ala Ile Thr Gln Ala Glu Val Ser Val Gly Ser Tyr Asn Trp Leu Gly
                725                 730                 735

Asn Ser Thr Val Ser Arg Tyr Leu Ser Val Ala Gly Thr Asp Thr Leu
            740                 745                 750

Tyr Gly Thr Gln Leu Glu Glu Phe Leu Asn Ala Thr Val Leu Ser Gln
        755                 760                 765

Met Arg Gly Leu Ala Ile Arg Leu Ser Ser Gln Glu Leu Lys Asp Gly
    770                 775                 780

Phe Asp Val Gln Leu Glu Ser Ser Cys Gln Asp Asn Leu Gln His Leu
785                 790                 795                 800

Leu Val Tyr Arg Ala Ser Arg Asp Leu Ala Ala Cys Lys Arg Ala Thr
                805                 810                 815

Cys Pro Ala Glu Leu Asp Pro Lys Ile Leu Val Leu Pro Ala Gly Ala
            820                 825                 830

Phe Ile Ala Ser Val Met Lys Met Ile Glu Arg Gly Asp Glu Pro Leu
        835                 840                 845

Ala Gly Ala Tyr Leu Arg His Arg Pro His Ser Phe Gly Trp Gln Ile
    850                 855                 860

Arg Val Arg Gly Val Ala Glu Val Gly Met Asp Gln Gly Thr Ala Leu
865                 870                 875                 880

Ala Phe Gln Lys Pro Thr Glu Ser Glu Pro Phe Lys Ile Lys Pro Phe
                885                 890                 895

Ser Ala Gln Tyr Gly Pro Val Leu Trp Leu Asn Ser Ser Ser Tyr Ser
            900                 905                 910

Gln Ser Gln Tyr Leu Asp Gly Phe Leu Ser Gln Pro Lys Asn Trp Ser
        915                 920                 925

Met Arg Val Leu Pro Gln Ala Gly Ser Val Arg Val Glu Gln Arg Val
    930                 935                 940

Ala Leu Ile Trp Asn Leu Gln Ala Gly Lys Met Arg Leu Glu Arg Ser
945                 950                 955                 960

Gly Ala Arg Ala Phe Phe Met Pro Val Pro Phe Ser Phe Arg Pro Ser
                965                 970                 975

Gly Ser Gly Asp Glu Ala Val Leu Ala Pro Asn Arg Tyr Leu Gly Leu
            980                 985                 990
```

Phe Pro His Ser Gly Gly Ile Glu Tyr Ala Val Val Asp Val Leu Asp
995 1000 1005

Ser Ala Gly Phe Lys Ile Leu Glu Arg Gly Thr Ile Ala Val Asn
1010 1015 1020

Gly Phe Ser Gln Lys Arg Gly Glu Arg Gln Glu Glu Ala His Arg
1025 1030 1035

Glu Lys Gln Arg Arg Gly Ile Ser Asp Ile Gly Arg Lys Lys Pro
1040 1045 1050

Val Gln Ala Glu Val Asp Ala Ala Asn Glu Leu His Arg Lys Tyr
1055 1060 1065

Thr Asp Val Ala Thr Arg Leu Gly Cys Arg Ile Val Val Gln Trp
1070 1075 1080

Ala Pro Gln Pro Lys Pro Gly Thr Ala Pro Thr Ala Gln Thr Val
1085 1090 1095

Tyr Ala Arg Ala Val Arg Thr Glu Ala Pro Arg Ser Gly Asn Gln
1100 1105 1110

Glu Asp His Ala Arg Met Lys Ser Ser Trp Gly Tyr Thr Trp Ser
1115 1120 1125

Thr Tyr Trp Glu Lys Arg Lys Pro Glu Asp Ile Leu Gly Ile Ser
1130 1135 1140

Thr Gln Val Tyr Trp Thr Gly Gly Ile Gly Glu Ser Cys Pro Ala
1145 1150 1155

Val Ala Val Ala Leu Leu Gly His Ile Arg Ala Thr Ser Thr Gln
1160 1165 1170

Thr Glu Trp Glu Lys Glu Glu Val Val Phe Gly Arg Leu Lys Lys
1175 1180 1185

Phe Phe Pro Ser
1190

<210> SEQ ID NO 159
<211> LENGTH: 1287
<212> TYPE: PRT
<213> ORGANISM: Unknown
<220> FEATURE:
<223> OTHER INFORMATION: Synthetic sequence

<400> SEQUENCE: 159

Met Lys Arg Ile Leu Asn Ser Leu Lys Val Ala Ala Leu Arg Leu Leu
1 5 10 15

Phe Arg Gly Lys Gly Ser Glu Leu Val Lys Thr Val Lys Tyr Pro Leu
20 25 30

Val Ser Pro Val Gln Gly Ala Val Glu Glu Leu Ala Glu Ala Ile Arg
35 40 45

His Asp Asn Leu His Leu Phe Gly Gln Lys Glu Ile Val Asp Leu Met
50 55 60

Glu Lys Asp Glu Gly Thr Gln Val Tyr Ser Val Val Asp Phe Trp Leu
65 70 75 80

Asp Thr Leu Arg Leu Gly Met Phe Phe Ser Pro Ser Ala Asn Ala Leu
85 90 95

Lys Ile Thr Leu Gly Lys Phe Asn Ser Asp Gln Val Ser Pro Phe Arg
100 105 110

Lys Val Leu Glu Gln Ser Pro Phe Phe Leu Ala Gly Arg Leu Lys Val
115 120 125

Glu Pro Ala Glu Arg Ile Leu Ser Val Glu Ile Arg Lys Ile Gly Lys
130 135 140

```
Arg Glu Asn Arg Val Glu Asn Tyr Ala Ala Asp Val Glu Thr Cys Phe
145                 150                 155                 160

Ile Gly Gln Leu Ser Ser Asp Glu Lys Gln Ser Ile Gln Lys Leu Ala
                165                 170                 175

Asn Asp Ile Trp Asp Ser Lys Asp His Glu Glu Gln Arg Met Leu Lys
            180                 185                 190

Ala Asp Phe Phe Ala Ile Pro Leu Ile Lys Asp Pro Lys Ala Val Thr
        195                 200                 205

Glu Glu Asp Pro Glu Asn Glu Thr Ala Gly Lys Gln Lys Pro Leu Glu
    210                 215                 220

Leu Cys Val Cys Leu Val Pro Glu Leu Tyr Thr Arg Gly Phe Gly Ser
225                 230                 235                 240

Ile Ala Asp Phe Leu Val Gln Arg Leu Thr Leu Leu Arg Asp Lys Met
                245                 250                 255

Ser Thr Asp Thr Ala Glu Asp Cys Leu Glu Tyr Val Gly Ile Glu Glu
            260                 265                 270

Glu Lys Gly Asn Gly Met Asn Ser Leu Leu Gly Thr Phe Leu Lys Asn
        275                 280                 285

Leu Gln Gly Asp Gly Phe Glu Gln Ile Phe Gln Phe Met Leu Gly Ser
    290                 295                 300

Tyr Val Gly Trp Gln Gly Lys Glu Asp Val Leu Arg Glu Arg Leu Asp
305                 310                 315                 320

Leu Leu Ala Glu Lys Val Lys Arg Leu Pro Lys Pro Lys Phe Ala Gly
                325                 330                 335

Glu Trp Ser Gly His Arg Met Phe Leu His Gly Gln Leu Lys Ser Trp
            340                 345                 350

Ser Ser Asn Phe Phe Arg Leu Phe Asn Glu Thr Arg Glu Leu Leu Glu
        355                 360                 365

Ser Ile Lys Ser Asp Ile Gln His Ala Thr Met Leu Ile Ser Tyr Val
    370                 375                 380

Glu Glu Lys Gly Gly Tyr His Pro Gln Leu Leu Ser Gln Tyr Arg Lys
385                 390                 395                 400

Leu Met Glu Gln Leu Pro Ala Leu Arg Thr Lys Val Leu Asp Pro Glu
                405                 410                 415

Ile Glu Met Thr His Met Ser Glu Ala Val Arg Ser Tyr Ile Met Ile
            420                 425                 430

His Lys Ser Val Ala Gly Phe Leu Pro Asp Leu Leu Glu Ser Leu Asp
        435                 440                 445

Arg Asp Lys Asp Arg Glu Phe Leu Leu Ser Ile Phe Pro Arg Ile Pro
    450                 455                 460

Lys Ile Asp Lys Lys Thr Lys Glu Ile Val Ala Trp Glu Leu Pro Gly
465                 470                 475                 480

Glu Pro Glu Glu Gly Tyr Leu Phe Thr Ala Asn Asn Leu Phe Arg Asn
                485                 490                 495

Phe Leu Glu Asn Pro Lys His Val Pro Arg Phe Met Ala Glu Arg Ile
            500                 505                 510

Pro Glu Asp Trp Thr Arg Leu Arg Ser Ala Pro Val Trp Phe Asp Gly
        515                 520                 525

Met Val Lys Gln Trp Gln Lys Val Val Asn Gln Leu Val Glu Ser Pro
    530                 535                 540

Gly Ala Leu Tyr Gln Phe Asn Glu Ser Phe Leu Arg Gln Arg Leu Gln
545                 550                 555                 560
```

```
Ala Met Leu Thr Val Tyr Lys Arg Asp Leu Gln Thr Glu Lys Phe Leu
                565                 570                 575

Lys Leu Leu Ala Asp Val Cys Arg Pro Leu Val Asp Phe Phe Gly Leu
            580                 585                 590

Gly Gly Asn Asp Ile Ile Phe Lys Ser Cys Gln Asp Pro Arg Lys Gln
        595                 600                 605

Trp Gln Thr Val Ile Pro Leu Ser Val Pro Ala Asp Val Tyr Thr Ala
    610                 615                 620

Cys Glu Gly Leu Ala Ile Arg Leu Arg Glu Thr Leu Gly Phe Glu Trp
625                 630                 635                 640

Lys Asn Leu Lys Gly His Glu Arg Glu Asp Phe Leu Arg Leu His Gln
                645                 650                 655

Leu Leu Gly Asn Leu Leu Phe Trp Ile Arg Asp Ala Lys Leu Val Val
            660                 665                 670

Lys Leu Glu Asp Trp Met Asn Asn Pro Cys Val Gln Glu Tyr Val Glu
        675                 680                 685

Ala Arg Lys Ala Ile Asp Leu Pro Leu Glu Ile Phe Gly Phe Glu Val
    690                 695                 700

Pro Ile Phe Leu Asn Gly Tyr Leu Phe Ser Glu Leu Arg Gln Leu Glu
705                 710                 715                 720

Leu Leu Leu Arg Arg Lys Ser Val Met Thr Ser Tyr Ser Val Lys Thr
                725                 730                 735

Thr Gly Ser Pro Asn Arg Leu Phe Gln Ile Val Tyr Leu Pro Leu Asn
            740                 745                 750

Pro Ser Asp Pro Glu Lys Lys Asn Ser Asn Asn Phe Gln Glu Arg Leu
        755                 760                 765

Asp Thr Pro Thr Gly Leu Ser Arg Arg Phe Leu Asp Leu Thr Leu Asp
    770                 775                 780

Ala Phe Ala Gly Lys Leu Leu Thr Asp Pro Val Thr Gln Glu Leu Lys
785                 790                 795                 800

Thr Met Ala Gly Phe Tyr Asp His Leu Phe Gly Phe Lys Leu Pro Cys
                805                 810                 815

Lys Leu Ala Ala Met Ser Asn His Pro Gly Ser Ser Ser Lys Met Val
            820                 825                 830

Val Leu Ala Lys Pro Lys Lys Gly Val Ala Ser Asn Ile Gly Phe Glu
        835                 840                 845

Pro Ile Pro Asp Pro Ala His Pro Val Phe Arg Val Arg Ser Ser Trp
    850                 855                 860

Pro Glu Leu Lys Tyr Leu Glu Gly Leu Leu Tyr Leu Pro Glu Asp Thr
865                 870                 875                 880

Pro Leu Thr Ile Glu Leu Ala Glu Thr Ser Val Ser Cys Gln Ser Val
                885                 890                 895

Ser Ser Val Ala Phe Asp Leu Lys Asn Leu Thr Thr Ile Leu Gly Arg
            900                 905                 910

Val Gly Glu Phe Arg Val Thr Ala Asp Gln Pro Phe Lys Leu Thr Pro
        915                 920                 925

Ile Ile Pro Glu Lys Glu Glu Ser Phe Ile Gly Lys Thr Tyr Leu Gly
    930                 935                 940

Leu Asp Ala Gly Glu Arg Ser Gly Val Gly Phe Ala Ile Val Thr Val
945                 950                 955                 960

Asp Gly Asp Gly Tyr Glu Val Gln Arg Leu Gly Val His Glu Asp Thr
                965                 970                 975

Gln Leu Met Ala Leu Gln Gln Val Ala Ser Lys Ser Leu Lys Glu Pro
```

-continued

```
            980                 985                 990

Val Phe Gln Pro Leu Arg Lys Gly  Thr Phe Arg Gln Gln  Glu Arg Ile
        995                 1000                1005

Arg Lys  Ser Leu Arg Gly Cys  Tyr Trp Asn Phe Tyr  His Ala Leu
    1010                 1015                 1020

Val Ile  Lys Tyr Arg Ala Lys  Val Val His Glu Glu  Ser Val Gly
    1025                 1030                 1035

Ser Ser  Gly Leu Val Gly Gln  Trp Leu Arg Ala Phe  Gln Lys Asp
    1040                 1045                 1050

Leu Lys  Lys Ala Asp Val Leu  Pro Lys Lys Gly Gly  Lys Asn Gly
    1055                 1060                 1065

Val Asp  Lys Lys Lys Arg Glu  Ser Ser Ala Gln Asp  Thr Leu Trp
    1070                 1075                 1080

Gly Gly  Ala Phe Ser Lys Lys  Glu Glu Gln Gln Ile  Ala Phe Glu
    1085                 1090                 1095

Val Gln  Ala Ala Cys Ser Ser  Gln Phe Cys Leu Lys  Cys Gly Trp
    1100                 1105                 1110

Trp Phe  Gln Leu Gly Met Arg  Glu Val Asn Arg Val  Gln Glu Ser
    1115                 1120                 1125

Gly Val  Val Leu Asp Trp Asn  Arg Ser Ile Val Thr  Phe Leu Ile
    1130                 1135                 1140

Glu Ser  Ser Gly Glu Lys Val  Tyr Gly Phe Ser Pro  Gln Gln Leu
    1145                 1150                 1155

Glu Lys  Gly Phe Arg Pro Asp  Ile Glu Thr Phe Lys  Lys Met Val
    1160                 1165                 1170

Arg Asp  Phe Met Arg Pro Pro  Met Phe Asp Arg Lys  Gly Arg Pro
    1175                 1180                 1185

Ala Ala  Ala Tyr Glu Arg Phe  Val Leu Gly Arg Arg  His Arg Arg
    1190                 1195                 1200

Tyr Arg  Phe Asp Lys Val Phe  Glu Glu Arg Phe Gly  Arg Ser Ala
    1205                 1210                 1215

Leu Phe  Ile Cys Pro Arg Val  Gly Cys Gly Asn Phe  Asp His Ser
    1220                 1225                 1230

Ser Glu  Gln Ser Ala Val Val  Leu Ala Leu Ile Gly  Tyr Ile Ala
    1235                 1240                 1245

Asp Lys  Glu Gly Met Ser Gly  Lys Lys Leu Val Tyr  Val Arg Leu
    1250                 1255                 1260

Ala Glu  Leu Met Ala Glu Trp  Lys Leu Lys Lys Leu  Glu Arg Ser
    1265                 1270                 1275

Arg Val  Glu Glu Gln Ser Ser  Ala Gln
    1280                 1285
```